US011952424B2

(12) United States Patent
de Kruif et al.

(10) Patent No.: US 11,952,424 B2
(45) Date of Patent: Apr. 9, 2024

(54) MULTIVALENT ANTIBODY

(71) Applicant: MERUS N.V., Utrecht (NL)

(72) Inventors: Cornelis Adriaan de Kruif, Utrecht (NL); Linda Johanna Aleida Hendriks, Utrecht (NL); Ton Logtenberg, Utrecht (NL)

(73) Assignee: merus n.v., Utrecht (NL)

( * ) Notice: Subject to any disclaimer, the term of this patent is extended or adjusted under 35 U.S.C. 154(b) by 0 days.

(21) Appl. No.: 16/370,346

(22) Filed: Mar. 29, 2019

(65) Prior Publication Data

US 2019/0352401 A1    Nov. 21, 2019

Related U.S. Application Data

(60) Provisional application No. 62/650,467, filed on Mar. 30, 2018.

(51) Int. Cl.
*C07K 16/28*    (2006.01)

(52) U.S. Cl.
CPC ...... *C07K 16/2827* (2013.01); *C07K 16/2809* (2013.01); *C07K 16/2851* (2013.01); *C07K 16/2863* (2013.01); *C07K 2317/31* (2013.01); *C07K 2317/35* (2013.01); *C07K 2317/522* (2013.01); *C07K 2317/53* (2013.01); *C07K 2317/55* (2013.01)

(58) Field of Classification Search
CPC ............ C07K 2317/55; C07K 2317/31; C07K 2317/35; C07K 2317/60
USPC ............................................ 424/133.1, 136.1
See application file for complete search history.

(56) References Cited

U.S. PATENT DOCUMENTS

| 7,612,181 | B2 | 11/2009 | Wu et al. | |
|---|---|---|---|---|
| 9,248,181 | B2 | 2/2016 | De Kruif et al. | |
| 9,358,286 | B2 | 6/2016 | De Kruif et al. | |
| 9,914,777 | B2* | 3/2018 | Bakker | A61P 35/00 |
| 10,266,593 | B2* | 4/2019 | Bakker | C07K 16/2851 |
| 10,266,608 | B2* | 4/2019 | Wu | A61P 1/16 |
| 10,519,251 | B2* | 12/2019 | Wu | A61P 13/12 |
| 10,544,212 | B2* | 1/2020 | Bloom | A61P 11/00 |
| 2010/0203056 | A1 | 8/2010 | Irving et al. | |
| 2015/0203591 | A1* | 7/2015 | Yancopoulos | C07K 16/2803 530/387.3 |
| 2016/0368988 | A1* | 12/2016 | Bakker | C07K 16/2809 |
| 2017/0204176 | A1 | 7/2017 | Bonvini et al. | |
| 2018/0237523 | A1* | 8/2018 | Bakker | A61K 39/39591 |
| 2019/0211100 | A1* | 7/2019 | Bakker | A61K 39/39591 |
| 2020/0017595 | A1* | 1/2020 | Geuijen | C07K 16/2827 |
| 2020/0102393 | A1* | 4/2020 | Throsby | A61K 39/39558 |
| 2020/0216539 | A1* | 7/2020 | Geuijen | C07K 16/2818 |
| 2020/0216540 | A1* | 7/2020 | Geuijen | C07K 16/1282 |
| 2020/0247892 | A1* | 8/2020 | Geuijen | A61P 35/00 |
| 2020/0291130 | A1* | 9/2020 | Throsby | C07K 16/32 |
| 2020/0325227 | A1* | 10/2020 | Geuijen | C07K 16/2818 |
| 2020/0384084 | A1* | 12/2020 | Bakker | A61K 45/06 |
| 2021/0054049 | A1* | 2/2021 | De Kruif | C07K 16/36 |
| 2021/0220404 | A1* | 7/2021 | Abujoub | A61P 35/00 |
| 2022/0073649 | A1* | 3/2022 | De Kruif | C07K 16/005 |
| 2023/0210988 | A1* | 7/2023 | Van Loo | A61K 39/3955 424/136.1 |

FOREIGN PATENT DOCUMENTS

| CN | 108602888 A * | 9/2018 |
|---|---|---|
| EP | 0517024 A2 | 12/1992 |
| WO | WO-9850431 A2 | 11/1998 |
| WO | WO-2001077342 A1 | 10/2001 |
| WO | WO-2002002781 A1 | 1/2002 |
| WO | WO-2004009618 A2 | 1/2004 |
| WO | WO-2008024188 A2 | 2/2008 |
| WO | WO-2009157771 A2 | 12/2009 |
| WO | WO-2010135558 A1 | 11/2010 |
| WO | WO-2011066389 A1 | 6/2011 |
| WO | WO-2011084255 A2 | 7/2011 |
| WO | WO-2011086091 A1 | 7/2011 |
| WO | WO-2012088290 A2 | 6/2012 |
| WO | WO-2013079174 A1 | 6/2013 |

(Continued)

OTHER PUBLICATIONS

Shiraiwa et al (Methods 154:10-20 (2019)).*
Gong et al (Methods 154:87-92 (2019)).*
Gong et al (MABS vol. 9, No. 7, 1118-1128 (2017)).*
Qi et al. (Frontiers in Immunology 10:1-13 (2019)).*
Spiess, C., et al., (Alternative molecular formats and therapeutic applications for bispecific antibodies. Mol. Immunol. (2015), http://dx.doi.org/10.1016/j.molimm.2015.01.003).*
Miller et al (J Immunol 2003; 170:4854-4861).*
Kontermann (mAbs 4:2, 182-197; Mar./Apr. 2012).*

(Continued)

*Primary Examiner* — Lynn A Bristol
(74) *Attorney, Agent, or Firm* — STERNE, KESSLER, GOLDSTEIN & FOX P.L.L.C.

(57) ABSTRACT

The invention relates to a multivalent antibody which comprises: a base antibody portion which comprises two binding domains; and at least one additional binding domain, wherein the base antibody portion is connected by a linker to the at least one additional binding domain, wherein each binding domain of the base antibody portion and each of the at least one additional binding domains all have a common variable region, and wherein the linker comprises a hinge sequence or a sequence derived from a hinge sequence. The invention also relates to a multivalent antibody which comprises: a base antibody portion which comprises two binding domains; and at least one additional binding domain, wherein at least one additional binding domain comprises a CH1 region and is connected to the base antibody portion by said linker, linking a variable region of the base antibody portion and the CH1 region, and wherein the multivalent antibody binds to at least three different epitopes.

47 Claims, 54 Drawing Sheets

Specification includes a Sequence Listing.

(56) References Cited

FOREIGN PATENT DOCUMENTS

| WO | WO-2013157953 A1 | 10/2013 |
|---|---|---|
| WO | WO-2013157954 A1 | 10/2013 |
| WO | WO-2013173223 A1 | 11/2013 |
| WO | WO-2013181634 A2 | 12/2013 |
| WO | WO-2014022540 A1 | 2/2014 |
| WO | WO-2014051433 A1 | 4/2014 |
| WO | WO-2014122144 A1 | 8/2014 |
| WO | WO-2014131711 A1 | 9/2014 |
| WO | WO-2014167022 A1 | 10/2014 |
| WO | WO-2015130172 A1 | 9/2015 |
| WO | WO-2015130173 A1 | 9/2015 |
| WO | WO-2016020332 A1 | 2/2016 |
| WO | WO-2016055592 A1 | 4/2016 |
| WO | WO-2016055593 A1 | 4/2016 |
| WO | WO-2016079177 A1 | 5/2016 |
| WO | WO-2016105450 A2 | 6/2016 |
| WO | WO-2016149201 A2 | 9/2016 |
| WO | WO-2017021450 A1 | 2/2017 |
| WO | WO-2017034916 A1 | 3/2017 |
| WO | WO-2017162890 A1 | 9/2017 |
| WO | WO-2017186950 A1 | 11/2017 |
| WO | WO-2018056821 A1 | 3/2018 |
| WO | WO-2018075692 A2 | 4/2018 |
| WO | WO-2018083204 A1 | 5/2018 |
| WO | WO-2019190327 A2 | 10/2019 |

OTHER PUBLICATIONS

Brinkmann; U. et al., "The Making of Bispecific Antibodies," MABS 9(2):182-212, Taylor & Francis Group, England (2017).

Capelle, M., et al., "Spectroscopic Characterization of Antibodies Adsorbed to Aluminium Adjuvants: Correlation With Antibody Vaccine Immunogenicity," Vaccine 23(14):1686-1694, Elsevier Science, Netherlands (Feb. 2005).

De Haard, H.J., et al., "A Large Non-immunized Human Fab Fragment Phage Library That Permits Rapid Isolation and Kinetic Analysis of High Affinity Antibodies," Journal of Biological Chemistry 274(26):18218-18230, American Society for Biochemistry and Molecular Biology, United States (Jun. 1999).

Demeule, B., et al., "Characterization of Protein Aggregation: the Case of a Therapeutic Immunoglobulin," Biochimica et Biophysica Acta 1774(1):146-153, Elsevier Publisher, Netherlands (Jan. 2007 ).

Demeule, B., et al., "Detection and Characterization of Protein Aggregates by Fluorescence Microscopy," International Journal of Pharmaceutics 329(1-2):37-45, Elsevier/North-Holland Biomedical Press, Netherlands (Feb. 2007 ).

Demeule, B., et al., "New methods allowing the detection of protein aggregates A case study on trastuzumab," MABs, 1(2):142-150, Landes Bioscience (Mar.-Apr. 2009).

Digiammarino; E.L. et al., "Ligand Association Rates to the Inner-Variable-Domain Immunoglobulin Are Significantly Impacted By Linker Design," MABS 3(5):487-94, Taylor & Francis (2011).

Eckhardt, B.M., et al., "A Turbidimetric Method to Determine Visual Appearance of Protein Solutions," Journal of Pharmaceutical Science and Technology, 48(2):64-70, Bethesda Md : Pda, United States (Mar.-Apr. 1994).

GenBank, Homo sapiens Epidermal Growth Factor Receptor (EGFR), Transcript Variant 1, mRNA, Accession No. NM005228.3, accessed at https://www.ncbi.nlm.nih.gov/nuccore/NM_005228.3/.

Gorelik, L., et al., Preclinical Characterization of a Novel Fully Human IgG1 anti-PD-L1 mAb CK-301, American Association for Cancer Research Annual Meeting (AACR), Abstract 4606 (Apr. 2016).

Gront, D., et al., "Generalized Fragment Picking in Rosetta: Design, Protocols and Applications," PLoS One, 6(8): e23294, Public Library of Science, United States (2011).

Gunasekaran, K., et al., "Enhancing Antibody Fc Heterodimer Formation Through Electrostatic Steering Effects: Applications to Bispecific Molecules and Monovalent IgG," Journal of Biological Chemistry 285(25):19637-19646, American Society for Biochemistry and Molecular Biology, United States (Jun. 2010).

Karplus, P.A and Schulz, G.E., "Prediction of Chain Flexibility in Proteins, " Natural Sciences, 72(4):212-213, Springer-Verlag (Apr. 1985).

Kontermann; R., "Dual Targeting Strategies With Bispecific Antibodies," MABS 4(2):182-97, Taylor & Francis, England (2012).

Kruskal, J. B and Liberman, M., The Symmetric Time-Warping Problem: From Continuous to Discrete, Chapter four, Edited by Sankoff, D and Kruskal, J. B, 1983, Addison-Wesley Publishing Company, Inc, 38 pages.

Luca, L., et al., "Physical Instability, Aggregation and Conformational Changes of Recombinant Human Bone morphogenetic protein-2 (rhBMP-2)," International Journal of Pharmaceutics, 391(1-2):48-54, Elsevier/North-Holland Biomedical Press, Netherlands (May 2010).

Marks, J.D., et al., "By-passing Immunization. Human Antibodies from V-gene Libraries Displayed on Phage," Journal of Molecular Biology 222(3):581-597, Academic Press Limited, United States (Dec. 1991).

Merchant; M.A. et al., "An Efficient Route to Human Bispecific IgG," Nature Biotechnology 16(7):677-81, Nature Publishing Group, England (1998).

Mulinacci, F., et al., "Enhanced Physical Stability of Human Calcitonin after Methionine Oxidation," European Journal of Pharmaceutics and Biopharmaceutics, 78(2):229-238, Elsevier Science, Netherlands (Jun. 2011).

Mulinacci, F., et al., "Influence of Methionine Oxidation on the Aggregation of Recombinant Human Growth Hormone," European Journal of Pharmaceutics and Biopharmaceutics, 85(1):42-52, Elsevier Science, Netherlands (Sep. 2013).

Mulinacci, F., et al., "Oxidized Recombinant Human Growth Hormone That Maintains Conformational Integrity," Journal of Pharmaceutical Sciences, 100(1):110-122, Elsevier, United States (Jan. 2011).

Mulinacci, F., et al., "Stability of Human Growth Hormone: Influence of Methionine Oxidation on Thermal Folding," Journal of Pharmaceutical Sciences, 100(2):451-463, Elsevier, United States (Feb. 2011).

Nardis, D.C., et al., "A New Approach for Generating Bispecific Antibodies Based on a Common Light Chain Format and the Stable Architecture of Human Immunoglobulin G1," Journal of Biological Chemistry, 292(35):14706-14717, American Society for Biochemistry and Molecular Biology, United States (Sep. 2017).

Needleman, S.B. and Wunsch, C.D., "A General Method Applicable to the Search for Similarities in the Amino Acid Sequence of Two Proteins," Journal of Molecular Biology 48(3):443-453, Academic Press, England (Mar. 1970).

Patois, E., et al., "Evaluation of Nanoparticle Tracking Analysis (NTA) in the Characterization of Therapeutic Antibodies and Seasonal Influenza Vaccines: Pros and Cons," Journal of Drug Delivery Science and Technology, 22(5): 427-433, Elsevier B.V (2012).

Patois, E., et al., "Stability of Seasonal Influenza Vaccines Investigated By Spectroscopy and Microscopy Methods," Vaccine, 29(43): 7404-7413, Elsevier Science, Netherlands (Oct. 2011).

Peters, E., et al., "Alkaline Phosphatase as a Treatment of Sepsis-associated Acute Kidney Injury," The Journal of Pharmacology and Experimental Therapeutics 344(1):2-7, American Society for Pharmacology and Experimental Therapeutics, United States (2013).

Sackett, D.L. and Wolff, J., "Nile Red as a Polarity-Sensitive Fluorescent Probe of Hydrophobic Protein Surfaces," Analytical Biochemistry, 167(2):228-234, Elsevier, United States (Dec. 1987).

Strohl, W.R., "Optimization of Fc-mediated Effector Functions of Monoclonal Antibodies," Current Opinion in Biotechnology 20(6):685-691, Elsevier, England (2009).

Version 2.8.0 or higher, EMBOSS: The European Molecular Biology Open Software Suite (2000) Rice, P. Longdenj and Bleasby, A. Trends in Genetics 16, (6) pp. 276-277, Retrieved from the Internet: (URL: http://emboss.bioinformatics.nl/).

Zhang, F., et al., "Structural Basis of a Novel PD-L1 Nanobody for Immune Checkpoint Blockade," Cell Discovery, 3:17004, Nature Publishing Group, England (Mar. 2017).

(56) References Cited

OTHER PUBLICATIONS

International Search Report and Written Opinion dated Oct. 14, 2019, in International Patent Application No. PCT/NL2019/050199, European Patent Office, Netherlands, 32 pages.

Grummt, M., et al., "Importance of a flexible hinge near the motor domain in kinesin-driven motility," EMBO J 17(19):5536-5542, Oxford University Press, United Kingdom (Oct. 1998).

Klement, M., et al., "Effect of linker flexibility and length on the functionality of a cytotoxic engineered antibody fragment," J Biotechnol 199:90-97, Elsevier, Netherlands (Apr. 2015).

Meehan, R. R., et al., "HP1 binding to native chromatin in vitro is determined by the hinge region and not by the chromodomain," EMBO J 22(12):3164-3174, Oxford University Press, United Kingdom (Jun. 2003).

Zhao, L., et al., "A JAK2 interdomain linker relays Epo receptor engagement signals to kinase activation," J Biol Chem 284(39):26988-26998, American Society for Biochemistry and Molecular Biology, United States (Sep. 2009).

\* cited by examiner

Fig. 11A (SEQ ID NO: 35)

DIQMTQSPSSLSASVGDRVTITCRASQSISSYLNWYQQKPGKAPKLLIYAASSLQSGVP
SRFSGSGSGTDFTLTISSLQPEDFATYYCQQSYSTPPTFGQGTKVEIK
RTVAAPSVFIFPPSDEQLKSGTASVVCLLNNFYPREAKVQWKVDNALQSGNSQESVTE
QDSKDSTYSLSSTLTLSKADYEKHKVYACEVTHQGLSSPVTKSFNRGEC

Fig. 11B (SEQ ID NOs: 36 and 37)

gacatccagatgacccagtctccatcctccctgtctgcatctgtaggagacagagtcacc
D I Q M T Q S P S S L S A S V G D R V T
atcacttgccgggcaagtcagagcattagcagctacttaaattggtatcagcagaaacca
I T C R A S Q S I S S Y L N W Y Q Q K P
gggaaagcccctaagctcctgatctatgctgcatccagtttgcaaagtggggtcccatca
G K A P K L L I Y A A S S L Q S G V P S
aggttcagtggcagtggatctgggacagatttcactctcaccatcagcagtctgcaacct
R F S G S G S G T D F T L T I S S L Q P
gaagattttgcaacttactactgtcaacagagttacagtaccccccaacgttcggccaa
E D F A T Y Y C Q Q S Y S T P P T F G Q
gggaccaaggtggagatcaaa
G T K V E I K

Fig. 11C (SEQ ID NOs: 38 and 39)

cgaactgtggctgcaccatctgtcttcatcttcccgccatctgatgagcagttgaaatct
R T V A A P S V F I F P P S D E Q L K S
ggaactgcctctgttgtgtgcctgctgaataacttctatcccagagaggccaaagtacag
G T A S V V C L L N N F Y P R E A K V Q
tggaaggtggataacgcccctccaatcgggtaactcccaggagagtgtcacagagcaggac
W K V D N A L Q S G N S Q E S V T E Q D Fig. 11C (continued)

agcaaggacagcacctacagcctcagcagcaccctgacgctgagcaaagcagactacgag
S K D S T Y S L S S T L T L S K A D Y E
aaacacaaagtctacgcctgcgaagtcacccatcagggcctgagctcgcccgtcacaaag
K H K V Y A C E V T H Q G L S S P V T K
agcttcaacaggggagagtgttag
S F N R G E C -

Fig. 11D (SEQ ID NO: 40)

DIQMTQSPSSLSASVGDRVTITCRASQSISSYLNWYQQKPGKAPKLLIYAASSLQSGVP
SRFSGSGSGTDFTLTISSLQPEDFATYYCQQSYSTPPITFGQGTRLEIK

Fig. 11E (SEQ ID NO: 41)

DIQMTQSPSSLSASVGDRVTITCRASQSISSYLNWYQQKPGKAPKLLIYAASSLQSGVP
SRFSGSGSGTDFTLTISSLQPEDFATYYCQQSYSTP

Fig. 12

Fig. 13
| IgG1 UH 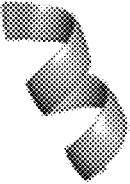 | SEQ ID NO: 2 | IgG2A H  | SEQ ID NO: 15 |
|---|---|---|---|
| IgG2A MH 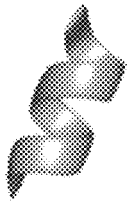 | SEQ ID NO: 4 | IgG2B H  | SEQ ID NO: 16 |
| IgG1 MH  | SEQ ID NO: 11 | IgG1 H  | SEQ ID NO:19 |
| IgG1G4  | SEQ ID NO: 12 | IgG2B R  | SEQ ID NO: 21 |

Fig. 14
14a
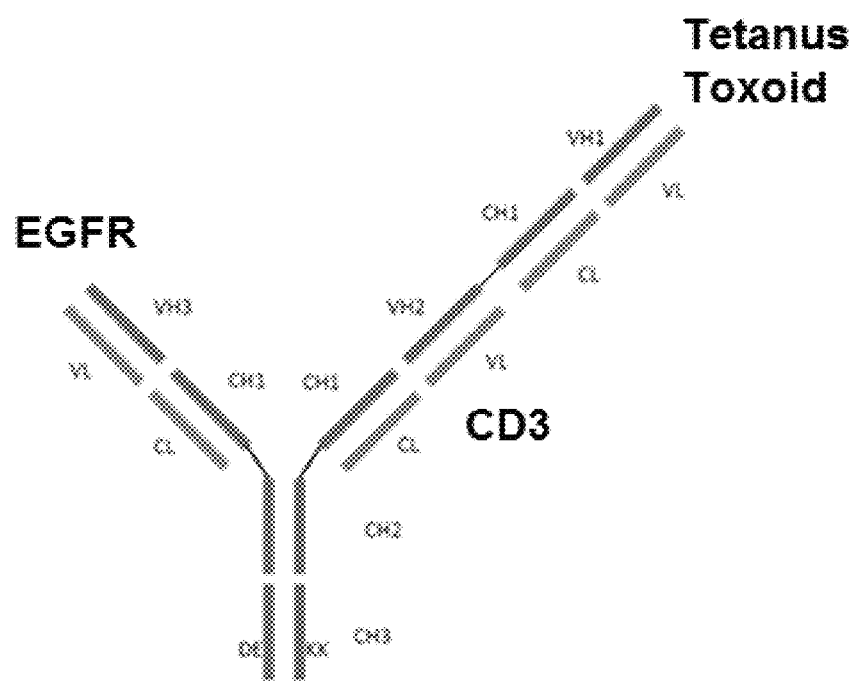
14b
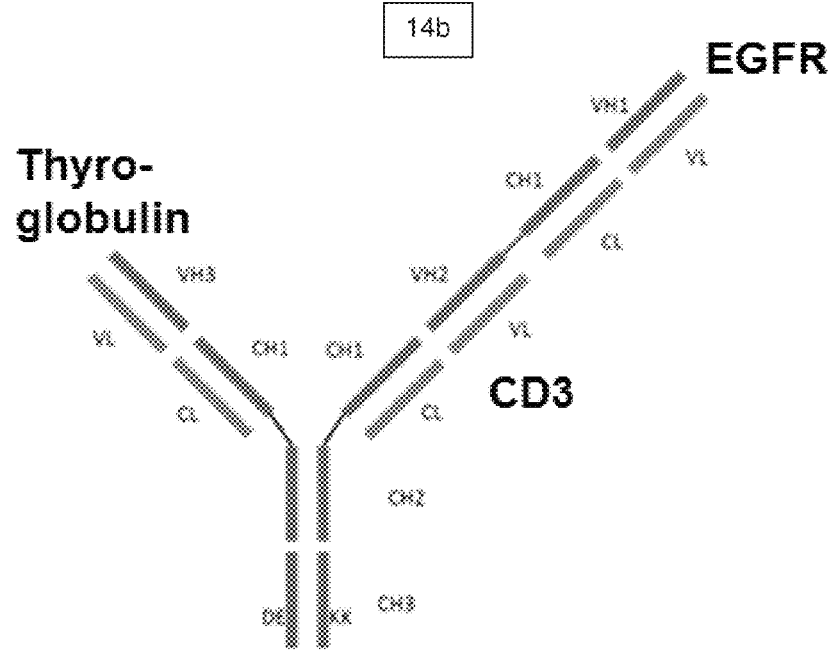

T cell Activation:

EGFRxCD3:TT

T cell Activation:

THYROxCD3:EGFR

T cell Cytotoxicity:

EGFRxCD3:TT

T cell Cytotoxicity:

THYROxCD3:EGFR

Fig. 23a

| FACS | Norm AUC | Mock | | | EGFR | | | |
|---|---|---|---|---|---|---|---|---|
| MDA PD-L1 | | | | MF9988 | | | | MF9891 |
| | - | 12 | N/A | 50 | 69 | 83 | | 146 |
| | - | 50 | 71 | 88 | 116 | 113 | | 148 |
| | - | 45 | 81 | N/A | 112 | 121 | | 148 |
| | - | 8 | 32 | 30 | 63 | N/A | | 104 |
| | MF5380 | 5 | 14 | N/A | 40 | 43 | | 71 |
| | MF5444 | 12 | 26 | 39 | 51 | 72 | | 102 |
| | Control EGFRxCD3 | | 28 | 25 | 26 | 60 | | 101 |

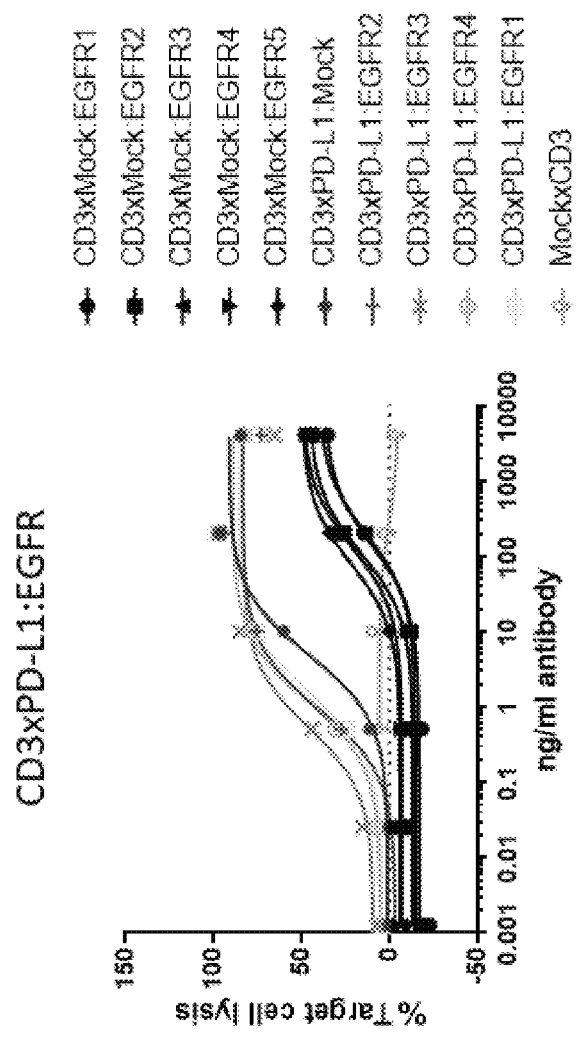

SEQUENCE LISTING

<160> NUMBER OF SEQ ID NOS: 314

<210> SEQ ID NO 1
<211> LENGTH: 7
<212> TYPE: PRT
<213> ORGANISM: Homo sapiens

<400> SEQUENCE: 1

Glu Ser Lys Tyr Gly Pro Pro
1               5

<210> SEQ ID NO 2
<211> LENGTH: 10
<212> TYPE: PRT
<213> ORGANISM: Homo sapiens

<400> SEQUENCE: 2

Glu Pro Lys Ser Cys Asp Lys Thr His Thr
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Linker

<400> SEQUENCE: 3

Gly Gly Gly Gly Ser Gly Gly Gly Gly Ser
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Linker

<400> SEQUENCE: 4

Glu Arg Lys Ser Ser Val Glu Ser Pro Pro Ser Pro
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Linker

<400> SEQUENCE: 5

Glu Arg Lys Cys Ser Val Glu Ser Pro Pro Ser Pro
1               5                   10

<210> SEQ ID NO 6
<211> LENGTH: 12
<212> TYPE: PRT
<213> ORGANISM: Homo sapiens

<400> SEQUENCE: 6

Glu Leu Lys Thr Pro Leu Gly Asp Thr Thr His Thr
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Linker

<400> SEQUENCE: 7

Glu Ser Lys Tyr Gly Pro Pro Ser Pro Ser Ser Pro
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Linker

<400> SEQUENCE: 8

Glu Arg Lys Ser Ser Val Glu Ala Pro Pro Val Ala Gly
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Linker

<400> SEQUENCE: 9

Glu Arg Lys Cys Ser Val Glu Ala Pro Pro Val Ala Gly
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Linker

<400> SEQUENCE: 10

Glu Ser Lys Tyr Gly Pro Pro Ala Pro Glu Phe Leu Gly Gly
1               5                   10

<210> SEQ ID NO 11
<211> LENGTH: 15
<212> TYPE: PRT
<213> ORGANISM: Artificial Sequence
<220> FEATURE:
<223> OTHER INFORMATION: Linker

<400> SEQUENCE: 11

Glu Pro Lys Ser Cys Asp Lys Thr His Thr Ser Pro Pro Ser Pro
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Linker

<400> SEQUENCE: 12

Glu Pro Lys Ser Cys Asp Gly Gly Gly Ser Gly Gly Gly Gly Ser
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Linker

<400> SEQUENCE: 13

Gly Gly Gly Gly Ser Gly Gly Gly Gly Ser Ala Pro Pro Val Ala Gly
1               5                   10                  15

<210> SEQ ID NO 14
<211> LENGTH: 17
<212> TYPE: PRT
<213> ORGANISM: Artificial Sequence
<220> FEATURE:
<223> OTHER INFORMATION: Linker

<400> SEQUENCE: 14

Glu Pro Lys Ser Cys Asp Lys Thr His Thr Ala Pro Glu Leu Leu Gly
1               5                   10                  15
Gly

<210> SEQ ID NO 15
<211> LENGTH: 18
<212> TYPE: PRT
<213> ORGANISM: Artificial Sequence
<220> FEATURE:
<223> OTHER INFORMATION: Linker

<400> SEQUENCE: 15

Glu Arg Lys Ser Ser Val Glu Ser Pro Pro Ser Pro Ala Pro Pro Val
1               5                   10                  15
Ala Gly

<210> SEQ ID NO 16
<211> LENGTH: 18
<212> TYPE: PRT
<213> ORGANISM: Artificial Sequence
<220> FEATURE:
<223> OTHER INFORMATION: Linker

<400> SEQUENCE: 16

Glu Arg Lys Cys Ser Val Glu Ser Pro Pro Ser Pro Ala Pro Pro Val
1               5                   10                  15
Ala Gly

<210> SEQ ID NO 17
<211> LENGTH: 19
<212> TYPE: PRT
<213> ORGANISM: Artificial Sequence
<220> FEATURE:
<223> OTHER INFORMATION: Linker

<400> SEQUENCE: 17

Glu Leu Lys Thr Pro Leu Gly Asp Thr Thr His Thr Ala Pro Glu Phe
1               5                   10                  15

Leu Gly Gly

<210> SEQ ID NO 18
<211> LENGTH: 19
<212> TYPE: PRT
<213> ORGANISM: Artificial Sequence
<220> FEATURE:
<223> OTHER INFORMATION: Linker

<400> SEQUENCE: 18

Glu Ser Lys Tyr Gly Pro Pro Ser Pro Ser Pro Ala Pro Glu Phe
1               5                   10                  15

Leu Gly Gly

<210> SEQ ID NO 19
<211> LENGTH: 22
<212> TYPE: PRT
<213> ORGANISM: Artificial Sequence
<220> FEATURE:
<223> OTHER INFORMATION: Linker

<400> SEQUENCE: 19

Glu Pro Lys Ser Cys Asp Lys Thr His Thr Ser Pro Pro Ser Pro Ala
1               5                   10                  15

Pro Glu Leu Leu Gly Gly
                20

<210> SEQ ID NO 20
<211> LENGTH: 23
<212> TYPE: PRT
<213> ORGANISM: Artificial Sequence
<220> FEATURE:
<223> OTHER INFORMATION: Linker

<400> SEQUENCE: 20

Glu Arg Lys Ser Ser Val Glu Glu Ala Ala Ala Lys Glu Ala Ala Ala
1               5                   10                  15

Lys Ala Pro Pro Val Ala Gly
                20

<210> SEQ ID NO 21
<211> LENGTH: 23
<212> TYPE: PRT
<213> ORGANISM: Artificial Sequence
<220> FEATURE:
<223> OTHER INFORMATION: Linker

<400> SEQUENCE: 21

Glu Arg Lys Cys Ser Val Glu Glu Ala Ala Lys Glu Ala Ala Ala
1               5                   10                  15

Lys Ala Pro Pro Val Ala Gly
                20

<210> SEQ ID NO 22
<211> LENGTH: 24
<212> TYPE: PRT
<213> ORGANISM: Artificial Sequence
<220> FEATURE:
<223> OTHER INFORMATION: Linker

<400> SEQUENCE: 22

Glu Ser Lys Tyr Gly Pro Pro Glu Ala Ala Ala Lys Glu Ala Ala Ala
1               5                   10                  15

Lys Ala Pro Glu Phe Leu Gly Gly
            20

<210> SEQ ID NO 23
<211> LENGTH: 27
<212> TYPE: PRT
<213> ORGANISM: Artificial Sequence
<220> FEATURE:
<223> OTHER INFORMATION: Linker

<400> SEQUENCE: 23

Glu Pro Lys Ser Cys Asp Lys Thr His Thr Glu Ala Ala Ala Lys Glu
1               5                   10                  15

Ala Ala Ala Lys Ala Pro Glu Leu Leu Gly Gly
            20                  25

<210> SEQ ID NO 24
<211> LENGTH: 29
<212> TYPE: PRT
<213> ORGANISM: Artificial Sequence
<220> FEATURE:
<223> OTHER INFORMATION: Linker

<400> SEQUENCE: 24

Glu Leu Lys Thr Pro Leu Gly Asp Thr Thr His Thr Glu Ala Ala Ala
1               5                   10                  15

Lys Glu Ala Ala Ala Lys Ala Pro Glu Phe Leu Gly Gly
            20                  25

<210> SEQ ID NO 25
<211> LENGTH: 1072
<212> TYPE: DNA
<213> ORGANISM: Artificial Sequence
<220> FEATURE:
<223> OTHER INFORMATION: DNA sequence of construct MF1337xIgG4 UHxMF1122

<400> SEQUENCE: 25
ggcccagccg gccatggccg aggtgcagct ggtggagact ggggctgagg tgaagaagcc      60
gggggcctca gtgaaggtct cctgcaaggc ttctgactac atcttcacca aatatgacat     120
caactgggtg cgccaggccc ctggacaagg cttgaatgg atgggatgga tgagcgctaa     180
cactggaaac acgggctatg cacagaagtt ccagggcaga gtcaccatga ccagggacac     240
gtccataaac acagcctaca tggagctgag cagcctgaca tctggtgaca cggccgttta     300
tttctgtgcg aggagtagtc tttcaagac agagacggcg ccctactatc acttcgctct     360
ggacgtctgg ggccaaggga ccacggtcac cgtctccagt gctagcacca agggcccag     420 cgtgttcccc ctggcccct gcagccgag caccagcgag agcaccgccg ccctgggctg     480
cctggtgaag gactacttcc ccgagcccgt gaccgtgagc tggaacagcg gcgccctgac     540
cagcggcgtg cacaccttcc ccgccgtgct gcagagcagc ggcctgtaca gcctgagcag     600
cgtggtgacg gtgcccagca gcagcctggg caccaagacc tacacctgca acgtggacca     660
caagcccagc aacaccaagg tggacaagcg ggtggagagc aagtacggcc cccccgaggt     720
gcagctggtg gagtctgggg gaggcgtggt ccagcctggg aggtccctga gactctcctg     780
tgcagcctct ggattcacct tcagtagcta tggcatgcac tgggtccgcc aggctccagg     840
caaggggctg gagtgggtgg cagttatatc atatgatgga agtaataaat actatgcaga     900
ctccgtgaag ggccgattca ccatctccag agacaattcc aagaacacgc tgtatctgca    960
aatgaacagc ctgagagctg aggacacggc cgtgtattac tgtgcaagag ccctcttcac   1020
gaccatcgcc atggactatt ggggccaagg taccctttgtc accgtctcga gt          1072

```
<210> SEQ ID NO 26
<211> LENGTH: 116
<212> TYPE: PRT
<213> ORGANISM: Artificial Sequence
<220> FEATURE:
<223> OTHER INFORMATION: Translation of MF1122

<400> SEQUENCE: 26
```

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Leu Phe Thr Thr Ile Ala Met Asp Tyr Trp Gly Gln Gly
            100                 105                 110

Thr Leu Val Thr
        115

```
<210> SEQ ID NO 27
<211> LENGTH: 115
<212> TYPE: PRT
<213> ORGANISM: Artificial Sequence
<220> FEATURE:
<223> OTHER INFORMATION: Translation of MF1025

<400> SEQUENCE: 27
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Asp Trp Trp Ala Thr Phe Asp Tyr Trp Gly Gln Gly Thr
            100                 105                 110

Leu Val Thr
        115

```
<210> SEQ ID NO 28
<211> LENGTH: 124
<212> TYPE: PRT
```

<213> ORGANISM: Artificial Sequence
<220> FEATURE:
<223> OTHER INFORMATION: Translation of MF1337

<400> SEQUENCE: 28

```
Glu Val Gln Leu Val Glu Thr Gly Ala Glu Val Lys Lys Pro Gly Ala
1               5                   10                  15

Ser Val Lys Val Ser Cys Lys Ala Ser Asp Tyr Ile Phe Thr Lys Tyr
            20                  25                  30

Asp Ile Asn Trp Val Arg Gln Ala Pro Gly Gln Gly Leu Glu Trp Met
        35                  40                  45

Gly Trp Met Ser Ala Asn Thr Gly Asn Thr Gly Tyr Ala Gln Lys Phe
    50                  55                  60

Gln Gly Arg Val Thr Met Thr Arg Asp Thr Ser Ile Asn Thr Ala Tyr
65                  70                  75                  80

Met Glu Leu Ser Ser Leu Thr Ser Gly Asp Thr Ala Val Tyr Phe Cys
                85                  90                  95

Ala Arg Ser Ser Leu Phe Lys Thr Glu Thr Ala Pro Tyr Tyr His Phe
            100                 105                 110

Ala Leu Asp Val Trp Gly Gln Gly Thr Thr Val Thr
            115                 120
```

<210> SEQ ID NO 29
<211> LENGTH: 214
<212> TYPE: PRT
<213> ORGANISM: Artificial Sequence
<220> FEATURE:
<223> OTHER INFORMATION: Translation of common light chain (cLC)

<400> SEQUENCE: 29

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205
```

```
Phe Asn Arg Gly Glu Cys
    210

<210> SEQ ID NO 30
<211> LENGTH: 21
<212> TYPE: PRT
<213> ORGANISM: Artificial Sequence
<220> FEATURE:
<223> OTHER INFORMATION: Primer

<400> SEQUENCE: 30

Cys Cys Thr Cys Ala Thr Gly Cys Ala Thr Cys Ala Cys Gly Gly Ala
1               5                   10                  15

Gly Cys Ala Thr Gly
            20

<210> SEQ ID NO 31
<211> LENGTH: 21
<212> TYPE: PRT
<213> ORGANISM: Artificial Sequence
<220> FEATURE:
<223> OTHER INFORMATION: Primer

<400> SEQUENCE: 31

Cys Ala Ala Ala Gly Gly Cys Cys Ala Ala Cys Thr Cys Thr Cys
1               5                   10                  15

Cys Ala Cys Thr Cys
            20

<210> SEQ ID NO 32
<211> LENGTH: 20
<212> TYPE: PRT
<213> ORGANISM: Artificial Sequence
<220> FEATURE:
<223> OTHER INFORMATION: Primer

<400> SEQUENCE: 32

Cys Gly Cys Thr Gly Thr Gly Cys Cys Cys Cys Ala Gly Ala Gly
1               5                   10                  15

Gly Thr Gly Cys
            20

<210> SEQ ID NO 33
<211> LENGTH: 19
<212> TYPE: DNA
<213> ORGANISM: Artificial Sequence
<220> FEATURE:
<223> OTHER INFORMATION: Primer

<400> SEQUENCE: 33
gtaccggtga attggccgg                                                19

<210> SEQ ID NO 34
<211> LENGTH: 25
<212> TYPE: PRT
<213> ORGANISM: Artificial Sequence
<220> FEATURE:
<223> OTHER INFORMATION: Primer

<400> SEQUENCE: 34

Gly Cys Gly Cys Cys Cys Thr Ala Cys Thr Ala Thr Cys Ala Cys Thr
1               5                   10                  15

Thr Cys Gly Cys Thr Cys Thr Gly Gly
            20                  25
```

```
<210> SEQ ID NO 35
<211> LENGTH: 214
<212> TYPE: PRT
<213> ORGANISM: Artificial Sequence
<220> FEATURE:
<223> OTHER INFORMATION: Common light chain

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 36
<211> LENGTH: 321
<212> TYPE: DNA
<213> ORGANISM: Artificial Sequence
<220> FEATURE:
<223> OTHER INFORMATION: common light chain variable domain (IGKV1-
      39/jk1)
<220> FEATURE:
<221> NAME/KEY: CDS
<222> LOCATION: (1)..(321)

<400> SEQUENCE: 36 gac atc cag atg acc cag tct cca tcc tcc ctg tct gca tct gta gga    48
Asp Ile Gln Met Thr Gln Ser Pro Ser Ser Leu Ser Ala Ser Val Gly
1               5                   10                  15 gac aga gtc acc atc act tgc cgg gca agt cag agc att agc agc tac    96
Asp Arg Val Thr Ile Thr Cys Arg Ala Ser Gln Ser Ile Ser Ser Tyr
            20                  25                  30 tta aat tgg tat cag cag aaa cca ggg aaa gcc cct aag ctc ctg atc   144
Leu Asn Trp Tyr Gln Gln Lys Pro Gly Lys Ala Pro Lys Leu Leu Ile
        35                  40                  45 tat gct gca tcc agt ttg caa agt ggg gtc cca tca agg ttc agt ggc   192
```

```
Tyr Ala Ala Ser Ser Leu Gln Ser Gly Val Pro Ser Arg Phe Ser Gly
        50                  55                  60 agt gga tct ggg aca gat ttc act ctc acc atc agc agt ctg caa cct      240
Ser Gly Ser Gly Thr Asp Phe Thr Leu Thr Ile Ser Ser Leu Gln Pro
65                  70                  75                  80 gaa gat ttt gca act tac tac tgt caa cag agt tac agt acc cct cca      288
Glu Asp Phe Ala Thr Tyr Tyr Cys Gln Gln Ser Tyr Ser Thr Pro Pro
                85                  90                  95 acg ttc ggc caa ggg acc aag gtg gag atc aaa                          321
Thr Phe Gly Gln Gly Thr Lys Val Glu Ile Lys
                100                 105

<210> SEQ ID NO 37
<211> LENGTH: 107
<212> TYPE: PRT
<213> ORGANISM: Artificial Sequence
<220> FEATURE:
<223> OTHER INFORMATION: Synthetic Construct

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys
                100                 105

<210> SEQ ID NO 38
<211> LENGTH: 324
<212> TYPE: DNA
<213> ORGANISM: Artificial Sequence
<220> FEATURE:
<223> OTHER INFORMATION: common light chain constant region
<220> FEATURE:
<221> NAME/KEY: CDS
<222> LOCATION: (1)..(324)

<400> SEQUENCE: 38 cga act gtg gct gca cca tct gtc ttc atc ttc ccg cca tct gat gag       48
Arg Thr Val Ala Ala Pro Ser Val Phe Ile Phe Pro Pro Ser Asp Glu
1               5                   10                  15 cag ttg aaa tct gga act gcc tct gtt gtg tgc ctg ctg aat aac ttc       96
Gln Leu Lys Ser Gly Thr Ala Ser Val Val Cys Leu Leu Asn Asn Phe
            20                  25                  30 tat ccc aga gag gcc aaa gta cag tgg aag gtg gat aac gcc ctc caa      144
Tyr Pro Arg Glu Ala Lys Val Gln Trp Lys Val Asp Asn Ala Leu Gln
        35                  40                  45 tcg ggt aac tcc cag gag agt gtc aca gag cag gac agc aag gac agc      192
Ser Gly Asn Ser Gln Glu Ser Val Thr Glu Gln Asp Ser Lys Asp Ser
    50                  55                  60 acc tac agc ctc agc agc acc ctg acg ctg agc aaa gca gac tac gag      240
Thr Tyr Ser Leu Ser Ser Thr Leu Thr Leu Ser Lys Ala Asp Tyr Glu
65                  70                  75                  80
```

```
aaa cac aaa gtc tac gcc tgc gaa gtc acc cat cag ggc ctg agc tcg    288
Lys His Lys Val Tyr Ala Cys Glu Val Thr His Gln Gly Leu Ser Ser
                85                  90                  95 ccc gtc aca aag agc ttc aac agg gga gag tgt tag                    324
Pro Val Thr Lys Ser Phe Asn Arg Gly Glu Cys
            100                 105
```

<210> SEQ ID NO 39
<211> LENGTH: 107
<212> TYPE: PRT
<213> ORGANISM: Artificial Sequence
<220> FEATURE:
<223> OTHER INFORMATION: Synthetic Construct

<400> SEQUENCE: 39

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 40
<211> LENGTH: 108
<212> TYPE: PRT
<213> ORGANISM: Artificial Sequence
<220> FEATURE:
<223> OTHER INFORMATION: IGKV1-39/jk5 common light chain variable domain

<400> SEQUENCE: 40

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105
```

<210> SEQ ID NO 41
<211> LENGTH: 95
<212> TYPE: PRT
<213> ORGANISM: Artificial Sequence
<220> FEATURE:
<223> OTHER INFORMATION: V-region IGKV1-39A

<400> SEQUENCE: 41

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95
```

```
<210> SEQ ID NO 42
<211> LENGTH: 22
<212> TYPE: PRT
<213> ORGANISM: Homo sapiens

<400> SEQUENCE: 42

Glu Pro Lys Ser Cys Asp Lys Thr His Thr Cys Pro Pro Cys Pro Ala
1               5                   10                  15

Pro Glu Leu Leu Gly Gly
            20
```

```
<210> SEQ ID NO 43
<211> LENGTH: 10
<212> TYPE: PRT
<213> ORGANISM: Homo sapiens

<400> SEQUENCE: 43

Glu Pro Lys Ser Cys Asp Lys Thr His Thr
1               5                   10
```

```
<210> SEQ ID NO 44
<211> LENGTH: 5
<212> TYPE: PRT
<213> ORGANISM: Homo sapiens

<400> SEQUENCE: 44

Cys Pro Pro Cys Pro
1               5
```

```
<210> SEQ ID NO 45
<211> LENGTH: 7
<212> TYPE: PRT
<213> ORGANISM: Homo sapiens

<400> SEQUENCE: 45

Ala Pro Glu Leu Leu Gly Gly
1               5
```

```
<210> SEQ ID NO 46
<211> LENGTH: 18
<212> TYPE: PRT
<213> ORGANISM: Homo sapiens

<400> SEQUENCE: 46

Glu Arg Lys Cys Cys Val Glu Cys Pro Pro Cys Pro Ala Pro Pro Val
1               5                   10                  15

Ala Gly
```

<210> SEQ ID NO 47
<211> LENGTH: 7
<212> TYPE: PRT
<213> ORGANISM: Homo sapiens

<400> SEQUENCE: 47

Glu Arg Lys Cys Cys Val Glu
1               5

<210> SEQ ID NO 48
<211> LENGTH: 5
<212> TYPE: PRT
<213> ORGANISM: Homo sapiens

<400> SEQUENCE: 48

Cys Pro Pro Cys Pro
1               5

<210> SEQ ID NO 49
<211> LENGTH: 6
<212> TYPE: PRT
<213> ORGANISM: Homo sapiens

<400> SEQUENCE: 49

Ala Pro Pro Val Ala Gly
1               5

<210> SEQ ID NO 50
<211> LENGTH: 69
<212> TYPE: PRT
<213> ORGANISM: Homo sapiens

<400> SEQUENCE: 50

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro Ala Pro
    50                  55                  60

Glu Phe Leu Gly Gly
65

<210> SEQ ID NO 51
<211> LENGTH: 12
<212> TYPE: PRT
<213> ORGANISM: Homo sapiens

<400> SEQUENCE: 51

Glu Leu Lys Thr Pro Leu Gly Asp Thr Thr His Thr
1               5                   10

<210> SEQ ID NO 52
<211> LENGTH: 50
<212> TYPE: PRT
<213> ORGANISM: Homo sapiens

<400> SEQUENCE: 52

Cys Pro Arg Cys Pro Glu Pro Lys Ser Cys Asp Thr Pro Pro Cys
1               5                   10                  15

Pro Arg Cys Pro Glu Pro Lys Ser Cys Asp Thr Pro Pro Cys Pro

```
                    20                  25                  30
Arg Cys Pro Glu Pro Lys Ser Cys Asp Thr Pro Pro Cys Pro Arg
            35                  40                  45

Cys Pro
    50

<210> SEQ ID NO 53
<211> LENGTH: 7
<212> TYPE: PRT
<213> ORGANISM: Homo sapiens

<400> SEQUENCE: 53

Ala Pro Glu Phe Leu Gly Gly
1               5

<210> SEQ ID NO 54
<211> LENGTH: 19
<212> TYPE: PRT
<213> ORGANISM: Homo sapiens

<400> SEQUENCE: 54

Glu Ser Lys Tyr Gly Pro Pro Cys Pro Ser Cys Pro Ala Pro Glu Phe
1               5                   10                  15

Leu Gly Gly

<210> SEQ ID NO 55
<211> LENGTH: 7
<212> TYPE: PRT
<213> ORGANISM: Homo sapiens

<400> SEQUENCE: 55

Glu Ser Lys Tyr Gly Pro Pro
1               5

<210> SEQ ID NO 56
<211> LENGTH: 5
<212> TYPE: PRT
<213> ORGANISM: Homo sapiens

<400> SEQUENCE: 56

Cys Pro Ser Cys Pro
1               5

<210> SEQ ID NO 57
<211> LENGTH: 7
<212> TYPE: PRT
<213> ORGANISM: Homo sapiens

<400> SEQUENCE: 57

Ala Pro Glu Phe Leu Gly Gly
1               5

<210> SEQ ID NO 58
<211> LENGTH: 52
<212> TYPE: PRT
<213> ORGANISM: Artificial Sequence
<220> FEATURE:
<223> OTHER INFORMATION: Synthetic construct

<400> SEQUENCE: 58

Asn Val Asn His Lys Pro Ser Asn Thr Lys Val Asp Lys Arg Val Glu
1               5                   10                  15

Pro Lys Ser Cys Asp Lys Thr His Thr Ser Pro Pro Ser Pro Ala Pro
```

```
                        20                  25                  30

Glu Leu Leu Gly Gly Glu Val Gln Leu Val Glu Ser Gly Gly Gly Val
            35                  40                  45

Val Gln Pro Gly
        50

<210> SEQ ID NO 59
<211> LENGTH: 45
<212> TYPE: PRT
<213> ORGANISM: Artificial Sequence
<220> FEATURE:
<223> OTHER INFORMATION: Synthetic construct

<400> SEQUENCE: 59

Asn Val Asn His Lys Pro Ser Asn Thr Lys Val Asp Lys Arg Val Glu
1               5                   10                  15

Pro Lys Ser Cys Asp Lys Thr His Thr Ser Pro Pro Ser Pro Glu Val
            20                  25                  30

Gln Leu Val Glu Ser Gly Gly Val Val Gln Pro Gly
        35                  40                  45

<210> SEQ ID NO 60
<211> LENGTH: 40
<212> TYPE: PRT
<213> ORGANISM: Artificial Sequence
<220> FEATURE:
<223> OTHER INFORMATION: Synthetic construct

<400> SEQUENCE: 60

Asn Val Asn His Lys Pro Ser Asn Thr Lys Val Asp Lys Arg Val Glu
1               5                   10                  15

Pro Lys Ser Cys Asp Lys Thr His Thr Glu Val Gln Leu Val Glu Ser
            20                  25                  30

Gly Gly Gly Val Val Gln Pro Gly
        35                  40

<210> SEQ ID NO 61
<211> LENGTH: 46
<212> TYPE: PRT
<213> ORGANISM: Artificial Sequence
<220> FEATURE:
<223> OTHER INFORMATION: Synthetic construct

<400> SEQUENCE: 61

Asn Val Asn His Lys Pro Ser Asn Thr Lys Val Asp Lys Arg Val Glu
1               5                   10                  15

Pro Lys Ser Cys Asp Gly Gly Gly Ser Gly Gly Gly Ser Glu
            20                  25                  30

Val Gln Leu Val Glu Ser Gly Gly Val Val Gln Pro Gly
        35                  40                  45

<210> SEQ ID NO 62
<211> LENGTH: 57
<212> TYPE: PRT
<213> ORGANISM: Artificial Sequence
<220> FEATURE:
<223> OTHER INFORMATION: Synthetic construct

<400> SEQUENCE: 62

Asn Val Asn His Lys Pro Ser Asn Thr Lys Val Asp Lys Arg Val Glu
1               5                   10                  15

Pro Lys Ser Cys Asp Lys Thr His Thr Glu Ala Ala Ala Lys Glu Ala
```

```
                    20                  25                  30

Ala Ala Lys Ala Pro Glu Leu Leu Gly Gly Glu Val Gln Leu Val Glu
            35                  40                  45

Ser Gly Gly Gly Val Val Gln Pro Gly
        50                  55

<210> SEQ ID NO 63
<211> LENGTH: 47
<212> TYPE: PRT
<213> ORGANISM: Artificial Sequence
<220> FEATURE:
<223> OTHER INFORMATION: Synthetic construct

<400> SEQUENCE: 63

Asn Val Asn His Lys Pro Ser Asn Thr Lys Val Asp Lys Arg Val Glu
1               5                   10                  15

Pro Lys Ser Cys Asp Lys Thr His Thr Ala Pro Glu Leu Leu Gly Gly
            20                  25                  30

Glu Val Gln Leu Val Glu Ser Gly Gly Gly Val Val Gln Pro Gly
        35                  40                  45

<210> SEQ ID NO 64
<211> LENGTH: 48
<212> TYPE: PRT
<213> ORGANISM: Artificial Sequence
<220> FEATURE:
<223> OTHER INFORMATION: Synthetic construct

<400> SEQUENCE: 64

Asn Val Asp His Lys Pro Ser Asn Thr Lys Val Asp Lys Thr Val Glu
1               5                   10                  15

Arg Lys Ser Ser Val Glu Ser Pro Pro Ser Pro Ala Pro Pro Val Ala
            20                  25                  30

Gly Glu Val Gln Leu Val Glu Ser Gly Gly Gly Val Val Gln Pro Gly
        35                  40                  45

<210> SEQ ID NO 65
<211> LENGTH: 42
<212> TYPE: PRT
<213> ORGANISM: Artificial Sequence
<220> FEATURE:
<223> OTHER INFORMATION: Synthetic construct

<400> SEQUENCE: 65

Asn Val Asp His Lys Pro Ser Asn Thr Lys Val Asp Lys Thr Val Glu
1               5                   10                  15

Arg Lys Ser Ser Val Glu Ser Pro Pro Ser Pro Glu Val Gln Leu Val
            20                  25                  30

Glu Ser Gly Gly Gly Val Val Gln Pro Gly
        35                  40

<210> SEQ ID NO 66
<211> LENGTH: 43
<212> TYPE: PRT
<213> ORGANISM: Artificial Sequence
<220> FEATURE:
<223> OTHER INFORMATION: Synthetic construct

<400> SEQUENCE: 66

Asn Val Asp His Lys Pro Ser Asn Thr Lys Val Asp Lys Thr Val Glu
1               5                   10                  15

Arg Lys Ser Ser Val Glu Ala Pro Pro Val Ala Gly Glu Val Gln Leu
```

```
                    20                  25                  30

Val Glu Ser Gly Gly Gly Val Val Gln Pro Gly
            35                  40

<210> SEQ ID NO 67
<211> LENGTH: 48
<212> TYPE: PRT
<213> ORGANISM: Artificial Sequence
<220> FEATURE:
<223> OTHER INFORMATION: Synthetic construct

<400> SEQUENCE: 67

Asn Val Asp His Lys Pro Ser Asn Thr Lys Val Asp Lys Thr Val Glu
1               5                   10                  15

Arg Lys Cys Ser Val Glu Ser Pro Pro Ser Pro Ala Pro Pro Val Ala
            20                  25                  30

Gly Glu Val Gln Leu Val Glu Ser Gly Gly Gly Val Val Gln Pro Gly
        35                  40                  45

<210> SEQ ID NO 68
<211> LENGTH: 42
<212> TYPE: PRT
<213> ORGANISM: Artificial Sequence
<220> FEATURE:
<223> OTHER INFORMATION: Synthetic construct

<400> SEQUENCE: 68

Asn Val Asp His Lys Pro Ser Asn Thr Lys Val Asp Lys Thr Val Glu
1               5                   10                  15

Arg Lys Cys Ser Val Glu Ser Pro Pro Ser Pro Glu Val Gln Leu Val
            20                  25                  30

Glu Ser Gly Gly Gly Val Val Gln Pro Gly
        35                  40

<210> SEQ ID NO 69
<211> LENGTH: 43
<212> TYPE: PRT
<213> ORGANISM: Artificial Sequence
<220> FEATURE:
<223> OTHER INFORMATION: Synthetic construct

<400> SEQUENCE: 69

Asn Val Asp His Lys Pro Ser Asn Thr Lys Val Asp Lys Thr Val Glu
1               5                   10                  15

Arg Lys Cys Ser Val Glu Ala Pro Pro Val Ala Gly Glu Val Gln Leu
            20                  25                  30

Val Glu Ser Gly Gly Gly Val Val Gln Pro Gly
        35                  40

<210> SEQ ID NO 70
<211> LENGTH: 46
<212> TYPE: PRT
<213> ORGANISM: Artificial Sequence
<220> FEATURE:
<223> OTHER INFORMATION: Synthetic construct

<400> SEQUENCE: 70

Asn Val Asp His Lys Pro Ser Asn Thr Lys Val Asp Lys Thr Val Gly
1               5                   10                  15

Gly Gly Gly Ser Gly Gly Gly Ser Ala Pro Pro Val Ala Gly Glu
            20                  25                  30

Val Gln Leu Val Glu Ser Gly Gly Gly Val Val Gln Pro Gly
```

<210> SEQ ID NO 71
<211> LENGTH: 40
<212> TYPE: PRT
<213> ORGANISM: Artificial Sequence
<220> FEATURE:
<223> OTHER INFORMATION: Synthetic construct

<400> SEQUENCE: 71

Asn Val Asp His Lys Pro Ser Asn Thr Lys Val Asp Lys Thr Val Gly
1               5                   10                  15

Gly Gly Gly Ser Gly Gly Gly Ser Glu Val Gln Leu Val Glu Ser
            20                  25                  30

Gly Gly Gly Val Val Gln Pro Gly
        35                  40

<210> SEQ ID NO 72
<211> LENGTH: 53
<212> TYPE: PRT
<213> ORGANISM: Artificial Sequence
<220> FEATURE:
<223> OTHER INFORMATION: Synthetic construct

<400> SEQUENCE: 72

Asn Val Asp His Lys Pro Ser Asn Thr Lys Val Asp Lys Thr Val Glu
1               5                   10                  15

Arg Lys Ser Ser Val Glu Glu Ala Ala Ala Lys Glu Ala Ala Ala Lys
            20                  25                  30

Ala Pro Pro Val Ala Gly Glu Val Gln Leu Val Glu Ser Gly Gly Gly
        35                  40                  45

Val Val Gln Pro Gly
    50

<210> SEQ ID NO 73
<211> LENGTH: 53
<212> TYPE: PRT
<213> ORGANISM: Artificial Sequence
<220> FEATURE:
<223> OTHER INFORMATION: Synthetic construct

<400> SEQUENCE: 73

Asn Val Asp His Lys Pro Ser Asn Thr Lys Val Asp Lys Thr Val Glu
1               5                   10                  15

Arg Lys Cys Ser Val Glu Glu Ala Ala Ala Lys Glu Ala Ala Ala Lys
            20                  25                  30

Ala Pro Pro Val Ala Gly Glu Val Gln Leu Val Glu Ser Gly Gly Gly
        35                  40                  45

Val Val Gln Pro Gly
    50

<210> SEQ ID NO 74
<211> LENGTH: 49
<212> TYPE: PRT
<213> ORGANISM: Artificial Sequence
<220> FEATURE:
<223> OTHER INFORMATION: Synthetic construct

<400> SEQUENCE: 74

Asn Val Asn His Lys Pro Ser Asn Thr Lys Val Asp Lys Arg Val Glu
1               5                   10                  15

Leu Lys Thr Pro Leu Gly Asp Thr Thr His Thr Ala Pro Glu Phe Leu

-continued

```
                20                  25                  30

Gly Gly Glu Val Gln Leu Val Glu Ser Gly Gly Gly Val Val Gln Pro
        35                  40                  45

Gly

<210> SEQ ID NO 75
<211> LENGTH: 42
<212> TYPE: PRT
<213> ORGANISM: Artificial Sequence
<220> FEATURE:
<223> OTHER INFORMATION: Synthetic construct

<400> SEQUENCE: 75

Asn Val Asn His Lys Pro Ser Asn Thr Lys Val Asp Lys Arg Val Glu
1               5                   10                  15

Leu Lys Thr Pro Leu Gly Asp Thr Thr His Thr Glu Val Gln Leu Val
            20                  25                  30

Glu Ser Gly Gly Gly Val Val Gln Pro Gly
        35                  40

<210> SEQ ID NO 76
<211> LENGTH: 59
<212> TYPE: PRT
<213> ORGANISM: Artificial Sequence
<220> FEATURE:
<223> OTHER INFORMATION: Synthetic construct

<400> SEQUENCE: 76

Asn Val Asn His Lys Pro Ser Asn Thr Lys Val Asp Lys Arg Val Glu
1               5                   10                  15

Leu Lys Thr Pro Leu Gly Asp Thr Thr His Thr Glu Ala Ala Ala Lys
            20                  25                  30

Glu Ala Ala Ala Lys Ala Pro Glu Phe Leu Gly Gly Glu Val Gln Leu
        35                  40                  45

Val Glu Ser Gly Gly Gly Val Val Gln Pro Gly
    50                  55

<210> SEQ ID NO 77
<211> LENGTH: 49
<212> TYPE: PRT
<213> ORGANISM: Artificial Sequence
<220> FEATURE:
<223> OTHER INFORMATION: Synthetic construct

<400> SEQUENCE: 77

Asn Val Asp His Lys Pro Ser Asn Thr Lys Val Asp Lys Arg Val Glu
1               5                   10                  15

Ser Lys Tyr Gly Pro Pro Ser Pro Ser Ser Pro Ala Pro Glu Phe Leu
            20                  25                  30

Gly Gly Glu Val Gln Leu Val Glu Ser Gly Gly Gly Val Val Gln Pro
        35                  40                  45

Gly

<210> SEQ ID NO 78
<211> LENGTH: 42
<212> TYPE: PRT
<213> ORGANISM: Artificial Sequence
<220> FEATURE:
<223> OTHER INFORMATION: Synthetic construct

<400> SEQUENCE: 78
```

-continued

Asn Val Asp His Lys Pro Ser Asn Thr Lys Val Asp Lys Arg Val Glu
1               5                   10                  15

Ser Lys Tyr Gly Pro Pro Ser Pro Ser Ser Pro Glu Val Gln Leu Val
            20                  25                  30

Glu Ser Gly Gly Gly Val Val Gln Pro Gly
        35                  40

<210> SEQ ID NO 79
<211> LENGTH: 44
<212> TYPE: PRT
<213> ORGANISM: Artificial Sequence
<220> FEATURE:
<223> OTHER INFORMATION: Synthetic construct

<400> SEQUENCE: 79

Asn Val Asp His Lys Pro Ser Asn Thr Lys Val Asp Lys Arg Val Glu
1               5                   10                  15

Ser Lys Tyr Gly Pro Pro Ala Pro Glu Phe Leu Gly Gly Glu Val Gln
            20                  25                  30

Leu Val Glu Ser Gly Gly Gly Val Val Gln Pro Gly
        35                  40

<210> SEQ ID NO 80
<211> LENGTH: 37
<212> TYPE: PRT
<213> ORGANISM: Artificial Sequence
<220> FEATURE:
<223> OTHER INFORMATION: Synthetic construct

<400> SEQUENCE: 80

Asn Val Asp His Lys Pro Ser Asn Thr Lys Val Asp Lys Arg Val Glu
1               5                   10                  15

Ser Lys Tyr Gly Pro Pro Glu Val Gln Leu Val Glu Ser Gly Gly Gly
            20                  25                  30

Val Val Gln Pro Gly
        35

<210> SEQ ID NO 81
<211> LENGTH: 54
<212> TYPE: PRT
<213> ORGANISM: Artificial Sequence
<220> FEATURE:
<223> OTHER INFORMATION: Synthetic construct

<400> SEQUENCE: 81

Asn Val Asp His Lys Pro Ser Asn Thr Lys Val Asp Lys Arg Val Glu
1               5                   10                  15

Ser Lys Tyr Gly Pro Pro Glu Ala Ala Ala Lys Glu Ala Ala Ala Lys
            20                  25                  30

Ala Pro Glu Phe Leu Gly Gly Glu Val Gln Leu Val Glu Ser Gly Gly
        35                  40                  45

Gly Val Val Gln Pro Gly
    50

<210> SEQ ID NO 82
<211> LENGTH: 52
<212> TYPE: PRT
<213> ORGANISM: Artificial Sequence
<220> FEATURE:
<223> OTHER INFORMATION: Synthetic construct

<400> SEQUENCE: 82

```
Asn Val Asn His Lys Pro Ser Asn Thr Lys Val Asp Lys Arg Val Glu
1               5                   10                  15

Pro Lys Ser Cys Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met
    50

<210> SEQ ID NO 83
<211> LENGTH: 369
<212> TYPE: DNA
<213> ORGANISM: Artificial Sequence
<220> FEATURE:
<223> OTHER INFORMATION: MF6744

<400> SEQUENCE: 83
gaggtgcagc tggtgcagtc tggagcagag gtgaaaaagc ccggggagtc actgaaaatc    60
tcctgtaagg gttctggata cagctttacc agctactgga tcggctgggt gcgccagatg   120
cccgggaaag gcctggagtg gatggggatc atctttcctg atgactctga taccagatac   180
agtccgtcct tccaaggcca ggtcaccatc tcagccgaca gtccatcag taccgcctac   240 ctgcagtgga gcagcctgaa accctcggac accgccatgt attactgtgt gagacttggt   300
ggatatagtg gctacgctga ggattttgtt gacttctggg gccagggaac cctggtcacc   360
gtctccagt                                                          369

<210> SEQ ID NO 84
<211> LENGTH: 30
<212> TYPE: PRT
<213> ORGANISM: Artificial Sequence
<220> FEATURE:
<223> OTHER INFORMATION: MF6744 FW1

<400> SEQUENCE: 84

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr
            20                  25                  30

<210> SEQ ID NO 85
<211> LENGTH: 14
<212> TYPE: PRT
<213> ORGANISM: Artificial Sequence
<220> FEATURE:
<223> OTHER INFORMATION: MF6744 FW2

<400> SEQUENCE: 85

Trp Val Arg Gln Met Pro Gly Lys Gly Leu Glu Trp Met Gly
1               5                   10

<210> SEQ ID NO 86
<211> LENGTH: 32
<212> TYPE: PRT
<213> ORGANISM: Artificial Sequence
<220> FEATURE:
<223> OTHER INFORMATION: MF6744 FW3

<400> SEQUENCE: 86

Gln Val Thr Ile Ser Ala Asp Lys Ser Ile Ser Thr Ala Tyr Leu Gln
1               5                   10                  15

Trp Ser Ser Leu Lys Pro Ser Asp Thr Ala Met Tyr Tyr Cys Val Arg
```

<210> SEQ ID NO 87
<211> LENGTH: 11
<212> TYPE: PRT
<213> ORGANISM: Artificial Sequence
<220> FEATURE:
<223> OTHER INFORMATION: FW4

<400> SEQUENCE: 87

Trp Gly Gln Gly Thr Leu Val Thr Val Ser Ser
1               5                   10

<210> SEQ ID NO 88
<211> LENGTH: 5
<212> TYPE: PRT
<213> ORGANISM: Artificial Sequence
<220> FEATURE:
<223> OTHER INFORMATION: MF6744 CDR1

<400> SEQUENCE: 88

Ser Tyr Trp Ile Gly
1               5

<210> SEQ ID NO 89
<211> LENGTH: 17
<212> TYPE: PRT
<213> ORGANISM: Artificial Sequence
<220> FEATURE:
<223> OTHER INFORMATION: MF6744 CDR2

<400> SEQUENCE: 89

Ile Ile Phe Pro Asp Asp Ser Asp Thr Arg Tyr Ser Pro Ser Phe Gln
1               5                   10                  15

Gly

<210> SEQ ID NO 90
<211> LENGTH: 14
<212> TYPE: PRT
<213> ORGANISM: Artificial Sequence
<220> FEATURE:
<223> OTHER INFORMATION: MF6744 CDR3

<400> SEQUENCE: 90

Leu Gly Gly Tyr Ser Gly Tyr Ala Glu Asp Phe Val Asp Phe
1               5                   10

<210> SEQ ID NO 91
<211> LENGTH: 123
<212> TYPE: PRT
<213> ORGANISM: Artificial Sequence
<220> FEATURE:
<223> OTHER INFORMATION: MF6744 VH

<400> SEQUENCE: 91

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Phe Pro Asp Asp Ser Asp Thr Arg Tyr Ser Pro Ser Phe
        50                  55                  60

Gln Gly Gln Val Thr Ile Ser Ala Asp Lys Ser Ile Ser Thr Ala Tyr

```
                65                  70                  75                  80
Leu Gln Trp Ser Ser Leu Lys Pro Ser Asp Thr Ala Met Tyr Tyr Cys
                    85                  90                  95

Val Arg Leu Gly Gly Tyr Ser Gly Tyr Ala Glu Asp Phe Val Asp Phe
                100                 105                 110

Trp Gly Gln Gly Thr Leu Val Thr Val Ser Ser
        115                 120
```

<210> SEQ ID NO 92
<211> LENGTH: 354
<212> TYPE: DNA
<213> ORGANISM: Artificial Sequence
<220> FEATURE:
<223> OTHER INFORMATION: MF8057

<400> SEQUENCE: 92

```
gaggtgcagc tggtgcagtc tggagctgag gtgaagaagc ctgggtcctc ggtgaaggtc    60
tcctgcaagg cttctggagg caccttccgc agctttggta tcagttgggt gcgacaggcc   120
cctggacaag gacttgagtg gatgggagga ttcatccctg tccttggtac agcaaactac   180
gcacagaaat tccagggcag agtgacgatt atcgcggaca atccacgaa cacagcctac    240 atggagctga gcagcctgag atctgaggac acggccgtgt attactgtgc gcgaagggggt   300 aactggaacc cgttcgaccc ctggggccag ggaaccctgg tcaccgtctc gagt         354
```

<210> SEQ ID NO 93
<211> LENGTH: 30
<212> TYPE: PRT
<213> ORGANISM: Artificial Sequence
<220> FEATURE:
<223> OTHER INFORMATION: MF8057 FW1

<400> SEQUENCE: 93

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg
            20                  25                  30
```

<210> SEQ ID NO 94
<211> LENGTH: 14
<212> TYPE: PRT
<213> ORGANISM: Artificial Sequence
<220> FEATURE:
<223> OTHER INFORMATION: MF8057 FW2

<400> SEQUENCE: 94

```
Trp Val Arg Gln Ala Pro Gly Gln Gly Leu Glu Trp Met Gly
1               5                   10
```

<210> SEQ ID NO 95
<211> LENGTH: 32
<212> TYPE: PRT
<213> ORGANISM: Artificial Sequence
<220> FEATURE:
<223> OTHER INFORMATION: MF8057 FW3

<400> SEQUENCE: 95

```
Arg Val Thr Ile Ile Ala Asp Lys Ser Thr Asn Thr Ala Tyr Met Glu
1               5                   10                  15

Leu Ser Ser Leu Arg Ser Glu Asp Thr Ala Val Tyr Tyr Cys Ala Arg
            20                  25                  30
```

```
<210> SEQ ID NO 96
<211> LENGTH: 11
<212> TYPE: PRT
<213> ORGANISM: Artificial Sequence
<220> FEATURE:
<223> OTHER INFORMATION: MF8057 FW4

<400> SEQUENCE: 96

Trp Gly Gln Gly Thr Leu Val Thr Val Ser Ser
1               5                   10

<210> SEQ ID NO 97
<211> LENGTH: 5
<212> TYPE: PRT
<213> ORGANISM: Artificial Sequence
<220> FEATURE:
<223> OTHER INFORMATION: MF8057 CDR1

<400> SEQUENCE: 97

Ser Phe Gly Ile Ser
1               5

<210> SEQ ID NO 98
<211> LENGTH: 17
<212> TYPE: PRT
<213> ORGANISM: Artificial Sequence
<220> FEATURE:
<223> OTHER INFORMATION: MF8057 CDR2

<400> SEQUENCE: 98

Gly Phe Ile Pro Val Leu Gly Thr Ala Asn Tyr Ala Gln Lys Phe Gln
1               5                   10                  15

Gly

<210> SEQ ID NO 99
<211> LENGTH: 9
<212> TYPE: PRT
<213> ORGANISM: Artificial Sequence
<220> FEATURE:
<223> OTHER INFORMATION: MF8057 CDR3

<400> SEQUENCE: 99

Arg Gly Asn Trp Asn Pro Phe Asp Pro
1               5

<210> SEQ ID NO 100
<211> LENGTH: 118
<212> TYPE: PRT
<213> ORGANISM: Artificial Sequence
<220> FEATURE:
<223> OTHER INFORMATION: MF8057 VH

<400> SEQUENCE: 100

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Ser Phe
            20                  25                  30

Gly Ile Ser Trp Val Arg Gln Ala Pro Gly Gln Gly Leu Glu Trp Met
        35                  40                  45

Gly Gly Phe Ile Pro Val Leu Gly Thr Ala Asn Tyr Ala Gln Lys Phe
    50                  55                  60

Gln Gly Arg Val Thr Ile Ile Ala Asp Lys Ser Thr Asn Thr Ala Tyr
65                  70                  75                  80

Met Glu Leu Ser Ser Leu Arg Ser Glu Asp Thr Ala Val Tyr Tyr Cys
```

85                  90                  95
Ala Arg Arg Gly Asn Trp Asn Pro Phe Asp Pro Trp Gly Gln Gly Thr
            100                 105                 110

Leu Val Thr Val Ser Ser
        115

<210> SEQ ID NO 101
<211> LENGTH: 360
<212> TYPE: DNA
<213> ORGANISM: Artificial Sequence
<220> FEATURE:
<223> OTHER INFORMATION: MF8058

<400> SEQUENCE: 101
caggtgcagc tggtgcagtc tggggctgag gtgaagaagc ctgggtcctc ggtgaaggtc      60
tcctgcaagg cttctggaga cgccttcaaa agcaaaacct ttactatcag ctgggtgcga     120
caggcccctg gacagggggct tgagtggctg gggggggatca tccctctttt tggtacaatt    180
acctacgcac agaagttcca gggcagagtc acgattaccg cggacaaatc cacgaacact     240
gccttcatgg aactgagcag cctgagatct gaggacacgg ccatgtatta ttgtacgcga     300 cggggggaact ggaaccccctt cgacccctgg ggccagggaa ccctggtcac cgtctcgagt    360

<210> SEQ ID NO 102
<211> LENGTH: 30
<212> TYPE: PRT
<213> ORGANISM: Artificial Sequence
<220> FEATURE:
<223> OTHER INFORMATION: MF8058 FW1

<400> SEQUENCE: 102

Gln Val Gln Leu Val Gln Ser Gly Ala Glu Val Lys Lys Pro Gly Ser
1               5                   10                  15

Ser Val Lys Val Ser Cys Lys Ala Ser Gly Asp Ala Phe Lys
            20                  25                  30

<210> SEQ ID NO 103
<211> LENGTH: 14
<212> TYPE: PRT
<213> ORGANISM: Artificial Sequence
<220> FEATURE:
<223> OTHER INFORMATION: MF8058 FW2

<400> SEQUENCE: 103

Trp Val Arg Gln Ala Pro Gly Gln Gly Leu Glu Trp Leu Gly
1               5                   10

<210> SEQ ID NO 104
<211> LENGTH: 32
<212> TYPE: PRT
<213> ORGANISM: Artificial Sequence
<220> FEATURE:
<223> OTHER INFORMATION: MF8058 FW3

<400> SEQUENCE: 104

Arg Val Thr Ile Thr Ala Asp Lys Ser Thr Asn Thr Ala Phe Met Glu
1               5                   10                  15

Leu Ser Ser Leu Arg Ser Glu Asp Thr Ala Met Tyr Tyr Cys Thr Arg
            20                  25                  30

<210> SEQ ID NO 105
<211> LENGTH: 11
<212> TYPE: PRT

```
<213> ORGANISM: Artificial Sequence
<220> FEATURE:
<223> OTHER INFORMATION: MF8058 FW4

<400> SEQUENCE: 105

Trp Gly Gln Gly Thr Leu Val Thr Val Ser Ser
1               5                   10

<210> SEQ ID NO 106
<211> LENGTH: 7
<212> TYPE: PRT
<213> ORGANISM: Artificial Sequence
<220> FEATURE:
<223> OTHER INFORMATION: MF8058 CDR1

<400> SEQUENCE: 106

Ser Lys Thr Phe Thr Ile Ser
1               5

<210> SEQ ID NO 107
<211> LENGTH: 17
<212> TYPE: PRT
<213> ORGANISM: Artificial Sequence
<220> FEATURE:
<223> OTHER INFORMATION: MF8058 CDR2

<400> SEQUENCE: 107

Gly Ile Ile Pro Leu Phe Gly Thr Ile Thr Tyr Ala Gln Lys Phe Gln
1               5                   10                  15

Gly

<210> SEQ ID NO 108
<211> LENGTH: 9
<212> TYPE: PRT
<213> ORGANISM: Artificial Sequence
<220> FEATURE:
<223> OTHER INFORMATION: MF8058 CDR3

<400> SEQUENCE: 108

Arg Gly Asn Trp Asn Pro Phe Asp Pro
1               5

<210> SEQ ID NO 109
<211> LENGTH: 120
<212> TYPE: PRT
<213> ORGANISM: Artificial Sequence
<220> FEATURE:
<223> OTHER INFORMATION: MF8058 VH

<400> SEQUENCE: 109

Gln Val Gln Leu Val Gln Ser Gly Ala Glu Val Lys Lys Pro Gly Ser
1               5                   10                  15

Ser Val Lys Val Ser Cys Lys Ala Ser Gly Asp Ala Phe Lys Ser Lys
                20                  25                  30

Thr Phe Thr Ile Ser Trp Val Arg Gln Ala Pro Gly Gln Gly Leu Glu
            35                  40                  45

Trp Leu Gly Gly Ile Ile Pro Leu Phe Gly Thr Ile Thr Tyr Ala Gln
    50                  55                  60

Lys Phe Gln Gly Arg Val Thr Ile Thr Ala Asp Lys Ser Thr Asn Thr
65                  70                  75                  80

Ala Phe Met Glu Leu Ser Ser Leu Arg Ser Glu Asp Thr Ala Met Tyr
                85                  90                  95

Tyr Cys Thr Arg Arg Gly Asn Trp Asn Pro Phe Asp Pro Trp Gly Gln
```

100                 105                 110
Gly Thr Leu Val Thr Val Ser Ser
            115                 120

<210> SEQ ID NO 110
<211> LENGTH: 360
<212> TYPE: DNA
<213> ORGANISM: Artificial Sequence
<220> FEATURE:
<223> OTHER INFORMATION: MF8078

<400> SEQUENCE: 110
gaggtgcagc tggtgcagtc tgggtctgag ttgaagaagc ctgggtcctc ggtgaaggtc    60
tcctgcaagg cttctggagt caccttcaac agcagaacct ttactatcag ttgggtgcga   120
caggcccctg gacaagggct tgagtggctg gggagtatca tccctatttt tggtacaata   180
acctacgcac agaagttcca gggcagagtc acgattaccg cggacaaatc cacgagcact   240
gccttcatgg aactgaccag cctgagatct gaggacacgg ccatatatta ttgtacgaga   300
cgggggaact ggaaccccct cgacccctgg ggccagggca ccctggtcac cgtctcgagt   360

<210> SEQ ID NO 111
<211> LENGTH: 30
<212> TYPE: PRT
<213> ORGANISM: Artificial Sequence
<220> FEATURE:
<223> OTHER INFORMATION: MF8078 FW1

<400> SEQUENCE: 111

Glu Val Gln Leu Val Gln Ser Gly Ser Glu Leu Lys Lys Pro Gly Ser
1               5                  10                  15

Ser Val Lys Val Ser Cys Lys Ala Ser Gly Val Thr Phe Asn
            20                  25                  30

<210> SEQ ID NO 112
<211> LENGTH: 14
<212> TYPE: PRT
<213> ORGANISM: Artificial Sequence
<220> FEATURE:
<223> OTHER INFORMATION: MF8078 FW2

<400> SEQUENCE: 112

Trp Val Arg Gln Ala Pro Gly Gln Gly Leu Glu Trp Leu Gly
1               5                  10

<210> SEQ ID NO 113
<211> LENGTH: 32
<212> TYPE: PRT
<213> ORGANISM: Artificial Sequence
<220> FEATURE:
<223> OTHER INFORMATION: MF8078 FW3

<400> SEQUENCE: 113

Arg Val Thr Ile Thr Ala Asp Lys Ser Thr Ser Thr Ala Phe Met Glu
1               5                  10                  15

Leu Thr Ser Leu Arg Ser Glu Asp Thr Ala Ile Tyr Tyr Cys Thr Arg
            20                  25                  30

<210> SEQ ID NO 114
<211> LENGTH: 11
<212> TYPE: PRT
<213> ORGANISM: Artificial Sequence
<220> FEATURE:
<223> OTHER INFORMATION: MF8078 FW4

```
<400> SEQUENCE: 114

Trp Gly Gln Gly Thr Leu Val Thr Val Ser Ser
1               5                   10

<210> SEQ ID NO 115
<211> LENGTH: 7
<212> TYPE: PRT
<213> ORGANISM: Artificial Sequence
<220> FEATURE:
<223> OTHER INFORMATION: MF8078 CDR1

<400> SEQUENCE: 115

Ser Arg Thr Phe Thr Ile Ser
1               5

<210> SEQ ID NO 116
<211> LENGTH: 17
<212> TYPE: PRT
<213> ORGANISM: Artificial Sequence
<220> FEATURE:
<223> OTHER INFORMATION: MF8078 CDR2

<400> SEQUENCE: 116

Ser Ile Ile Pro Ile Phe Gly Thr Ile Thr Tyr Ala Gln Lys Phe Gln
1               5                   10                  15
Gly

<210> SEQ ID NO 117
<211> LENGTH: 9
<212> TYPE: PRT
<213> ORGANISM: Artificial Sequence
<220> FEATURE:
<223> OTHER INFORMATION: MF8078 CDR3

<400> SEQUENCE: 117

Arg Gly Asn Trp Asn Pro Phe Asp Pro
1               5

<210> SEQ ID NO 118
<211> LENGTH: 120
<212> TYPE: PRT
<213> ORGANISM: Artificial Sequence
<220> FEATURE:
<223> OTHER INFORMATION: MF8078 VH

<400> SEQUENCE: 118

Glu Val Gln Leu Val Gln Ser Gly Ser Glu Leu Lys Lys Pro Gly Ser
1               5                   10                  15

Ser Val Lys Val Ser Cys Lys Ala Ser Gly Val Thr Phe Asn Ser Arg
            20                  25                  30

Thr Phe Thr Ile Ser Trp Val Arg Gln Ala Pro Gly Gln Gly Leu Glu
        35                  40                  45

Trp Leu Gly Ser Ile Ile Pro Ile Phe Gly Thr Ile Thr Tyr Ala Gln
    50                  55                  60

Lys Phe Gln Gly Arg Val Thr Ile Thr Ala Asp Lys Ser Thr Ser Thr
65                  70                  75                  80

Ala Phe Met Glu Leu Thr Ser Leu Arg Ser Glu Asp Thr Ala Ile Tyr
                85                  90                  95

Tyr Cys Thr Arg Arg Gly Asn Trp Asn Pro Phe Asp Pro Trp Gly Gln
            100                 105                 110

Gly Thr Leu Val Thr Val Ser Ser
```

<210> SEQ ID NO 119
<211> LENGTH: 369
<212> TYPE: DNA
<213> ORGANISM: Artificial Sequence
<220> FEATURE:
<223> OTHER INFORMATION: MF8397

<400> SEQUENCE: 119

```
caggtgcagc tggtgcagtc tgggggaggc ctggtacagc ctggggggtc cctgagactc      60
tcctgtgcaa cctctggatt caaattcagt agctatgccc tgagctgggt ccgccaggca     120
ccagggaagg gactggagtg ggtctcaggt attagtggta gtggtcgcac cacatggtat     180
gcagactccg tgaagggccg gttcaccatc tccagagaca attccaagaa cacgctgtat     240
ctgcaaatga acagcctgag agccgaggac acggccgtat attactgtgc gagagacggt     300
ggatacagct atggccctta ctggtacttc gatctctggg gccgtggaac cctggtcacc     360
gtctccagt                                                             369
```

<210> SEQ ID NO 120
<211> LENGTH: 30
<212> TYPE: PRT
<213> ORGANISM: Artificial Sequence
<220> FEATURE:
<223> OTHER INFORMATION: MF8397 FW1

<400> SEQUENCE: 120

Gln Val Gln Leu Val Gln Ser Gly Gly Gly Leu Val Gln Pro Gly Gly
1               5                   10                  15
Ser Leu Arg Leu Ser Cys Ala Thr Ser Gly Phe Lys Phe Ser
            20                  25                  30

<210> SEQ ID NO 121
<211> LENGTH: 14
<212> TYPE: PRT
<213> ORGANISM: Artificial Sequence
<220> FEATURE:
<223> OTHER INFORMATION: MF8397 FW2

<400> SEQUENCE: 121

Trp Val Arg Gln Ala Pro Gly Lys Gly Leu Glu Trp Val Ser
1               5                   10

<210> SEQ ID NO 122
<211> LENGTH: 32
<212> TYPE: PRT
<213> ORGANISM: Artificial Sequence
<220> FEATURE:
<223> OTHER INFORMATION: MF8397 FW3

<400> SEQUENCE: 122

Arg Phe Thr Ile Ser Arg Asp Asn Ser Lys Asn Thr Leu Tyr Leu Gln
1               5                   10                  15
Met Asn Ser Leu Arg Ala Glu Asp Thr Ala Val Tyr Tyr Cys Ala Arg
            20                  25                  30

<210> SEQ ID NO 123
<211> LENGTH: 11
<212> TYPE: PRT
<213> ORGANISM: Artificial Sequence
<220> FEATURE:
<223> OTHER INFORMATION: MF8397 FW4

-continued

<400> SEQUENCE: 123

Trp Gly Arg Gly Thr Leu Val Thr Val Ser Ser
1               5                   10

<210> SEQ ID NO 124
<211> LENGTH: 5
<212> TYPE: PRT
<213> ORGANISM: Artificial Sequence
<220> FEATURE:
<223> OTHER INFORMATION: MF8397 CDR1

<400> SEQUENCE: 124

Ser Tyr Ala Leu Ser
1               5

<210> SEQ ID NO 125
<211> LENGTH: 17
<212> TYPE: PRT
<213> ORGANISM: Artificial Sequence
<220> FEATURE:
<223> OTHER INFORMATION: MF8397 CDR2

<400> SEQUENCE: 125

Gly Ile Ser Gly Ser Gly Arg Thr Thr Trp Tyr Ala Asp Ser Val Lys
1               5                   10                  15

Gly

<210> SEQ ID NO 126
<211> LENGTH: 14
<212> TYPE: PRT
<213> ORGANISM: Artificial Sequence
<220> FEATURE:
<223> OTHER INFORMATION: MF8397 CDR3

<400> SEQUENCE: 126

Asp Gly Gly Tyr Ser Tyr Gly Pro Tyr Trp Tyr Phe Asp Leu
1               5                   10

<210> SEQ ID NO 127
<211> LENGTH: 123
<212> TYPE: PRT
<213> ORGANISM: Artificial Sequence
<220> FEATURE:
<223> OTHER INFORMATION: MF8397 VH

<400> SEQUENCE: 127

Gln Val Gln Leu Val Gln Ser Gly Gly Gly Leu Val Gln Pro Gly Gly
1               5                   10                  15

Ser Leu Arg Leu Ser Cys Ala Thr Ser Gly Phe Lys Phe Ser Ser Tyr
            20                  25                  30

Ala Leu Ser Trp Val Arg Gln Ala Pro Gly Lys Gly Leu Glu Trp Val
        35                  40                  45

Ser Gly Ile Ser Gly Ser Gly Arg Thr Thr Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gly Tyr Ser Tyr Gly Pro Tyr Trp Tyr Phe Asp Leu
            100                 105                 110

Trp Gly Arg Gly Thr Leu Val Thr Val Ser Ser
        115                 120

<210> SEQ ID NO 128
<211> LENGTH: 372
<212> TYPE: DNA
<213> ORGANISM: Artificial Sequence
<220> FEATURE:
<223> OTHER INFORMATION: MF8508

<400> SEQUENCE: 128

```
gaggtgcagc tggtggagtc tgggggagga ttggtacagc ctggcaggtc cctgagactc      60
tcctgtgcaa cctctggatt caactttgat gattatacca tgcactgggt ccggcaagct     120
ccagggaagg gcctggagtg gtctcagat attagttgga gtagtggtag cataggctat     180
gcggactctg tgaagggccg attcaccatc tccagagaca cgccaagaa ctccctgtgg     240 ctgcaaatga acagtctgag aactgaggac acggccttgt atttctgtgc aaaagatcat     300
agggggtacg gtgactacga gggtggtggc tttgactact ggggccaggg aaccctggtc     360
accgtctcca gt                                                         372
```

<210> SEQ ID NO 129
<211> LENGTH: 30
<212> TYPE: PRT
<213> ORGANISM: Artificial Sequence
<220> FEATURE:
<223> OTHER INFORMATION: MF8508 FW1

<400> SEQUENCE: 129

Glu Val Gln Leu Val Glu Ser Gly Gly Gly Leu Val Gln Pro Gly Arg
1               5                   10                  15

Ser Leu Arg Leu Ser Cys Ala Thr Ser Gly Phe Asn Phe Asp
            20                  25                  30

<210> SEQ ID NO 130
<211> LENGTH: 14
<212> TYPE: PRT
<213> ORGANISM: Artificial Sequence
<220> FEATURE:
<223> OTHER INFORMATION: MF8508 FW2

<400> SEQUENCE: 130

Trp Val Arg Gln Ala Pro Gly Lys Gly Leu Glu Trp Val Ser
1               5                   10

<210> SEQ ID NO 131
<211> LENGTH: 32
<212> TYPE: PRT
<213> ORGANISM: Artificial Sequence
<220> FEATURE:
<223> OTHER INFORMATION: MF8508 FW3

<400> SEQUENCE: 131

Arg Phe Thr Ile Ser Arg Asp Asn Ala Lys Asn Ser Leu Trp Leu Gln
1               5                   10                  15

Met Asn Ser Leu Arg Thr Glu Asp Thr Ala Leu Tyr Phe Cys Ala Lys
            20                  25                  30

<210> SEQ ID NO 132
<211> LENGTH: 11
<212> TYPE: PRT
<213> ORGANISM: Artificial Sequence
<220> FEATURE:
<223> OTHER INFORMATION: MF8508 FW4

<400> SEQUENCE: 132

```
Trp Gly Gln Gly Thr Leu Val Thr Val Ser Ser
1               5                   10

<210> SEQ ID NO 133
<211> LENGTH: 5
<212> TYPE: PRT
<213> ORGANISM: Artificial Sequence
<220> FEATURE:
<223> OTHER INFORMATION: MF8508 CDR1

<400> SEQUENCE: 133

Asp Tyr Thr Met His
1               5

<210> SEQ ID NO 134
<211> LENGTH: 17
<212> TYPE: PRT
<213> ORGANISM: Artificial Sequence
<220> FEATURE:
<223> OTHER INFORMATION: MF8508 CDR2

<400> SEQUENCE: 134

Asp Ile Ser Trp Ser Ser Gly Ser Ile Gly Tyr Ala Asp Ser Val Lys
1               5                   10                  15

Gly

<210> SEQ ID NO 135
<211> LENGTH: 15
<212> TYPE: PRT
<213> ORGANISM: Artificial Sequence
<220> FEATURE:
<223> OTHER INFORMATION: MF8508 CDR3

<400> SEQUENCE: 135

Asp His Arg Gly Tyr Gly Asp Tyr Glu Gly Gly Phe Asp Tyr
1               5                   10                  15

<210> SEQ ID NO 136
<211> LENGTH: 124
<212> TYPE: PRT
<213> ORGANISM: Artificial Sequence
<220> FEATURE:
<223> OTHER INFORMATION: MF8508 VH

<400> SEQUENCE: 136

Glu Val Gln Leu Val Glu Ser Gly Gly Gly Leu Val Gln Pro Gly Arg
1               5                   10                  15

Ser Leu Arg Leu Ser Cys Ala Thr Ser Gly Phe Asn Phe Asp Asp Tyr
            20                  25                  30

Thr Met His Trp Val Arg Gln Ala Pro Gly Lys Gly Leu Glu Trp Val
        35                  40                  45

Ser Asp Ile Ser Trp Ser Ser Gly Ser Ile Gly Tyr Ala Asp Ser Val
    50                  55                  60

Lys Gly Arg Phe Thr Ile Ser Arg Asp Asn Lys Asn Ser Leu Trp
65                  70                  75                  80

Leu Gln Met Asn Ser Leu Arg Thr Glu Asp Thr Ala Leu Tyr Phe Cys
                85                  90                  95

Ala Lys Asp His Arg Gly Tyr Gly Asp Tyr Glu Gly Gly Phe Asp
            100                 105                 110

Tyr Trp Gly Gln Gly Thr Leu Val Thr Val Ser Ser
        115                 120
```

<210> SEQ ID NO 137
<211> LENGTH: 378
<212> TYPE: DNA
<213> ORGANISM: Artificial Sequence
<220> FEATURE:
<223> OTHER INFORMATION: MF9249

<400> SEQUENCE: 137

```
gaggtgcagc tggtgcagtc tggagcagaa gtgaaaaagc ccggggagtc tctgaagatc      60
tcctgtaagg gttctggata cagttttact aggttttgga tcggctgggt gcgccagatg     120
cccgggaaag gcctggagtg gatggggatc atctatcctg gtgactctga taccagatac     180
agcccgtcct tccaaggcca ggtcaccatc tcagccgaca gtccaccag taccgcctac      240
ctgcagtgga gcagcctgaa ggcctcggac accggcatgt attattgtgt gagacatata     300
cgatattttg actggtcgga agactaccac tattacctgg acgtctgggg caaagggacc     360
acggtcaccg tctccagt                                                   378
```

<210> SEQ ID NO 138
<211> LENGTH: 30
<212> TYPE: PRT
<213> ORGANISM: Artificial Sequence
<220> FEATURE:
<223> OTHER INFORMATION: MF9249 FW1

<400> SEQUENCE: 138

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr
            20                  25                  30

<210> SEQ ID NO 139
<211> LENGTH: 14
<212> TYPE: PRT
<213> ORGANISM: Artificial Sequence
<220> FEATURE:
<223> OTHER INFORMATION: MF9249 FW2

<400> SEQUENCE: 139

Trp Val Arg Gln Met Pro Gly Lys Gly Leu Glu Trp Met Gly
1               5                   10

<210> SEQ ID NO 140
<211> LENGTH: 32
<212> TYPE: PRT
<213> ORGANISM: Artificial Sequence
<220> FEATURE:
<223> OTHER INFORMATION: MF9249 FW3

<400> SEQUENCE: 140

Gln Val Thr Ile Ser Ala Asp Lys Ser Thr Ser Thr Ala Tyr Leu Gln
1               5                   10                  15

Trp Ser Ser Leu Lys Ala Ser Asp Thr Gly Met Tyr Tyr Cys Val Arg
            20                  25                  30

<210> SEQ ID NO 141
<211> LENGTH: 11
<212> TYPE: PRT
<213> ORGANISM: Artificial Sequence
<220> FEATURE:
<223> OTHER INFORMATION: MF9249 FW4

<400> SEQUENCE: 141

```
Trp Gly Lys Gly Thr Thr Val Thr Val Ser Ser
 1               5                  10
```

<210> SEQ ID NO 142
<211> LENGTH: 5
<212> TYPE: PRT
<213> ORGANISM: Artificial Sequence
<220> FEATURE:
<223> OTHER INFORMATION: MF9249 CDR1

<400> SEQUENCE: 142

```
Arg Phe Trp Ile Gly
 1               5
```

<210> SEQ ID NO 143
<211> LENGTH: 17
<212> TYPE: PRT
<213> ORGANISM: Artificial Sequence
<220> FEATURE:
<223> OTHER INFORMATION: MF9249 CDR2

<400> SEQUENCE: 143

```
Ile Ile Tyr Pro Gly Asp Ser Asp Thr Arg Tyr Ser Pro Ser Phe Gln
 1               5                  10                  15
Gly
```

<210> SEQ ID NO 144
<211> LENGTH: 17
<212> TYPE: PRT
<213> ORGANISM: Artificial Sequence
<220> FEATURE:
<223> OTHER INFORMATION: MF9249 CDR3

<400> SEQUENCE: 144

```
His Ile Arg Tyr Phe Asp Trp Ser Glu Asp Tyr His Tyr Tyr Leu Asp
 1               5                  10                  15
Val
```

<210> SEQ ID NO 145
<211> LENGTH: 126
<212> TYPE: PRT
<213> ORGANISM: Artificial Sequence
<220> FEATURE:
<223> OTHER INFORMATION: MF9249 VH

<400> SEQUENCE: 145

```
Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Arg Phe
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Thr Ser Thr Ala Tyr
65                  70                  75                  80

Leu Gln Trp Ser Ser Leu Lys Ala Ser Asp Thr Gly Met Tyr Tyr Cys
                85                  90                  95

Val Arg His Ile Arg Tyr Phe Asp Trp Ser Glu Asp Tyr His Tyr Tyr
                100                 105                 110

Leu Asp Val Trp Gly Lys Gly Thr Thr Val Thr Val Ser Ser
            115                 120                 125
```

<210> SEQ ID NO 146
<211> LENGTH: 378
<212> TYPE: DNA
<213> ORGANISM: Artificial Sequence
<220> FEATURE:
<223> OTHER INFORMATION: MF9267

<400> SEQUENCE: 146

```
gaggtgcagc tggtggagtc tggggcagag gtgaaaaagc ccggggagtc tctgaagatc    60
tcctgtaagg gttctggata cagttttact aggtattgga tcggctgggt gcgccagatg   120
cccgggaaag gcctggagtg gatggggatc atctatcctg gtgactctga taccagatac   180
agcccgtcct ccaaggcca ggtcaccatc tcagccgaca gtccatcag tactgcctac    240
ctgcagtgga gcagcctgaa ggcctcggac accgccatgt attattgtgt gagaaatata   300
cgatattttg tctggtcgga ggactaccac tactacatgg acgtctgggg caaagggacc   360
acggtcaccg tctccagt                                                 378
```

<210> SEQ ID NO 147
<211> LENGTH: 30
<212> TYPE: PRT
<213> ORGANISM: Artificial Sequence
<220> FEATURE:
<223> OTHER INFORMATION: MF9267 FW1

<400> SEQUENCE: 147

Glu Val Gln Leu Val Glu Ser Gly Ala Glu Val Lys Lys Pro Gly Glu
1               5                   10                  15

Ser Leu Lys Ile Ser Cys Lys Gly Ser Gly Tyr Ser Phe Thr
            20                  25                  30

<210> SEQ ID NO 148
<211> LENGTH: 14
<212> TYPE: PRT
<213> ORGANISM: Artificial Sequence
<220> FEATURE:
<223> OTHER INFORMATION: MF9267 FW2

<400> SEQUENCE: 148

Trp Val Arg Gln Met Pro Gly Lys Gly Leu Glu Trp Met Gly
1               5                   10

<210> SEQ ID NO 149
<211> LENGTH: 32
<212> TYPE: PRT
<213> ORGANISM: Artificial Sequence
<220> FEATURE:
<223> OTHER INFORMATION: MF9267 FW3

<400> SEQUENCE: 149

Gln Val Thr Ile Ser Ala Asp Lys Ser Ile Ser Thr Ala Tyr Leu Gln
1               5                   10                  15

Trp Ser Ser Leu Lys Ala Ser Asp Thr Ala Met Tyr Tyr Cys Val Arg
            20                  25                  30

<210> SEQ ID NO 150
<211> LENGTH: 11
<212> TYPE: PRT
<213> ORGANISM: Artificial Sequence
<220> FEATURE:
<223> OTHER INFORMATION: MF9267 FW4

<400> SEQUENCE: 150

Trp Gly Lys Gly Thr Thr Val Thr Val Ser Ser
1               5                   10

<210> SEQ ID NO 151
<211> LENGTH: 5
<212> TYPE: PRT
<213> ORGANISM: Artificial Sequence
<220> FEATURE:
<223> OTHER INFORMATION: MF9267 CDR1

<400> SEQUENCE: 151

Arg Tyr Trp Ile Gly
1               5

<210> SEQ ID NO 152
<211> LENGTH: 17
<212> TYPE: PRT
<213> ORGANISM: Artificial Sequence
<220> FEATURE:
<223> OTHER INFORMATION: MF9267 CDR2

<400> SEQUENCE: 152

Ile Ile Tyr Pro Gly Asp Ser Asp Thr Arg Tyr Ser Pro Ser Phe Gln
1               5                   10                  15
Gly

<210> SEQ ID NO 153
<211> LENGTH: 17
<212> TYPE: PRT
<213> ORGANISM: Artificial Sequence
<220> FEATURE:
<223> OTHER INFORMATION: MF9267 CDR3

<400> SEQUENCE: 153

Asn Ile Arg Tyr Phe Val Trp Ser Glu Asp Tyr His Tyr Tyr Met Asp
1               5                   10                  15
Val

<210> SEQ ID NO 154
<211> LENGTH: 126
<212> TYPE: PRT
<213> ORGANISM: Artificial Sequence
<220> FEATURE:
<223> OTHER INFORMATION: MF9267 VH

<400> SEQUENCE: 154

Glu Val Gln Leu Val Glu Ser Gly Ala Glu Val Lys Lys Pro Gly Glu
1               5                   10                  15

Ser Leu Lys Ile Ser Cys Lys Gly Ser Gly Tyr Ser Phe Thr Arg Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Val Arg Asn Ile Arg Tyr Phe Val Trp Ser Glu Asp Tyr His Tyr Tyr
            100                 105                 110

Met Asp Val Trp Gly Lys Gly Thr Thr Val Thr Val Ser Ser

<210> SEQ ID NO 155
<211> LENGTH: 363
<212> TYPE: DNA
<213> ORGANISM: Artificial Sequence
<220> FEATURE:
<223> OTHER INFORMATION: MF5377

<400> SEQUENCE: 155

```
gaggtgcagc tggtgcagtc tggagctgag gtgaagaagc ctgggtcctc ggtgaaggtc      60
tcctgcaagg cttctggagg catcttcagc acctatgcta tcagctgggt gcgacaggcc     120
cctggacaag ggcttgagtg gatgggaggg atcatcccta tctttgatac accaaactac     180
gcacagaagt tccagggcag agtcacgatt accgcggaca atccacgag cacagcctac      240
atggacctga gcagcctgag atctgaggac acggccgtat attactgtgc gaaaaacgtg     300
cgtggatata gtgcctacga ccttgactac tggggccagg gcaccctggt caccgtctcc     360
agt                                                                     363
```

<210> SEQ ID NO 156
<211> LENGTH: 30
<212> TYPE: PRT
<213> ORGANISM: Artificial Sequence
<220> FEATURE:
<223> OTHER INFORMATION: MF5377 FW1

<400> SEQUENCE: 156

Glu Val Gln Leu Val Gln Ser Gly Ala Glu Val Lys Lys Pro Gly Ser
1               5                   10                  15
Ser Val Lys Val Ser Cys Lys Ala Ser Gly Gly Ile Phe Ser
            20                  25                  30

<210> SEQ ID NO 157
<211> LENGTH: 14
<212> TYPE: PRT
<213> ORGANISM: Artificial Sequence
<220> FEATURE:
<223> OTHER INFORMATION: MF5377 FW2

<400> SEQUENCE: 157

Trp Val Arg Gln Ala Pro Gly Gln Gly Leu Glu Trp Met Gly
1               5                   10

<210> SEQ ID NO 158
<211> LENGTH: 32
<212> TYPE: PRT
<213> ORGANISM: Artificial Sequence
<220> FEATURE:
<223> OTHER INFORMATION: MF5377 FW3

<400> SEQUENCE: 158

Arg Val Thr Ile Thr Ala Asp Lys Ser Thr Ser Thr Ala Tyr Met Asp
1               5                   10                  15
Leu Ser Ser Leu Arg Ser Glu Asp Thr Ala Val Tyr Tyr Cys Ala Lys
            20                  25                  30

<210> SEQ ID NO 159
<211> LENGTH: 11
<212> TYPE: PRT
<213> ORGANISM: Artificial Sequence
<220> FEATURE:
<223> OTHER INFORMATION: MF5377 FW4

```
<400> SEQUENCE: 159

Trp Gly Gln Gly Thr Leu Val Thr Val Ser Ser
1               5                   10

<210> SEQ ID NO 160
<211> LENGTH: 5
<212> TYPE: PRT
<213> ORGANISM: Artificial Sequence
<220> FEATURE:
<223> OTHER INFORMATION: MF5377 CDR1

<400> SEQUENCE: 160

Thr Tyr Ala Ile Ser
1               5

<210> SEQ ID NO 161
<211> LENGTH: 17
<212> TYPE: PRT
<213> ORGANISM: Artificial Sequence
<220> FEATURE:
<223> OTHER INFORMATION: MF5377 CDR2

<400> SEQUENCE: 161

Gly Ile Ile Pro Ile Phe Asp Thr Pro Asn Tyr Ala Gln Lys Phe Gln
1               5                   10                  15

Gly

<210> SEQ ID NO 162
<211> LENGTH: 12
<212> TYPE: PRT
<213> ORGANISM: Artificial Sequence
<220> FEATURE:
<223> OTHER INFORMATION: MF5377 CDR3

<400> SEQUENCE: 162

Asn Val Arg Gly Tyr Ser Ala Tyr Asp Leu Asp Tyr
1               5                   10

<210> SEQ ID NO 163
<211> LENGTH: 121
<212> TYPE: PRT
<213> ORGANISM: Artificial Sequence
<220> FEATURE:
<223> OTHER INFORMATION: MF5377 VH

<400> SEQUENCE: 163

Glu Val Gln Leu Val Gln Ser Gly Ala Glu Val Lys Lys Pro Gly Ser
1               5                   10                  15

Ser Val Lys Val Ser Cys Lys Ala Ser Gly Gly Ile Phe Ser Thr Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Asp Thr Pro Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Asp Leu Ser Ser Leu Arg Ser Glu Asp Thr Ala Val Tyr Tyr Cys
                85                  90                  95

Ala Lys Asn Val Arg Gly Tyr Ser Ala Tyr Asp Leu Asp Tyr Trp Gly
            100                 105                 110

Gln Gly Thr Leu Val Thr Val Ser Ser
        115                 120
```

<210> SEQ ID NO 164
<211> LENGTH: 363
<212> TYPE: DNA
<213> ORGANISM: Artificial Sequence
<220> FEATURE:
<223> OTHER INFORMATION: MF5444

<400> SEQUENCE: 164

```
caggtgcagc tggtgcaatc tgggtctgag ttgaagaagc ctggggcctc agtgaaggtt      60
tcctgcaagg cttctggata caccttcact agctattcta tgaattgggt gcgacaggcc     120
cctggacaag gcttgagtg gatgggatgg atcaacacca cactgggaa cccaacgtat       180
gcccagggct tcacaggacg gtttgtcttc tccttggaca cctctgtcag cacggcatat     240
ctgcagatca gcagcctaaa ggctgaggac actgccgtgt attactgtgc gagagatcac     300
gattttcgga ctgggagggc ttttgatatc tggggccaag gaccacggt caccgtctcc      360
agt                                                                   363
```

<210> SEQ ID NO 165
<211> LENGTH: 30
<212> TYPE: PRT
<213> ORGANISM: Artificial Sequence
<220> FEATURE:
<223> OTHER INFORMATION: MF5444 FW1

<400> SEQUENCE: 165

Gln Val Gln Leu Val Gln Ser Gly Ser Glu Leu Lys Lys Pro Gly Ala
1               5                   10                  15
Ser Val Lys Val Ser Cys Lys Ala Ser Gly Tyr Thr Phe Thr
            20                  25                  30

<210> SEQ ID NO 166
<211> LENGTH: 14
<212> TYPE: PRT
<213> ORGANISM: Artificial Sequence
<220> FEATURE:
<223> OTHER INFORMATION: MF5444 FW2

<400> SEQUENCE: 166

Trp Val Arg Gln Ala Pro Gly Gln Gly Leu Glu Trp Met Gly
1               5                   10

<210> SEQ ID NO 167
<211> LENGTH: 32
<212> TYPE: PRT
<213> ORGANISM: Artificial Sequence
<220> FEATURE:
<223> OTHER INFORMATION: MF5444 FW3

<400> SEQUENCE: 167

Arg Phe Val Phe Ser Leu Asp Thr Ser Val Ser Thr Ala Tyr Leu Gln
1               5                   10                  15
Ile Ser Ser Leu Lys Ala Glu Asp Thr Ala Val Tyr Tyr Cys Ala Arg
            20                  25                  30

<210> SEQ ID NO 168
<211> LENGTH: 11
<212> TYPE: PRT
<213> ORGANISM: Artificial Sequence
<220> FEATURE:
<223> OTHER INFORMATION: MF5444 FW4

<400> SEQUENCE: 168

```
Trp Gly Gln Gly Thr Thr Val Thr Val Ser Ser
1               5                   10

<210> SEQ ID NO 169
<211> LENGTH: 5
<212> TYPE: PRT
<213> ORGANISM: Artificial Sequence
<220> FEATURE:
<223> OTHER INFORMATION: MF5444 CDR1

<400> SEQUENCE: 169

Ser Tyr Ser Met Asn
1               5

<210> SEQ ID NO 170
<211> LENGTH: 17
<212> TYPE: PRT
<213> ORGANISM: Artificial Sequence
<220> FEATURE:
<223> OTHER INFORMATION: MF5444 CDR2

<400> SEQUENCE: 170

Trp Ile Asn Thr Asn Thr Gly Asn Pro Thr Tyr Ala Gln Gly Phe Thr
1               5                   10                  15

Gly

<210> SEQ ID NO 171
<211> LENGTH: 12
<212> TYPE: PRT
<213> ORGANISM: Artificial Sequence
<220> FEATURE:
<223> OTHER INFORMATION: MF5444 CDR3

<400> SEQUENCE: 171

Asp His Asp Phe Arg Thr Gly Arg Ala Phe Asp Ile
1               5                   10

<210> SEQ ID NO 172
<211> LENGTH: 121
<212> TYPE: PRT
<213> ORGANISM: Artificial Sequence
<220> FEATURE:
<223> OTHER INFORMATION: MF5444 VH

<400> SEQUENCE: 172

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ser Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp His Asp Phe Arg Thr Gly Arg Ala Phe Asp Ile Trp Gly
            100                 105                 110

Gln Gly Thr Thr Val Thr Val Ser Ser
        115                 120
```

<210> SEQ ID NO 173
<211> LENGTH: 372
<212> TYPE: DNA
<213> ORGANISM: Artificial Sequence
<220> FEATURE:
<223> OTHER INFORMATION: MF5380

<400> SEQUENCE: 173

```
gaggtgcagc tggtggagtc tgggggagac gtggtccagc ctggggaggtc cctgagactc      60
tcctgtgcag cctctggatt caccttcagt agctatggca tgcactgggt ccgccaggct     120
ccaggcaagg gctggagtg gtggcagtt atatcatatg atggaagtaa taaatactat      180
gcagactccg tgaagggccg attcaccatc tccagagaca actccaagag cacgctgttt     240
ctgcaaatga acagcctgag agctgaggac acggctgtgt atttctgtgt gagaggcctc     300
cccataacta tggttcgggg agcgtactcc tttgactact ggggccaggg cacctggtc     360
accgtctcca gt                                                          372
```

<210> SEQ ID NO 174
<211> LENGTH: 30
<212> TYPE: PRT
<213> ORGANISM: Artificial Sequence
<220> FEATURE:
<223> OTHER INFORMATION: MF5380 FW1

<400> SEQUENCE: 174

```
Glu Val Gln Leu Val Glu Ser Gly Gly Asp Val Val Gln Pro Gly Arg
1               5                   10                  15
Ser Leu Arg Leu Ser Cys Ala Ala Ser Gly Phe Thr Phe Ser
            20                  25                  30
```

<210> SEQ ID NO 175
<211> LENGTH: 14
<212> TYPE: PRT
<213> ORGANISM: Artificial Sequence
<220> FEATURE:
<223> OTHER INFORMATION: MF5380 FW2

<400> SEQUENCE: 175

```
Trp Val Arg Gln Ala Pro Gly Lys Gly Leu Glu Trp Val Ala
1               5                   10
```

<210> SEQ ID NO 176
<211> LENGTH: 32
<212> TYPE: PRT
<213> ORGANISM: Artificial Sequence
<220> FEATURE:
<223> OTHER INFORMATION: MF5380 FW3

<400> SEQUENCE: 176

```
Arg Phe Thr Ile Ser Arg Asp Asn Ser Lys Ser Thr Leu Phe Leu Gln
1               5                   10                  15
Met Asn Ser Leu Arg Ala Glu Asp Thr Ala Val Tyr Phe Cys Val Arg
            20                  25                  30
```

<210> SEQ ID NO 177
<211> LENGTH: 11
<212> TYPE: PRT
<213> ORGANISM: Artificial Sequence
<220> FEATURE:
<223> OTHER INFORMATION: MF5380 FW4

<400> SEQUENCE: 177

```
Trp Gly Gln Gly Thr Leu Val Thr Val Ser Ser
1               5                   10
```

<210> SEQ ID NO 178
<211> LENGTH: 5
<212> TYPE: PRT
<213> ORGANISM: Artificial Sequence
<220> FEATURE:
<223> OTHER INFORMATION: MF5380 CDR1

<400> SEQUENCE: 178

```
Ser Tyr Gly Met His
1               5
```

<210> SEQ ID NO 179
<211> LENGTH: 17
<212> TYPE: PRT
<213> ORGANISM: Artificial Sequence
<220> FEATURE:
<223> OTHER INFORMATION: MF5380 CDR2

<400> SEQUENCE: 179

```
Val Ile Ser Tyr Asp Gly Ser Asn Lys Tyr Tyr Ala Asp Ser Val Lys
1               5                   10                  15

Gly
```

<210> SEQ ID NO 180
<211> LENGTH: 15
<212> TYPE: PRT
<213> ORGANISM: Artificial Sequence
<220> FEATURE:
<223> OTHER INFORMATION: MF5380 CDR3

<400> SEQUENCE: 180

```
Gly Leu Pro Ile Thr Met Val Arg Gly Ala Tyr Ser Phe Asp Tyr
1               5                   10                  15
```

<210> SEQ ID NO 181
<211> LENGTH: 124
<212> TYPE: PRT
<213> ORGANISM: Artificial Sequence
<220> FEATURE:
<223> OTHER INFORMATION: MF5380 VH

<400> SEQUENCE: 181

```
Glu Val Gln Leu Val Glu Ser Gly Gly Asp Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Thr Leu Phe
65                  70                  75                  80

Leu Gln Met Asn Ser Leu Arg Ala Glu Asp Thr Ala Val Tyr Phe Cys
                85                  90                  95

Val Arg Gly Leu Pro Ile Thr Met Val Arg Gly Ala Tyr Ser Phe Asp
            100                 105                 110

Tyr Trp Gly Gln Gly Thr Leu Val Thr Val Ser Ser
        115                 120
```

<210> SEQ ID NO 182
<211> LENGTH: 366
<212> TYPE: DNA
<213> ORGANISM: Artificial Sequence
<220> FEATURE:
<223> OTHER INFORMATION: MF8233

<400> SEQUENCE: 182

```
caggttcagc tggtgcagtc tggagctgag gtgaagaagc ctggggcctc agtgaaggtc      60
tcctgcaagg cttctggtta cacctttacc agctatggta tcagctgggt gcgacaggcc    120
cctggacaag ggcttgagtg gatgggatgg atcagcgctt acaatgccaa cacaaactat    180
gcacagaagc tccagggcag agtcaccatg accacagaca catccacgag cacagcctac    240
atggagctga ggagcctgag atctgacgac acggctgtgt attactgtgc aaaagatcgt    300
cattggcatt ggtggctgga cgcctttgat tattggggcc aaggtaccct ggtcaccgtc    360
tccagt                                                                366
```

<210> SEQ ID NO 183
<211> LENGTH: 30
<212> TYPE: PRT
<213> ORGANISM: Artificial Sequence
<220> FEATURE:
<223> OTHER INFORMATION: MF8233 FW1

<400> SEQUENCE: 183

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr
            20                  25                  30

<210> SEQ ID NO 184
<211> LENGTH: 14
<212> TYPE: PRT
<213> ORGANISM: Artificial Sequence
<220> FEATURE:
<223> OTHER INFORMATION: MF8233 FW2

<400> SEQUENCE: 184

Trp Val Arg Gln Ala Pro Gly Gln Gly Leu Glu Trp Met Gly
1               5                   10

<210> SEQ ID NO 185
<211> LENGTH: 32
<212> TYPE: PRT
<213> ORGANISM: Artificial Sequence
<220> FEATURE:
<223> OTHER INFORMATION: MF8233 FW3

<400> SEQUENCE: 185

Arg Val Thr Met Thr Thr Asp Thr Ser Thr Ser Thr Ala Tyr Met Glu
1               5                   10                  15
Leu Arg Ser Leu Arg Ser Asp Asp Thr Ala Val Tyr Tyr Cys Ala Lys
            20                  25                  30

<210> SEQ ID NO 186
<211> LENGTH: 11
<212> TYPE: PRT
<213> ORGANISM: Artificial Sequence
<220> FEATURE:
<223> OTHER INFORMATION: MF8233 FW4

<400> SEQUENCE: 186

Trp Gly Gln Gly Thr Leu Val Thr Val Ser Ser

```
<210> SEQ ID NO 187
<211> LENGTH: 5
<212> TYPE: PRT
<213> ORGANISM: Artificial Sequence
<220> FEATURE:
<223> OTHER INFORMATION: MF8233 CDR1

<400> SEQUENCE: 187

Ser Tyr Gly Ile Ser
1               5

<210> SEQ ID NO 188
<211> LENGTH: 17
<212> TYPE: PRT
<213> ORGANISM: Artificial Sequence
<220> FEATURE:
<223> OTHER INFORMATION: MF8233 CDR2

<400> SEQUENCE: 188

Trp Ile Ser Ala Tyr Asn Ala Asn Thr Asn Tyr Ala Gln Lys Leu Gln
1               5                   10                  15

Gly

<210> SEQ ID NO 189
<211> LENGTH: 13
<212> TYPE: PRT
<213> ORGANISM: Artificial Sequence
<220> FEATURE:
<223> OTHER INFORMATION: MF8233 CDR3

<400> SEQUENCE: 189

Asp Arg His Trp His Trp Trp Leu Asp Ala Phe Asp Tyr
1               5                   10

<210> SEQ ID NO 190
<211> LENGTH: 122
<212> TYPE: PRT
<213> ORGANISM: Artificial Sequence
<220> FEATURE:
<223> OTHER INFORMATION: MF8233 VH

<400> SEQUENCE: 190

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Ala Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Lys Asp Arg His Trp His Trp Trp Leu Asp Ala Phe Asp Tyr Trp
            100                 105                 110

Gly Gln Gly Thr Leu Val Thr Val Ser Ser
        115                 120

<210> SEQ ID NO 191
```

```
<211> LENGTH: 366
<212> TYPE: DNA
<213> ORGANISM: Artificial Sequence
<220> FEATURE:
<223> OTHER INFORMATION: MF9891

<400> SEQUENCE: 191
caggttcagc tggtgcagtc tggagctgag gtgaagaagc ctggggcctc agtgaaggtc      60
tcctgcaagg cttctggtta cacctttacc agctatggta tcagctgggt gcgacaggcc     120
cctggacaag ggcttgagtg gatgggatgg atcagcgctt acaatgccaa cacaaactat     180
gcacagaagc tccagggcag agtcaccatg accacagaca catccacgag cacagcctac     240
atggagctga ggagcctgag atctgacgac acggctgtgt attactgtgc aaaagatctg     300
tacggtcatt ggtggctgga tgcctttgat tattggggcc aaggtaccct ggtcaccgtc     360
tccagt                                                                366

<210> SEQ ID NO 192
<211> LENGTH: 30
<212> TYPE: PRT
<213> ORGANISM: Artificial Sequence
<220> FEATURE:
<223> OTHER INFORMATION: MF9891 FW1

<400> SEQUENCE: 192

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 193
<211> LENGTH: 14
<212> TYPE: PRT
<213> ORGANISM: Artificial Sequence
<220> FEATURE:
<223> OTHER INFORMATION: MF9891 FW2

<400> SEQUENCE: 193

Trp Val Arg Gln Ala Pro Gly Gln Gly Leu Glu Trp Met Gly
1               5                   10

<210> SEQ ID NO 194
<211> LENGTH: 32
<212> TYPE: PRT
<213> ORGANISM: Artificial Sequence
<220> FEATURE:
<223> OTHER INFORMATION: MF9891 FW3

<400> SEQUENCE: 194

Arg Val Thr Met Thr Thr Asp Thr Ser Thr Ser Thr Ala Tyr Met Glu
1               5                   10                  15

Leu Arg Ser Leu Arg Ser Asp Asp Thr Ala Val Tyr Tyr Cys Ala Lys
            20                  25                  30

<210> SEQ ID NO 195
<211> LENGTH: 11
<212> TYPE: PRT
<213> ORGANISM: Artificial Sequence
<220> FEATURE:
<223> OTHER INFORMATION: MF9891 FW4

<400> SEQUENCE: 195

Trp Gly Gln Gly Thr Leu Val Thr Val Ser Ser
1               5                   10
```

-continued

```
<210> SEQ ID NO 196
<211> LENGTH: 5
<212> TYPE: PRT
<213> ORGANISM: Artificial Sequence
<220> FEATURE:
<223> OTHER INFORMATION: MF9891 CDR1

<400> SEQUENCE: 196

Ser Tyr Gly Ile Ser
1               5

<210> SEQ ID NO 197
<211> LENGTH: 17
<212> TYPE: PRT
<213> ORGANISM: Artificial Sequence
<220> FEATURE:
<223> OTHER INFORMATION: MF9891 CDR2

<400> SEQUENCE: 197

Trp Ile Ser Ala Tyr Asn Ala Asn Thr Asn Tyr Ala Gln Lys Leu Gln
1               5                   10                  15

Gly

<210> SEQ ID NO 198
<211> LENGTH: 13
<212> TYPE: PRT
<213> ORGANISM: Artificial Sequence
<220> FEATURE:
<223> OTHER INFORMATION: MF9891 CDR3

<400> SEQUENCE: 198

Asp Leu Tyr Gly His Trp Trp Leu Asp Ala Phe Asp Tyr
1               5                   10

<210> SEQ ID NO 199
<211> LENGTH: 122
<212> TYPE: PRT
<213> ORGANISM: Artificial Sequence
<220> FEATURE:
<223> OTHER INFORMATION: MF9891 VH

<400> SEQUENCE: 199

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Ala Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Lys Asp Leu Tyr Gly His Trp Trp Leu Asp Ala Phe Asp Tyr Trp
            100                 105                 110

Gly Gln Gly Thr Leu Val Thr Val Ser Ser
        115                 120

<210> SEQ ID NO 200
<211> LENGTH: 366
```

-continued

```
<212> TYPE: DNA
<213> ORGANISM: Artificial Sequence
<220> FEATURE:
<223> OTHER INFORMATION: MF9886

<400> SEQUENCE: 200
caggttcagc tggtgcagtc tggagctgag gtgaagaagc ctggggcctc agtgaaggtc      60
tcctgcaagg cttctggtta cacctttacc agctatggta tcagctgggt gcgacaggcc     120
cctggacaag ggcttgagtg gatgggatgg atcagcgctt acaatgccaa cacaaactat     180
gcacagaagc tccagggcag agtcaccatg accacagaca catccacgag cacagcctac     240
atggagctga ggagcctgag atctgacgac acggctgtgt attactgtgc aaaaggtcca     300
ggttctcatt ggtggctgga tgcctttgat tattggggcc aaggtaccct ggtcaccgtc     360
tccagt                                                                366

<210> SEQ ID NO 201
<211> LENGTH: 30
<212> TYPE: PRT
<213> ORGANISM: Artificial Sequence
<220> FEATURE:
<223> OTHER INFORMATION: MF9886 FW1

<400> SEQUENCE: 201

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 202
<211> LENGTH: 14
<212> TYPE: PRT
<213> ORGANISM: Artificial Sequence
<220> FEATURE:
<223> OTHER INFORMATION: MF9886 FW2

<400> SEQUENCE: 202

Trp Val Arg Gln Ala Pro Gly Gln Gly Leu Glu Trp Met Gly
1               5                   10

<210> SEQ ID NO 203
<211> LENGTH: 32
<212> TYPE: PRT
<213> ORGANISM: Artificial Sequence
<220> FEATURE:
<223> OTHER INFORMATION: MF9886 FW3

<400> SEQUENCE: 203

Arg Val Thr Met Thr Thr Asp Thr Ser Thr Ser Thr Ala Tyr Met Glu
1               5                   10                  15

Leu Arg Ser Leu Arg Ser Asp Asp Thr Ala Val Tyr Tyr Cys Ala Lys
            20                  25                  30

<210> SEQ ID NO 204
<211> LENGTH: 11
<212> TYPE: PRT
<213> ORGANISM: Artificial Sequence
<220> FEATURE:
<223> OTHER INFORMATION: MF9886 FW4

<400> SEQUENCE: 204

Trp Gly Gln Gly Thr Leu Val Thr Val Ser Ser
1               5                   10
```

-continued

```
<210> SEQ ID NO 205
<211> LENGTH: 5
<212> TYPE: PRT
<213> ORGANISM: Artificial Sequence
<220> FEATURE:
<223> OTHER INFORMATION: MF9886 CDR1

<400> SEQUENCE: 205

Ser Tyr Gly Ile Ser
1               5

<210> SEQ ID NO 206
<211> LENGTH: 17
<212> TYPE: PRT
<213> ORGANISM: Artificial Sequence
<220> FEATURE:
<223> OTHER INFORMATION: MF9886 CDR2

<400> SEQUENCE: 206

Trp Ile Ser Ala Tyr Asn Ala Asn Thr Asn Tyr Ala Gln Lys Leu Gln
1               5                   10                  15

Gly

<210> SEQ ID NO 207
<211> LENGTH: 13
<212> TYPE: PRT
<213> ORGANISM: Artificial Sequence
<220> FEATURE:
<223> OTHER INFORMATION: MF9886 CDR3

<400> SEQUENCE: 207

Gly Pro Gly Ser His Trp Trp Leu Asp Ala Phe Asp Tyr
1               5                   10

<210> SEQ ID NO 208
<211> LENGTH: 122
<212> TYPE: PRT
<213> ORGANISM: Artificial Sequence
<220> FEATURE:
<223> OTHER INFORMATION: MF9886 VH

<400> SEQUENCE: 208

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Ala Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Lys Gly Pro Gly Ser His Trp Trp Leu Asp Ala Phe Asp Tyr Trp
            100                 105                 110

Gly Gln Gly Thr Leu Val Thr Val Ser Ser
        115                 120

<210> SEQ ID NO 209
<211> LENGTH: 366
<212> TYPE: DNA
```

<213> ORGANISM: Artificial Sequence
<220> FEATURE:
<223> OTHER INFORMATION: MF9873

<400> SEQUENCE: 209

```
caggttcagc tggtgcagtc tggagctgag gtgaagaagc ctggggcctc agtgaaggtc      60
tcctgcaagg cttctggtta cacctttacc agctatggta tcagctgggt gcgacaggcc     120
cctggacaag gcttgagtg gatgggatgg atcagcgctt acaatgccaa cacaaactat      180
gcacagaagc tccagggcag agtcaccatg accacagaca catccacgag cacagcctac     240
atggagctga ggagcctgag atctgacgac acggctgtgt attactgtgc aaaagataga     300
ggttggcatt ggtggctgga tgcctttgat tattggggcc aaggtaccct ggtcaccgtc     360
tccagt                                                                366
```

<210> SEQ ID NO 210
<211> LENGTH: 30
<212> TYPE: PRT
<213> ORGANISM: Artificial Sequence
<220> FEATURE:
<223> OTHER INFORMATION: MF9873 FW1

<400> SEQUENCE: 210

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr
            20                  25                  30

<210> SEQ ID NO 211
<211> LENGTH: 14
<212> TYPE: PRT
<213> ORGANISM: Artificial Sequence
<220> FEATURE:
<223> OTHER INFORMATION: MF9873 FW2

<400> SEQUENCE: 211

Trp Val Arg Gln Ala Pro Gly Gln Gly Leu Glu Trp Met Gly
1               5                   10

<210> SEQ ID NO 212
<211> LENGTH: 32
<212> TYPE: PRT
<213> ORGANISM: Artificial Sequence
<220> FEATURE:
<223> OTHER INFORMATION: MF9873 FW3

<400> SEQUENCE: 212

Arg Val Thr Met Thr Thr Asp Thr Ser Thr Ser Thr Ala Tyr Met Glu
1               5                   10                  15
Leu Arg Ser Leu Arg Ser Asp Asp Thr Ala Val Tyr Tyr Cys Ala Lys
            20                  25                  30

<210> SEQ ID NO 213
<211> LENGTH: 11
<212> TYPE: PRT
<213> ORGANISM: Artificial Sequence
<220> FEATURE:
<223> OTHER INFORMATION: MF9873 FW4

<400> SEQUENCE: 213

Trp Gly Gln Gly Thr Leu Val Thr Val Ser Ser
1               5                   10

-continued

```
<210> SEQ ID NO 214
<211> LENGTH: 5
<212> TYPE: PRT
<213> ORGANISM: Artificial Sequence
<220> FEATURE:
<223> OTHER INFORMATION: MF9873 CDR1

<400> SEQUENCE: 214

Ser Tyr Gly Ile Ser
1               5

<210> SEQ ID NO 215
<211> LENGTH: 17
<212> TYPE: PRT
<213> ORGANISM: Artificial Sequence
<220> FEATURE:
<223> OTHER INFORMATION: MF9873 CDR2

<400> SEQUENCE: 215

Trp Ile Ser Ala Tyr Asn Ala Asn Thr Asn Tyr Ala Gln Lys Leu Gln
1               5                   10                  15

Gly

<210> SEQ ID NO 216
<211> LENGTH: 13
<212> TYPE: PRT
<213> ORGANISM: Artificial Sequence
<220> FEATURE:
<223> OTHER INFORMATION: MF9873 CDR3

<400> SEQUENCE: 216

Asp Arg Gly Trp His Trp Trp Leu Asp Ala Phe Asp Tyr
1               5                   10

<210> SEQ ID NO 217
<211> LENGTH: 122
<212> TYPE: PRT
<213> ORGANISM: Artificial Sequence
<220> FEATURE:
<223> OTHER INFORMATION: MF9873 VH

<400> SEQUENCE: 217

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Ala Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Lys Asp Arg Gly Trp His Trp Trp Leu Asp Ala Phe Asp Tyr Trp
            100                 105                 110

Gly Gln Gly Thr Leu Val Thr Val Ser Ser
        115                 120

<210> SEQ ID NO 218
<211> LENGTH: 375
<212> TYPE: DNA
<213> ORGANISM: Artificial Sequence
```

<220> FEATURE:
<223> OTHER INFORMATION: MF9988

<400> SEQUENCE: 218

```
caggttcagc tggtgcagtc tggagctgag gtgaagaagc ctggggcctc agtgaaggtc    60
tcctgcaagg cttctggtta caccttacc agctatggta tcagctgggt gcgacaggcc   120
cctggacaag ggcttgagtg gatgggatgg atcagcgctt acaatgccaa cacaaactat   180
gcacagaagc tccagggcag agtcaccatg accacagaca catccacgag cacagcctac   240
atggagctga ggagcctgag atctgacgac acggctgtgt attactgtgc aaaagatcgt   300
cattggcatt ggtggctgga cggctttgat tattggggcc aaggtaccct ggtcaccgtc   360
tcgagtgtct ccagt                                                    375
```

<210> SEQ ID NO 219
<211> LENGTH: 30
<212> TYPE: PRT
<213> ORGANISM: Artificial Sequence
<220> FEATURE:
<223> OTHER INFORMATION: MF9988 FW1

<400> SEQUENCE: 219

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr
            20                  25                  30

<210> SEQ ID NO 220
<211> LENGTH: 14
<212> TYPE: PRT
<213> ORGANISM: Artificial Sequence
<220> FEATURE:
<223> OTHER INFORMATION: MF9988 FW2

<400> SEQUENCE: 220

Trp Val Arg Gln Ala Pro Gly Gln Gly Leu Glu Trp Met Gly
1               5                   10

<210> SEQ ID NO 221
<211> LENGTH: 32
<212> TYPE: PRT
<213> ORGANISM: Artificial Sequence
<220> FEATURE:
<223> OTHER INFORMATION: MF9988 FW3

<400> SEQUENCE: 221

Arg Val Thr Met Thr Thr Asp Thr Ser Thr Ser Thr Ala Tyr Met Glu
1               5                   10                  15
Leu Arg Ser Leu Arg Ser Asp Asp Thr Ala Val Tyr Tyr Cys Ala Lys
            20                  25                  30

<210> SEQ ID NO 222
<211> LENGTH: 11
<212> TYPE: PRT
<213> ORGANISM: Artificial Sequence
<220> FEATURE:
<223> OTHER INFORMATION: MF9988 FW4

<400> SEQUENCE: 222

Trp Gly Gln Gly Thr Leu Val Thr Val Ser Ser
1               5                   10

<210> SEQ ID NO 223

```
<211> LENGTH: 5
<212> TYPE: PRT
<213> ORGANISM: Artificial Sequence
<220> FEATURE:
<223> OTHER INFORMATION: MF9988 CDR1

<400> SEQUENCE: 223

Ser Tyr Gly Ile Ser
1               5

<210> SEQ ID NO 224
<211> LENGTH: 17
<212> TYPE: PRT
<213> ORGANISM: Artificial Sequence
<220> FEATURE:
<223> OTHER INFORMATION: MF9988 CDR2

<400> SEQUENCE: 224

Trp Ile Ser Ala Tyr Asn Ala Asn Thr Asn Tyr Ala Gln Lys Leu Gln
1               5                   10                  15

Gly

<210> SEQ ID NO 225
<211> LENGTH: 13
<212> TYPE: PRT
<213> ORGANISM: Artificial Sequence
<220> FEATURE:
<223> OTHER INFORMATION: MF9988 CDR3

<400> SEQUENCE: 225

Asp Arg His Trp His Trp Trp Leu Asp Gly Phe Asp Tyr
1               5                   10

<210> SEQ ID NO 226
<211> LENGTH: 122
<212> TYPE: PRT
<213> ORGANISM: Artificial Sequence
<220> FEATURE:
<223> OTHER INFORMATION: MF9988 VH

<400> SEQUENCE: 226

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Ala Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Lys Asp Arg His Trp His Trp Trp Leu Asp Gly Phe Asp Tyr Trp
                100                 105                 110

Gly Gln Gly Thr Leu Val Thr Val Ser Ser
            115                 120

<210> SEQ ID NO 227
<211> LENGTH: 381
<212> TYPE: DNA
<213> ORGANISM: Artificial Sequence
<220> FEATURE:
```

<223> OTHER INFORMATION: MF1337

<400> SEQUENCE: 227

```
gaggtgcagc tggtggagac tgggctgag gtgaagaagc cgggggcctc agtgaaggtc      60
tcctgcaagg cttctgacta catcttcacc aaatatgaca tcaactgggt gcgccaggcc    120
cctggacaag ggcttgaatg gatgggatgg atgagcgcta acactggaaa cacgggctat    180
gcacagaagt tccagggcag agtcaccatg accagggaca cgtccataaa cacagcctac    240
atggagctga gcagcctgac atctggtgac acggccgttt atttctgtgc gaggagtagt    300
cttttcaaga cagagacggc gccctactat cacttcgctc tggacgtctg ggccaaggg    360
accacggtca ccgtctccag t                                              381
```

<210> SEQ ID NO 228
<211> LENGTH: 30
<212> TYPE: PRT
<213> ORGANISM: Artificial Sequence
<220> FEATURE:
<223> OTHER INFORMATION: MF1337 FW1

<400> SEQUENCE: 228

Glu Val Gln Leu Val Glu Thr Gly Ala Glu Val Lys Lys Pro Gly Ala
1               5                   10                  15
Ser Val Lys Val Ser Cys Lys Ala Ser Asp Tyr Ile Phe Thr
            20                  25                  30

<210> SEQ ID NO 229
<211> LENGTH: 14
<212> TYPE: PRT
<213> ORGANISM: Artificial Sequence
<220> FEATURE:
<223> OTHER INFORMATION: MF1337 FW2

<400> SEQUENCE: 229

Trp Val Arg Gln Ala Pro Gly Gln Gly Leu Glu Trp Met Gly
1               5                   10

<210> SEQ ID NO 230
<211> LENGTH: 32
<212> TYPE: PRT
<213> ORGANISM: Artificial Sequence
<220> FEATURE:
<223> OTHER INFORMATION: MF1337 FW3

<400> SEQUENCE: 230

Arg Val Thr Met Thr Arg Asp Thr Ser Ile Asn Thr Ala Tyr Met Glu
1               5                   10                  15
Leu Ser Ser Leu Thr Ser Gly Asp Thr Ala Val Tyr Phe Cys Ala Arg
            20                  25                  30

<210> SEQ ID NO 231
<211> LENGTH: 11
<212> TYPE: PRT
<213> ORGANISM: Artificial Sequence
<220> FEATURE:
<223> OTHER INFORMATION: MF1337 FW4

<400> SEQUENCE: 231

Trp Gly Gln Gly Thr Thr Val Thr Val Ser Ser
1               5                   10

<210> SEQ ID NO 232
<211> LENGTH: 5

```
<212> TYPE: PRT
<213> ORGANISM: Artificial Sequence
<220> FEATURE:
<223> OTHER INFORMATION: CDR1

<400> SEQUENCE: 232

Lys Tyr Asp Ile Asn
1               5

<210> SEQ ID NO 233
<211> LENGTH: 17
<212> TYPE: PRT
<213> ORGANISM: Artificial Sequence
<220> FEATURE:
<223> OTHER INFORMATION: MF1337 CDR2

<400> SEQUENCE: 233

Trp Met Ser Ala Asn Thr Gly Asn Thr Gly Tyr Ala Gln Lys Phe Gln
1               5                   10                  15

Gly

<210> SEQ ID NO 234
<211> LENGTH: 18
<212> TYPE: PRT
<213> ORGANISM: Artificial Sequence
<220> FEATURE:
<223> OTHER INFORMATION: MF1337 CDR3

<400> SEQUENCE: 234

Ser Ser Leu Phe Lys Thr Glu Thr Ala Pro Tyr Tyr His Phe Ala Leu
1               5                   10                  15

Asp Val

<210> SEQ ID NO 235
<211> LENGTH: 127
<212> TYPE: PRT
<213> ORGANISM: Artificial Sequence
<220> FEATURE:
<223> OTHER INFORMATION: MF1337 VH

<400> SEQUENCE: 235

Glu Val Gln Leu Val Glu Thr Gly Ala Glu Val Lys Lys Pro Gly Ala
1               5                   10                  15

Ser Val Lys Val Ser Cys Lys Ala Ser Asp Tyr Ile Phe Thr Lys Tyr
            20                  25                  30

Asp Ile Asn Trp Val Arg Gln Ala Pro Gly Gln Gly Leu Glu Trp Met
        35                  40                  45

Gly Trp Met Ser Ala Asn Thr Gly Asn Thr Gly Tyr Ala Gln Lys Phe
    50                  55                  60

Gln Gly Arg Val Thr Met Thr Arg Asp Thr Ser Ile Asn Thr Ala Tyr
65                  70                  75                  80

Met Glu Leu Ser Ser Leu Thr Ser Gly Asp Thr Ala Val Tyr Phe Cys
                85                  90                  95

Ala Arg Ser Ser Leu Phe Lys Thr Glu Thr Ala Pro Tyr Tyr His Phe
            100                 105                 110

Ala Leu Asp Val Trp Gly Gln Gly Thr Thr Val Thr Val Ser Ser
        115                 120                 125

<210> SEQ ID NO 236
<211> LENGTH: 357
<212> TYPE: DNA
<213> ORGANISM: Artificial Sequence
```

<220> FEATURE:
<223> OTHER INFORMATION: MF1122

<400> SEQUENCE: 236

```
gaggtgcagc tggtggagtc tggggggaggc gtggtccagc ctgggaggtc cctgagactc    60
tcctgtgcag cctctggatt caccttcagt agctatggca tgcactgggt ccgccaggct   120
ccaggcaagg ggctggagtg ggtggcagtt atatcatatg atggaagtaa taaatactat   180
gcagactccg tgaagggccg attcaccatc tccagagaca attccaagaa cacgctgtat   240
ctgcaaatga acagcctgag agctgaggac acggccgtgt attactgtgc aagagccctc   300
ttcacgacca tcgccatgga ctattggggc caaggtaccc tggtcaccgt ctccagt     357
```

<210> SEQ ID NO 237
<211> LENGTH: 30
<212> TYPE: PRT
<213> ORGANISM: Artificial Sequence
<220> FEATURE:
<223> OTHER INFORMATION: MF1122 FW1

<400> SEQUENCE: 237

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser
            20                  25                  30
```

<210> SEQ ID NO 238
<211> LENGTH: 14
<212> TYPE: PRT
<213> ORGANISM: Artificial Sequence
<220> FEATURE:
<223> OTHER INFORMATION: MF1122 FW2

<400> SEQUENCE: 238

```
Trp Val Arg Gln Ala Pro Gly Lys Gly Leu Glu Trp Val Ala
1               5                   10
```

<210> SEQ ID NO 239
<211> LENGTH: 32
<212> TYPE: PRT
<213> ORGANISM: Artificial Sequence
<220> FEATURE:
<223> OTHER INFORMATION: MF1122 FW3

<400> SEQUENCE: 239

```
Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30
```

<210> SEQ ID NO 240
<211> LENGTH: 11
<212> TYPE: PRT
<213> ORGANISM: Artificial Sequence
<220> FEATURE:
<223> OTHER INFORMATION: MF1122 FW4

<400> SEQUENCE: 240

```
Trp Gly Gln Gly Thr Leu Val Thr Val Ser Ser
1               5                   10
```

<210> SEQ ID NO 241
<211> LENGTH: 5
<212> TYPE: PRT

```
<213> ORGANISM: Artificial Sequence
<220> FEATURE:
<223> OTHER INFORMATION: MF1122 CDR1

<400> SEQUENCE: 241

Ser Tyr Gly Met His
1               5

<210> SEQ ID NO 242
<211> LENGTH: 17
<212> TYPE: PRT
<213> ORGANISM: Artificial Sequence
<220> FEATURE:
<223> OTHER INFORMATION: MF1122 CDR2

<400> SEQUENCE: 242

Val Ile Ser Tyr Asp Gly Ser Asn Lys Tyr Tyr Ala Asp Ser Val Lys
1               5                   10                  15

Gly

<210> SEQ ID NO 243
<211> LENGTH: 10
<212> TYPE: PRT
<213> ORGANISM: Artificial Sequence
<220> FEATURE:
<223> OTHER INFORMATION: MF1122 CDR3

<400> SEQUENCE: 243

Ala Leu Phe Thr Thr Ile Ala Met Asp Tyr
1               5                   10

<210> SEQ ID NO 244
<211> LENGTH: 119
<212> TYPE: PRT
<213> ORGANISM: Artificial Sequence
<220> FEATURE:
<223> OTHER INFORMATION: MF1122 VH

<400> SEQUENCE: 244

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Leu Phe Thr Thr Ile Ala Met Asp Tyr Trp Gly Gln Gly
            100                 105                 110

Thr Leu Val Thr Val Ser Ser
        115

<210> SEQ ID NO 245
<211> LENGTH: 354
<212> TYPE: DNA
<213> ORGANISM: Artificial Sequence
<220> FEATURE:
<223> OTHER INFORMATION: MF1025
```

-continued

```
<400> SEQUENCE: 245
gaggtgcagc tggtggagtc tgggggaggc ttggtacagc ctgggggtc cctgagactc        60 tcctgtgcag cctctggatt cacctttagc agctatgcca tgagctgggt ccgccaggct       120
ccagggaagg gctggagtg gtctcagct attagtggta gtggtggtag cacatactac         180
gcagactccg tgaagggccg gttcaccatc tccagagaca attccaagaa cacgctgtat       240
ctgcaaatga acagcctgag agccgaggac acggccgtgt attactgtgc aagggccgat       300
tggtgggcga cttttgacta ctgggggccaa ggtaccctgg tcaccgtctc cagt            354

<210> SEQ ID NO 246
<211> LENGTH: 30
<212> TYPE: PRT
<213> ORGANISM: Artificial Sequence
<220> FEATURE:
<223> OTHER INFORMATION: MF1025 FW1

<400> SEQUENCE: 246

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 247
<211> LENGTH: 14
<212> TYPE: PRT
<213> ORGANISM: Artificial Sequence
<220> FEATURE:
<223> OTHER INFORMATION: MF1025 FW2

<400> SEQUENCE: 247

Trp Val Arg Gln Ala Pro Gly Lys Gly Leu Glu Trp Val Ser
1               5                   10

<210> SEQ ID NO 248
<211> LENGTH: 32
<212> TYPE: PRT
<213> ORGANISM: Artificial Sequence
<220> FEATURE:
<223> OTHER INFORMATION: MF1025 FW3

<400> SEQUENCE: 248

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 249
<211> LENGTH: 11
<212> TYPE: PRT
<213> ORGANISM: Artificial Sequence
<220> FEATURE:
<223> OTHER INFORMATION: MF1025 FW4

<400> SEQUENCE: 249

Trp Gly Gln Gly Thr Leu Val Thr Val Ser Ser
1               5                   10

<210> SEQ ID NO 250
<211> LENGTH: 5
<212> TYPE: PRT
<213> ORGANISM: Artificial Sequence
<220> FEATURE:
<223> OTHER INFORMATION: MF1025 CDR1
```

-continued

<400> SEQUENCE: 250

Ser Tyr Ala Met Ser
1               5

<210> SEQ ID NO 251
<211> LENGTH: 17
<212> TYPE: PRT
<213> ORGANISM: Artificial Sequence
<220> FEATURE:
<223> OTHER INFORMATION: MF1025 CDR2

<400> SEQUENCE: 251

Ala Ile Ser Gly Ser Gly Gly Ser Thr Tyr Tyr Ala Asp Ser Val Lys
1               5                   10                  15

Gly

<210> SEQ ID NO 252
<211> LENGTH: 9
<212> TYPE: PRT
<213> ORGANISM: Artificial Sequence
<220> FEATURE:
<223> OTHER INFORMATION: MF1025 CDR3

<400> SEQUENCE: 252

Ala Asp Trp Trp Ala Thr Phe Asp Tyr
1               5

<210> SEQ ID NO 253
<211> LENGTH: 118
<212> TYPE: PRT
<213> ORGANISM: Artificial Sequence
<220> FEATURE:
<223> OTHER INFORMATION: MF1025 VH

<400> SEQUENCE: 253

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Asp Trp Trp Ala Thr Phe Asp Tyr Trp Gly Gln Gly Thr
            100                 105                 110

Leu Val Thr Val Ser Ser
        115

<210> SEQ ID NO 254
<211> LENGTH: 6
<212> TYPE: PRT
<213> ORGANISM: Artificial Sequence
<220> FEATURE:
<223> OTHER INFORMATION: Light chain CDR1

<400> SEQUENCE: 254

Gln Ser Ile Ser Ser Tyr 1               5

<210> SEQ ID NO 255
<211> LENGTH: 3
<212> TYPE: PRT
<213> ORGANISM: Artificial Sequence
<220> FEATURE:
<223> OTHER INFORMATION: Light chain CDR2

<400> SEQUENCE: 255

Ala Ala Ser
1

<210> SEQ ID NO 256
<211> LENGTH: 7
<212> TYPE: PRT
<213> ORGANISM: Artificial Sequence
<220> FEATURE:
<223> OTHER INFORMATION: Light chain CDR3

<400> SEQUENCE: 256

Gln Gln Ser Tyr Ser Thr Pro
1               5

<210> SEQ ID NO 257
<211> LENGTH: 290
<212> TYPE: PRT
<213> ORGANISM: Homo sapiens

<400> SEQUENCE: 257

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His

```
                225                 230                 235                 240
Leu Val Ile Leu Gly Ala Ile Leu Leu Cys Leu Gly Val Ala Leu Thr
                    245                 250                 255

Phe Ile Phe Arg Leu Arg Lys Gly Arg Met Met Asp Val Lys Lys Cys
                    260                 265                 270

Gly Ile Gln Asp Thr Asn Ser Lys Lys Gln Ser Asp Thr His Leu Glu
                    275                 280                 285

Glu Thr
    290

<210> SEQ ID NO 258
<211> LENGTH: 1210
<212> TYPE: PRT
<213> ORGANISM: Homo sapiens

<400> SEQUENCE: 258

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
                100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
                180                 185                 190

Ser Cys Pro Asn Gly Ser Cys Trp Gly Ala Gly Glu Asn Cys Gln
            195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
                260                 265                 270

Thr Thr Tyr Gln Met Asp Val Asn Pro Glu Gly Lys Tyr Ser Phe Gly
            275                 280                 285

Ala Thr Cys Val Lys Lys Cys Pro Arg Asn Tyr Val Val Thr Asp His
            290                 295                 300
```

```
Gly Ser Cys Val Arg Ala Cys Gly Ala Asp Ser Tyr Glu Met Glu Glu
305                 310                 315                 320

Asp Gly Val Arg Lys Cys Lys Cys Glu Gly Pro Cys Arg Lys Val
            325                 330                 335

Cys Asn Gly Ile Gly Ile Gly Glu Phe Lys Asp Ser Leu Ser Ile Asn
                340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
                420                 425                 430

His Gly Gln Phe Ser Leu Ala Val Val Ser Leu Asn Ile Thr Ser Leu
            435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
            515                 520                 525

Val Ser Arg Gly Arg Glu Cys Val Asp Lys Cys Asn Leu Leu Glu Gly
            530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
                660                 665                 670

Ile Val Arg Lys Arg Thr Leu Arg Arg Leu Leu Gln Glu Arg Glu Leu
            675                 680                 685

Val Glu Pro Leu Thr Pro Ser Gly Glu Ala Pro Asn Gln Ala Leu Leu
            690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
```

```
                725                 730                 735
Lys Val Lys Ile Pro Val Ala Ile Lys Glu Leu Arg Glu Ala Thr Ser
                740                 745                 750

Pro Lys Ala Asn Lys Glu Ile Leu Asp Glu Ala Tyr Val Met Ala Ser
                755                 760                 765

Val Asp Asn Pro His Val Cys Arg Leu Leu Gly Ile Cys Leu Thr Ser
                770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
                820                 825                 830

Leu Val His Arg Asp Leu Ala Ala Arg Asn Val Leu Val Lys Thr Pro
                835                 840                 845

Gln His Val Lys Ile Thr Asp Phe Gly Leu Ala Lys Leu Leu Gly Ala
                850                 855                 860

Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
                900                 905                 910

Lys Pro Tyr Asp Gly Ile Pro Ala Ser Glu Ile Ser Ser Ile Leu Glu
                915                 920                 925

Lys Gly Glu Arg Leu Pro Gln Pro Ile Cys Thr Ile Asp Val Tyr
930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
                980                 985                 990

Thr Asp Ser Asn Phe Tyr Arg Ala Leu Met Asp Glu Glu Asp Met Asp
                995                1000                1005

Asp Val Val Asp Ala Asp Glu Tyr Leu Ile Pro Gln Gln Gly Phe
                1010                1015                1020

Phe Ser Ser Pro Ser Thr Ser Arg Thr Pro Leu Leu Ser Ser Leu
                1025                1030                1035

Ser Ala Thr Ser Asn Asn Ser Thr Val Ala Cys Ile Asp Arg Asn
                1040                1045                1050

Gly Leu Gln Ser Cys Pro Ile Lys Glu Asp Ser Phe Leu Gln Arg
                1055                1060                1065

Tyr Ser Ser Asp Pro Thr Gly Ala Leu Thr Glu Asp Ser Ile Asp
                1070                1075                1080

Asp Thr Phe Leu Pro Val Pro Glu Tyr Ile Asn Gln Ser Val Pro
                1085                1090                1095

Lys Arg Pro Ala Gly Ser Val Gln Asn Pro Val Tyr His Asn Gln
                1100                1105                1110

Pro Leu Asn Pro Ala Pro Ser Arg Asp Pro His Tyr Gln Asp Pro
                1115                1120                1125

His Ser Thr Ala Val Gly Asn Pro Glu Tyr Leu Asn Thr Val Gln
                1130                1135                1140
```

Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
    1190                1195                1200

Ser Ser Glu Phe Ile Gly Ala
    1205                1210

<210> SEQ ID NO 259
<211> LENGTH: 124
<212> TYPE: PRT
<213> ORGANISM: Artificial Sequence
<220> FEATURE:
<223> OTHER INFORMATION: Translation of IgG1H

<400> SEQUENCE: 259

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Ser Pro Pro Ser
            100                 105                 110

Pro Ala Pro Glu Leu Leu Gly Gly Glu Val Gln Leu
        115                 120

<210> SEQ ID NO 260
<211> LENGTH: 117
<212> TYPE: PRT
<213> ORGANISM: Artificial Sequence
<220> FEATURE:
<223> OTHER INFORMATION: Translation of IgG1MH

<400> SEQUENCE: 260

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Ser Pro Pro Ser

```
                    100                 105                 110

Pro Glu Val Gln Leu
            115

<210> SEQ ID NO 261
<211> LENGTH: 112
<212> TYPE: PRT
<213> ORGANISM: Artificial Sequence
<220> FEATURE:
<223> OTHER INFORMATION: Translation of IgG1 UH

<400> SEQUENCE: 261

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Glu Val Gln Leu
            100                 105                 110

<210> SEQ ID NO 262
<211> LENGTH: 118
<212> TYPE: PRT
<213> ORGANISM: Artificial Sequence
<220> FEATURE:
<223> OTHER INFORMATION: Translation of IgG1G4S

<400> SEQUENCE: 262

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Gly Gly Gly Ser Gly Gly Gly
            100                 105                 110

Gly Ser Glu Val Gln Leu
            115

<210> SEQ ID NO 263
<211> LENGTH: 119
<212> TYPE: PRT
<213> ORGANISM: Artificial Sequence
<220> FEATURE:
<223> OTHER INFORMATION: Translation of IgG1UL

<400> SEQUENCE: 263
```

-continued

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Ala Pro Glu Leu
            100                 105                 110

Leu Gly Gly Glu Val Gln Leu
        115
```

<210> SEQ ID NO 264
<211> LENGTH: 129
<212> TYPE: PRT
<213> ORGANISM: Artificial Sequence
<220> FEATURE:
<223> OTHER INFORMATION: Translation of IgG1R

<400> SEQUENCE: 264

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Glu Ala Ala Ala
            100                 105                 110

Lys Glu Ala Ala Ala Lys Ala Pro Glu Leu Leu Gly Gly Glu Val Gln
        115                 120                 125

Leu
```

<210> SEQ ID NO 265
<211> LENGTH: 120
<212> TYPE: PRT
<213> ORGANISM: Artificial Sequence
<220> FEATURE:
<223> OTHER INFORMATION: Translation of IgG2AH

<400> SEQUENCE: 265

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

Gly Val His Thr Phe Pro Ala Val Leu Gln Ser Ser Gly Leu Tyr Ser
            50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                    85                  90                  95

Thr Val Glu Arg Lys Ser Ser Val Ser Pro Pro Ser Pro Ala Pro
                100                 105                 110

Pro Val Ala Gly Glu Val Gln Leu
                115                 120

<210> SEQ ID NO 266
<211> LENGTH: 114
<212> TYPE: PRT
<213> ORGANISM: Artificial Sequence
<220> FEATURE:
<223> OTHER INFORMATION: Translation of Ig G2AMH

<400> SEQUENCE: 266

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                    85                  90                  95

Thr Val Glu Arg Lys Ser Ser Val Glu Ser Pro Pro Ser Pro Glu Val
                100                 105                 110

Gln Leu

<210> SEQ ID NO 267
<211> LENGTH: 115
<212> TYPE: PRT
<213> ORGANISM: Artificial Sequence
<220> FEATURE:
<223> OTHER INFORMATION: Translation of IgG2AUL

<400> SEQUENCE: 267

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                    85                  90                  95

Thr Val Glu Arg Lys Ser Ser Val Glu Ala Pro Pro Val Ala Gly Glu
                100                 105                 110

Val Gln Leu
        115

<210> SEQ ID NO 268
<211> LENGTH: 112
<212> TYPE: PRT
<213> ORGANISM: Artificial Sequence
<220> FEATURE:
<223> OTHER INFORMATION: Translation of IgG2AG4SS

<400> SEQUENCE: 268

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Gly Gly Gly Gly Ser Gly Gly Gly Ser Glu Val Gln Leu
            100                 105                 110

<210> SEQ ID NO 269
<211> LENGTH: 118
<212> TYPE: PRT
<213> ORGANISM: Artificial Sequence
<220> FEATURE:
<223> OTHER INFORMATION: Translation of IgG2AG4SL

<400> SEQUENCE: 269

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Gly Gly Gly Gly Ser Gly Gly Gly Ser Ala Pro Pro Val
            100                 105                 110

Ala Gly Glu Val Gln Leu
        115

<210> SEQ ID NO 270
<211> LENGTH: 125
<212> TYPE: PRT
<213> ORGANISM: Artificial Sequence
<220> FEATURE:
<223> OTHER INFORMATION: Translation of IgG2AR

<400> SEQUENCE: 270

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Ser Val Glu Glu Ala Ala Ala Lys Glu Ala
            100                 105                 110

Ala Ala Lys Ala Pro Pro Val Ala Gly Glu Val Gln Leu
            115                 120                 125

<210> SEQ ID NO 271
<211> LENGTH: 120
<212> TYPE: PRT
<213> ORGANISM: Artificial Sequence
<220> FEATURE:
<223> OTHER INFORMATION: Translation of IgG2BH

<400> SEQUENCE: 271

Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Ser Val Glu Ser Pro Pro Ser Pro Ala Pro
            100                 105                 110

Pro Val Ala Gly Glu Val Gln Leu
            115                 120

<210> SEQ ID NO 272
<211> LENGTH: 114
<212> TYPE: PRT
<213> ORGANISM: Artificial Sequence
<220> FEATURE:
<223> OTHER INFORMATION: Translation of IgG2BMH

<400> SEQUENCE: 272

Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60
```

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Ser Val Glu Ser Pro Pro Ser Pro Glu Val
            100                 105                 110

Gln Leu

<210> SEQ ID NO 273
<211> LENGTH: 115
<212> TYPE: PRT
<213> ORGANISM: Artificial Sequence
<220> FEATURE:
<223> OTHER INFORMATION: Translation of IgG2BUL

<400> SEQUENCE: 273

Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Ser Val Glu Ala Pro Pro Val Ala Gly Glu
            100                 105                 110

Val Gln Leu
        115

<210> SEQ ID NO 274
<211> LENGTH: 125
<212> TYPE: PRT
<213> ORGANISM: Artificial Sequence
<220> FEATURE:
<223> OTHER INFORMATION: Translation of IgG2BR

<400> SEQUENCE: 274

Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Ser Val Glu Glu Ala Ala Lys Glu Ala
            100                 105                 110

Ala Ala Lys Ala Pro Pro Val Ala Gly Glu Val Gln Leu
        115                 120                 125

<210> SEQ ID NO 275
<211> LENGTH: 121
<212> TYPE: PRT
<213> ORGANISM: Artificial Sequence
<220> FEATURE:
<223> OTHER INFORMATION: Translation of IgG3ULH

<400> SEQUENCE: 275

```
Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Ala Pro
            100                 105                 110

Glu Phe Leu Gly Gly Glu Val Gln Leu
        115                 120
```

<210> SEQ ID NO 276
<211> LENGTH: 114
<212> TYPE: PRT
<213> ORGANISM: Artificial Sequence
<220> FEATURE:
<223> OTHER INFORMATION: Translation of IgG3UH

<400> SEQUENCE: 276

```
Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Glu Val
            100                 105                 110

Gln Leu
```

<210> SEQ ID NO 277
<211> LENGTH: 131
<212> TYPE: PRT
<213> ORGANISM: Artificial Sequence
<220> FEATURE:
<223> OTHER INFORMATION: Translation of IgG3R

<400> SEQUENCE: 277

```
Ala Ser Thr Lys Gly Pro Ser Val Phe Pro Leu Ala Pro Cys Ser Arg
```

```
                1               5                   10                  15
            Ser Thr Ser Gly Gly Thr Ala Ala Leu Gly Cys Leu Val Lys Asp Tyr
                        20                  25                  30

Phe Pro Glu Pro Val Thr Val Ser Trp Asn Ser Gly Ala Leu Thr Ser
                        35                  40                  45

Gly Val His Thr Phe Pro Ala Val Leu Gln Ser Ser Gly Leu Tyr Ser
                        50                  55                  60

Leu Ser Ser Val Val Thr Val Pro Ser Ser Ser Leu Gly Thr Gln Thr
             65                 70                  75                  80

Tyr Thr Cys Asn Val Asn His Lys Pro Ser Asn Thr Lys Val Asp Lys
                            85                  90                  95

Arg Val Glu Leu Lys Thr Pro Leu Gly Asp Thr Thr His Thr Glu Ala
                        100                 105                 110

Ala Ala Lys Glu Ala Ala Ala Lys Ala Pro Glu Phe Leu Gly Gly Glu
                        115                 120                 125

Val Gln Leu
                        130
```

<210> SEQ ID NO 278
<211> LENGTH: 121
<212> TYPE: PRT
<213> ORGANISM: Artificial Sequence
<220> FEATURE:
<223> OTHER INFORMATION: Translation of IgG4H

<400> SEQUENCE: 278

```
            Ala Ser Thr Lys Gly Pro Ser Val Phe Pro Leu Ala Pro Cys Ser Arg
             1               5                   10                  15

Ser Thr Ser Glu Ser Thr Ala Ala Leu Gly Cys Leu Val Lys Asp Tyr
                        20                  25                  30

Phe Pro Glu Pro Val Thr Val Ser Trp Asn Ser Gly Ala Leu Thr Ser
                        35                  40                  45

Gly Val His Thr Phe Pro Ala Val Leu Gln Ser Ser Gly Leu Tyr Ser
                        50                  55                  60

Leu Ser Ser Val Val Thr Val Pro Ser Ser Ser Leu Gly Thr Lys Thr
             65                 70                  75                  80

Tyr Thr Cys Asn Val Asp His Lys Pro Ser Asn Thr Lys Val Asp Lys
                            85                  90                  95

Arg Val Glu Ser Lys Tyr Gly Pro Pro Ser Pro Ser Pro Ala Pro
                        100                 105                 110

Glu Phe Leu Gly Gly Glu Val Gln Leu
                        115                 120
```

<210> SEQ ID NO 279
<211> LENGTH: 109
<212> TYPE: PRT
<213> ORGANISM: Artificial Sequence
<220> FEATURE:
<223> OTHER INFORMATION: Translation of IgG4UH

<400> SEQUENCE: 279

```
            Ala Ser Thr Lys Gly Pro Ser Val Phe Pro Leu Ala Pro Cys Ser Arg
             1               5                   10                  15

Ser Thr Ser Glu Ser Thr Ala Ala Leu Gly Cys Leu Val Lys Asp Tyr
                        20                  25                  30

Phe Pro Glu Pro Val Thr Val Ser Trp Asn Ser Gly Ala Leu Thr Ser
                        35                  40                  45
```

Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Glu Val Gln Leu
             100                 105

<210> SEQ ID NO 280
<211> LENGTH: 114
<212> TYPE: PRT
<213> ORGANISM: Artificial Sequence
<220> FEATURE:
<223> OTHER INFORMATION: Translation of IgG4MH

<400> SEQUENCE: 280

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Ser Pro Ser Pro Glu Val
             100                 105                 110

Gln Leu

<210> SEQ ID NO 281
<211> LENGTH: 126
<212> TYPE: PRT
<213> ORGANISM: Artificial Sequence
<220> FEATURE:
<223> OTHER INFORMATION: Translation of IgG4R

<400> SEQUENCE: 281

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Glu Ala Ala Lys Glu Ala
             100                 105                 110

Ala Ala Lys Ala Pro Glu Phe Leu Gly Gly Glu Val Gln Leu
         115                 120                 125

<210> SEQ ID NO 282
<211> LENGTH: 116
<212> TYPE: PRT
<213> ORGANISM: Artificial Sequence
<220> FEATURE:
<223> OTHER INFORMATION: Translation of IgG4UL

<400> SEQUENCE: 282

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Ala Pro Glu Phe Leu Gly Gly
            100                 105                 110

Glu Val Gln Leu
        115

<210> SEQ ID NO 283
<211> LENGTH: 107
<212> TYPE: PRT
<213> ORGANISM: Artificial Sequence
<220> FEATURE:
<223> OTHER INFORMATION: Consensus

<400> SEQUENCE: 283

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
                85                  90                  95

Arg Val Glu Lys Ser Thr Ser Glu Val Gln Leu
            100                 105

<210> SEQ ID NO 284
<211> LENGTH: 1053
<212> TYPE: DNA
<213> ORGANISM: Artificial Sequence
<220> FEATURE:
<223> OTHER INFORMATION: DNA sequence of construct MF1337xIgG4 UHxMF1122
<220> FEATURE:
<221> NAME/KEY: CDS
<222> LOCATION: (1)..(1053)

<400> SEQUENCE: 284 gag gtg cag ctg gtg gag act ggg gct gag gtg aag aag ccg ggg gcc        48

```
                                                                              -continued Glu Val Gln Leu Val Glu Thr Gly Ala Glu Val Lys Lys Pro Gly Ala
 1               5                  10                  15 tca gtg aag gtc tcc tgc aag gct tct gac tac atc ttc acc aaa tat      96
Ser Val Lys Val Ser Cys Lys Ala Ser Asp Tyr Ile Phe Thr Lys Tyr
             20                  25                  30 gac atc aac tgg gtg cgc cag gcc cct gga caa ggg ctt gaa tgg atg     144
Asp Ile Asn Trp Val Arg Gln Ala Pro Gly Gln Gly Leu Glu Trp Met
         35                  40                  45 gga tgg atg agc gct aac act gga aac acg ggc tat gca cag aag ttc     192
Gly Trp Met Ser Ala Asn Thr Gly Asn Thr Gly Tyr Ala Gln Lys Phe
     50                  55                  60 cag ggc aga gtc acc atg acc agg gac acg tcc ata aac aca gcc tac     240
Gln Gly Arg Val Thr Met Thr Arg Asp Thr Ser Ile Asn Thr Ala Tyr
 65                  70                  75                  80 atg gag ctg agc agc ctg aca tct ggt gac acg gcc gtt tat ttc tgt     288
Met Glu Leu Ser Ser Leu Thr Ser Gly Asp Thr Ala Val Tyr Phe Cys
                 85                  90                  95 gcg agg agt agt ctt ttc aag aca gag acg gcg ccc tac tat cac ttc     336
Ala Arg Ser Ser Leu Phe Lys Thr Glu Thr Ala Pro Tyr Tyr His Phe
            100                 105                 110 gct ctg gac gtc tgg ggc caa ggg acc acg gtc acc gtc tcc agt gct     384
Ala Leu Asp Val Trp Gly Gln Gly Thr Thr Val Thr Val Ser Ser Ala
        115                 120                 125 agc acc aag ggc ccc agc gtg ttc ccc ctg gcc ccc tgc agc cgg agc     432
Ser Thr Lys Gly Pro Ser Val Phe Pro Leu Ala Pro Cys Ser Arg Ser
    130                 135                 140 acc agc gag agc acc gcc gcc ctg ggc tgc ctg gtg aag gac tac ttc     480
Thr Ser Glu Ser Thr Ala Ala Leu Gly Cys Leu Val Lys Asp Tyr Phe
145                 150                 155                 160 ccc gag ccc gtg acc gtg agc tgg aac agc ggc gcc ctg acc agc ggc     528
Pro Glu Pro Val Thr Val Ser Trp Asn Ser Gly Ala Leu Thr Ser Gly
                165                 170                 175 gtg cac acc ttc ccc gcc gtg ctg cag agc agc ggc ctg tac agc ctg     576
Val His Thr Phe Pro Ala Val Leu Gln Ser Ser Gly Leu Tyr Ser Leu
            180                 185                 190 agc agc gtg gtg acg gtg ccc agc agc agc ctg ggc acc aag acc tac     624
Ser Ser Val Val Thr Val Pro Ser Ser Ser Leu Gly Thr Lys Thr Tyr
        195                 200                 205 acc tgc aac gtg gac cac aag ccc agc aac acc aag gtg gac aag cgg     672
Thr Cys Asn Val Asp His Lys Pro Ser Asn Thr Lys Val Asp Lys Arg
    210                 215                 220 gtg gag agc aag tac ggc ccc ccc gag gtg cag ctg gtg gag tct ggg     720
Val Glu Ser Lys Tyr Gly Pro Pro Glu Val Gln Leu Val Glu Ser Gly
225                 230                 235                 240 gga ggc gtg gtc cag cct ggg agg tcc ctg aga ctc tcc tgt gca gcc     768
Gly Gly Val Val Gln Pro Gly Arg Ser Leu Arg Leu Ser Cys Ala Ala
                245                 250                 255 tct gga ttc acc ttc agt agc tat ggc atg cac tgg gtc cgc cag gct     816
Ser Gly Phe Thr Phe Ser Ser Tyr Gly Met His Trp Val Arg Gln Ala
            260                 265                 270 cca ggc aag ggg ctg gag tgg gtg gca gtt ata tca tat gat gga agt     864
Pro Gly Lys Gly Leu Glu Trp Val Ala Val Ile Ser Tyr Asp Gly Ser
        275                 280                 285 aat aaa tac tat gca gac tcc gtg aag ggc cga ttc acc atc tcc aga     912
Asn Lys Tyr Tyr Ala Asp Ser Val Lys Gly Arg Phe Thr Ile Ser Arg
    290                 295                 300 gac aat tcc aag aac acg ctg tat ctg caa atg aac agc ctg aga gct     960
Asp Asn Ser Lys Asn Thr Leu Tyr Leu Gln Met Asn Ser Leu Arg Ala
305                 310                 315                 320
```

```
gag gac acg gcc gtg tat tac tgt gca aga gcc ctc ttc acg acc atc    1008
Glu Asp Thr Ala Val Tyr Tyr Cys Ala Arg Ala Leu Phe Thr Thr Ile
            325                 330                 335 gcc atg gac tat tgg ggc caa ggt acc ctt gtc acc gtc tcg agt        1053
Ala Met Asp Tyr Trp Gly Gln Gly Thr Leu Val Thr Val Ser Ser
                340                 345                 350

<210> SEQ ID NO 285
<211> LENGTH: 351
<212> TYPE: PRT
<213> ORGANISM: Artificial Sequence
<220> FEATURE:
<223> OTHER INFORMATION: Synthetic Construct

<400> SEQUENCE: 285

Glu Val Gln Leu Val Glu Thr Gly Ala Glu Val Lys Lys Pro Gly Ala
1               5                   10                  15

Ser Val Lys Val Ser Cys Lys Ala Ser Asp Tyr Ile Phe Thr Lys Tyr
                20                  25                  30

Asp Ile Asn Trp Val Arg Gln Ala Pro Gly Gln Gly Leu Glu Trp Met
            35                  40                  45

Gly Trp Met Ser Ala Asn Thr Gly Asn Thr Gly Tyr Ala Gln Lys Phe
        50                  55                  60

Gln Gly Arg Val Thr Met Thr Arg Asp Thr Ser Ile Asn Thr Ala Tyr
65                  70                  75                  80

Met Glu Leu Ser Ser Leu Thr Ser Gly Asp Thr Ala Val Tyr Phe Cys
                85                  90                  95

Ala Arg Ser Ser Leu Phe Lys Thr Glu Thr Ala Pro Tyr Tyr His Phe
            100                 105                 110

Ala Leu Asp Val Trp Gly Gln Gly Thr Thr Val Thr Val Ser Ser Ala
        115                 120                 125

Ser Thr Lys Gly Pro Ser Val Phe Pro Leu Ala Pro Cys Ser Arg Ser
130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Lys Thr Tyr
        195                 200                 205

Thr Cys Asn Val Asp His Lys Pro Ser Asn Thr Lys Val Asp Lys Arg
210                 215                 220

Val Glu Ser Lys Tyr Gly Pro Pro Glu Val Gln Leu Val Glu Ser Gly
225                 230                 235                 240

Gly Gly Val Val Gln Pro Gly Arg Ser Leu Arg Leu Ser Cys Ala Ala
                245                 250                 255

Ser Gly Phe Thr Phe Ser Ser Tyr Gly Met His Trp Val Arg Gln Ala
            260                 265                 270

Pro Gly Lys Gly Leu Glu Trp Val Ala Val Ile Ser Tyr Asp Gly Ser
        275                 280                 285

Asn Lys Tyr Tyr Ala Asp Ser Val Lys Gly Arg Phe Thr Ile Ser Arg
            290                 295                 300

Asp Asn Ser Lys Asn Thr Leu Tyr Leu Gln Met Asn Ser Leu Arg Ala
305                 310                 315                 320

Glu Asp Thr Ala Val Tyr Tyr Cys Ala Arg Ala Leu Phe Thr Thr Ile
```

```
                    325                 330                 335
Ala Met Asp Tyr Trp Gly Gln Gly Thr Leu Val Thr Val Ser Ser
            340                 345                 350

<210> SEQ ID NO 286
<211> LENGTH: 119
<212> TYPE: PRT
<213> ORGANISM: Artificial Sequence
<220> FEATURE:
<223> OTHER INFORMATION: Translation of MF1122

<400> SEQUENCE: 286

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Leu Phe Thr Thr Ile Ala Met Asp Tyr Trp Gly Gln Gly
            100                 105                 110

Thr Leu Val Thr Val Ser Ser
        115

<210> SEQ ID NO 287
<211> LENGTH: 118
<212> TYPE: PRT
<213> ORGANISM: Artificial Sequence
<220> FEATURE:
<223> OTHER INFORMATION: Translation of MF1025

<400> SEQUENCE: 287

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Asp Trp Trp Ala Thr Phe Asp Tyr Trp Gly Gln Gly Thr
            100                 105                 110

Leu Val Thr Val Ser Ser
        115

<210> SEQ ID NO 288
<211> LENGTH: 127
<212> TYPE: PRT
<213> ORGANISM: Artificial Sequence
<220> FEATURE:
```

<223> OTHER INFORMATION: Translation of MF1337

<400> SEQUENCE: 288

| | | | | | | | | | | | | | | |
|---|---|---|---|---|---|---|---|---|---|---|---|---|---|---|
| Glu | Val | Gln | Leu | Val | Glu | Thr | Gly | Ala | Glu | Val | Lys | Lys | Pro | Gly | Ala |
| 1 | | | | 5 | | | | | 10 | | | | | 15 | |

Ser Val Lys Val Ser Cys Lys Ala Ser Asp Tyr Ile Phe Thr Lys Tyr
           20                    25                30

Asp Ile Asn Trp Val Arg Gln Ala Pro Gly Gln Gly Leu Glu Trp Met
           35                    40                45

Gly Trp Met Ser Ala Asn Thr Gly Asn Thr Gly Tyr Ala Gln Lys Phe
 50                       55                    60

Gln Gly Arg Val Thr Met Thr Arg Asp Thr Ser Ile Asn Thr Ala Tyr
65                    70                  75                80

Met Glu Leu Ser Ser Leu Thr Ser Gly Asp Thr Ala Val Tyr Phe Cys
           85                    90                95

Ala Arg Ser Ser Leu Phe Lys Thr Glu Thr Ala Pro Tyr Tyr His Phe
          100                 105             110

Ala Leu Asp Val Trp Gly Gln Gly Thr Thr Val Thr Val Ser Ser
          115                 120             125

<210> SEQ ID NO 289
<211> LENGTH: 267
<212> TYPE: PRT
<213> ORGANISM: Homo sapiens

<400> SEQUENCE: 289

Met Trp Gly Val Phe Leu Leu Tyr Val Ser Met Lys Met Gly Gly Thr
1                 5                   10                15

Thr Gly Gln Asn Ile Asp Gln Pro Thr Glu Met Thr Ala Thr Glu Gly
          20                    25                30

Ala Ile Val Gln Ile Asn Cys Thr Tyr Gln Thr Ser Gly Phe Asn Gly
             35                   40                45

Leu Phe Trp Tyr Gln Gln His Ala Gly Glu Ala Pro Thr Phe Leu Ser
 50                      55                   60

Tyr Asn Val Leu Asp Gly Leu Glu Glu Lys Gly Arg Phe Ser Ser Phe
65                    70                  75                80

Leu Ser Arg Ser Lys Gly Tyr Ser Tyr Leu Leu Leu Lys Glu Leu Gln
             85                    90              95

Met Lys Asp Ser Ala Ser Tyr Leu Cys Ala Val Met Asp Ser Asn Tyr
          100                 105             110

Gln Leu Ile Trp Gly Ala Gly Thr Lys Leu Ile Ile Lys Pro Asp Ile
          115                 120             125

Gln Asn Pro Asp Pro Ala Val Tyr Gln Leu Arg Asp Ser Lys Ser Ser
 130                    135                  140

Asp Lys Ser Val Cys Leu Phe Thr Asp Phe Asp Ser Gln Thr Asn Val
145                   150                 155              160

Ser Gln Ser Lys Asp Ser Asp Val Tyr Ile Thr Asp Lys Thr Val Leu
          165                 170             175

Asp Met Arg Ser Met Asp Phe Lys Ser Asn Ser Ala Val Ala Trp Ser
          180                 185             190

Asn Lys Ser Asp Phe Ala Cys Ala Asn Ala Phe Asn Asn Ser Ile Ile
          195                 200             205

Pro Glu Asp Thr Phe Phe Pro Ser Pro Glu Ser Ser Cys Asp Val Lys
 210                    215                  220

Leu Val Glu Lys Ser Phe Glu Thr Asp Thr Asn Leu Asn Phe Gln Asn

```
                225                 230                 235                 240
Leu Ser Val Ile Gly Phe Arg Ile Leu Leu Lys Val Ala Gly Phe
                    245                 250                 255

Asn Leu Leu Met Thr Leu Arg Leu Trp Ser Ser
                    260                 265

<210> SEQ ID NO 290
<211> LENGTH: 310
<212> TYPE: PRT
<213> ORGANISM: Homo sapiens

<400> SEQUENCE: 290

Met Arg Ile Arg Leu Leu Cys Cys Val Ala Phe Ser Leu Leu Trp Ala
1               5                   10                  15

Gly Pro Val Ile Ala Gly Ile Thr Gln Ala Pro Thr Ser Gln Ile Leu
            20                  25                  30

Ala Ala Gly Arg Arg Met Thr Leu Arg Cys Thr Gln Asp Met Arg His
        35                  40                  45

Asn Ala Met Tyr Trp Tyr Arg Gln Asp Leu Gly Leu Gly Leu Arg Leu
    50                  55                  60

Ile His Tyr Ser Asn Thr Ala Gly Thr Thr Gly Lys Gly Glu Val Pro
65                  70                  75                  80

Asp Gly Tyr Ser Val Ser Arg Ala Asn Thr Asp Asp Phe Pro Leu Thr
                85                  90                  95

Leu Ala Ser Ala Val Pro Ser Gln Thr Ser Val Tyr Phe Cys Ala Ser
            100                 105                 110

Ser Glu Ala Gly Gly Asn Thr Gly Glu Leu Phe Phe Gly Glu Gly Ser
        115                 120                 125

Arg Leu Thr Val Leu Glu Asp Leu Asn Lys Val Phe Pro Pro Glu Val
130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Val Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Phe
305                 310

<210> SEQ ID NO 291
<211> LENGTH: 294
```

<212> TYPE: DNA
<213> ORGANISM: Artificial Sequence
<220> FEATURE:
<223> OTHER INFORMATION: VH-CH1
<220> FEATURE:
<221> NAME/KEY: CDS
<222> LOCATION: (1)..(294)

<400> SEQUENCE: 291

| | | | | | | | | | | | | | | | | |
|---|---|---|---|---|---|---|---|---|---|---|---|---|---|---|---|---|
| gct | agc | acc | aag | ggc | cca | tcg | gtc | ttc | ccc | ctg | gca | ccc | tcc | tcc | aag | 48 |
| Ala | Ser | Thr | Lys | Gly | Pro | Ser | Val | Phe | Pro | Leu | Ala | Pro | Ser | Ser | Lys | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| agc | acc | tct | ggg | ggc | aca | gcg | gcc | ctg | ggc | tgc | ctg | gtc | aag | gac | tac | 96 |
| Ser | Thr | Ser | Gly | Gly | Thr | Ala | Ala | Leu | Gly | Cys | Leu | Val | Lys | Asp | Tyr | |
| | | | 20 | | | | | 25 | | | | | 30 | | | |

| | | | | | | | | | | | | | | | | |
|---|---|---|---|---|---|---|---|---|---|---|---|---|---|---|---|---|
| ttc | ccc | gaa | ccg | gtg | acg | gtg | tcg | tgg | aac | tca | ggc | gcc | ctg | acc | agc | 144 |
| Phe | Pro | Glu | Pro | Val | Thr | Val | Ser | Trp | Asn | Ser | Gly | Ala | Leu | Thr | Ser | |
| | | | 35 | | | | | 40 | | | | | 45 | | | |

| | | | | | | | | | | | | | | | | |
|---|---|---|---|---|---|---|---|---|---|---|---|---|---|---|---|---|
| ggc | gtg | cac | acc | ttc | ccg | gct | gtc | cta | cag | tcc | tca | gga | ctc | tac | tcc | 192 |
| Gly | Val | His | Thr | Phe | Pro | Ala | Val | Leu | Gln | Ser | Ser | Gly | Leu | Tyr | Ser | |
| | | 50 | | | | | 55 | | | | | 60 | | | | |

| | | | | | | | | | | | | | | | | |
|---|---|---|---|---|---|---|---|---|---|---|---|---|---|---|---|---|
| ctc | agc | agc | gtc | gtg | acc | gtg | ccc | tcc | agc | agc | ttg | ggc | acc | cag | acc | 240 |
| Leu | Ser | Ser | Val | Val | Thr | Val | Pro | Ser | Ser | Ser | Leu | Gly | Thr | Gln | Thr | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| tac | atc | tgc | aac | gtg | aat | cac | aag | ccc | agc | aac | acc | aag | gtg | gac | aag | 288 |
| Tyr | Ile | Cys | Asn | Val | Asn | His | Lys | Pro | Ser | Asn | Thr | Lys | Val | Asp | Lys | |
| | | | | 85 | | | | | 90 | | | | | 95 | | |

| | | |
|---|---|---|
| aga | gtt | 294 |
| Arg | Val | |

<210> SEQ ID NO 292
<211> LENGTH: 98
<212> TYPE: PRT
<213> ORGANISM: Artificial Sequence
<220> FEATURE:
<223> OTHER INFORMATION: Synthetic Construct

<400> SEQUENCE: 292

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val

<210> SEQ ID NO 293
<211> LENGTH: 45
<212> TYPE: DNA
<213> ORGANISM: Artificial Sequence
<220> FEATURE:
<223> OTHER INFORMATION: VH-hinge
<220> FEATURE:
<221> NAME/KEY: CDS
<222> LOCATION: (1)..(45)

<400> SEQUENCE: 293

```
gag ccc aaa tct tgt gac aaa act cac aca tgc cca ccg tgc cca        45
Glu Pro Lys Ser Cys Asp Lys Thr His Thr Cys Pro Pro Cys Pro
1               5                   10                  15
```

<210> SEQ ID NO 294
<211> LENGTH: 15
<212> TYPE: PRT
<213> ORGANISM: Artificial Sequence
<220> FEATURE:
<223> OTHER INFORMATION: Synthetic Construct

<400> SEQUENCE: 294

```
Glu Pro Lys Ser Cys Asp Lys Thr His Thr Cys Pro Pro Cys Pro
1               5                   10                  15
```

<210> SEQ ID NO 295
<211> LENGTH: 330
<212> TYPE: DNA
<213> ORGANISM: Artificial Sequence
<220> FEATURE:
<223> OTHER INFORMATION: VH-CH2
<220> FEATURE:
<221> NAME/KEY: CDS
<222> LOCATION: (1)..(330)

<400> SEQUENCE: 295

```
gca cct gaa ctc ctg ggg gga ccg tca gtc ttc ctc ttc ccc cca aaa        48
Ala Pro Glu Leu Leu Gly Gly Pro Ser Val Phe Leu Phe Pro Pro Lys
1               5                   10                  15 ccc aag gac acc ctc atg atc tcc cgg acc cct gag gtc aca tgc gtg        96
Pro Lys Asp Thr Leu Met Ile Ser Arg Thr Pro Glu Val Thr Cys Val
                20                  25                  30 gtg gtg gac gtg agc cac gaa gac cct gag gtc aag ttc aac tgg tac       144
Val Val Asp Val Ser His Glu Asp Pro Glu Val Lys Phe Asn Trp Tyr
            35                  40                  45 gtg gac ggc gtg gag gtg cat aat gcc aag aca aag ccg cgg gag gag       192
Val Asp Gly Val Glu Val His Asn Ala Lys Thr Lys Pro Arg Glu Glu
        50                  55                  60 cag tac aac agc acg tac cgt gtg gtc agc gtc ctc acc gtc ctg cac       240
Gln Tyr Asn Ser Thr Tyr Arg Val Val Ser Val Leu Thr Val Leu His
65                  70                  75                  80 cag gac tgg ctg aat ggc aag gag tac aag tgc aag gtc tcc aac aaa       288
Gln Asp Trp Leu Asn Gly Lys Glu Tyr Lys Cys Lys Val Ser Asn Lys
                85                  90                  95 gcc ctc cca gcc ccc atc gag aaa acc atc tcc aaa gcc aaa               330
Ala Leu Pro Ala Pro Ile Glu Lys Thr Ile Ser Lys Ala Lys
                100                 105                 110
```

<210> SEQ ID NO 296
<211> LENGTH: 110
<212> TYPE: PRT
<213> ORGANISM: Artificial Sequence
<220> FEATURE:
<223> OTHER INFORMATION: Synthetic Construct

<400> SEQUENCE: 296

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
```

```
              50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys
             100                 105                 110

<210> SEQ ID NO 297
<211> LENGTH: 330
<212> TYPE: DNA
<213> ORGANISM: Artificial Sequence
<220> FEATURE:
<223> OTHER INFORMATION: VH-CH2 L235G G236R
<220> FEATURE:
<221> NAME/KEY: CDS
<222> LOCATION: (1)..(330)

<400> SEQUENCE: 297 gca cct gaa ctc ggc agg gga ccg tca gtc ttc ctc ttc ccc cca aaa       48
Ala Pro Glu Leu Gly Arg Gly Pro Ser Val Phe Leu Phe Pro Pro Lys
  1               5                  10                  15 ccc aag gac acc ctc atg atc tcc cgg acc cct gag gtc aca tgc gtg       96
Pro Lys Asp Thr Leu Met Ile Ser Arg Thr Pro Glu Val Thr Cys Val
             20                  25                  30 gtg gtg gac gtg agc cac gaa gac cct gag gtc aag ttc aac tgg tac      144
Val Val Asp Val Ser His Glu Asp Pro Glu Val Lys Phe Asn Trp Tyr
         35                  40                  45 gtg gac ggc gtg gag gtg cat aat gcc aag aca aag ccg cgg gag gag      192
Val Asp Gly Val Glu Val His Asn Ala Lys Thr Lys Pro Arg Glu Glu
     50                  55                  60 cag tac aac agc acg tac cgt gtg gtc agc gtc ctc acc gtc ctg cac      240
Gln Tyr Asn Ser Thr Tyr Arg Val Val Ser Val Leu Thr Val Leu His
 65                  70                  75                  80 cag gac tgg ctg aat ggc aag gag tac aag tgc aag gtc tcc aac aaa      288
Gln Asp Trp Leu Asn Gly Lys Glu Tyr Lys Cys Lys Val Ser Asn Lys
                 85                  90                  95 gcc ctc cca gcc ccc atc gag aaa acc atc tcc aaa gcc aaa              330
Ala Leu Pro Ala Pro Ile Glu Lys Thr Ile Ser Lys Ala Lys
             100                 105                 110

<210> SEQ ID NO 298
<211> LENGTH: 110
<212> TYPE: PRT
<213> ORGANISM: Artificial Sequence
<220> FEATURE:
<223> OTHER INFORMATION: Synthetic Construct

<400> SEQUENCE: 298

Ala Pro Glu Leu Gly Arg Gly Pro Ser Val Phe Leu Phe Pro Pro Lys
  1               5                  10                  15

Pro Lys Asp Thr Leu Met Ile Ser Arg Thr Pro Glu Val Thr Cys Val
             20                  25                  30

Val Val Asp Val Ser His Glu Asp Pro Glu Val Lys Phe Asn Trp Tyr
         35                  40                  45

Val Asp Gly Val Glu Val His Asn Ala Lys Thr Lys Pro Arg Glu Glu
     50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95
```

Ala Leu Pro Ala Pro Ile Glu Lys Thr Ile Ser Lys Ala Lys
             100                 105                 110

<210> SEQ ID NO 299
<211> LENGTH: 321
<212> TYPE: DNA
<213> ORGANISM: Artificial Sequence
<220> FEATURE:
<223> OTHER INFORMATION: VH-CH3
<220> FEATURE:
<221> NAME/KEY: CDS
<222> LOCATION: (1)..(321)

<400> SEQUENCE: 299

| ggg cag ccc cga gaa cca cag gtg tac acc aag ccc cca tcc cgg gag | 48 |
|---|---|
| Gly Gln Pro Arg Glu Pro Gln Val Tyr Thr Lys Pro Pro Ser Arg Glu | |
| 1               5                   10                  15 | |

| gag atg acc aag aac cag gtc agc ctg aag tgc ctg gtc aaa ggc ttc | 96 |
|---|---|
| Glu Met Thr Lys Asn Gln Val Ser Leu Lys Cys Leu Val Lys Gly Phe | |
|             20                  25                  30 | |

| tat ccc agc gac atc gcc gtg gag tgg gag agc aat ggg cag ccg gag | 144 |
|---|---|
| Tyr Pro Ser Asp Ile Ala Val Glu Trp Glu Ser Asn Gly Gln Pro Glu | |
|         35                  40                  45 | |

| aac aac tac aag acc acg cct ccc gtg ctg gac tcc gac ggc tcc ttc | 192 |
|---|---|
| Asn Asn Tyr Lys Thr Thr Pro Pro Val Leu Asp Ser Asp Gly Ser Phe | |
|     50                  55                  60 | |

| ttc ctc tat agc aag ctc acc gtg gac aag agc agg tgg cag cag ggg | 240 |
|---|---|
| Phe Leu Tyr Ser Lys Leu Thr Val Asp Lys Ser Arg Trp Gln Gln Gly | |
| 65                  70                  75                  80 | |

| aac gtc ttc tca tgc tcc gtg atg cat gag gct ctg cac aac cac tac | 288 |
|---|---|
| Asn Val Phe Ser Cys Ser Val Met His Glu Ala Leu His Asn His Tyr | |
|                 85                  90                  95 | |

| acg cag aag agc ctc tcc ctg tct ccg ggt tga | 321 |
|---|---|
| Thr Gln Lys Ser Leu Ser Leu Ser Pro Gly | |
|             100                 105 | |

<210> SEQ ID NO 300
<211> LENGTH: 106
<212> TYPE: PRT
<213> ORGANISM: Artificial Sequence
<220> FEATURE:
<223> OTHER INFORMATION: Synthetic Construct

<400> SEQUENCE: 300

Gly Gln Pro Arg Glu Pro Gln Val Tyr Thr Lys Pro Pro Ser Arg Glu
1               5                   10                  15

Glu Met Thr Lys Asn Gln Val Ser Leu Lys Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 301
<211> LENGTH: 321

<212> TYPE: DNA
<213> ORGANISM: Artificial Sequence
<220> FEATURE:
<223> OTHER INFORMATION: VH-CH3
<220> FEATURE:
<221> NAME/KEY: CDS
<222> LOCATION: (1)..(321)

<400> SEQUENCE: 301

```
ggg cag ccc cga gaa cca cag gtg tac acc gac ccc tcc cgg gag      48
Gly Gln Pro Arg Glu Pro Gln Val Tyr Thr Asp Pro Pro Ser Arg Glu
1               5                   10                  15 gag atg acc aag aac cag gtc agc ctg acc tgc gag gtc aaa ggc ttc  96
Glu Met Thr Lys Asn Gln Val Ser Leu Thr Cys Glu Val Lys Gly Phe
                20                  25                  30 tat ccc agc gac atc gcc gtg gag tgg gag agc aat ggg cag ccg gag 144
Tyr Pro Ser Asp Ile Ala Val Glu Trp Glu Ser Asn Gly Gln Pro Glu
            35                  40                  45 aac aac tac aag acc acg cct ccc gtg ctg gac tcc gac ggc tcc ttc 192
Asn Asn Tyr Lys Thr Thr Pro Pro Val Leu Asp Ser Asp Gly Ser Phe
        50                  55                  60 ttc ctc tat agc aag ctc acc gtg gac aag agc agg tgg cag cag ggg 240
Phe Leu Tyr Ser Lys Leu Thr Val Asp Lys Ser Arg Trp Gln Gln Gly
65                  70                  75                  80 aac gtc ttc tca tgc tcc gtg atg cat gag gct ctg cac aac cac tac 288
Asn Val Phe Ser Cys Ser Val Met His Glu Ala Leu His Asn His Tyr
                85                  90                  95 acg cag aag agc ctc tcc ctg tct ccg ggt tga                      321
Thr Gln Lys Ser Leu Ser Leu Ser Pro Gly
                100                 105
```

<210> SEQ ID NO 302
<211> LENGTH: 106
<212> TYPE: PRT
<213> ORGANISM: Artificial Sequence
<220> FEATURE:
<223> OTHER INFORMATION: Synthetic Construct

<400> SEQUENCE: 302

Gly Gln Pro Arg Glu Pro Gln Val Tyr Thr Asp Pro Pro Ser Arg Glu
1               5                   10                  15

Glu Met Thr Lys Asn Gln Val Ser Leu Thr Cys Glu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
                100                 105

<210> SEQ ID NO 303
<211> LENGTH: 5
<212> TYPE: PRT
<213> ORGANISM: Artificial Sequence
<220> FEATURE:
<223> OTHER INFORMATION: synthetic linker

<400> SEQUENCE: 303

```
Gly Gly Gly Gly Ser
1               5

<210> SEQ ID NO 304
<211> LENGTH: 10
<212> TYPE: PRT
<213> ORGANISM: Artificial Sequence
<220> FEATURE:
<223> OTHER INFORMATION: multivalent antibody

<400> SEQUENCE: 304

Glu Ala Ala Ala Lys Glu Ala Ala Ala Lys
1               5                   10

<210> SEQ ID NO 305
<211> LENGTH: 5
<212> TYPE: PRT
<213> ORGANISM: Artificial Sequence
<220> FEATURE:
<223> OTHER INFORMATION: IgG1

<400> SEQUENCE: 305

Glu Pro Lys Ser Cys
1               5

<210> SEQ ID NO 306
<211> LENGTH: 5
<212> TYPE: PRT
<213> ORGANISM: Artificial Sequence
<220> FEATURE:
<223> OTHER INFORMATION: synthetic linker
<220> FEATURE:
<221> NAME/KEY: MISC_FEATURE
<222> LOCATION: (1)..(5)
<223> OTHER INFORMATION: Sequence can be repeated N number of times

<400> SEQUENCE: 306

Gly Gly Gly Gly Ser
1               5

<210> SEQ ID NO 307
<211> LENGTH: 5
<212> TYPE: PRT
<213> ORGANISM: Artificial Sequence
<220> FEATURE:
<223> OTHER INFORMATION: hinge region

<400> SEQUENCE: 307

Cys Pro Ser Pro Cys
1               5

<210> SEQ ID NO 308
<211> LENGTH: 5
<212> TYPE: PRT
<213> ORGANISM: Artificial Sequence
<220> FEATURE:
<223> OTHER INFORMATION: linker

<400> SEQUENCE: 308

Ser Pro Ser Pro Cys
1               5

<210> SEQ ID NO 309
<211> LENGTH: 5
<212> TYPE: PRT
<213> ORGANISM: Artificial Sequence
<220> FEATURE:
<223> OTHER INFORMATION: linker
```

```
<400> SEQUENCE: 309

Cys Pro Ser Pro Ser
1               5

<210> SEQ ID NO 310
<211> LENGTH: 5
<212> TYPE: PRT
<213> ORGANISM: Artificial Sequence
<220> FEATURE:
<223> OTHER INFORMATION: linker

<400> SEQUENCE: 310

Ser Pro Ser Pro Ser
1               5

<210> SEQ ID NO 311
<211> LENGTH: 5
<212> TYPE: PRT
<213> ORGANISM: Artificial Sequence
<220> FEATURE:
<223> OTHER INFORMATION: hinge region

<400> SEQUENCE: 311

Cys Pro Pro Cys Pro
1               5

<210> SEQ ID NO 312
<211> LENGTH: 6
<212> TYPE: PRT
<213> ORGANISM: Artificial Sequence
<220> FEATURE:
<223> OTHER INFORMATION: light chain variable region

<400> SEQUENCE: 312

Gln Ser Ile Ser Ser Tyr
1               5

<210> SEQ ID NO 313
<211> LENGTH: 7
<212> TYPE: PRT
<213> ORGANISM: Artificial Sequence
<220> FEATURE:
<223> OTHER INFORMATION: light chain variable region CDR3

<400> SEQUENCE: 313

Gln Gln Ser Tyr Ser Thr Pro
1               5

<210> SEQ ID NO 314
<211> LENGTH: 8
<212> TYPE: PRT
<213> ORGANISM: Artificial Sequence
<220> FEATURE:
<223> OTHER INFORMATION: Linker

<400> SEQUENCE: 314

Glu Ala Ala Lys Glu Ala Ala Lys
1               5
```

MULTIVALENT ANTIBODY

CROSS-REFERENCE TO RELATED APPLICATIONS

This application claims priority to U.S. Provisional Application No. 62/650,467, filed Mar. 30, 2018, the contents of which are hereby incorporated by reference.

REFERENCE TO SEQUENCE LISTING SUBMITTED ELECTRONICALLY VIA EFS-WEB

The content of the electronically submitted sequence listing (Name: "4096-0180001_SL_ST25.txt"; Size: 183,320 bytes; Date of Creation: Jun. 30, 2021) submitted in this application is incorporated herein by reference in its entirety.

FIELD

The invention relates to multivalent antibodies having three or more binding domains and to a method for making such multivalent antibodies. The invention further relates to constituent polypeptides of the multivalent antibodies and to linkers that can be used to connect one or more binding domains of the multivalent antibody. The invention in addition relates to nucleic acids that encode such multivalent antibodies, linkers and to vectors comprising such nucleic acids, as well as to host cells that produce the multivalent antibodies. The invention also relates to multivalent antibodies which are capable of simultaneously binding three antigens or targets at once, including to target antigens present on cancer cells or tumor cell antigens and targets that engage immune effector cells. Also the invention relates to a pharmaceutical composition which comprises the multivalent antibody and to the multivalent antibody for use in the treatment of the human or animal by therapy. Also, the invention relates to a method for the treatment of a human or animal using the antibody.

BACKGROUND

Multivalent antibodies, such as bispecific antibodies, capable of binding two antigens or two epitopes are known in the art. Such multivalent binding proteins can be generated using various technologies, including cell fusion, chemical conjugation or recombinant DNA techniques.

Antibodies typically are multimers comprised of four proteins, including two identical heavy chains and two identical light chains, wherein the heavy chain is comprised of a variable domain (VH), and three constant regions (CH1, CH2, CH3), and wherein the light chain is comprised of a variable light chain domain (VL) and a constant region (CL). Typically, the light chain pairs with the heavy chain through the influence of many noncovalent interactions and also via disulphide bonds. The two heavy chains pair at the hinge region that connects CH1 to CH2 and/or through amino acid interactions in the interface between the two CH3 domains. The pairing of the VH with VL forms an antigen binding domain, and typically variability is found in three superficial-loop forming regions in the VH and VL domains, which are the complementarity determining regions or CDRs.

Certain multivalent antibody formats are known in the art, such as antibodies having two different binding domains, such as in bispecific antibodies, that may bind two different antigens, or two different epitopes within the same antigen. Such a format may allow for the use of calibrated binding that will allow the multivalent antibody to be selectively targeted to cells or targets that express two antigens or epitopes such as a tumor cell whilst not targeting healthy cells expressing one antigen, or to target such healthy cells expressing one antigen at lower expression levels. Similarly, having two different binding domains on a multivalent antibody, such as a bispecific antibody, may permit binding of different antigens, such that said multivalent antibody could be used to target both an inhibitory and a stimulatory molecule on a single cell or on two interacting cells to result in enhanced potency of the multivalent antibody. A multivalent antibody could also be used to redirect cells, for example immunomodulatory cells, that could be redirected to a tumor.

The incorporation of more than two binding domains in a single antibody may allow for a broader array of beneficial combinations of targets and efficacy. For example, a multivalent antibody having three or more binding domains may target the same antigen and epitope, permitting specificity for a given target and/or saturation of a target at a lower ratio of antibody to target. A multivalent antibody may contain two or more identical antigen binding domains to allow for high avidity binding to a target cell. This can be used to specifically target antigens such as gangliosides that are over-expressed on tumor cells. These tumor associated antigens are present on normal cells but at much higher density on tumor cells. A multivalent antibody containing several lower affinity binding regions may allow for specific targeting to tumor cells while not reacting with healthy cells or doing so at a lower ratio and at the same time activating or blocking additional receptors. Ultimately, three or more binding regions are useful in such applications.

While certain multivalent antibodies have been described in the art, there is a need in the art for new formats, and new linkers, that permit the efficient production of multivalent antibodies, for which binding domains to an array of antigens can be readily made and converted into a multivalent antibody efficiently, stably, and that are capable of binding a wide array of antigens and epitopes. Engineering an antibody that contains more than two binding domains traditionally has been time-consuming, inefficient, and costly. Indeed, there are numerous impediments to efficiently producing high quality, low immunogenic multivalent antibodies that can be generated to target a variety of antigens.

For example, existing multivalent formats containing three or four binding domains rely on synthetic linkers such as $Gly_4Ser$ ($G_4S$) (SEQ ID NO:303) repeats that contain sequence domains which firstly tend to restrict access to all binding domains in the molecule and secondly which may also be problematic for developability.

Existing multivalent antibody formats also rely on different heavy and light chains which are associated by disulphide bonds and amino acid interactions or can by joined by short linkers in the case of single-chain fragment variables (scFvs). Yet the need to use differential variable chains (heavy and/or light) in each of the multiple variable domains used in a multispecific format of three or more binding specificities requires extensive engineering of such molecules to prevent mispairing of the heavy chains and light chains. Invariably this has an impact on complexity, stability, immunogenicity and production levels of these molecules.

Multivalent antibody formats may rely on the use of the same light chain for each binding domain, where one or more of the cognate variable regions paired with said light chain are forced to pair through chemical modifications, rather than the cognate chain being formed with and paired with a common light chain in response to antigenic exposure, and the processes of co-evolution that occurs during B-cell development.

Multivalent antibody formats may also rely on the light chain from an existing monospecific antibody that binds one antigen, which is then used in a library to identify heavy chains capable of pairing said light chain, while also binding a distinct epitope or antigen.

Such pseudo-common light chains are not preferred for use in the present invention. Preferred common light chains for the present invention are those that are capable of pairing with a diversity of cognate chains and are obtained from, derived from or based on common chains that pair with a rearranged cognate chain, which is encoded by DNA having undergone somatic recombination, and preferably somatic hypermutation in response to antigenic exposure.

A pseudo light chain approach limits the range of available cognate chains. Forcing the pairing of heavy and light chains, which were not formed together in a response to antigenic exposure results in loss of specificity and affinity limiting the utility. Further, it is typically rare for any given antibody to allow shuffling of VH and VL and conserve affinity and specificity.

Forcing light chain pairing with a heavy chain where the two have not co-evolved in the immune response while maintaining the capacity to bind an antigen is not trivial and may limit the flexibility of this approach.

Similarly, reusing a light chain of one antibody to identify heavy chains that are capable of binding said light chain and also bind a distinct antibody of interest, limits the range of available heavy chains, and becomes increasingly unlikely to identify suitable additional heavy chains the more antigens or epitopes sought to be bound. That is, one may use a light chain that pairs with a heavy chain to form a Fab that binds a given antigen to identify a subsequent heavy chain that pairs with said light chain, and is capable of binding a second antigen. However, use of that light chain a third time, to identify third heavy chain capable of pairing to said light chain while binding a third antigen or epitope become increasingly rare, and rarer still the more heavy chains are sought to be identified capable of pairing with said light chain, while also binding distinct epitopes or antigens.

A preferred embodiment of the invention described herein employs a common chain, which pairs with a diversity of heavy chains in response to an antigen, and does not require reuse of an existing light chain from a monospecific antibody or forced pairing of a light chain to a cognate chain through chemical modification.

The successful construction of multivalent antibodies relies on the proper choice of protein linkers between the different domains as direct fusion of two domains can lead to compromised biological activity. The biophysical characteristics of the linker or linkers such as charge, rigidity or flexibility as well as the distance between the binding domains and the spatial conformation between binding regions can impact epitope access and the ability of the multivalent protein to bind its targets. Thus there is a need for a multivalent format that in a modular fashion can employ a variety of linkers with different characteristics to permit construction of multivalent antibodies that allow simultaneous binding to different combinations of epitopes that may be located on different molecules and/or on different cells.

Accordingly, there is a need in the art for the design of a set of linkers containing different characteristics of rigidity, flexibility, length that can be employed in a modular fashion depending on the combination of targets, while maintaining stability, low immunogenicity and ease of developability.

Accordingly, there is a need for new and useful formats for multivalent antibodies having three or more binding domains and linkers for the production of such antibodies which are widely applicable to the rapid and robust generation of a broad range of antibodies which comprise more than two binding domains.

SUMMARY

The invention is based on new, modular, formats for a multivalent antibody comprising three or more binding domains which may be a multispecific antibody. In these formats, at least one binding domain is connected to a base antibody portion, said base antibody portion comprising two binding domains. The additional binding domain may comprise a variable region, Fv domain, a Fab domain or a modified Fab domain or a functional fragment of any thereof. The base antibody portion may be, for example, a full length antibody or fragment thereof, but in each case comprises two binding domains.

The one or more additional binding domains are connected to the base antibody portion via a linker(s), providing one or more binding moieties in addition to those of the base antibody portion.

A linker is used to connect the one or more additional binding domains to the base antibody portion. The linker comprises a peptide region, for example one or more hinge regions and/or one or more regions derived from a hinge region. The combination of the linker and a constant region (e.g., CH1) to which it is connected may be critical in determining the properties of the multivalent antibody and allow correct functionality of the antibody and/or orientation of the one or more additional binding domains to the base antibody. Thus, if a linker sequence is based on a hinge of a given subtype it may be preferable that the constant region of the additional binding domain to which it is attached is of the same subtype.

The one or more additional binding domain(s) may comprise a variable region, Fv domain, a Fab domain or modified Fab domain.

Fab domains in particular constitute beneficial additional binding domains since they comprise protein domains having predictable behavior which is useful for the manufacture of multivalent molecules which are stable and can be readily manufactured.

Facilitating efficient production and developability of the multivalent antibody of the invention, said multivalent antibody may comprise a common variable region, which can be an immunoglobulin heavy chain variable region (VH) or a light chain variable region (VL), but is typically a common light chain (cLC) variable region.

The common variable region is typically paired with a cognate variable region that is encoded by a nucleic acid that has undergone somatic recombination and preferably affinity maturation or is based on or derived from a rearranged variable region that is encoded by a nucleic acid that has undergone the process of somatic recombination and preferably affinity maturation, and/or is based on or derived from known antibody generation techniques, such as phage display, immunization of animals, including transgenic animals with humanized immune systems and other techniques well known in the art.

The use of a common variable region that is essentially identical in each binding domain of the multivalent antibody of the invention facilitates the development and manufacture of such antibodies.

The choice of the common variable region for use in a multivalent antibody of the invention should thus be one which can be used widely with many different cognate heavy or light regions.

An identical, or substantially identical, common variable region, for example a cLC variable region, allows the use of complete, or substantially complete, Fab domains for all three or more binding regions without the need for extensive engineering as used in Crossmab technology or for linkers to prevent heavy and light chain mispairing, such as those used in scFv domains. Also, since essentially germline encoded and non-immunogenic common variable regions are known (see WO2009/157771), using it in each of the three or more Fab domains may provide for reduced immunogenicity.

An additional benefit of the format described herein for producing multivalent antibodies permits the use of transgenic animals, preferably transgenic rodents, that have within their genomes a common variable region, capable of pairing with a diversity of cognate variable regions (e.g., common light chain variable region pairing with a diversity of heavy chain variable regions) (see WO2009/157771), that permits the DNA encoding the cognate variable regions formed from exposure to different antigens to be introduced into a host cell with the DNA encoding the common variable region, which can each be expressed for the generation of multivalent antibodies.

For example, a transgenic mouse comprising in its germline, DNA encoding a common variable region and DNA encoding an unrearranged immunoglobulin locus that can rearrange to form a cognate variable region and is capable of undergoing somatic recombination, can be exposed to one or more antigens, such that the rearranged variable regions produced based on exposure to the three or more antigens can then be used to generate a multivalent antibody of the present invention. Nucleic acid sequences encoding the common variable region, and the three or more rearranged variable regions can be transformed into a host cell, to express a multivalent antibody of the present invention.

Thus, the formats described herein for producing multivalent antibodies make use of three or more binding domains that all may comprise a common variable region, preferably a common light chain variable region.

The formats of the present invention comprise one or more binding domains in addition to those of the base antibody portion. Such an additional binding domain may be a Fv domain, a Fab domain or a modified Fab domain preferably comprising a CH1 domain and a variable domain, which is connected to the base antibody portion via a linker. In a modified Fab domain, the CH1 domain is not paired with a CL. A suitable CH1 domain may be one which is engineered to remove one or more hydrophobic regions or may be one derived from a camelid animal or a shark. Alternatively, an additional binding domain may comprise a CL domain and a variable domain which is connected to the base antibody portion via a linker. The CL domain can either be a Ckappa or a Clambda domain.

Typically, the additional binding domain(s) is/are connected to one or both binding domains of the base antibody portion at the N-terminal region of either a common variable portion or a rearranged variable region of the binding domain of the base antibody portion or both.

Alternatively, an additional binding domain may be connected to the base antibody portion via a linker connecting both a common chain and a rearranged variable domain of the binding domain of the base antibody portion to a CH1 and CL region of the additional binding domain. Where an additional binding domain lacks a constant region, novel linkers disclosed herein may connect both a common chain and a rearranged variable domain of the binding domain of the base antibody portion to the common chain and/or rearranged variable region of the additional binding domain.

Alternatively, an additional binding domain may be a VH and VL region, i.e. a Fv domain, which is connected by a single linker peptide to the base antibody portion. Typically, this type of additional binding domain(s) is/are attached to one or both binding domains of the base antibody portion at the N-terminal region of either the common variable portion or the rearranged variable region of the binding domain of the base antibody portion.

This format, when used with linkers of the invention disclosed herein, including different lengths, structures and degrees of rigidity, is surprisingly flexible. Thus, the invention provides a repertoire of linkers with different properties for use in the disclosed multivalent antibody formats that render it developmentally facile to combine three or more binding domains into a multivalent antibody.

By way of the linkers disclosed herein, the invention thus provides a modular approach in which selection of the appropriate linker together with selection of a corresponding set of binding domains, such as Fab domains, allows those binding domains to function together in a multivalent antibody for a variety of efficacy.

A multivalent antibody of the invention may be used in therapy, in particular, as a so-called "engager" antibody whereby the antibody is capable of forming a link between an immune effector cell and a tumor cell.

According to the invention, there is thus provided a multivalent antibody which comprises:
  a base antibody portion which comprises two binding domains; and
  at least one additional binding domain,
  wherein the base antibody portion is connected by a linker to the at least one additional binding domain,
  wherein each binding domain of the base antibody portion and each of the at least one additional binding domains all have a common variable region, and
  wherein the linker comprises a hinge sequence or a sequence derived from a hinge sequence.

The invention also provides a multivalent antibody which comprises:
  a base antibody portion which comprises two binding domains; and
  at least one additional binding domain,
  wherein at least one additional binding domain comprises a CH1 region and is connected to the base antibody portion by said linker, linking a variable region of the base antibody portion and the CH1 region, and
  wherein the multivalent antibody binds to at least three different epitopes.

Preferably, each binding domain of the base antibody portion and each of the at least one additional binding domains may all have a common variable region, Variety of the One or More Additional Binding Domain A preferred embodiment is a multivalent antibody, wherein one or more binding domains is a Fv domain comprising a heavy chain variable region (VH) and a light chain variable region (VL).

A further preferred embodiment is a multivalent antibody, wherein one or more binding domains is a Fab domain comprising a heavy chain variable region (VH) and a light chain variable region (VL), said heavy chain variable region of said Fab domain comprising a CH1 region (VH-CH1) and said light chain variable region of said Fab comprising a CL region (VL-CL). Said Fab domain may contain a VL-CL that is either a Vkappa-Ckappa, Vlambda-Clambda, Vlambda-Ckappa or Vkappa-Clambda.

Another embodiment is a multivalent antibody, wherein the one or more additional binding domains is a modified Fab domain consisting of a VH-CH1 and VL. Alternatively, an embodiment is a multivalent antibody, wherein the one or more additional binding domain is a modified Fab domain consisting of a VL-CL and a VH. In such modified Fab domains, a constant region, CH1 or CL, is present which is not paired with its cognate region and/or a variable region VH or VL, is present, which is not paired with its cognate region.

Common Chain

A preferred embodiment is a multivalent antibody wherein the one or more additional binding domain comprises a Fab domain comprising a common rearranged variable region paired to a rearranged variable region which has undergone somatic rearrangement following exposure to an antigen or is encoded by nucleic acids obtained from, derived from, or based on a sequence, which is the result of somatic rearrangement. Alternatively, the rearranged variable region could be one obtained from, derived from, or based on a synthetic repertoire where diversity is introduced into a repertoire using molecular biology techniques known in the art, including the use of synthetic phage display libraries. Preferably, said Fab domain comprises a common light chain variable region paired to a counterpart rearranged heavy chain variable region. Preferably, said common light chain variable region is connected to a CL region and said rearranged heavy chain variable region is connected to a CH1 region. Preferably, said common light chain is paired to said heavy chain variable region via joining of the CL and CH1 regions. Alternatively, wherein the common chain is a heavy chain, the rearranged variable region is a light chain, and said chains may comprise a CH1 and CL domain respectively and may be paired via joining of the CL and CH1 regions.

A preferred embodiment is a multivalent antibody wherein the three or more binding domains each comprise the same common chain, but wherein the three or more binding domains comprise different rearranged variable cognate chains, more preferably, wherein the said same common chain is a common light chain.

A preferred embodiment is a multivalent antibody, wherein the three or more binding domains comprise rearranged variable regions encoded by nucleic acids obtained from, derived from, or based on nucleic acid sequences of a transgenic animal comprising a common light chain and unrearranged heavy chain variable region, which has been exposed to an antigen and has produced antibodies comprising a rearranged heavy chain variable region paired to a common light chain. Alternatively, in an embodiment of a multivalent antibody, the three or more binding domains comprise rearranged variable regions encoded by nucleic acids obtained from, derived from, or based on nucleic acid sequences of a transgenic animal comprising a common heavy chain and unrearranged light chain variable region, which has been exposed to an antigen and has produced antibodies comprising a rearranged light chain variable region paired to a common heavy chain.

Linker Composition

A preferred embodiment is said multivalent antibody, wherein said linker is a naturally occurring sequence, or based on a naturally occurring sequence. More specifically, said linker is a hinge sequence or comprises a sequence based on a hinge sequence. More specifically said linker may comprise a hinge region based on an IgG1 hinge region, an IgG2 hinge region, an IgG3 hinge region or an IgG4 hinge region.

Alternatively, said linker comprises a peptide region comprising one or more of the following:

```
                                        (SEQ ID NO: 1)
ESKYGPP (SEQ ID NO: 2)
EPKSCDKTHT (SEQ ID NO: 3)
GGGGSGGGGS (SEQ ID NO: 4)
ERKSSVESPPSP (SEQ ID NO: 5)
ERKCSVESPPSP (SEQ ID NO: 6)
ELKTPLGDTTHT (SEQ ID NO: 7)
ESKYGPPSPSSP (SEQ ID NO: 8)
ERKSSVEAPPVAG (SEQ ID NO: 9)
ERKCSVEAPPVAG (SEQ ID NO: 10)
ESKYGPPAPEFLGG (SEQ ID NO: 11)
EPKSCDKTHTSPPSP (SEQ ID NO: 12)
EPKSCDGGGGSGGGGS (SEQ ID NO: 13)
GGGGSGGGGSAPPVAG (SEQ ID NO: 14)
EPKSCDKTHTAPELLGG (SEQ ID NO: 15)
ERKSSVESPPSPAPPVAG (SEQ ID NO: 16)
ERKCSVESPPSPAPPVAG (SEQ ID NO: 17)
ELKTPLGDTTHTAPEFLGG (SEQ ID NO 18)
ESKYGPPSPSSPAPEFLGG (SEQ ID NO: 19)
EPKSCDKTHTSPPSPAPELLGG (SEQ ID NO: 20)
ERKSSVEEAAAKEAAAKAPPVAG (SEQ ID NO: 21)
ERKCSVEEAAAKEAAAKAPPVAG (SEQ ID NO: 22)
ESKYGPPEAAAKEAAAKAPEFLGG (SEQ ID NO: 23)
EPKSCDKTHTEAAAKEAAAKAPELLGG (SEQ ID NO: 24)
ELKTPLGDTTHTEAAAKEAAAKAPEFLGG
``` or a sequence having at least about 85% sequence identity to any one thereto.

Preferably, a multivalent antibody of the invention comprises a linker that connects the base antibody portion to the one or more binding domains by comprising an amino acid sequence of any one of SEQ ID NOs: 1 to 24 or a polypeptide comprising an amino acid sequence having at least about 85% sequence identity to any of SEQ ID NOs: 1 to 24.

Table 1 illustrates how such linkers may be connected to a CH1 region.

A preferred multivalent antibody of the invention, comprises a linker that is rigid. More preferably, said multivalent antibody comprises a linker that comprises a helix-forming sequence.

A preferred multivalent antibody of the invention comprises a linker comprising a peptide sequence comprising a (EAAK)$_2$ (SEQ ID NO:314) motif.

A preferred multivalent antibody of the invention, comprises a linker that is flexible.

A preferred multivalent antibody of the invention, comprises a linker comprising three or more amino acid residues that correspond to a hinge region of a subtype of a constant region to which it is connected of said multivalent antibody.

A preferred multivalent antibody of the invention comprises a linker comprising a sequence of SEQ ID NOs: 1 to 24 that corresponds to a hinge region of a subtype of a constant region to which it is connected of said multivalent antibody.

Linker Location/Orientation

A preferred embodiment is a multivalent antibody, wherein the base antibody portion is connected to the one or more additional binding domains by a linker, wherein said linker joins an N-terminal end of a variable region of said base antibody portion to the C-terminal end of the one or more additional binding domains. Preferably, the base antibody portion comprises a Fab domain and the one or more additional binding domain comprises a Fab domain comprising a CH1 domain and CL domain and the linker connects an N-terminal end of a variable region of the Fab of the base antibody portion to either or both of a C-terminal end of the CH1 domain and CL domain of the Fab domain of the one or more additional binding domain.

A preferred embodiment of the invention is a multivalent antibody comprising a common chain at each binding domain of the base antibody portion and each of the one or more additional binding domains and a linker which connects a N-terminal end of a rearranged variable region of the base antibody portion to a C-terminal end of a rearranged variable region of the one or more additional binding domain. More preferably, the one or more additional binding domain comprises a Fab domain comprising a CH1 domain and CL domain and the linker connects an N-terminal end of a variable region of the Fab domain of the base antibody portion to the CH1 domain or CL domain of the Fab domain of the one or more additional binding domain.

Pairing of the Regions Comprising the Additional Binding Domain

Antibody assembly occurs through association of the light and heavy chains, namely the association (pairing) of VH with VL and CH1 with CL, which is based on interacting residues in the interface between VH and VL, and between CH1 and CL. Typically, pairing is further stabilized, whereby a light chain is covalently connected to the heavy chain by a disulfide bond between a cysteine residue of the light chain in the CL, and a cysteine residue of the heavy chain at the CH1 or hinge, depending on the subtype.

Thus, in a multivalent antibody of the invention, an additional one or more binding domain(s) is connected to the base antibody portion via a linker(s), wherein the one or more binding domain(s) comprises a Fv domain, a Fab domain or a modified Fab domain, and the counterpart immunoglobulin chains that comprise the binding domain (typically a heavy and light chain region) are paired together in a stable association.

For multivalent antibodies of the present invention that contain an additional binding domain, wherein the binding domain is a Fv or Fab domain a cysteine residue may be present or engineered into the heavy and light chain domains, such that a disulfide bond forms to stabilize the pairing between the heavy and light chain of the additional binding domain. Where the multivalent antibody of the invention includes an additional binding domain comprising an IgG1 subclass, an upper hinge of IgG1 (EPKSC) (SEQ ID NO:305) of the heavy chain may be used that is connected to and upstream (n-terminal side) of an artificial linker, such as (G4S)n (SEQ ID NO:306), to provide a cysteine to covalently pair with the light chain of the additional binding domain. For other subclasses used in the additional binding domain, the skilled artisan will recognize the ability to engineer a cysteine residue in the linker employed to stabilize the pairing of light and heavy chain domains of the additional binding domain and to form a disulfide bridge between said light chain and heavy chain used.

The wild-type IgG1 hinge region has the sequence: EPKSCDKTHTCPPCPAPELLGG (SEQ ID NO: 42). The underlined C residue is Cys220 which in the IgG1 heavy chain pairs with Cys214 of the light chain. Where a multivalent antibody of the invention comprises a linker based on such a hinge, preferably any Cys residues other than Cys220 are substituted with an amino acid residue which cannot form a disulphide bond, for example Ser.

The wild type IgG2 hinge region has the sequence: ERKCCVECPPCPAPPVAG (SEQ ID NO: 46). The underlined C residue is Cys219 which in the IgG2-B heavy chain pairs with Cys214 of the light chain. In IgG2-A, Cys127 in the heavy chain pairs with Cys214. Where a multivalent antibody of the invention comprises a linker based on such a hinge, preferably any Cys residues other than Cys215 are substituted with an amino acid residue which cannot form a disulphide bond, for example Ser.

The wild type IgG3 hinge region has the sequence: ELKTPLGDTTHTCPRCPEPKSCDTPPPCPRCPEPKS- CDTPPPCPRCPEPKSCDTPPPCPRCP APEFLGG (SEQ ID NO: 50). In IgG3, Cys131 in the heavy chain pairs with Cys214 of the light chain.

The IgG4 hinge region has the sequence: ESKYGPPCP- SCPAPEFLGG (SEQ ID NO: 54). In IgG4, Cys131 in the heavy chain pairs with Cys214 of the light chain. Where a multivalent antibody of the invention comprises a linker based on such a hinge, preferably one or both of the Cys residues in the CPSPC (SEQ ID NO:307) region of the hinge are substituted with an amino acid residue which cannot form a disulphide bond, for example Ser (i.e., SPSPC, SEQ ID NO:308; CPSPS, SEQ ID NO:309; SPSPS, SEQ ID NO:310).

As set out herein, to generate multivalent constructs, including trivalent constructs, based on an IgG structure capable of binding simultaneously three different epitopes, linkers are employed based on IgG hinges from different subclasses to connect a binding domain of a base antibody portion to an additional binding domain that comprise a heavy chain constant region. To ensure stabilization of the covalent bond between a cysteine in the light chain and a cysteine in the heavy chain of the additional binding domain, the invention matches a linker comprising a hinge region or based on a hinge region of a particular subtype with the CH1 of the additional binding domain that is from the same subtype.

Where the multivalent antibody comprises an additional binding domain comprised of pair regions (e.g., VH-CH1 paired with VL-CL, or VH paired with VL), stabilizing the interface between the regions may be accomplished in the present invention in a variety of ways. Where the one or more additional binding domain is a Fab domain comprised of a variable heavy chain region and variable light chain region, a CH1 can be connected to the variable heavy chain region. The CH1 can be paired to a CL with a covalent bond, typically a disulphide bridge, that is connected to the variable light chain region. In addition heavy and light chains of a Fab domain are paired via non-covalent interactions. Alternatively, the linker that connects the one or more additional binding domains to the base antibody portion can also be used to pair the variable heavy chain region to the variable light chain region of the additional binding domain by forming a peptide bond with either chain and a covalent linkage with the counterpart chain. This can be accomplished by designing a cysteine at or near the N-terminus of the linker and a cysteine at or near the C-termini of the variable heavy chain and/or variable light chain regions of the one or more additional binding domains, thereby forming a covalent bond between the linker and the variable heavy chain and/or variable light chain regions of the one or more additional binding domains. Other means of pairing the domains that comprise the one or more additional binding domain, such as a Fab domain, are known to persons of ordinary skill in the art and described further in detail below.

A preferred embodiment is a multivalent antibody, comprising a base antibody portion and one or more additional binding domains. Where the one or more additional binding domain is a Fv domain comprising a heavy chain variable (VH) region and light chain variable (VL) region, a linker of the invention connects the base antibody portion to said Fv, while pairing the heavy chain variable region and light chain variable region of the Fv.

Alternatively, the binding domain is a Fab domain comprising a variable heavy region comprising a CH1 region and a variable light region comprising a CL region. A linker of the invention connects the base antibody portion to the Fab domain at the CH1 region or CL region or both while pairing the CH1 and CL region of the Fab domain.

Pairing of the Base Antibody Portion

Different techniques are known in the art to pair and cause heterodimerization of heavy chain constant regions (e.g., CH2 and CH3) of a base antibody portion. The use of, for example, DEKK mutations to cause heterodimerization of antibody heavy chains (WO2013/157954 and De Nardis et al., J. Biol. Chem. (2017) 292(35) 14706-14717 incorporated herein by reference), further allows for efficient heterodimer formation, stable Fc region and ease of manufacture. This approach leaves the Fc region of the molecule functional and capable of engaging with immune receptors such as Fc receptors, complement and FcRn. Accordingly, certain multivalent antibody embodiments of the invention employ the DEKK modifications, or other Fc modifications known to skilled artisans, to preferentially heterodimerize the heavy chains of the base antibody portion.

Further, for certain embodiments of multivalent antibodies, it may be desirable not to engage the immune system's effector function (e.g. to limit antibody-dependent cellular cytotoxicity, antibody-mediated phagocytosis and/or cellular-dependent cytotoxicity), such as using a multivalent antibody to engage, stimulate and/or co-stimulate T-cells, in which case additional modifications may be employed to the Fc region to eliminate or mitigate effector function. Accordingly, certain multivalent antibody embodiments of the invention contain modifications to the heavy chain constant regions of the base antibody portion that eliminate or mitigate effector function(s).

An additional preferred embodiment of the invention is a multivalent antibody comprising a base antibody portion comprised of two heavy chains that lack CH2 or CH3 region, wherein said heavy chains are bound together at the hinge region.

The invention also provides a method for the preparation of a multivalent antibody, which method comprises providing a cell which comprises one or more nucleic acid sequences encoding polypeptides which are capable of assembly into a multivalent antibody of the invention. The cell may be cultivated under conditions to provide for expression of the base antibody portion, the at least one additional binding domain and the at least one linker and for their assembly into a multivalent antibody of the invention.

The invention also provides nucleic acids that encode for the constituent proteins of a multivalent antibody of the invention and the multivalent antibody they produce.

The invention also provides a vector comprising a nucleic acid sequence of the invention.

The invention also provides host cells that express said nucleic acids and produce said multivalent antibodies.

The invention also provides methods of generating said multivalent antibody, including through the use of transgenic animals comprising a common chain in its germline that produce common chain antibodies having diversity at a cognate chain, wherein said multivalent antibody comprises one or more binding domains having a rearranged variable region encoded by a nucleic acid obtained from, derived from or based on one or more cognate chains of the common chain antibodies expressed by the transgenic animal exposed to an antigen.

The invention also provides a non-human transgenic animal comprising a common human light chain variable region capable of pairing with a diversity of human heavy chain variable regions, wherein the nucleic acids encoding the common light chain variable region and human heavy chain variable regions are present at the non-human transgenic animal's endogenous variable region loci (light and heavy respectively or vice-versa) and/or are stably integrated elsewhere in the germline of the said transgenic animal (e.g., the Rosa locus), wherein contacting said transgenic animal with an antigen generates an array of rearranged human heavy chain variable regions that pair with said common light chain variable region, wherein a nucleic acid encoding said rearranged human heavy chain variable regions is transformed into a host cell capable of producing a multivalent antibody of the invention, and the multivalent antibody comprises one or more binding domains comprising said rearranged human heavy chain variable region encoded by a nucleic acid obtained from, derived from or based on one or more rearranged human heavy chain variable regions produced by the transgenic animal exposed to an antigen.

The invention also provides a pharmaceutical composition which comprises an antibody of the invention and a pharmaceutically acceptable carrier and/or diluent.

The invention also provides an antibody of the invention for use in the treatment of the human or animal body by therapy.

The invention also provides a method for the treatment of a human or animal suffering from a medical indication, which method comprises administering to the human or animal a therapeutically effective amount of an antibody of the invention.

BRIEF DESCRIPTION OF THE DRAWINGS

For ease of reference, for Figures fifteen through twenty-eight, when describing trispecific molecules, the following format is used MFAxMFB:MFC or AntigenAxAntigenB:AntigenC, such that MFA or AntigenA followed by x constitutes the "short arm", while the x denotes the dimerization, followed by MFB or AntigenB describes the interior position of the long arm, followed by a ":" designating a linker followed by MFC or AntigenC describes MFC or AntigenC at the distal domain of the long arm. Where the term "mock" is used in the context of a multivalent molecule, it refers to a binding domain of such molecule, which is capable of binding an antigen not present in the given assay in which it is tested. Typically, mock binding domains used herein bind tetanus toxin (TT), fibrinogen (Fibri) or thyroglobulin (Thyro).

FIG. 5 sets out the alignment of sequences of inserts used for cloning into MV1626. Note the alignment covers only CH1-linker for clarity purposes.

FIG. 9 sets out screening data of 24 multivalent constructs.

FIG. 10 sets out screening data of 18 multivalent constructs.

FIG. 11A: Common light chain amino acid sequence. FIG. 11B: Common light chain variable domain DNA sequence and translation (IGKV1-39/jk1). FIG. 11C: Common light chain constant region DNA sequence and translation. FIG. 11D: IGKV1-39/jk5 common light chain variable domain translation. FIG. 11E: V-region IGKV1-39A; FIG. 11F: CDR1, CDR2 and CDR3 of the common light chain.

FIG. 12: Stability analysis of 18 multivalent IgG constructs and 4 control antibodies analyzed under 4 different conditions.

FIG. 13: Bioinformatic modeling of 8 linkers.

FIG. 14: Two engager trispecific formats, with a long arm interior immune cell binding domain and a short arm tumor cell antigen binding domain (14a) or long arm distal tumor cell antigen binding domain and a short arm tumor cell antigen binding domain (14b).

FIG. 23a: FACS data against MDA-MB-231 cells is shown as area under the curve (AUC) for a range of PD-L1 affinities and a range of EGFR affinities, demonstrating dual-antigen binding correlated with increasing affinity of the tumor antigen binding domains.

FIG. 23b: T-cell cytotoxicity activity data is provided against BxPC3 cells demonstrating for certain trispecific molecules having the format of CD3xPD-L1:EGFR. Simultaneous dual antigen binding and immune cell engagement occurred with an additive effect on cytotoxicity over molecules binding a single antigen and CD3 (either CD3xEGFR:Mock or CD3xMock:PD-L1). Specific heavy chain sequences not shown.

DETAILED DESCRIPTION

Figure 1A:
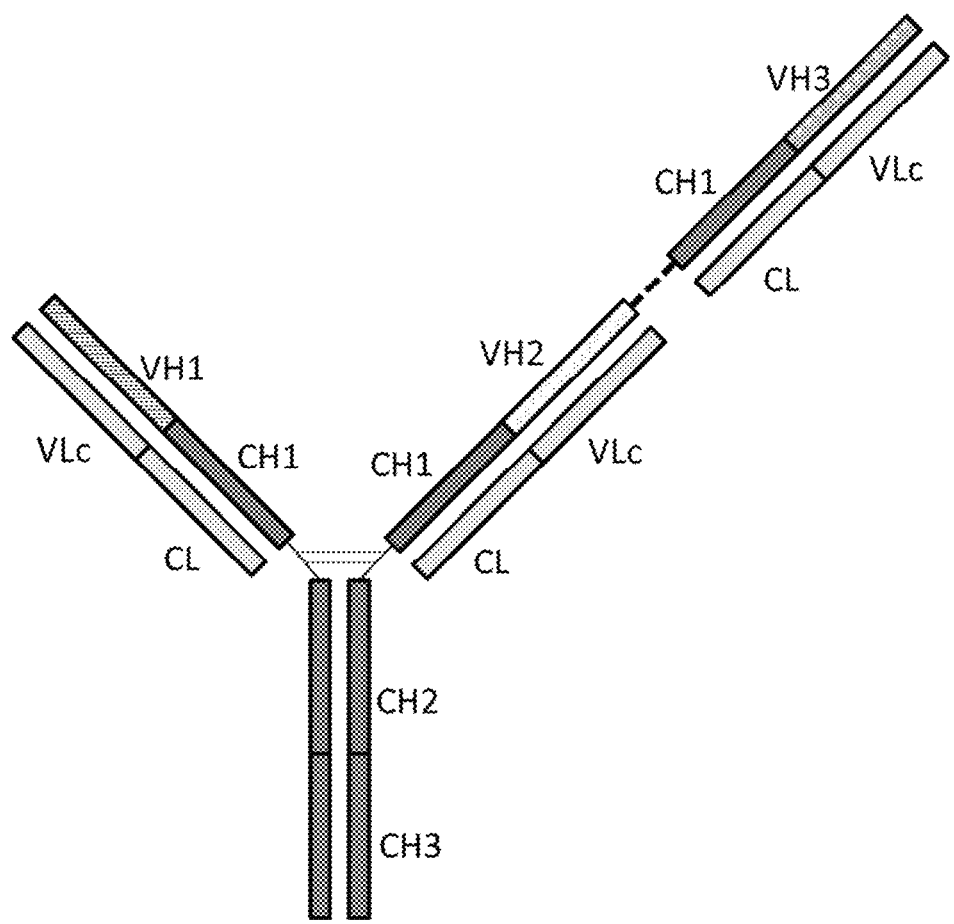
FIG. 1(a-u) sets out formats of multivalent antibodies of the invention, including different binding domain structures, linkers and base antibody portions.

An "antibody" is a proteinaceous molecule belonging to the immunoglobulin class of proteins, containing one or more domains that bind an epitope on an antigen, where such domains are derived from or share sequence homology with the variable region of an antibody. Antibody binding has different qualities including specificity and affinity. The specificity determines which antigen or epitope thereof is specifically bound by the binding domain. The affinity is a measure for the strength of binding to a particular antigen or epitope. It is convenient to note here that the 'specificity' of an antibody refers to its selectivity for a particular antigen, whereas 'affinity' refers to the strength of the interaction between the antibody's antigen binding site and the epitope it binds.

Thus, the "binding specificity" as used herein refers to the ability of an individual antibody binding site to react with an antigenic determinant. Typically, the binding site of the antibody of the invention is located in the Fab domains and is constructed from a hypervariable region of a heavy and/or light chains.

"Affinity" is the strength of the interaction between a single antigen-binding site and its antigen. A single antigen-binding site of an antibody of the invention for an antigen may be expressed in terms of the dissociation constant (KD). Typically, antibodies for therapeutic applications may have affinities of up to $1 \times 10^{10}$ M or even higher.

An "antigen" is a molecule capable of inducing an immune response (to produce an antibody) in a host organism and/or being targeted by an antibody. At the molecular level, an antigen is characterized by its ability to be bound by the antigen-binding site of an antibody. Also mixtures of antigens can be regarded as an 'antigen', i.e. the skilled person would appreciate that sometimes a lysate of tumor cells, or viral particles may be indicated as 'antigen' whereas such tumor cell lysate or viral particle preparation exists of many antigenic determinants. An antigen comprises at least one, but often more, epitopes.

An "epitope" or "antigenic determinant" is a site on an antigen to which an immunoglobulin or antibody specifically binds. Epitopes can be formed from contiguous amino acids or noncontiguous amino acids juxtaposed by tertiary folding of a protein (so-called linear and conformational epitopes, respectively). Epitopes formed from contiguous, linear amino acids are typically retained on exposure to denaturing solvents, whereas epitopes formed by tertiary folding, conformation are typically lost on treatment with denaturing solvents. An epitope may typically include 3, 4, 5, 6, 7, 8, 9, 10, 11, 12, 13, 14 or 15 amino acids in a unique spatial conformation.

The term "heavy chain" or "immunoglobulin heavy chain" includes an immunoglobulin heavy chain constant region sequence from any organism, and unless otherwise specified includes a heavy chain variable domain. The term heavy chain variable domains include three heavy chain CDRs and four FR regions, unless otherwise specified. Fragments of heavy chains include CDRs, CDRs and FRs, and combinations thereof. A typical heavy chain has, following the variable domain (from N-terminal to C-terminal), a CH1 domain, a hinge, a CH2 domain, and a CH3 domain. A functional fragment of a heavy chain includes a fragment that is capable of specifically recognizing an antigen and that comprises at least one CDR.

The term "light chain" includes an immunoglobulin light chain variable domain, or $V_L$ (or functional fragment thereof); and an immunoglobulin constant domain, or $C_L$ (or functional fragment thereof) sequence from any organism. Unless otherwise specified, the term light chain may include a light chain selected from a human kappa, lambda, and a combination thereof. Light chain variable ($V_L$) domains typically include three light chain CDRs and four framework (FR) regions, unless otherwise specified. Generally, a full-length light chain includes, from N-terminus to C-terminus, a $V_L$ domain that includes FR1-CDR1-FR2-CDR2-FR3-CDR3-FR4, and a light chain constant domain. Light chains that can be used with this invention include those, e.g., that do not selectively bind an epitope selectively bound by the heavy chains.

Suitable light chains for use in a multivalent antibody invention include a common light chain, such as those that can be identified by screening for the most commonly employed light chains in existing antibody libraries (wet libraries or in silico), where the light chains do not substantially interfere with the affinity and/or selectivity of the epitope-binding domains of the heavy chains, but are also suitable to pair with an array of heavy chains. For example, a suitable light chain includes one from a transgenic animal, such as a transgenic rodent, comprising the common light chain integrated into its genome and which can be used to generate large panels of common light chain antibodies having diversity at the heavy chain upon exposure to an antigen.

The term "common light chain" according to the invention refers to light chains which may be identical or have some amino acid sequence differences while the binding specificity of the an antibody of the invention is not affected, i.e. the differences do not materially influence the formation of functional binding regions.

It is for instance possible within the scope of the definition of common chains as used herein, to prepare or find variable chains that are not identical but still functionally equivalent, e.g., by introducing and testing conservative amino acid changes, changes of amino acids in regions that do not or only partly contribute to binding specificity when paired with a cognate chain, and the like. Such variants are thus also capable of binding different cognate chains and forming functional antigen binding domains. The term 'common light chain' as used herein thus refers to light chains which may be identical or have some amino acid sequence differences while retaining the binding specificity of the resulting antibody after pairing with a heavy chain. A combination of a certain common light chain and such functionally equivalent variants is encompassed within the term "common light chain".

A "Fv domain" means a binding domain comprising a heavy chain variable region (VH) and a light chain variable region (VL).

A "Fab domain" means a binding domain comprising a variable region, typically a binding domain comprising a paired heavy chain variable region and light chain variable region. A Fab domain may comprise constant region domains, including a CH1 and a VH domain paired with a constant light domain (CL) and VL domain. Such pairing may take place, for example, as covalent linkage via a disulfide bridge at the CH1 and CL domains.

A "modified Fab domain" means a binding domain comprising a CH1 and a VH domain, wherein the VH is paired with a VL domain and no CL domain is present. Alternatively, a modified Fab domain is a binding domain comprising a CL and a VL domain, wherein the VL is paired with a VH domain and no CH1 domain is present. In order that the CH1 or CL region can be present in a non-paired form, it may be necessary to remove or reduce the lengths of regions of hydrophobicity. CH1 regions from species of animal that naturally express single-chain antibodies, for example from a camelid animal, such as a llama or a camel, or from a shark may be used. Other examples of a modified Fab domain include a constant region, CH1 or CL, which is not paired with its cognate region and/or a variable region VH or VL, is present, which is not paired with its cognate region.

The term "immune effector cell" or 'effector cell' as used herein refers to a cell within the natural repertoire of cells in the mammalian immune system which can be activated to affect the viability of a target cell. Immune effector cells include cells of the lymphoid lineage such as natural killer (NK) cells, T cells including cytotoxic T cells, or B cells, but also cells of the myeloid lineage can be regarded as immune effector cells, such as monocytes or macrophages, dendritic cells and neutrophilic granulocytes. Hence, said effector cell is preferably an NK cell, a T cell, a B cell, a monocyte, a macrophage, a dendritic cell or a neutrophilic granulocyte.

"Percent (%) identity" as referring to nucleic acid or amino acid sequences herein is defined as the percentage of residues in a candidate sequence that are identical with the residues in a selected sequence, after aligning the sequences for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/based or amino acids. The sequence identity is the percentage of identical matches between the two sequences over the reported aligned region.

A comparison of sequences and determination of percentage of sequence identity between two sequences can be accomplished using a mathematical algorithm. The skilled person will be aware of the fact that several different computer programs are available to align two sequences and determine the identity between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent sequence identity between two amino acid sequences or nucleic acid sequences may be determined using the Needleman and Wunsch algorithm for the alignment of two sequences. (Needleman, S. B. and Wunsch, C. D. (1970) J. Mol. Biol. 48, 443-453). The Needleman-Wunsch algorithm has been implemented in the computer program NEEDLE. For the purpose of this invention the NEEDLE program from the EMBOSS package is used to determine percent identity of amino acid and nucleic acid sequences (version 2.8.0 or higher, EMBOSS: The European Molecular Biology Open Software Suite (2000) Rice, P. Longden J. and Bleasby, A. Trends in Genetics 16, (6) pp 276-277, http://emboss.bioinformatics.nl/). For protein sequences, EBLOSUM62 is used for the substitution matrix. For DNA sequences, DNAFULL is used. The parameters used are a gap-open penalty of 10 and a gap extension penalty of 0.5.

After alignment by the program NEEDLE as described above the percentage of sequence identity between a query sequence and a sequence of the invention is calculated as follows: Number of corresponding positions in the alignment showing an identical amino acid or identical nucleotide in both sequences divided by the total length of the alignment after subtraction of the total number of gaps in the alignment.

Herein, the term "connected" refers to domains which are joined to each other by way of peptide bonds at the primary amino acid sequence. For example, a heavy chain of a base antibody portion comprising VH-CH1-CH2-CH3 may be connected to a heavy chain of an additional binding domain VH-CH1 (or an additional binding domain to an additional binding domain) via a linker (connecting the heavy chain of the additional binding domain at the CH1 to the VH region of the base antibody portion), which together constitutes one polypeptide chain. Similarly, a CH1 domain may be connected to a variable heavy region and a CL domain may be connected to a variable light region.

"Pairing" refers to interactions between the polypeptides constituting a multivalent antibody of the invention such that they may multimerize. For example, an additional binding domain may comprise a heavy chain region (VH-CH1) paired to a light chain region (VL-CL), where the CH1 and CL pair to form said binding domain. As described herein, pairing of antibody domains (e.g., heavy and light) occurs due to noncovalent interactions and also via disulphide bonds, and can be engineered through techniques disclosed herein and by methods known in the art.

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

The invention provides a multivalent antibody which comprises:
  a base antibody portion which comprises two binding domains; and
  at least one additional binding domain,
  wherein the base antibody portion is connected by a linker to the at least one additional binding domain,
  wherein each binding domain of the base antibody portion and each of the at least one additional binding domains all have a common variable region, and wherein the linker comprises a hinge sequence or a sequence derived from a hinge sequence.

The invention also provides a multivalent antibody which comprises:
- a base antibody portion which comprises two binding domains; and
- at least one additional binding domain, wherein at least one additional binding domain comprises a CH1 region and is connected to the base antibody portion by said linker, linking a variable region of the base antibody portion and the CH1 region, and wherein the multivalent antibody binds to at least three different epitopes.

In such a multivalent antibody, each binding domain of the base antibody portion and each of the at least one additional binding domains may all have a common variable region, The invention thus provides a multivalent antibody which is typically capable of binding to its target or targets via at least three binding domains, i.e. the antibody is a multivalent antibody. The multivalent antibody may optionally be a multispecific antibody. That is to say, an antibody of the invention may be capable of binding two or more different epitopes or two or more different antigens, for example two, three, four or more different epitopes or antigens.

Different Formats of the Multivalent Antibodies

It should be noted that other features and aspects of the invention are apparent from the detailed description, taken in conjunction with the accompanying drawings, which illustrate, by way of example, the features in accordance with embodiments of the invention. The figures are exemplary and are not intended to nor do they limit the scope of the invention, which is defined by the claims and the full extent of the detailed disclosure, which describe and enable the inventions set out herein. A multivalent antibody of the invention may comprise a base antibody portion and an additional binding domain, preferably a Fab domain comprising a VH-CH1 region paired to a VL-CL region. Said multivalent antibody comprises three VH regions, and three VL regions. Either of the VH or VL may be a common variable region (VHc or VLc) paired to a rearranged variable region of the cognate chain. For example, the three VL regions may be a common chain (VLc), and each VH region (VH1-VH3) may comprise a rearranged variable region, wherein said VH1, VH2 and VH3 regions may bind the same epitope or up to three different epitopes. Wherein, the multivalent antibody comprises a common light chain (VLc) and three heavy chain variable regions (VH1-VH3), the additional Fab domain comprised of a VH3-CH1 paired with a VLc-CL may be connected to the base antibody via a linker positioned between a VH1 or VH2 region of the base antibody portion and CH1 of the additional Fab domain. See, for example, FIG. 1a.

Alternatively, the additional Fab domain may be connected to the base antibody via a linker positioned between the common light chain region (VLc) of the base antibody and the CL region of the additional Fab domain. See, for example, FIG. 1b. In another aspect of the invention, the three VH regions may be a common chain (VHc), and each VL region may comprise a rearranged variable region, wherein said three VL regions may bind the same or differing epitopes (VL1-VL3). Wherein the multivalent antibody comprises a common heavy chain (VHc) and three light chain variable regions (VL1-VL3), the additional Fab domain may be connected to the base antibody via a linker positioned between a VL1 or VL2 region of the base antibody portion and CL of the additional Fab domain. See, for example, FIG. 1c. Alternatively, the additional Fab domain may be connected to the base antibody via a linker positioned between the common heavy chain region (VHc) of the base antibody and the CH1 region of the additional Fab domain. See, for example, FIG. 1d.

Alternatively, the additional Fab domain may be connected to the base antibody via a linker positioned between both the heavy and light variable regions of the base antibody and the CH1 and CL regions of the additional Fab domain, irrespective of whether the common chain is heavy or light. See, for example, FIG. 1e.

A multivalent antibody of the invention may comprise a base antibody portion and more than one additional binding domain, for example two Fab domains. Either the VH or VL regions of said multivalent antibody may be a common variable region (e.g., VHc or VLc) with the cognate chain comprising a rearranged variable region binding the same or different antigen or epitope (e.g., VHc and VL1-VL4; or VH1-VH4 and VLc). The additional Fab domains may be connected to the base antibody portion via a linker positioned between the common chain of the base antibody portion (VHc or VLc) and the respective constant region of the common variable region of the additional Fab domains, or the rearranged variable domains (VH1 and VH2; or VL1 and VL2) of the base antibody and the respective constant region of the rearranged variable domain of the additional Fab domains. For example, FIG. 1f depicts a multivalent antibody of the invention comprising a base antibody and two additional Fab domains, wherein the antibody comprises a common light chain (VLc), and four heavy chain variable regions (VH1-VH4), wherein a linker connects the base antibody to the additional Fab domains at rearranged heavy chain variable regions of the base antibody (VH2 and VH3) and the CH1 regions of the additional Fab domains. Alternatively, FIG. 1g depicts a multivalent antibody of the invention, wherein the base antibody is connected to two additional Fab domains at a first rearranged heavy chain region (VH2) to the CH1 region of the first additional Fab domain, and a common light chain variable region (VLc) of the base antibody to the CL region of the second additional Fab domain. Alternatively, FIG. 1h depicts a multivalent antibody of the invention, wherein the base antibody is connected to two additional Fab domains via a linker connecting both common light chain regions (VLc) of the base antibody to the CL regions of the two additional Fab domains. Alternatively, FIG. 1j depicts a multivalent antibody of the invention, wherein the base antibody is connected to a first additional Fab domain via a linker connecting both the rearranged heavy chain variable region (VH3) and the common light chain region (VLc) of the base antibody to the first additional Fab domain at CH1 and CL respectively, and the second additional Fab domain is connected via a linker to the second rearranged heavy chain variable region (VH2) of the base antibody at the CH1 region of the second additional Fab domain. Alternatively, (FIG. 1i) the second additional Fab domain is connected via a linker to the common light chain variable region (VLc) of the base antibody to the CL region of the second additional Fab domain. Alternatively, (FIG. 1k), the second additional Fab domain is connected via a linker to both the second rearranged heavy chain variable region (VH2) and the common light chain (VLc) of the base antibody portion at the CH1 and CL regions of the second additional Fab domain, respectively. The formats described herein and depicted at FIGS. 1f-1k also apply to where the common chain is a heavy chain (VHc) and the multivalent antibody comprises four rearranged light chain variable regions (VL1-VL4) comprising up to four different binding specificities.

Further, two or more additional binding domains may be connected via linkers to only one binding domain of a base antibody portion, such that a first Fab domain is connected to a second Fab domain via a linker, which is then connected to the base antibody portion. That is to say, a first linker is positioned between the base antibody portion and one of the additional Fab domains and a second linker is positioned between the two additional Fab domains. The two linkers may be the same or different.

In another aspect of the invention, the individual proteins that make up the multivalent antibody can mix heavy and light chains within the same protein. For example, a multivalent antibody may be comprised of a first protein comprising the additional Fab domain linked to the base antibody in order from N-terminus to C-terminus of VLc-CL-VH2-CH1-CH2-CH3, such that a linker connects the VLc-CL region of the additional Fab domain to the base antibody portion at VH2-CL. A second protein comprising VH1-CH1, which pairs with the VLc-CL of the first protein. A third protein comprising in order from N-terminus to C-terminus VH3-CH1-CH2-CH3 such that the third and first proteins pair below their respective CH1 regions. And a fourth protein comprises in order from N-terminus to C-terminus VLc-CL, which pairs with the VH2-CH1 of the first protein and VH3-CH1 of the third protein. See for example, FIG. 1*l*.

While the format described and depicted in FIG. 1*l* illustrates use of a common light chain and at least three rearranged heavy chain variable regions (VH1-VH3) comprising up to three different binding specificities, it should be understood that this format applies where the common chain is a heavy chain (VHc) and the multivalent antibody comprises three or more rearranged light chain variable regions (VL1-VL3) comprising up to three different binding specificities.

Another aspect of the invention is a multivalent antibody comprising four proteins, where the common chain is a common light chain. The multivalent antibody is comprised of four proteins in order of N-terminus to C-terminus comprising: a first protein of VH1-CH1-VLc-CL, wherein a linker connects the CH1 to VLc; a second protein of VLc-CL that pairs with the VH1-CH1 to form an additional Fab domain; a third protein comprising VH2-CH1-CH2-CH3, wherein the CH1 of the third protein pairs with the CL of the second protein; and a fourth protein comprising VH3-CH1-CH2-CH3, wherein the third and fourth proteins are paired below the CH1 region, and the second protein (VLc-CL) is paired with the fourth protein at the CH1 region of the fourth protein. See, for example, FIG. 1*m*.

A multivalent antibody of the invention may comprise a base antibody portion and an additional Fab domain, wherein either the VH or VL regions of the multivalent antibody may be a common variable region, and wherein the additional Fab domain may be connected to the base antibody portion via a linker positioned either at the VH (FIG. 1*n*) or VL (FIG. 1o) of the base antibody, wherein said linker simultaneously connects the base antibody to the Fab domain and also pairs the cognate chains of the Fab domain. In such instances said Fab domain may optionally lack a CH1-CL domain, and use the linker to pair the variable domains of the Fab domain.

A multivalent antibody of the invention may comprise a base antibody portion and an additional binding domain which comprises a paired VH and VL. Said additional binding domain which comprises a VH and VL may be paired via a cysteine bridge, formed between the VH and VL, such that it may not require the presence of a CH1 or CL region. See, for example, FIG. 1*p*. Note, a cysteine bridge is depicted in FIG. 1*p*, although the person of ordinary skill in the art understands that additional cysteine bridges are typically present at the CH1/CL interface (not shown in the figures).

A multivalent antibody of the invention may comprise a base antibody portion and an additional modified Fab domain. The modified Fab domain may comprise a modified CH1 such that it does not need to pair with a CL. For example, the CH1 could be a camelid CH1 or based on a camelid CH1, or be modified to lack hydrophobic residues through techniques known in the art. Each VH or VL may be a common or rearranged variable region. The additional modified Fab domain may be connected to the base antibody portion via a linker positioned between the VH2 of the base antibody portion and CH1 of the modified Fab domain. The VH and VL of the modified Fab domain may be paired via a cysteine bridge, or alternatively non-covalent interactions. See, for example, FIG. 1*q*. Alternatively, the additional modified Fab domain may be connected to the base antibody portion via a linker positioned between the VL of the base antibody portion and CH1 of the modified Fab domain. The VH and VL of the modified Fab domain may be paired via a cysteine bridge. See, for example, FIG. 1*r*.

A multivalent antibody of the invention may comprise a base antibody portion and an additional modified Fab domain, wherein the modified Fab domain may comprise a modified CL such that it does not need to pair with a CH1. For example, the CL could be engineered to remove hydrophobic regions. Each VH or VL of the modified Fab domain may be a common or rearranged variable region. The additional modified Fab domain may be connected to the base antibody portion via a linker positioned between the VL of the base antibody portion and CL of the modified Fab domain. The VH and VL of the modified Fab domain may be paired via a cysteine bridge. See, for example, FIG. 1*s*.

A multivalent antibody of the invention may comprise a base antibody portion and an additional modified Fab domain, wherein the modified Fab domain may comprise a modified CL such that it does not need to pair with a CH1. For example, the CL could be engineered to remove hydrophobic regions. Each VH or VL of the modified Fab domain may be a common or rearranged variable region. The additional modified Fab domain may be connected to the base antibody portion via a linker positioned between the VH2 of the base antibody portion and CL of the modified Fab domain. The VH and VL of the modified Fab domain may be paired via a cysteine bridge. See, for example, Figure 1*t*.

Base Antibody Portion of the Invention

Figure 1B:
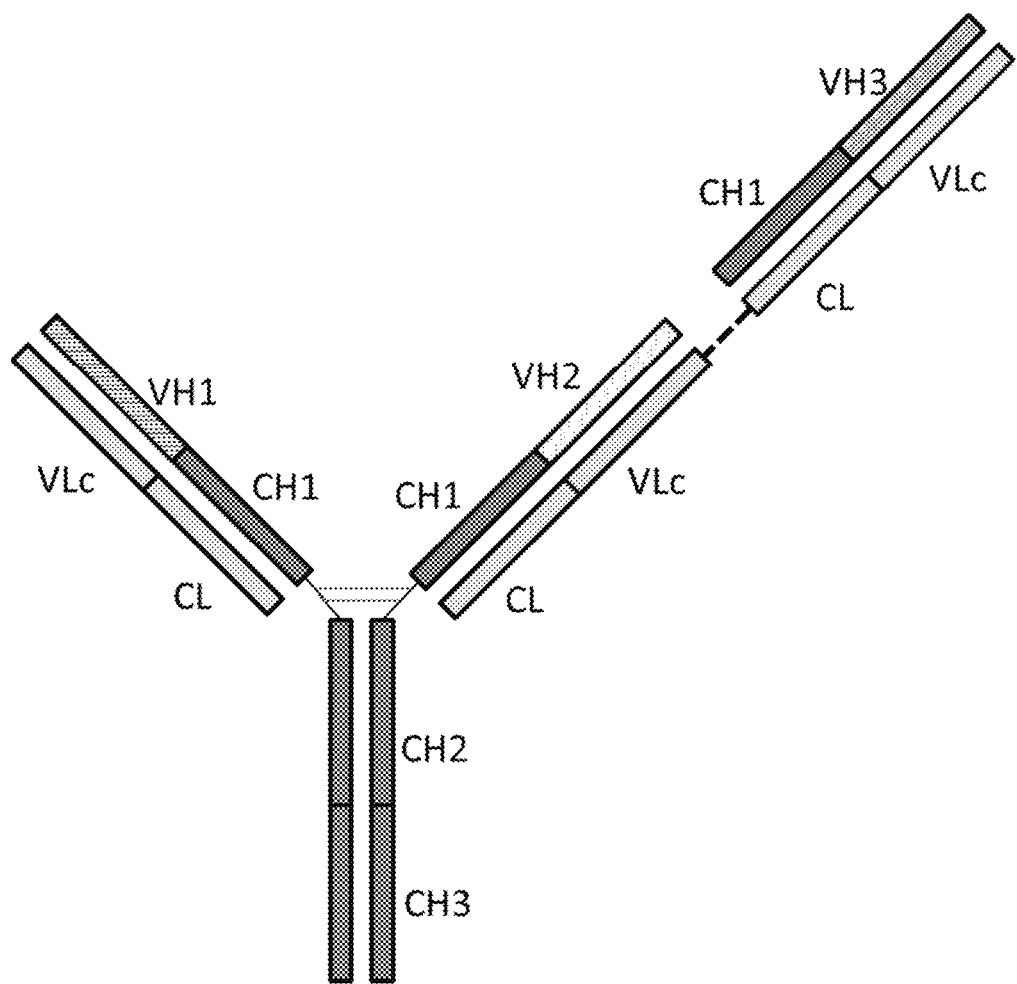
Figure 1C:
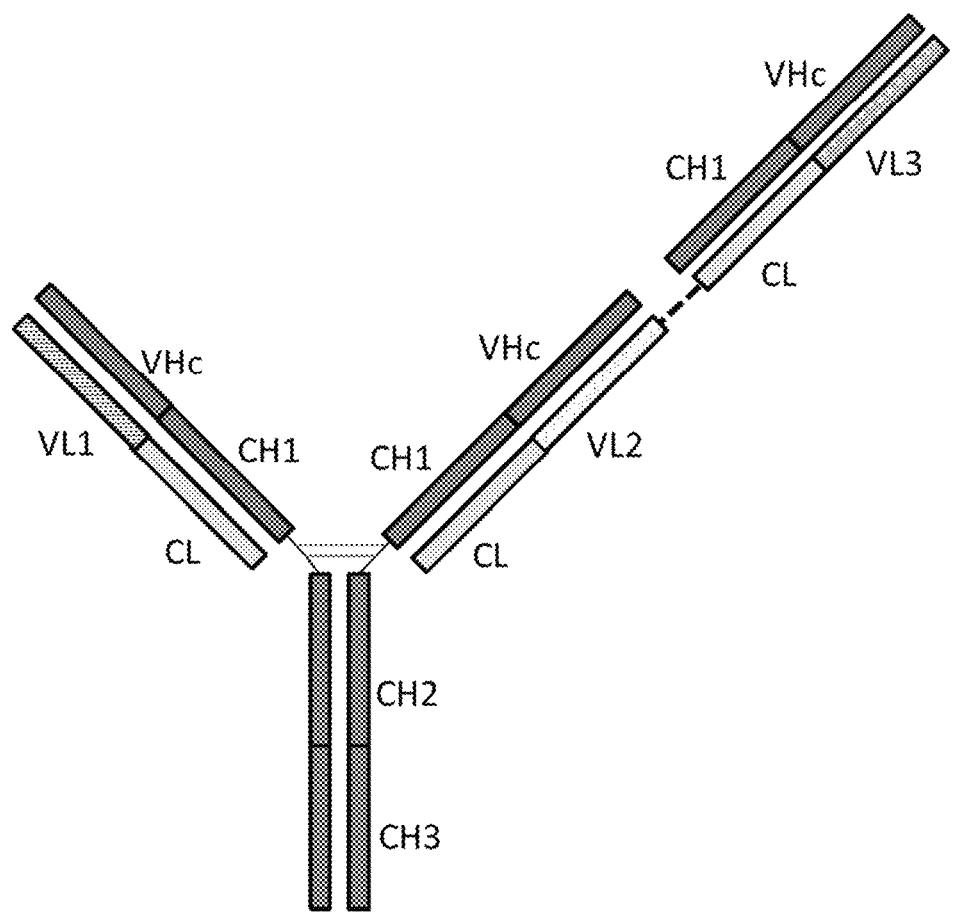
Figure 1D:
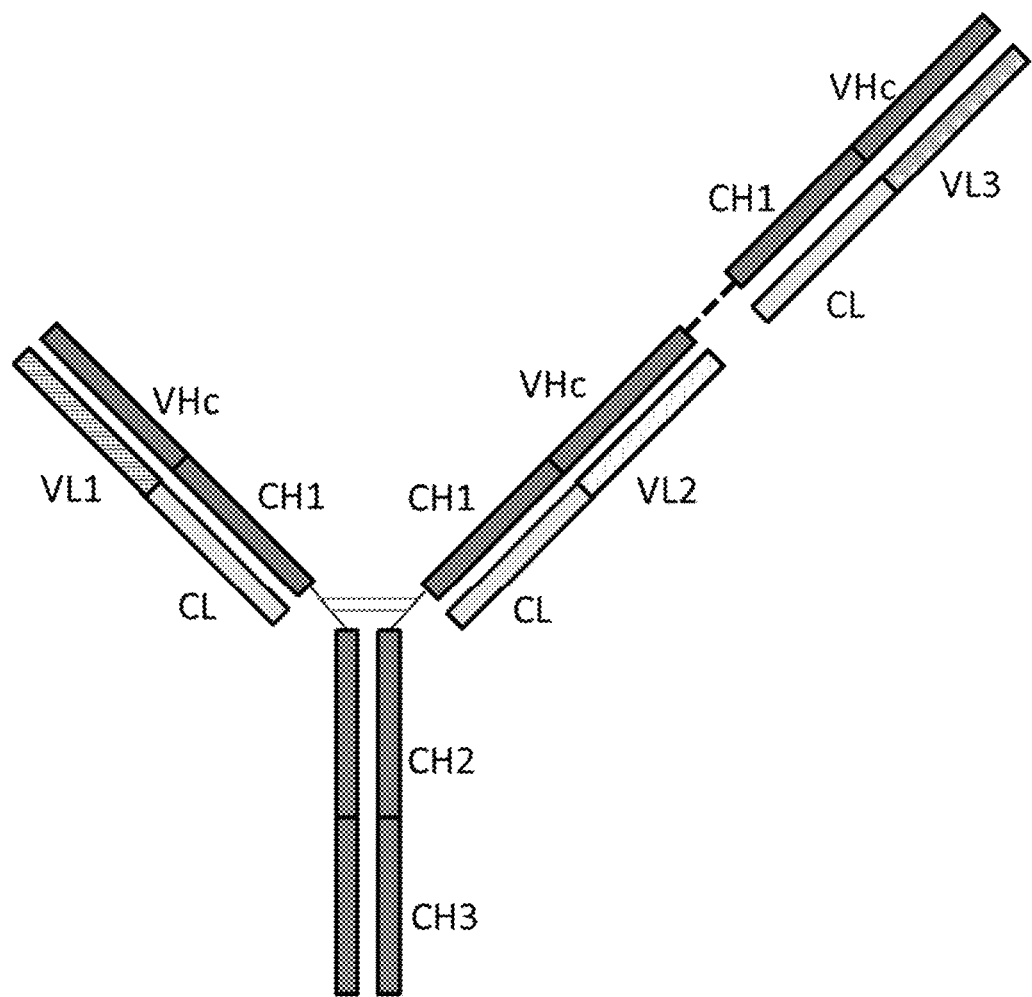
Figure 1E:
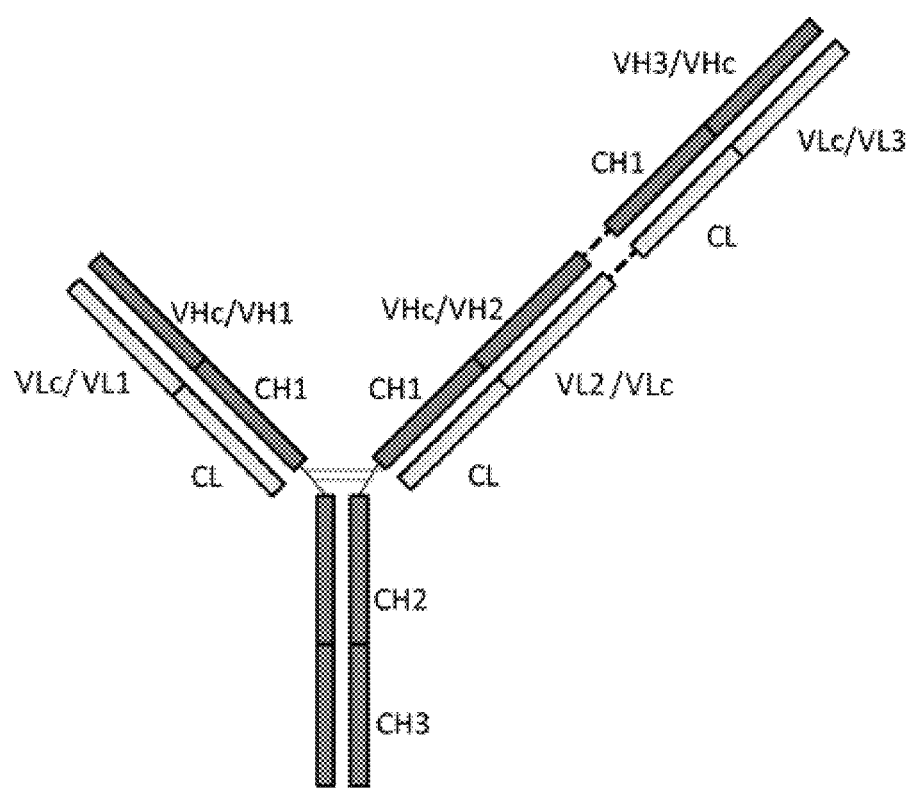
Figure 1F:
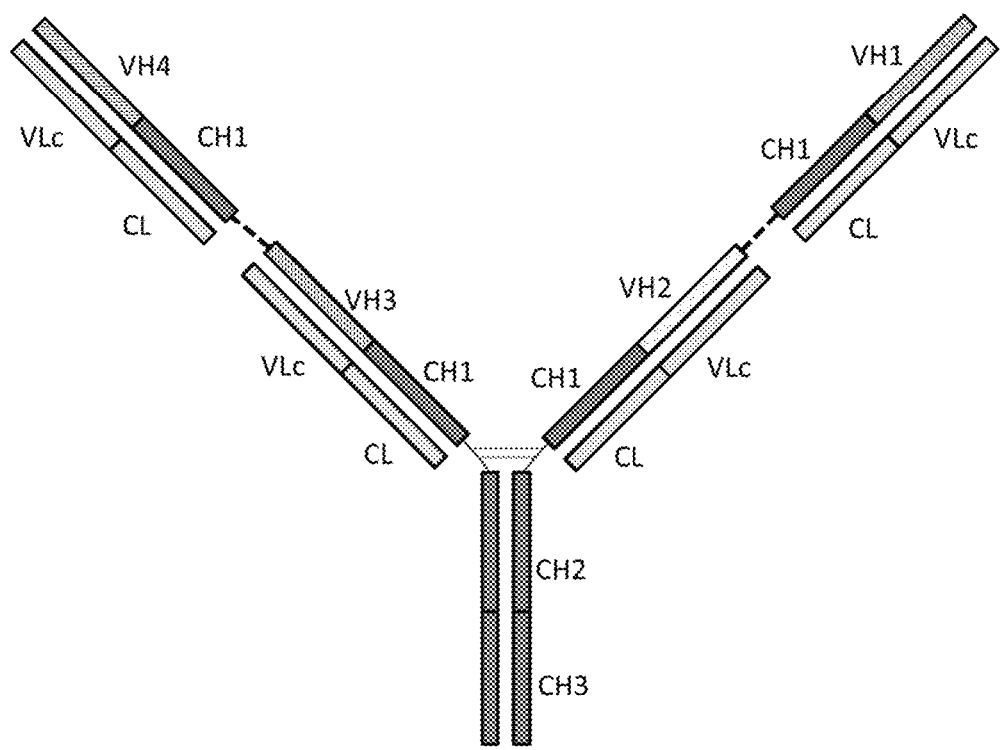
Figure 1G:
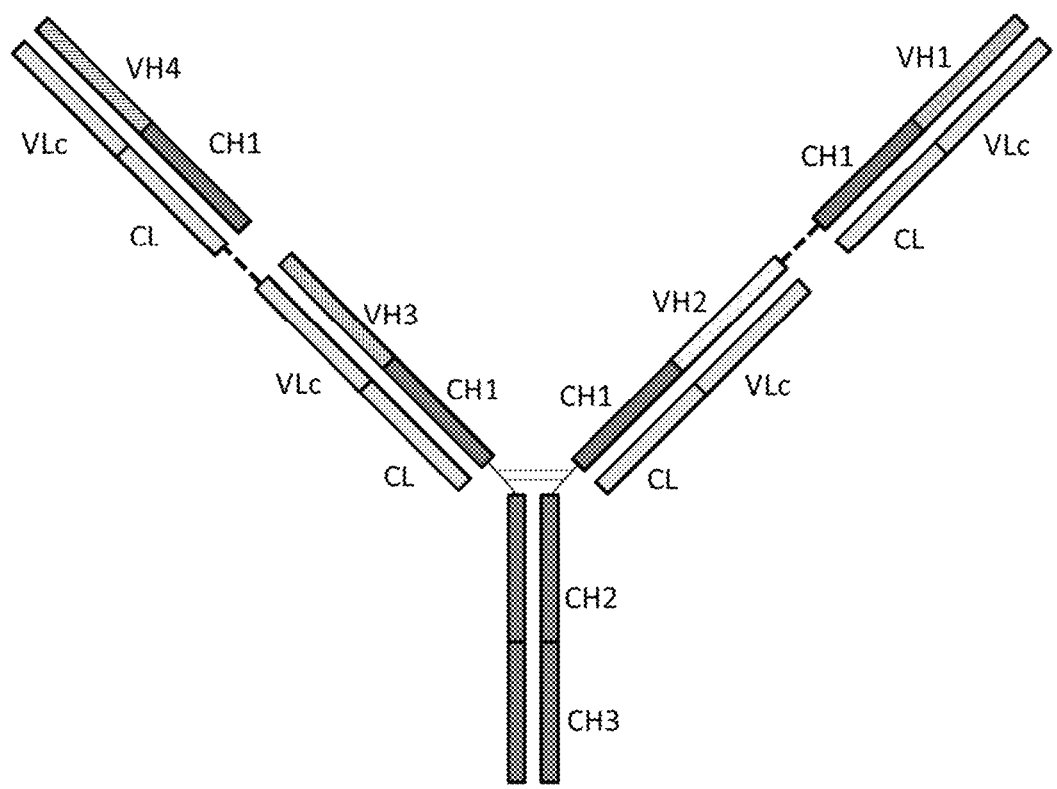
Figure 1H:
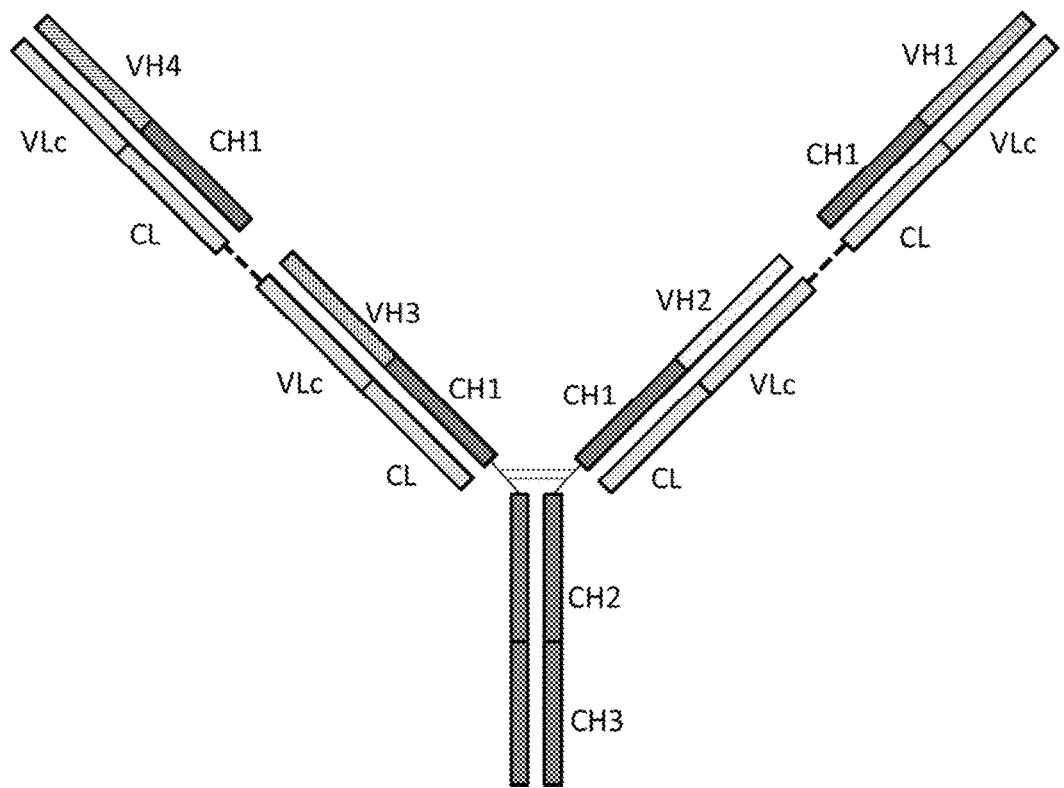
Figure 1I:
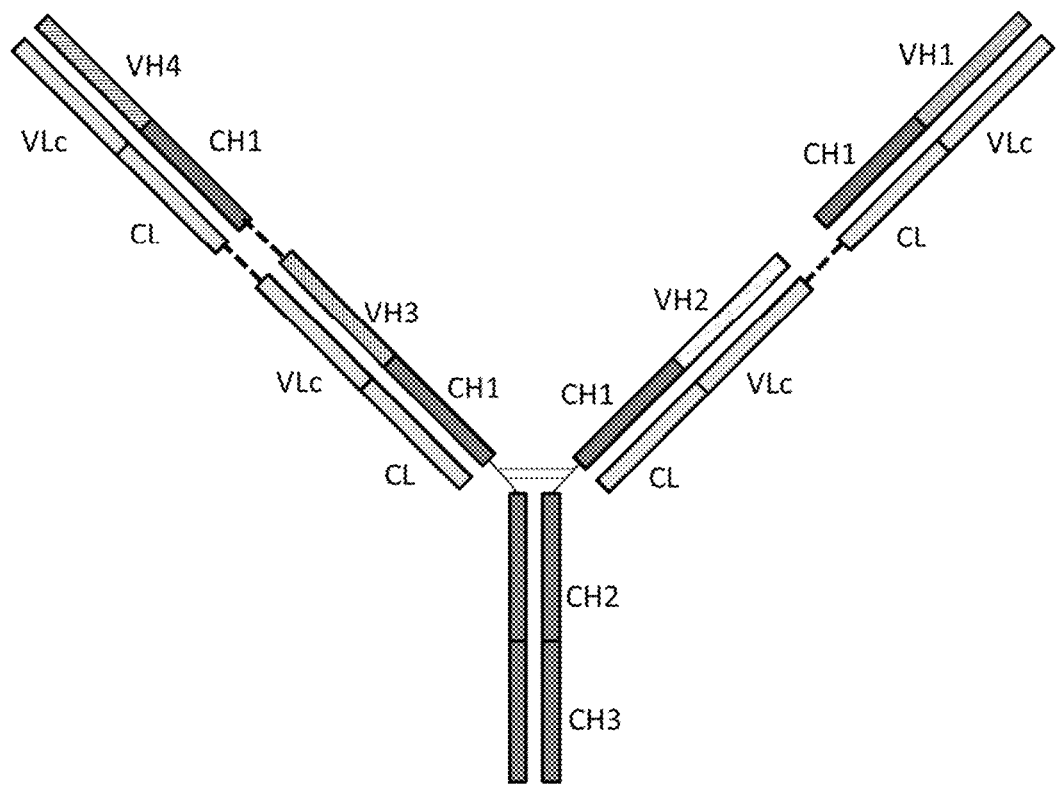
Figure 1J:
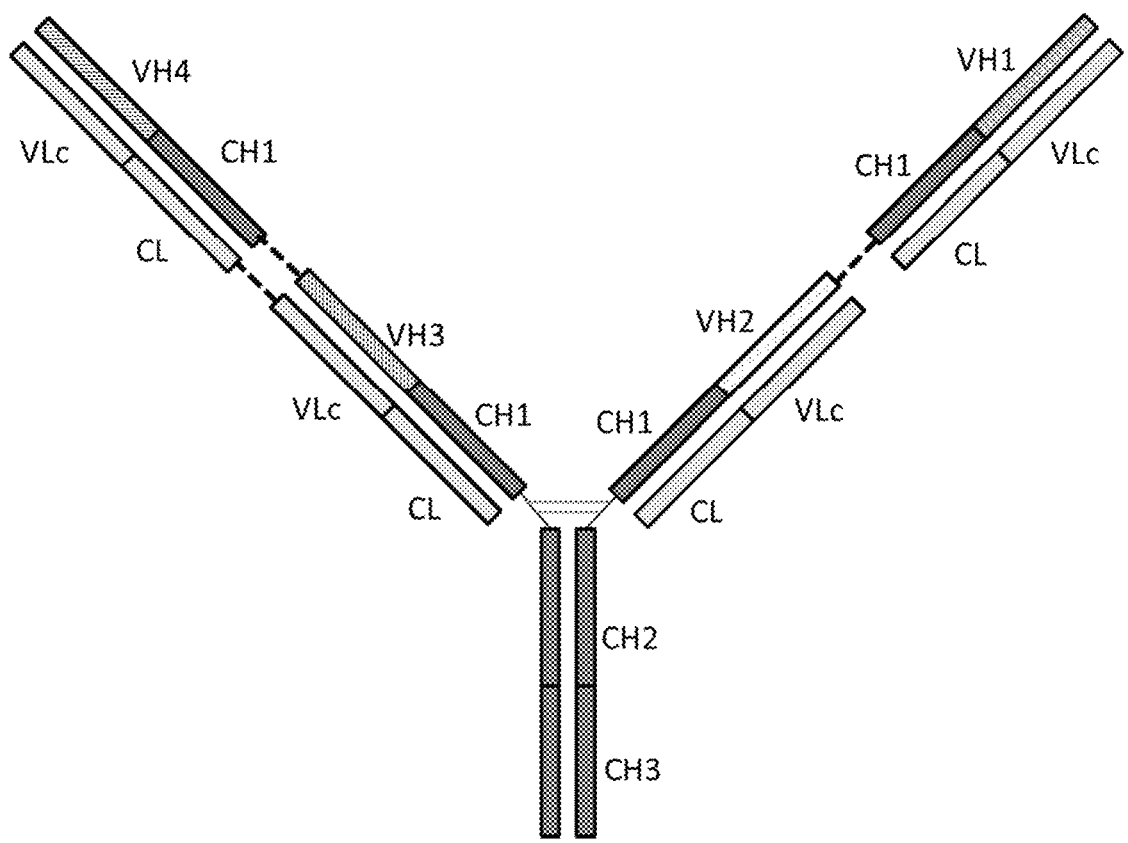
Figure 1K:
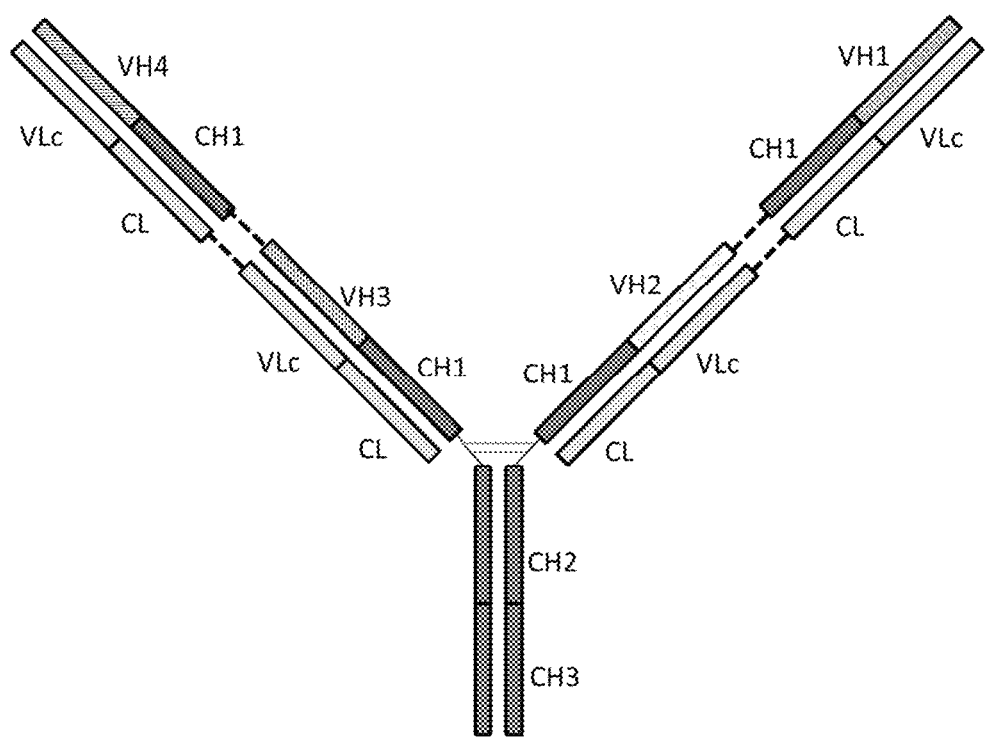
Figure 1I:
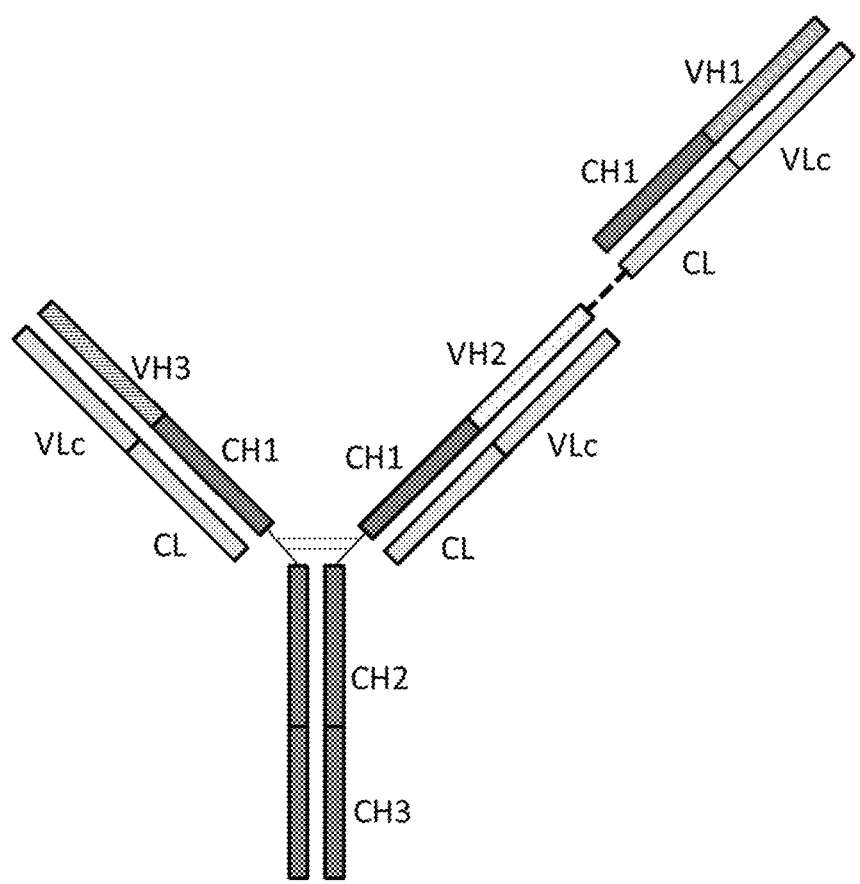
Figure 1M:
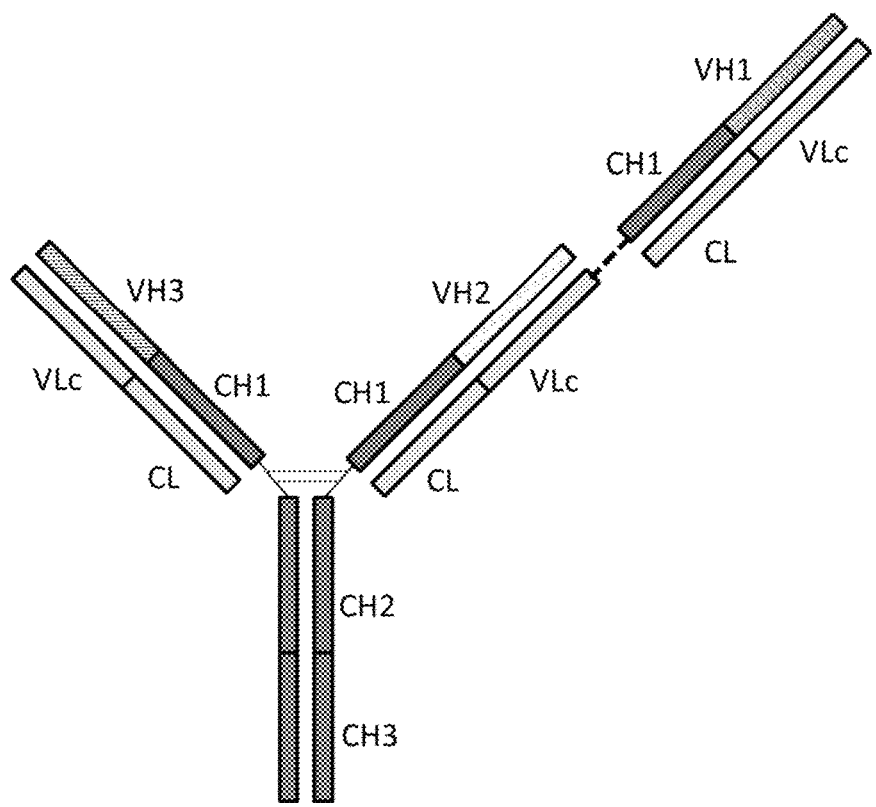
Figure 1N:
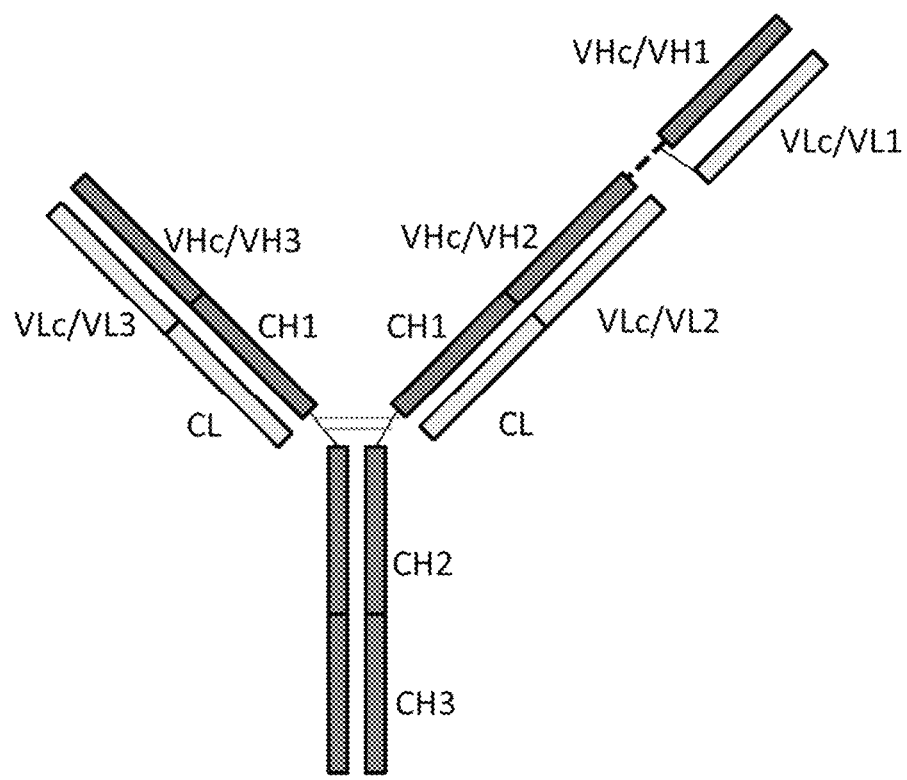
Figure 1O:
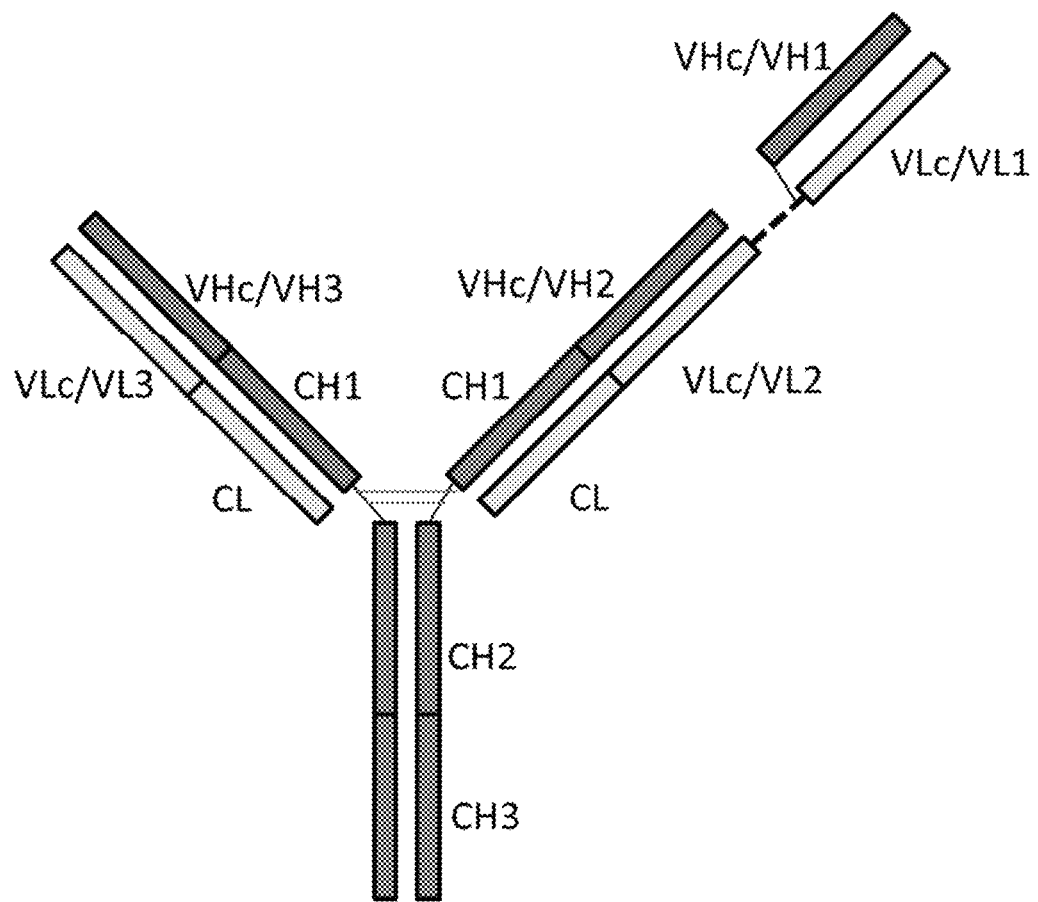
Figure 1P:
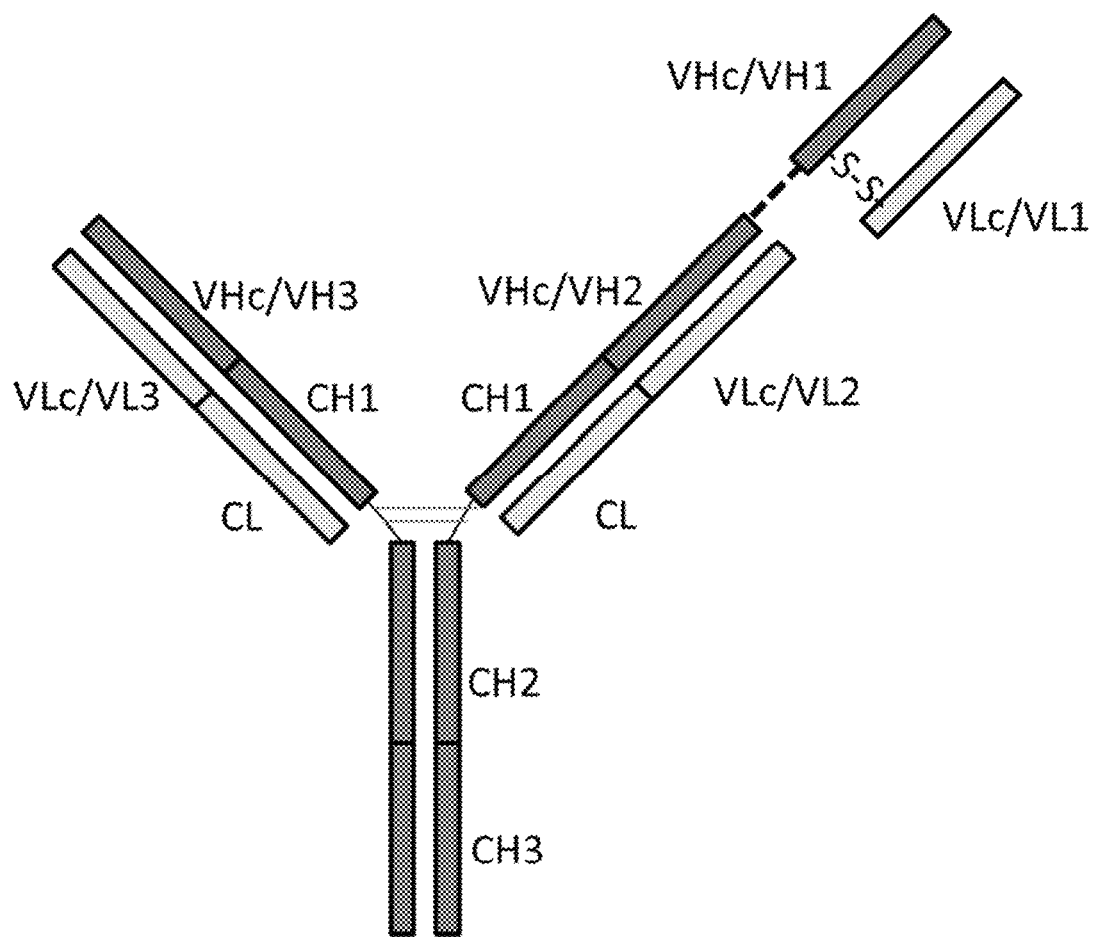
Figure 1Q:
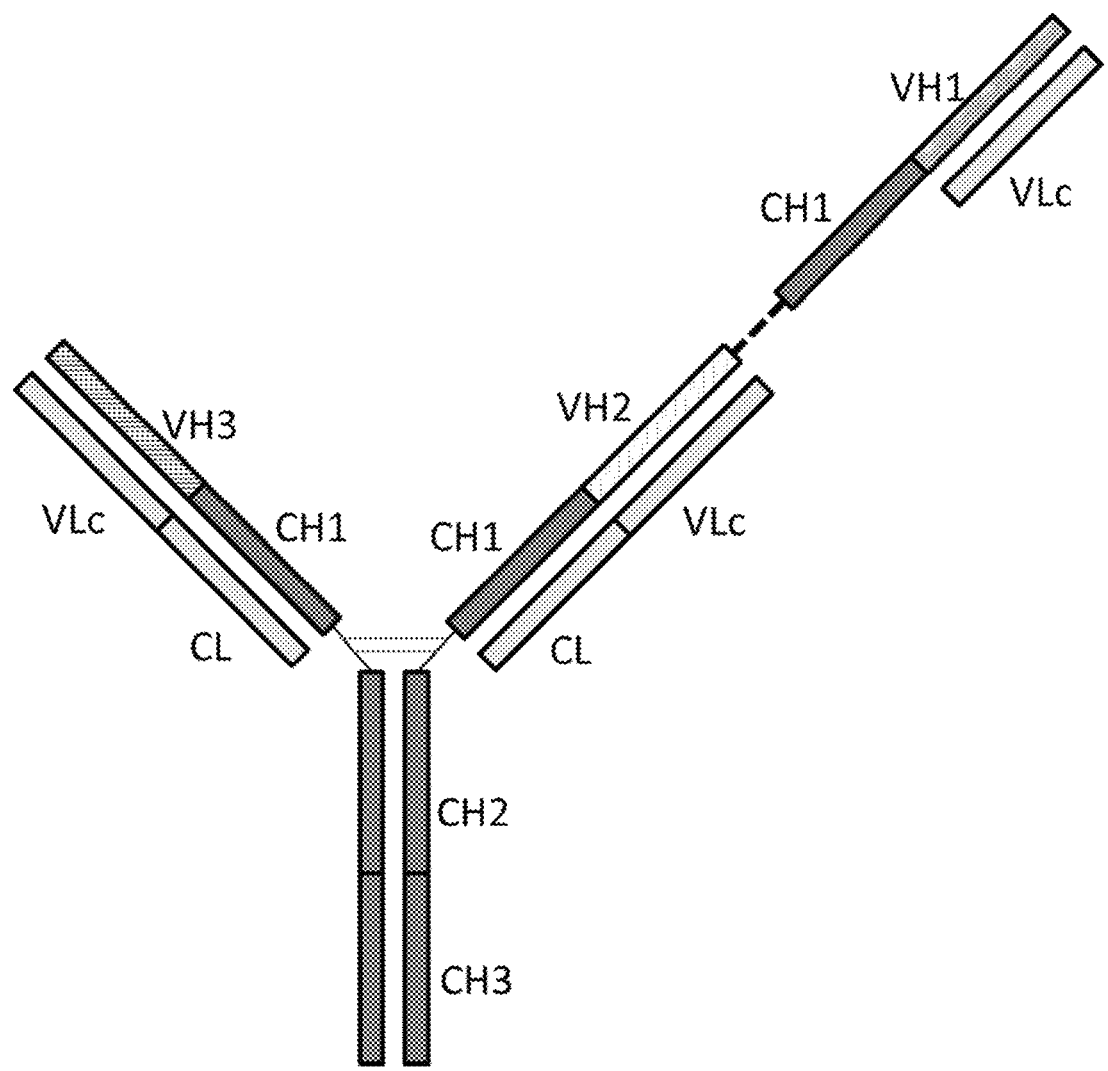
Figure 1R:
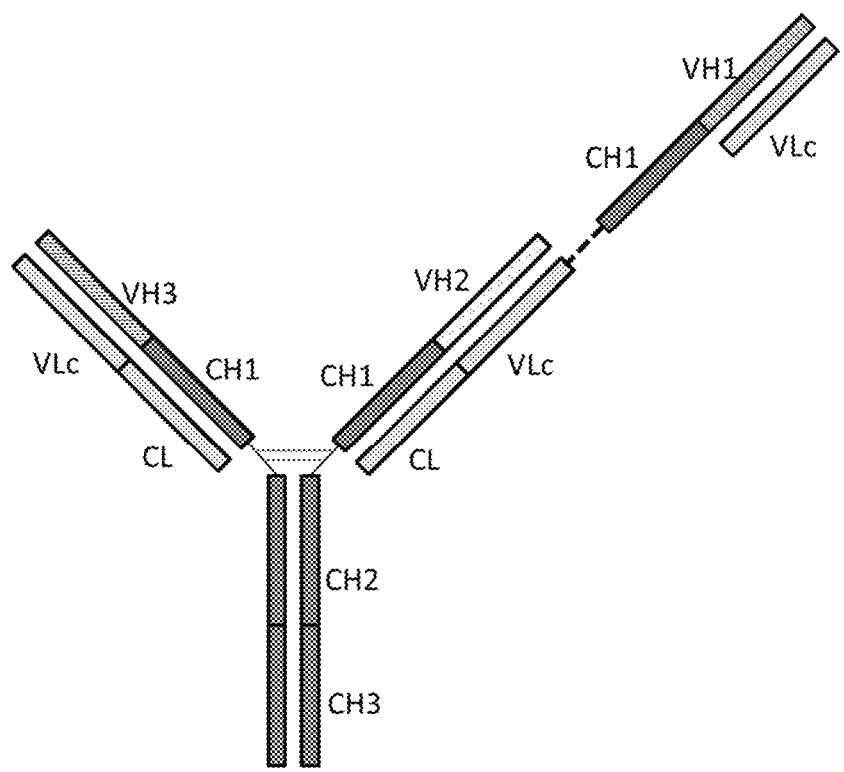
Figure 1S:
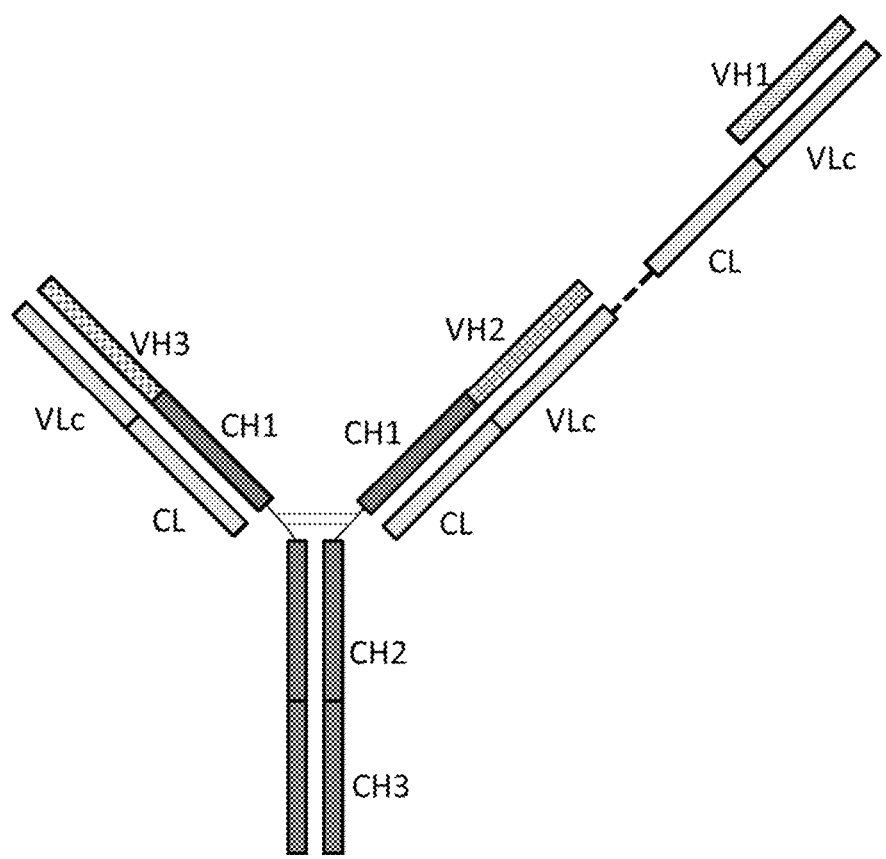
Figure 1T:
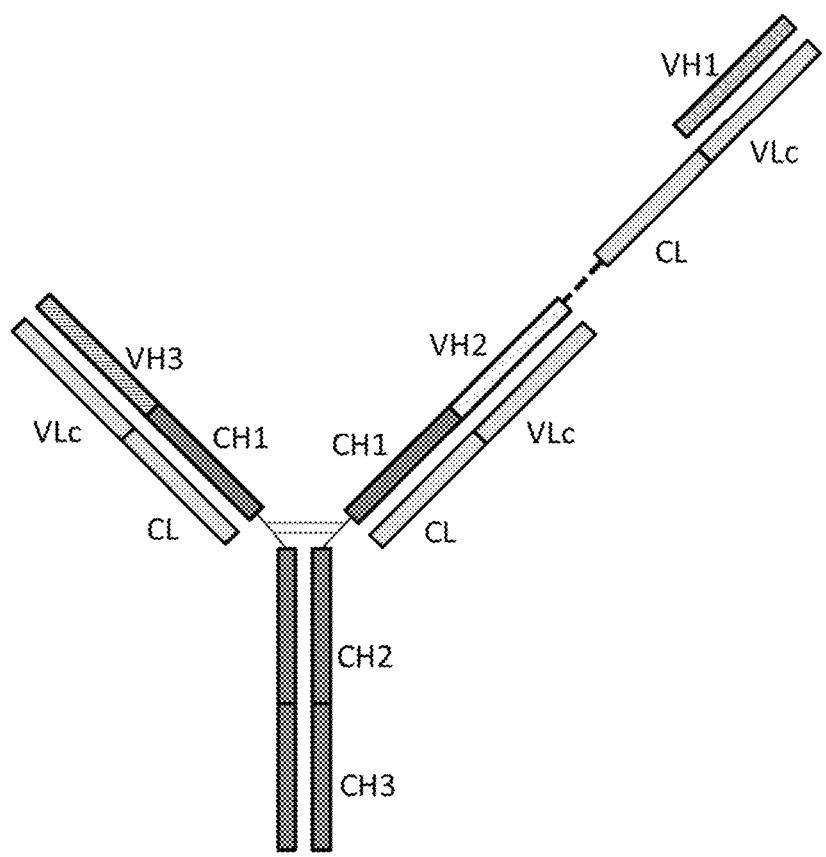
Figure 1U:
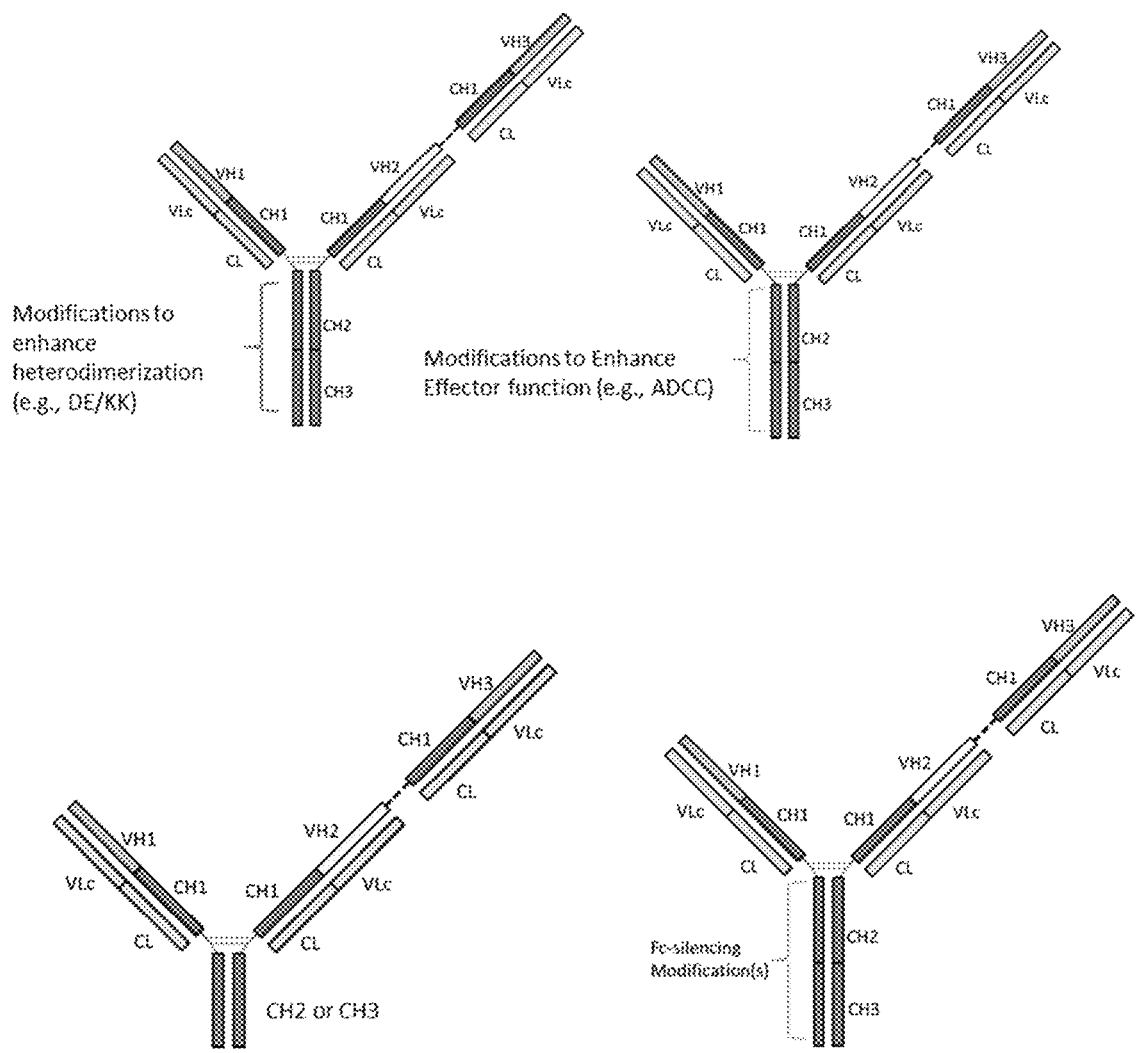

It should be noted that while FIGS. 1*a*-1*u* depict a base antibody portion of the multivalent antibody as including paired heavy chain constant regions comprising CH2 and CH3 regions, these regions are shown merely for illustrative purposes and the invention is not limited to these embodiments. Herein is described different formats for the base antibody portion and additional binding domain suitable for use in the antibodies disclosed.

The base antibody portion of the multivalent antibody of the invention may be a full length immunoglobulin, for example a full length IgG, IgA, IgE, IgD or IgM portion, but preferably IgG, and more preferably IgG1.

In any antibody of the invention, at least one of the additional binding domains, preferably a Fab domain, may comprise a CH1 domain of an immunoglobulin subclass different from that of the CH1 domain(s) of the base antibody portion of the antibody and/or may have a light chain of a different class. For example, where the base portion of the antibody is a full length IgG1, at least one of the additional binding domains may comprise a CH1 domain of the subclass IgG2a, IgG2b, IgG3 or IgG4 and/or where the base portion of the antibody includes a kappa light chain, at least one of the additional binding domain may include a lambda light chain.

The heavy chains of the base antibody may be designed to preferentially pair through techniques known to those of skill in the art, such as engineering the DEKK modifications in the CH3 regions of the base antibody. See WO2013/157954 and De Nardis et al., J. Biol. Chem. (2017) 292(35) 14706-14717 incorporated herein by reference, demonstrating engineering in the CH3 region for driving heterodimerization of the heavy chains. Alternative approaches for driving heterodimerization which may be used in the invention include the knob-in-hole format (WO1998/050431) and use of charge engineering (Gunasekaran, J B C 2010, vol 285, pp 19637-19646).

The Fc region mediates effector functions of an antibody, such as complement-dependent cytotoxicity (CDC), antibody-dependent cellular cytotoxicity (ADCC) and antibody-dependent cell phagocytosis (ADCP). Depending on the multivalent antibody, it may be desired to either reduce or increase the effector function. Reduced effector function can be desired when an immune response is to be activated, enhanced or stimulated as in some of the embodiments of the invention. Antibodies with reduced effector functions can be used to target cell-surface molecules of immune cells, among others. Increased effector function can be desired when an antibody is targeting harmful cells, thereby boosting the ability of immune effector cells or the complement cascade to eliminate or lyse such targets.

The effector function of the heavy chain Fc region can be mitigated or eliminated through modifications known to those of ordinary skill in the art. Similarly, the effector function of the heavy chain Fc region can be enhanced through modifications known to those of ordinary skill in the art. For example, ADCC may be enhanced via the genetic modification of the CH2 domain. See, for example, Strohl, Curr. Opin. Biotechnol. 2009 (6) 685-91.

A multivalent antibody of the invention can in one embodiment be afucosylated. A multivalent antibody of the invention preferably comprises a reduced amount of fucosylation of the N-linked carbohydrate structure in the Fc region, when compared to the same antibody produced in a normal CHO cell.

An aspect of the multivalent antibody of the invention also includes a base antibody, which lacks a CH2 or CH3 region, wherein said heavy chains of the base antibody portion may be joined by a cysteine covalent bridge below the CH1 region.

Aspects of the invention, including variations to the base antibody portion of the invention are illustrated at FIG. 1u.

Herein is described a repertoire of linkers that can be used to connect the base portion of the antibody of the invention with one or more binding domains. One or more binding domains, such as a variable region, an Fv domain, a Fab domain or a modified Fab domain, may be connected to the base antibody portion of an antibody of the invention.

The antibody of the invention comprises a base antibody portion and, attached thereto, via a linker or linkers, one or more binding domains.

Multivalent antibodies comprising a full length IgG base antibody portion are preferred because such structures typically have beneficial properties such as a favorable half-life, predictable biophysical behavior and lower immunogenicity. Antibodies of the invention are typically suitable for therapeutic use and therefore are comprised of human sequences for the use of human therapeutics. Alternatively, said antibodies have sequences of the species for which the therapeutic is being used or based on consensus sequences within that given species, using techniques well known to those of ordinary skill in the art.

Where the base antibody portion of an antibody of the invention is a full length IgG, the full length IgG may comprise mutations that provide desired characteristics. Such mutations are typically not deletions of substantial portions of any of the regions. However, full-length IgG portions wherein one or several amino acid residues are inserted, deleted or substituted, without essentially altering the binding characteristics of the resulting IgG portion, are embraced within the term "full length IgG". For instance, such IgG portions can have one or more insertions, deletions or substitutions of between 1 and 10 amino acid residues, preferably in non-CDR regions, wherein the inserted, deleted or substituted amino acids are not essential for the binding specificity of the IgG.

IgG1 may be favored based on its long circulatory half-life in man. Also, in order to mitigate immunogenicity in humans, it is preferred that the base antibody portion of an antibody according to the invention is a human antibody.

The base portion of the antibody of the invention may be a full length immunoglobulin which is defined as comprising an essentially complete antibody. Such an essentially complete antibody may not necessarily have all the functions of an intact antibody.

A full length base portion of an antibody as described herein comprises two heavy and two light chains. Each chain contains constant (C) and variable (V) regions, which can be broken down into domains designated CH1, CH2, CH3, VH for the heavy chain, and CL, VL for the light chain. The antibody can interact with molecules and cells of the immune system through the constant domains, typically through the Fc portion.

The constant region of an antibody of the present invention, including a bispecific or multispecific antibody, is preferably a human constant region. The constant region may contain one or more, preferably not more than 10, preferably not more than 5 amino-acid differences with the constant region of a naturally occurring human antibody. Various variable domains of antibodies produced herein are derived from a human antibody variable domain library. As such these variable domains are human. The unique CDR regions may be derived from humans, be synthetic or derived from another organism. An antibody or bispecific antibody of the invention is preferably a human or humanized antibody. Suitable heavy chain constant regions are non-limitingly exemplified in Table 21.

An antibody of the invention typically has an intact Fc region that maintains half-life and stability of the multispecific antibody. The Fc may also allow interaction with immune effector molecules such as Fc receptors, complement and FcRn. As understood by persons of skill in the art, techniques are available to design an Fc region to prevent or mitigate interactions with Fc receptors or to enhance interactions with Fc receptor.

The base antibody portion and one or more additional binding domains, for example, Fab domains are connected via one or more linkers. The at least one additional Fab domain may be of a given isotype or subclass, eg, IgG1, 2a, 2d, 3 or 4: at least one additional Fab may be of a different subclass to that of the Fab domains of the full length IgG portion or may carry a light chain of a different class (kappa or lambda).

Linkers for use in the Multivalent Antibody Format

An antibody of the invention comprises one or more linkers which connect the one or more additional binding domains to the base antibody portion. The linker together with the binding domain to which the linker is connected determines, at least in part, the functionality of the multivalent antibody.

In an antibody of the invention, the peptide region of a linker may comprise a hinge sequence or comprise a sequence based on a hinge sequence. Thus, the amino acid sequence of a suitable peptide region may comprise a naturally-occurring sequence or comprise a sequence based on a naturally-occurring sequence. The use of such sequences may help developability of multivalent antibodies of the invention and help to ensure low immunogenicity.

A hinge region is a flexible amino acid stretch in the central part of the heavy chains of the IgG and IgA immunoglobulin classes (i.e., that portion which connects the Fab to the Fc), which pairs these two heavy chains by disulfide bonds. It is rich in cysteine and proline amino acids, and bears little resemblance to any other immunoglobulin region.

Accordingly, a suitable linker to connect the one or more additional binding domains to the base antibody portion for use in a multivalent antibody of the invention may be derived from an IgG or IgA hinge sequence. The linker region may be based on an IgG1 hinge region, an IgG2 hinge region, an IgG3 hinge region or an IgG4 hinge region.

Typically, the type of the hinge region used is matched with the type of the constant region, for example the CH1, of the additional Fab domain to which the linker is connected. That is to say, if a linker is based on a sequence or sequences from a IgG1 hinge region, the CH1 of the additional Fab domain to which it is connected is a CH1 from a IgG1.

A linker of an antibody may be based on an upper, middle or lower hinge region, or a subset of such a region.

The IgG1 hinge region has the sequence: EPKSCDKTHTCPPCPAPELLGG (SEQ ID NO: 42).

The upper hinge region is defined as: EPKSCDKTHT (SEQ ID NO: 43)

The middle hinge region is defined as: CPPCP (SEQ ID NO: 44)

The lower hinge region is defined as: APELLGG (SEQ ID NO: 45)

Thus, in an antibody of the invention, the linker may comprise one or more of these sequences and/or a sequence based on one or more of these sequences.

The IgG2 hinge region has the sequence: ERKCCVECPPCPAPPVAG (SEQ ID NO: 46).

The upper hinge region is defined as: ERKCCVE (SEQ ID NO: 47)

The middle hinge region is defined as: CPPCP (SEQ ID NO: 48)

The lower hinge region is defined as: APPVAG (SEQ ID NO: 49)

Thus, in an antibody of the invention, the linker may comprise one or more of these sequences and/or a sequence based on one or more of these sequences.

The IgG3 hinge region has the sequence: ELKTPLGDTTHTCPRCPEPKSCDTPPPCPRCPEPKSCDTPPPCPRCPEPKSCDTPPPCPRCP APEFLGG (SEQ ID NO: 50) The upper hinge region is defined as: ELKTPLGDTTHT (SEQ ID NO: 51)

The middle hinge region is defined as: CPRCPEPKSCDTPPPCPRCPEPKSCDTPPPCPRCPEPKSCDTPPPCPRCP (SEQ ID NO: 52)

The lower hinge region is defined as: APEFLGG (SEQ ID NO: 53)

The IgG4 hinge region has the sequence: ESKYGPPCPSCPAPEFLGG (SEQ ID NO: 54).

The upper hinge region is defined as: ESKYGPP (SEQ ID NO: 55)

The middle hinge region is defined as: CPSCP (SEQ ID NO: 56)

The lower hinge region is defined as: APEFLGG (SEQ ID NO: 57).

The middle region with consensus sequence CXXC connects both IgG heavy chains in the context of a wildtype IgG and is rigid. These disulfide bridges are not required for the current application and, therefore, where a linker comprises a middle hinge sequence, preferably, one or both Cys residues in the CXXC consensus are substituted, for example with a Ser residue. Thus, in a preferred embodiment CxxC may be SxxS.

A linker suitable for use in a multivalent antibody of the invention may be one based on a middle hinge sequence, for example a sequence which comprises a middle hinge sequence, but which does not comprise a lower and/or an upper hinge sequence. A linker suitable for use in a multivalent antibody of the invention may be one based on an upper hinge sequence, for example a sequence which comprises an upper hinge sequence, but which does not comprise a lower and/or a middle hinge sequence. A linker suitable for use in a multivalent antibody of the invention may be one which does not comprise a middle hinge sequence, for example a sequence which comprises a combination of lower and upper hinge sequences.

Accordingly, the invention provides a linker comprising an amino acid sequence of one of SEQ ID NOs: 3 to 5, 7 to 11 or 13 to 24.

Thus, in an antibody of the invention, the linker may comprise one or more of these sequences and/or a sequence based on one or more of these sequences. A peptide region may consist essentially of a middle region sequence or be based on such as sequence or consist essentially of an upper and a lower region sequence or be based on such sequences.

A linker suitable for use in an antibody of the invention may be defined with reference to a sequence comprising the amino acid sequence of any linker sequence as set out herein in which from 0 to 5 amino acid insertions, deletions, substitutions or additions (or a combination thereof) is made. In some embodiments, the linker comprises an amino acid sequence comprising from 0 to 4, preferably from 0 to 3, preferably from 0 to 2, preferably from 0 to 1 and preferably 0 amino acid insertions, deletions, substitutions or additions (or a combination thereof) with respect to a linker sequence as set out herein.

A suitable linker may be from about 7 to about 29 amino acids in length, for example from about 10 to about 20 amino acids in length. However, a suitable linker may be a short linker, for example from about 7 to about 10 amino acids in length or may be a long linker, for example from about 20 to about 29 amino acids in length.

The linker may comprise an Ig hinge region or comprise a sequence based on an IgG hinge region connected to a CH1 region of the same subclass as the linker and may comprise cysteines for covalent linkage of the common light chain.

A linker suitable for use in an antibody of the invention may be based on an IgG1 hinge region, an IgG2 hinge region, an IgG3 hinge region or an IgG4 hinge region.

If a $(G_4S)_n$ sequence is to be used, preferably it is used in combination with a hinge sequence from an isotype other than IgG or a subclass other than IgG1 and includes a CH1 region.

In an antibody of the invention, the linker may be rigid or flexible may comprise a charged sequence, may be straight or bent.

A rigid sequence for the purposes of this invention is sequence having a Karplus and Schulz flexibility Prediction of about 1.015 or less. A partially flexible sequence is one having a Karplus and Schulz flexibility Prediction of from about 1.015 to about 1.04. A flexible sequence for the purposes of this invention is sequence having a Karplus and Schulz flexibility Prediction of at least about 1.015 (Karplus P A, Schulz G E. Prediction of Chain Flexibility in Proteins—A tool for the Selection of Peptide Antigens. Naturwissenschaften 1985; 72:212-3; http://tools.immuneepitope.org/bcell/). The flexibility prediction is calculated over consecutive windows of 7 residues along the sequence (1 residue step) yielding the predicted "flexibility" index per window. The overall flexibility over the linker sequence is given as the average over the whole sequence.

Removal or Substitution of Cys residues in an IgG hinge region may make a linker based on that hinge more flexible including through replacement of the Cys residue with a serine (Ser). Alternatively, a linker may be a rigid linker in view of the presence of a helix-forming sequence. Accordingly, a middle hinge region, for example the conserved CPPCP (SEQ ID NO:311) motif, may be replaced by a helix-forming sequence, for example (EAAAK)$_2$ (SEQ ID NO:304), which will result in a short rigid helix in the linker. Therefore, in an antibody of the invention, the linker may comprise a helix-forming sequence, for example comprising the amino acid sequence (EAAAK)$_2$ (SEQ ID NO:304). The use of such a sequence may help to add rigidity.

A linker of the invention may, preferably comprise an amino acid sequence as set out in any one of SEQ ID NOs: 3 to 5, 7 to 11 or 13 to 24 or an amino acid sequence having at least about 90% sequence identity to any one thereto, preferably at least about 95% sequence identity to any one thereto, more preferably at least 97% sequence identity to any one thereto, more preferably at least about 98% sequence identity to any one thereto, more preferably at least about 99% sequence identity to any one thereto.

For example, a linker suitable for use in a multivalent antibody of the invention may be defined with reference to a sequence comprising the amino acid sequence of any one of SEQ ID NOs: 1 to 24 in which from 0 to 5 amino acid insertions, deletions, substitutions or additions (or a combination thereof) is made. In some embodiments, the linker comprises an amino acid sequence having from 0 to 4, preferably from 0 to 3, preferably from 0 to 2, preferably from 0 to 1 and preferably 0 amino acid insertions, deletions, substitutions or additions (or a combination thereof) with respect to a sequence set out in SEQ ID NOs: 3 to 5, 7 to 11 or 13 to 24.

A linker suitable for use in a multivalent antibody of the invention may be defined with reference to a sequence comprising the amino acid sequence of any one of SEQ ID NOs: 1 to 24 or an amino acid sequence having at least about 85% sequence identity to any one thereto, such as at least about 90% sequence identity to any one thereto, for example at least about 95% sequence identity to any one thereto, such as at least about 98% sequence identity to any one thereto, for example at least about 99% sequence identity to any one thereto.

Table 1 illustrates how a linker sequence may be connected to CH1 and VH2 regions.

TABLE 1

The underlined sequence is the linker sequence; the flanking sequences are the CH1 region of the additional Fab's CH1 region and the VH2 region of a following heavy chain VH region

| # | Name | Linker sequences (underlined) containing CH1 region and VH sequence preceding and following the linker sequence respectively. In the control IgG1 sequence the CH2 region is present (underlined) |
|---|------|---|
| 1 | IgG1 H | NVNHKPSNTKVDKRVEPKSCDKTHTSPPSPAPELLGGEVQLVESGG GVVQPG (SEQ ID NO: 58) |
| 2 | IgG1 MH | NVNHKPSNTKVDKRVEPKSCDKTHTSPPSPEVQLVESGGGVVQPG (SEQ ID NO: 59) |
| 3 | IgG1 UH | NVNHKPSNTKVDKRVEPKSCDKTHTEVQLVESGGGVVQPG (SEQ ID NO: 60) |
| 4 | IgG1 G4S | NVNHKPSNTKVDKRVEPKSCDGGGGSGGGGSEVQLVESGGGVVQ PG (SEQ ID NO: 61) |
| 5 | IgG1 R | NVNHKPSNTKVDKRVEPKSCDKTHTEAAAKEAAAKAPELLGGEVQL VESGGGVVQPG (SEQ ID NO: 62) |
| 6 | IgG1 UL | NVNHKPSNTKVDKRVEPKSCDKTHTAPELLGGEVQLVESGGGVVQ PG (SEQ ID NO: 63) |
| 7 | IgG2A H | NVDHKPSNTKVDKTVERKSSVESPPSPAPPVAGEVQLVESGGGVV QPG (SEQ ID NO: 64) |
| 8 | IgG2A MH | NVDHKPSNTKVDKTVERKSSVESPPSPEVQLVESGGGVVQPG (SEQ ID NO: 65) |

TABLE 1 -continued

The underlined sequence is the linker sequence;
the flanking sequences are the CH1 region of
the additional Fab's CH1 region and the VH2 region
of a following heavy chain VH region

| # | Name | Linker sequences (underlined) containing CH1 region and VH sequence preceding and following the linker sequence respectively. In the control IgG1 sequence the CH2 region is present (underlined) |
|---|---|---|
| 9 | IgG2A UL | NVDHKPSNTKVDKTV<u>ERKSSVEAPPVAG</u>EVQLVESGGGVVQPG (SEQ ID NO: 66) |
| 10 | IgG2B H | NVDHKPSNTKVDKTV<u>ERKCSVESPPSPAPPVAG</u>EVQLVESGGGVVQPG (SEQ ID NO: 67) |
| 11 | IgG2B MH | NVDHKPSNTKVDKTV<u>ERKCSVESPPSP</u>EVQLVESGGGVVQPG (SEQ ID NO: 68) |
| 12 | IgG2B UL | NVDHKPSNTKVDKTV<u>ERKCSVEAPPVAG</u>EVQLVESGGGVVQPG (SEQ ID NO: 69) |
| 13 | IgG2A G4SL | NVDHKPSNTKVDKTV<u>GGGGSGGGGSAPPVAG</u>EVQLVESGGGVVQPG (SEQ ID NO: 70) |
| 14 | IgG2A G4SS | NVDHKPSNTKVDKTV<u>GGGGSGGGGS</u>EVQLVESGGGVVQPG (SEQ ID NO: 71) |
| 15 | IgG2A R | NVDHKPSNTKVDKTV<u>ERKSSVEEAAAKEAAAKAPPVAG</u>EVQLVESGGGVVQPG (SEQ ID NO: 72) |
| 16 | IgG2B R | NVDHKPSNTKVDKTV<u>ERKCSVEEAAAKEAAAKAPPVAG</u>EVQLVESGGGVVQPG (SEQ ID NO: 73) |
| 17 | IgG3 ULH | NVNHKPSNTKVDKRV<u>ELKTPLGDTTHTAPEFLGG</u>EVQLVESGGGVVQPG (SEQ ID NO: 74) |
| 18 | IgG3 UH | NVNHKPSNTKVDKRV<u>ELKTPLGDTTHT</u>EVQLVESGGGVVQPG (SEQ ID NO: 75) |
| 19 | IgG3 R | NVNHKPSNTKVDKRV<u>ELKTPLGDTTHTEAAAKEAAAKAPEFLGG</u>EVQLVESGGGVVQPG (SEQ ID NO: 76) |
| 20 | IgG4 H | NVDHKPSNTKVDKRV<u>ESKYGPPSPSSPAPEFLGG</u>EVQLVESGGGVVQPG (SEQ ID NO: 77) |
| 21 | IgG4 MH | NVDHKPSNTKVDKRV<u>ESKYGPPSPSSP</u>EVQLVESGGGVVQPG (SEQ ID NO: 78) |
| 22 | IgG4 UL | NVDHKPSNTKVDKRV<u>ESKYGPPAPEFLGG</u>EVQLVESGGGVVQPG (SEQ ID NO: 79) |
| 23 | IgG4 UH | NVDHKPSNTKVDKRV<u>ESKYGPP</u>EVQLVESGGGVVQPG (SEQ ID NO: 80) |
| 24 | IgG4 R | NVDHKPSNTKVDKRV<u>ESKYGPPEAAAKEAAAKAPEFLGG</u>EVQLVESGGGVVQPG (SEQ ID NO: 81) |
| 25 | IgG1 hinge | NVNHKPSNTKVDKRV<u>EPKSCDKTHTCPPCPAPELLGGPSVFLFPPKPKDTLM</u> (SEQ ID NO: 82) |

Note,
the VH2 sequence, following the linker (underscored above) may vary, depending on the specific variable region used. In other embodiments, the sequence following the linker may be a light chain variable region, including a common light chain.

Use of Linkers to Pair Regions of the Additional Binding Domain

The linkers used herein may connect the base antibody portion to the at least one additional binding domain. In addition, where the at least one additional binding domain is a Fab domain or is comprised of pairing of a heavy chain variable region and a light chain variable region, the linker may pair the heavy and light chains via covalent linkage, typically via a disulphide bridge. The disulphide bridge may form between a cysteine residue in the linker and a variable region of the additional binding domain(s). Such pairing caused by the linker may apply to an additional binding domain, comprising a Fab domain comprising a common light chain and a counterpart rearranged heavy chain variable region or comprising a common heavy chain and a counterpart rearranged light chain variable region.

Multivalency and Multispecificity

Where the two binding domains of the base antibody of a multivalent protein of the invention bind different antigens, said first and second antigens may be two different molecules or moieties that are located on one cell or on different cell types. Antibodies comprising two binding domains that mediate cytotoxicity by recruiting and activating endogenous immune cells are an emerging class of antibody therapeutics. This can be achieved by combining antigen binding specificities for target cells (i.e., tumor cells) and effector cells (i.e., T cells, NK cells, and macrophages) in one molecule (see, for example, WO2014/051433). An antibody of the invention comprises at least three binding domains. The base antibody portion will typically comprise two different binding domains (although the two binding domains may have the same sequence or bind the same epitope). A multivalent antibody comprising three or more binding domains may target one, two, three or more tumor associated antigens, permitting a specific targeting of deleterious cells over healthy cells. For example, one binding domain or two binding domains of the multivalent antibody may bind an antigen on an aberrant (tumor) cell, whereas a second or third binding domain of the multivalent antibody may bind an antigen on an immune effector cell that can cause directed killing of the tumor cell expressing the one or more tumor associated antigens. Alternatively, two binding domains of the multivalent antibody may bind specifically to two different epitopes on an identical antigen or different antigens expressed on tumor cells while the affinities of these arms are attenuated to mitigate binding to cells expressing only one antigen or where only one binding domain of the multivalent antibody is engaged. Or three binding domains of the multivalent antibody of the invention may bind to three different antigens or to identical antigens, but at different epitopes of immune effector cells.

Similarly, a multivalent antibody comprising three or more binding domains may bind a functional target such as a ligand or enzyme, triggering a biological response or blocking the function of the target, resulting in inhibitory or agonistic cellular activity. At least one binding domain of a multivalent antibody of the invention is connected via a linker to a binding domain of the base antibody portion. Where the binding domain of the base antibody portion is a Fab domain, this may take the form, for example, of VH-CH1-linker-VH-CH1, wherein the linker connects the heavy chain of the base antibody portion to the at least one additional binding domain, preferably a Fab domain.

Alternatively, this may take the form, for example, of VL-CL-linker-VL-CL, wherein the linker connects the light chain of the base antibody portion to the at least one additional binding domain, preferably a Fab domain.

An additional binding domain, such as a Fab domain, may be connected to each of the binding domains of the base antibody portion, each via a separate linker. The two or more linkers connecting the additional binding domains to the base antibody portion or additional binding domains may be the same or different. Further, the linkers may allow pairing of the cognate chains of the binding domain.

If an antibody of the invention comprises more than one linker, those linkers may be the same or different or a combination thereof. An example of the latter situation is where a multispecific antibody comprises three linkers, two of which are the same and a third which is different (from the other two).

Further a binding domain connected via a linker to a binding domain of a base antibody portion, may itself be attached to a binding domain connected via a linker described herein, wherein the base antibody portion may be extended in a modular fashion by connecting through a linker to an additional binding domain, and connecting that binding domain to a second additional binding domain through a linker and so on.

In this way an antibody of the invention may be capable of binding three or more epitopes. Thus, a multispecific antibody of the invention may be capable of specifically binding to three or more epitopes.

An antibody of the invention may be capable of binding two, three or more antigens. A multispecific antibody of the invention may thus be capable of specifically binding to two, three or more antigens.

An antibody of the invention may comprise two or more binding domains, such as two or more Fab domains, which are capable of binding to different epitopes on one antigen Accordingly, an antibody of the invention comprises at least three binding domains, such as two or more Fab domains which are different.

Another aspect of the invention comprises a multivalent antibody comprising at least three Fab domains and therefore is capable of binding to three epitopes which are typically all different from each other.

An antibody of the invention may be multivalent. An antibody of the invention may also be multispecific. Multivalent indicates that the antibody has at least three binding domains and therefore has at least three antigen-binding sites. Multispecific indicates that the antibody is capable of binding at least two different epitopes, for example two different antigens or two epitopes on the same antigen. Trispecific indicates that the antibody is capable of binding three different epitopes. Quadspecific indicates that the antibody is capable of binding four different epitopes and so on.

An antibody of the invention may bind target epitopes which are located on the same molecule. This may allow for more efficient counteraction of the (biological) function of said target molecule as compared to a situation wherein only one epitope is targeted. For example, an antibody of the invention may simultaneously bind to 2 or 3 or more epitopes present on an antigen cell, e.g., growth factor receptors or soluble molecules critical for tumors cells to proliferate, thereby effectively blocking several independent signaling pathways leading to uncontrolled proliferation.

Any combination of at least two antibodies of the invention may simultaneously bind to 2, 3, 4 or more epitopes present on a target molecule, such as a growth factor receptor or soluble molecule.

The target moiety may be a soluble molecule or may be a membrane-bound moiety or may be a moiety present on a cell-surface that internalizes upon binding.

The target epitopes may be located on different moieties, for example on two (i.e. two or more target epitopes on a first moiety and one or more target epitopes on a second moiety) or three different moieties (i.e. at least one target epitope on each of three moieties). In this case, each of the different target moieties may either be a soluble moiety or a membrane-bound moiety or a moiety present on a cell-surface that internalizes upon binding. In one embodiment, the different target moieties are soluble moieties. Alternatively, at least one target moiety is a soluble moiety whereas and at least one target moiety is a membrane bound moiety. In yet another alternative, all target moieties are membrane bound moieties. In one embodiment, the different target moieties are expressed on the same cell, whereas in other embodiments the different target moieties are expressed on different cells.

As a non-limiting example, any antibody of the invention or any combination of an antibody of the invention and an additional antibody may be suitable for simultaneously blocking multiple membrane-bound receptors, neutralizing multiple soluble molecules such as cytokines or growth factors for tumor cells or for neutralizing different viral serotypes or viral strains.

In an antibody of the invention, at least one target epitope may be located on a tumor cell. Alternatively, or additionally, at least a target epitope may be located on the surface of an effector cell. This is for instance suitable for recruitment of T cells or NK cells for tumor cell killing. For instance, an antibody of the invention may be capable of recruiting immune effector cells, preferably human immune effector cells, by specifically binding to a target molecule located on immune effector cells. In a further embodiment, said immune effector cell is activated upon binding of the antibody of the invention to the target molecule. Recruitment of effector mechanisms may for instance encompass the redirection of immune modulated cytotoxicity by administering an Ig-like molecule produced by a method according to the invention that is capable of binding to a cytotoxic trigger molecule such as the T cell receptor or an Fc gamma receptor, thereby activating downstream immune effector pathways or immune effector cells.

Immune Cell Engagers

A multivalent multimer, such as an antibody of the invention may be an immune effector cell engager antibody. That is to say, a multivalent antibody of the invention may be one which comprises at least one binding domain which binds specifically to an antigen on an immune effector cell, such as a T cell, and also comprises at least one binding domain which binds specifically to an antigen on an aberrant cell, such as a cancer or tumor cell.

A multivalent multimer of the invention, such as a trispecific antibody, may be one having three binding domains bringing three cells together in an engager complex, including a tumor cell, and two immune effector cells.

A multivalent multimer of the invention, such as a trispecific antibody, may further be one having three binding domains targeting two cells and a soluble molecule.

For the embodiments set out here, the Fc may be a wild-type Fc, may be enhanced for ADCC or binding of Cq1 based on means known to persons of skill in the art, or may be abrogated for such activity based on means known to persons of skill in the art.

The components of such immune cell engaging multivalent antibodies can be arranged with respect to each other in a variety of configurations. Exemplary configurations are depicted in FIGS. 1a-1u. In particular embodiments, the present invention is directed to an immune cell engaging multivalent antibody wherein a third binding domain is linked at the C-terminus of the Fab heavy chain to the N-terminus of a first or second binding domain of the base antibody.

In one embodiment, an immune cell engaging multivalent antibody comprises three binding domains, i.e. a base antibody portion and one additional binding domain, so that the said multivalent antibody is trispecific, One of the binding domains of the base antibody portion may be bind an antigen on an immune effector cell. Alternatively, the additional binding domain may bind an antigen of an immune effector cell. That is to say, the binding domain for an antigen on an immune effector cell may be at position 1, 2 or 3, wherein these positions correspond to the VH1, VH2 and VH3 indicated in FIG. 1a. Alternatively, where a common heavy chain is used, the binding domain for an antigen on an immune effector cell may be at position 1, 2 or 3, wherein these positions correspond to the VL1, VL2 and VL3, for example, as indicated in FIG. 1c.

In an immune effector cell engager antibody of the invention, at least one of the binding domains may specifically bind to an antigen on an aberrant cell. Typically, at least two binding domains bind to an antigen on an aberrant cell, typically at least two binding domains bind to at least two different antigens or epitopes on a an antigen on an aberrant cell. In an immune effector cell engager antibody of the invention, two or more binding domains may bind the same target, including antigen and epitope, and another binding domain engaging an immune effector cell.

In a preferred embodiment of the invention, a multivalent antibody of the invention specifically binds to an antigen on an immune effector cell and also binds specifically to two different antigens on an aberrant cell, such as a tumor cell.

In one embodiment of the invention, the T cell engaging multivalent antibody is capable of simultaneous binding to a target cell antigen, particularly a tumor cell antigen, and a surface antigen of a human T cell. In one embodiment, the T cell engaging multivalent antibody is capable of simultaneously binding to a target cell antigen, particularly a tumor cell antigen, and human CD3. In one embodiment, the T cell engaging multivalent antibody is capable of crosslinking a T cell and a target cell by simultaneous binding to a target cell antigen and CD3. In another embodiment, the simultaneous binding results in lysis of the target cell, particularly a tumor cell. In one embodiment, the simultaneous binding results in activation of the T cell. In other embodiments, the simultaneous binding results in a cellular response of a T lymphocyte, particularly a cytotoxic T lymphocyte, selected from the group of: proliferation, differentiation, cytokine secretion, cytotoxic effector molecule release, cytotoxic activity, and expression of activation markers. In one embodiment, binding of the T cell engaging polypeptide to CD3 without simultaneous binding to the target cell antigen does not result in T cell activation, where, for example the remaining binding domains do not bind a tumor cell antigen.

In one embodiment, the T cell engaging multivalent antibody is capable of re-directing cytotoxic activity of a T cell to a target cell. In one embodiment, the re-direction is independent of MHC-mediated peptide antigen presentation by the target cell and and/or specificity of the T cell. In one embodiment, the T cell is a cytotoxic T cell. In another embodiment, the T cell is a $CD4^+$ or a $CD8^+$ T cell. In another embodiment the T cell is a $CD8^+$ T cell.

The T cell engaging multivalent antibody of the invention comprises at least one antigen binding domain capable of binding to a surface antigen of a human T cell. In one embodiment, the binding domain binds CD3 (also referred to herein as an "CD3 antigen binding domain").

The term "CD3" (cluster of differentiation 3) refers a protein complex, which is composed of a CD3γ chain (SwissProt P09693), a CD36 chain (SwissProt P04234), CD3ε chains (SwissProt P07766), and a CD3 zeta chain homodimer (SwissProt P20963). CD3ε is known under various aliases some of which are: "CD3e Molecule, Epsilon (CD3-TCR Complex)"; "CD3e Antigen, Epsilon Polypeptide (TiT3 Complex)"; T-Cell Surface Antigen T3/Leu-4 Epsilon Chain; T3E; T-Cell Antigen Receptor Complex, Epsilon Subunit Of T3; CD3e Antigen; CD3-Epsilon 3; IMD18; TCRE. Ids for CD3E Gene are HGNC: 1674; Entrez Gene: 916; Ensembl: ENSG00000198851; OMIM: 186830 and UniProtKB: P07766. These chains associate with the T-cell receptor (TCR) and the ζ-chain to form a TCR complex that can upon mitogenic signaling generates an activation signal in T lymphocytes. CD3 is expressed on T cells and NK T cells. Where reference is made to CD3 herein, the reference is to human CD3, unless specifically stated otherwise.

In a particular embodiment, the T cell engaging polypeptide comprises not more than one binding domain capable of specific binding to CD3. In one embodiment the T cell engaging polypeptide provides monovalent binding to CD3. In one embodiment, the T cell engaging polypeptide comprises one member of a supercluster of CD3 binding binding domains. A 'super-cluster' is used hereinto to refer to variable regions having amino acid changes that are tolerated, for example, with respect to heavy chain variable regions, including a VH or VL and/or CDR therein of the present invention without losing binding specificity to the particular antigen. More specifically, a 'super-cluster' is a group of clones sharing the same VH V-gene usage and having at least 70% sequence identity in HCDR3 and the same HCDR3 length. The clones in a supercluster are expected to bind the same antigen potentially with different affinities and/or different location on the epitope.

The CD3 binding domain may range in affinity, epitope and other characteristics. Specific variable domains that can bind an extracellular part of CD3 are variable domains that comprise the amino acid sequence of the VH of MF8057, MF8058, MF8078 and variable regions of this supercluster, MF8397 and variable regions of this supercluster, MF8508 and variable regions of this supercluster, and MF9249 and MF9267 and variable regions of this supercluster.

The CD3 antigen binding domain comprises at least one heavy chain complementarity determining region (CDR) selected from the group consisting VH of MF8057, MF8058, MF8078 and variable regions of this supercluster, MF8397 and variable regions of this supercluster, MF8508 and variable regions of this supercluster, and MF9249 and MF9267 and variable regions of this supercluster (SEQ ID NO: 97, SEQ ID NO:106, SEQ ID NO:115, SEQ ID NO:124, SEQ ID NO:133, SEQ ID NO:142, SEQ ID NO:98, SEQ ID NO:107, SEQ ID NO:116, SEQ ID NO:125, SEQ ID NO:134 SEQ ID NO:143 SEQ ID NO:152SEQ ID NO: 99, SEQ ID NO:108, SEQ ID NO:117, SEQ ID NO:126, SEQ ID NO:135, SEQ ID NO:144 and/or SEQ ID NO:153) and at least one light chain CDR selected from the group of SEQ ID NO: 254, SEQ ID NO: 255, SEQ ID NO: 256.

In one embodiment the CD3 antigen binding domain comprises the heavy chain CDR1 of SEQ ID NO: 97, SEQ ID NO:106, SEQ ID NO:115, SEQ ID NO:124, SEQ ID NO:133, or SEQ ID NO:142, the heavy chain CDR2 of SEQ ID NO:98, SEQ ID NO:107, SEQ ID NO:116, SEQ ID NO:125, SEQ ID NO:134 SEQ ID NO:143 or SEQ ID NO:152, the heavy chain CDR3 of SEQ ID NO: 99, SEQ ID NO:108, SEQ ID NO:117, SEQ ID NO:126, SEQ ID NO:135, SEQ ID NO:144 or SEQ ID NO:153, the light chain CDR1 of SEQ ID NO: 254, the light chain CDR2 of SEQ ID NO: 255, and the light chain CDR3 of SEQ ID NO: 256.

In one embodiment the CD3 antigen binding domain comprises a heavy chain variable region sequence that is at least about 95%, 96%, 97%, 98%, 99% or 100% identical to an amino acid sequence selected from the group of: SEQ ID NO: 100, SEQ ID NO:109, SEQ ID NO:118, SEQ ID NO:127, SEQ ID NO:135, SEQ ID NO:145 and SEQ ID NO:154, and a light chain variable region sequence that is at least about 95%, 96%, 97%, 98%, 99% or 100% identical to an amino acid sequence selected from the group of: SEQ ID NO: 37 and SEQ ID NO: 40.

In one embodiment the CD3 antigen binding domain comprises the heavy chain variable region of SEQ ID NO: 100, SEQ ID NO:109, SEQ ID NO:118, SEQ ID NO:127, SEQ ID NO:135, SEQ ID NO:145 or SEQ ID NO:154 and the light chain variable region comprising the amino acid sequence of SEQ ID NO: 37 or SEQ ID NO:40.

The positions of the binding domains in the multivalent antibody can be defined. When the binding or variable domains of the base antibody are termed binding domains 1 and 2, the additional one or more binding domains can be referred to as binding domains 3, 4 etc. A binding domain is also referred to as BD. BD3 may be linked to BD1 or BD2. When BD3 is linked to one of BD1 or 2, BD4, when present, is linked to the other of BD1 and 2.

The T cell engaging multivalent antibody of the invention comprises at least two antigen binding domains capable of binding to a target cell antigen (also referred to herein as an "target cell antigen binding domain" or "second" or "third" antigen binding domain). In certain embodiments, the T cell engaging multivalent antibody comprises two antigen binding domains capable of binding to a target cell antigen. In one embodiment, each of these antigen binding domains specifically binds to the same antigenic determinant. In another embodiment, the target cell antigen binding domains are identical. In one embodiment, the T cell engager polypeptide comprises not more than two target cell antigen binding domains capable of binding to a target cell antigen.

In one embodiment the multivalent antibody comprises an BD1 which is a CD3 binding domain, an BD2 which is a binding domain that binds a first target cell antigen, further referred TA1 and an BD3 which is a binding domain that binds a second target cell antigen, further referred TA2. In this embodiment BD3 can be linked to BD1 or BD2. In one embodiment TA2 binding BD3 is linked to CD3 binding BD1. In another embodiment the TA2 binding BD3 is linked to TA1 binding BD2.

In one embodiment the multivalent antibody comprises a TA1 binding BD1, a TA2 binding BD2, and a CD3 binding BD3. In this embodiment BD3 can be linked to BD1 or BD2. In one embodiment the CD3 binding BD3 is linked to TA1 binding BD1. In another embodiment CD3 binding BD3 is linked to TA2 binding BD2.

In one embodiment the invention provides a multivalent antibody wherein the base antibody comprises binding domains 1 and 2 (BD1 and 2) and wherein the additional binding domain 3 (BD3) is linked to binding domain 1 (BD1) and wherein an optional additional binding domain 4 (BD4) is linked to binding domain 2 (BD2). In one embodiment binding domain 1 is a CD3 binding domain and binding domains 2 and 3 bind to different target cell antigens. In another embodiment binding domain 2 is a CD3 binding domain and binding domains 1 and 3 bind to different target cell antigens. In a further embodiment binding domain 3 is a CD3 binding domain and binding domains 1 and 2 bind to different target cell antigens.

In a preferred embodiment the multivalent antibody comprises a binding domain 4 that binds yet a further different target cell antigen.

The invention further provides a multivalent antibody as described herein wherein the base antibody comprises binding domains 1 and 2 and wherein the additional binding domain 3 is linked to binding domain 1 and wherein an optional additional binding domain 4 is linked to binding domain 2. In one embodiment binding domain 1 is a CD3 binding domain and binding domains 2 and 3 bind to different target cell antigens. In another embodiment binding domain 2 is a CD3 binding domain and binding domains 1 and 3 bind to different target cell antigens. In a further embodiment binding domain 3 is a CD3 binding domain and binding domains 1 and 2 bind to different target cell antigens.

When comprising a binding domain 4 the domain preferably binds yet a further different target cell antigen.

In one embodiment a first of said target cell antigen binding domain binds PD-L1, EGFR, CD137, CLEC12A, fibrinogen, or thyroglobulin. In one embodiment a first and a second of said target cell antigen binding domains bind antigens selected from PD-L1, EGFR, CD137, CLEC12A fibrinogen, and thyroglobulin. The first and second target cell binding domain preferably bind different antigens.

A CD3 binding domain preferably comprises a heavy chain variable region comprising a CDR1, CDR2 and CDR3 with the amino acid sequence of the CDR1, CDR2 and CDR3 of MF8057, or of MF8058, or of MF8078, or of MF8397, or of MF8508, or of MF9249 or of MF9267. The CD3 binding domain preferably comprises a heavy chain variable region with the amino acid sequence of the VH of MF8057, of MF8058, of MF8078, of MF8397, of MF8508, of MF9249 or of MF9267 with 0-10, preferably 0-5 amino acid insertions, deletions, substitutions, additions or a combination thereof at one or more positions other than the CDRs.

A target cell antigen binding domain can be a PD-L1 binding domain. If present the PD-L1 binding domain preferably comprises a heavy chain variable region comprising a CDR1, CDR2 and CDR3 with the amino acid sequence of the CDR1, CDR2 and CDR3 of MF5377, or of MF5444, or of MF5380. The PD-L1 binding domain preferably comprises a heavy chain variable region with the amino acid sequence of the VH of MF5377, of MF5444, or of MF5380 with 0-10, preferably 0-5 amino acid insertions, deletions, substitutions, additions or a combination thereof at one or more positions other than the CDRs.

A target cell antigen binding domain can be an EGFR binding domain. If present the EGFR binding domain preferably comprises a heavy chain variable region comprising a CDR1, CDR2 and CDR3 with the amino acid sequence of the CDR1, CDR2 and CDR3 of MF8233, or of MF9891, or of MF9886, or of MF9873, or of MF9988. The EGFR binding domain preferably comprises a heavy chain variable region with the amino acid sequence of the VH of MF8233, of MF9891, of MF9886, of MF9873, or of MF9988 with 0-10, preferably 0-5 amino acid insertions, deletions, substitutions, additions or a combination thereof at one or more positions other than the CDRs.

A target cell antigen binding domain can be a CLEC12A binding domain. If present the CLEC12A binding domain preferably comprises a heavy chain variable region comprising a CDR1, CDR2 and CDR3 with the amino acid sequence of the CDR1, CDR2 and CDR3 of MF4327. The CLEC12A binding domain preferably comprises a heavy chain variable region with the amino acid sequence of the VH of MF4327 with 0-10, preferably 0-5 amino acid insertions, deletions, substitutions, additions or a combination thereof at one or more positions other than the CDRs.

In one embodiment the multivalent antibody comprises a CD3 binding domain, an EGFR binding domain and a PD-L1 binding domain.

The binding domains with the indicated heavy chain variable regions comprise a light chain variable region. The light chain variable region preferably comprises a CDR1, CDR2, and CDR3 region comprising the amino acid sequence CDR1-QSISSY (SEQ ID NO:312), CDR2-AAS, CDR3-QQSYSTP (SEQ ID NO:313), i.e. the CDRs of IGKV1-39 (according to IMGT). The amino acid variations, insertions, deletions, substitutions, additions or combination thereof are preferably not in the CDR3 region of the light chain variable region, preferably not in the CDR1 or CDR2 region of the light chain variable region. In a preferred embodiment the light chain variable region does not comprise a deletion, addition or insertion with respect to the sequence indicated. In this embodiment the light chain variable region can have 0-5 amino acid substitutions with respect to the indicated amino acid sequence. An amino acid substitution is preferably a conservative amino acid substitution. The CDR1, CDR2 and CDR3 of a light chain of an antibody of the invention preferably comprises respectively the amino acid sequence CDR1-QSISSY (SEQ ID NO:312), CDR2-AAS, CDR3-QQSYSTP (SEQ ID NO:313), i.e. the CDRs of IGKV1-39 (according to IMGT).as described elsewhere herein. The light chains of the binding domains with the indicated heavy chain variable regions preferably all comprise the same light chain. Preferably a common light chain as defined elsewhere herein.

Amino acid insertions, deletions, substitutions, additions or combination thereof are preferably not in the CDR3 region of the heavy chain variable region, preferably not in the CDR1 and/or CDR2 region of the heavy chain variable region. In a preferred embodiment the heavy chain variable region does not comprise a deletion, addition or insertion with respect to the sequence indicated. In one embodiment the heavy chain variable region can have 0-10, preferably 0-5 amino acid substitutions with respect to the indicated amino acid sequence. In a preferred embodiment the heavy chain variable region comprises 0-9, 0-8, 0-7, 0-6, 0-5, 0-4, preferably 0-3, preferably 0-2, preferably 0-1 and preferably 0 amino acid insertions, deletions, substitutions, additions with respect to the indicated amino acid sequence, or a combination thereof at positions other than the CDRs. A combination of an insertion, addition, deletion or substitution is a combination as claimed if aligned sequences do not differ at more than 10, preferably no more than 5 positions. A gap in one of the aligned sequences counts for as many amino acids as skipped in the other sequence. An amino acid substitution, if any, is preferably a conservative amino acid substitution.

In one embodiment, the target cell antigen binding domain is a Fab molecule. In one embodiment, the target cell antigen binding domain is a Fab molecule that binds to a specific antigenic determinant and is able to direct the T cell engaging multivalent antibody to a target site, for example to a specific type of tumor cell that bears the antigenic determinant. In certain embodiments the target cell antigen binding specifically binds Programmed Cell Death 1 protein (PD-L1), preferably human PD-L1 (SEQ ID NO: 257).

PD-L1 is a type 1 transmembrane protein that plays a role in suppressing an immune response during particular events such as pregnancy, tissue allografts, autoimmune disease and other disease states such as hepatitis. The binding of PDL1 to PD-1 or B7.1 (CD80) transmits an inhibitory signal which reduces the proliferation of the PD-1 expressing T cells. PD-1 is thought to be able to control the accumulation of foreign antigen specific T cells through apoptosis. PD-L1 is expressed by a variety of cancer cells and the expression thereof is thought to be at least in part responsible for a dampening of an immune response against the cancer cell. PD-L1 is a member of the B7-family of protein and is known under a variety of other names such as CD274 Molecule; CD274 Antigen; B7 Homolog 1; PDCD1 Ligand 1; PDCD1 LG1; PDCD1L1; B7H1; PDL1; Programmed Cell Death 1 Ligand 1; Programmed Death Ligand 1; B7-H1; and B7-H.

External Ids for CD274 are HGNC: 17635; Entrez Gene: 29126; Ensembl: ENSG00000120217; OMIM: 605402; UniProtKB: Q9NZQ7.

The PD-L1 binding domain may range in affinity, epitope and other characteristics. Specific variable domains that can bind an extracellular part of PD-L1 are variable domains that comprise the amino acid sequence of the VH of MF5377, MF5444 or MF5380.

The PD-L1 antigen binding domain comprises at least one heavy chain CDR selected from the group consisting of VH of SEQ ID NO: 160, SEQ ID NO:169, SEQ ID NO:178, SEQ ID NO: 161, SEQ ID NO:170, SEQ ID NO:179 SEQ ID NO: 162, SEQ ID NO:171 and SEQ ID NO:180 and at least one light chain CDR selected from the group of SEQ ID NO: 254, SEQ ID NO: 255, and SEQ ID NO: 256.

In one embodiment the PD-L1 antigen binding domain comprises the heavy chain CDR1 of SEQ ID NO: 160, SEQ ID NO:169 or SEQ ID NO:178, the heavy chain CDR2 of SEQ ID NO: 161, SEQ ID NO:170 or SEQ ID NO:179, the heavy chain CDR3 of SEQ ID NO: 162, SEQ ID NO:171 or SEQ ID NO:180, the light chain CDR1 of SEQ ID NO: 254, the light chain CDR2 of SEQ ID NO: 255, and the light chain CDR3 of SEQ ID NO: 256.

In one embodiment the PD-L1 antigen binding domain comprises a heavy chain variable region sequence that is at least about 95%, 96%, 97%, 98%, 99% or 100% identical to an amino acid sequence selected from the group of: SEQ ID NO: 163, SEQ ID NO:172 and SEQ ID NO:181, and a light chain variable region sequence that is at least about 95%, 96%, 97%, 98%, 99% or 100% identical to an amino acid sequence selected from the group of: SEQ ID NO: 37 and SEQ ID NO: 40.

In one embodiment the PD-L1 antigen binding domain comprises the heavy chain variable region of SEQ ID NO: 163, SEQ ID NO:172 or SEQ ID NO:181 and the light chain variable region comprising the amino acid sequence of SEQ ID NO: 37 or SEQ ID NO:40.

In certain embodiments, the PD-L1 antigen binding domain comprises the heavy and light chain variable regions of the PD-L1 antibodies comprising the amino acid sequences disclosed for MPDL3280A, RG7446, see US 2010/0203056 A1; MEDI-4736, see WO 2011/066389; MSB-0010718C, see WO 2013/079174; STI-1014 see WO2013/181634; CX-072, see WO2016/149201; KN035, see Zhang et al., Cell Discov. 7:3 (March 2017); LY3300054, see, e.g., WO 2017/034916; and CK-301, see Gorelik et al., AACR:Abstract 4606 (April 2016)), and 12A4 or MDX-1105, see, e.g., WO 2013/173223.

In certain embodiments, the PD-L1 antigen binding domain binds the same epitope as the heavy and light chain variable regions of the PD-L1 antibodies MPDL3280A, RG7446, see US 2010/0203056 A1; MEDI-4736, see WO 2011/066389; MSB-0010718C, see WO 2013/079174; STI-1014 see WO2013/181634; CX-072, see WO2016/149201; KN035, see Zhang et al., Cell Discov. 7:3 (March 2017); LY3300054, see, e.g., WO 2017/034916; and CK-301, see Gorelik et al., AACR:Abstract 4606 (April 2016)), and 12A4 or MDX-1105, see, e.g., WO 2013/173223.

In certain embodiments, the PD-L1 antigen binding domain competes for binding to PD-L1 with the heavy and light chain variable regions of the PD-L1 antibodies MPDL3280A, RG7446, see US 2010/0203056 A1; MEDI-4736, see WO 2011/066389; MSB-0010718C, see WO 2013/079174; STI-1014 see WO2013/181634; CX-072, see WO2016/149201; KN035, see Zhang et al., Cell Discov. 7:3 (March 2017); LY3300054, see, e.g., WO 2017/034916; and CK-301, see Gorelik et al., AACR:Abstract 4606 (April 2016)), and 12A4 or MDX-1105, see, e.g., WO 2013/173223.

In certain embodiments the target cell antigen binding specifically binds human epidermal growth factor receptor (EGFR) (SEQ ID NO: 258). 'ErbB1' or 'EGFR' is a member of a family of four receptor tyrosine kinases (RTKs), named Her- or cErbB-1, -2, -3 and -4. The EGFR has an extracellular domain (ECD) that is composed of four sub-domains, two of which are involved in ligand binding and one of which is involved in homo-dimerisation and heterodimerisation. The reference numbers used in this section refer to the numbering of the references in the list headed "References cited in the specification". EGFR integrates extracellular signals from a variety of ligands to yield diverse intracellular responses. The major signal transduction pathway activated by EGFR is composed of the Ras-mitogen-activated protein kinase (MAPK) mitogenic signalling cascade. Activation of this pathway is initiated by the recruitment of Grb2 to tyrosine phosphorylated EGFR. This leads to activation of Ras through the Grb2-bound Ras-guanine nucleotide exchange factor Son of Sevenless (SOS). In addition, the PI3-kinase-Akt signal transduction pathway is also activated by EGFR, although this activation is much stronger in case there is co-expression of Her3. The EGFR is implicated in several human epithelial malignancies, notably cancers of the breast, bladder, non-small cell lung cancer lung, colon, ovarian head and neck and brain. Activating mutations in the gene have been found, as well as over-expression of the receptor and of its ligands, giving rise to autocrine activation loops. This RTK has therefore been extensively used as target for cancer therapy. Both small-molecule inhibitors targeting the RTK and monoclonal antibodies (mAbs) directed to the extracellular ligand-binding domains have been developed and have shown hitherto several clinical successes, albeit mostly for a select group of patients. A database accession number for the human EGFR protein and the gene encoding it is (GenBank NM_005228.3). The accession number is primarily given to provide a further method of identification of EGFR protein as a target, the actual sequence of the EGFR protein bound by an antibody may vary, for instance because of a mutation in the encoding gene such as those occurring in some cancers or the like. Where reference herein is made to EGFR, the reference refers to human EGFR unless otherwise stated. The antigen-binding site that binds EGFR, binds EGFR and a variety of variants thereof such as those expressed on some EGFR positive tumors.

The EGFR binding domain may range in affinity, epitope and other characteristics. Specific variable domains that can bind an extracellular part of EGFR are variable domains that comprise the amino acid sequence of the VH of MF8233, MF9891, MF9886, MF9873, MF9988.

The EGFR antigen binding domain comprises at least one heavy chain CDR selected from the group consisting of SEQ ID NO: 187, SEQ ID NO:196, SEQ ID NO:205, SEQ ID NO:214, SEQ ID NO:223, SEQ ID NO: 188, SEQ ID NO:197, SEQ ID NO:206, SEQ ID NO:215, SEQ ID NO:224 SEQ ID NO: 189, SEQ ID NO:198, SEQ ID NO:207, SEQ ID NO:216 and SEQ ID NO:225 and at least one light chain CDR selected from the group of SEQ ID NO: 254, SEQ ID NO: 255, SEQ ID NO: 256.

In one embodiment the EGFR antigen binding domain comprises the heavy chain CDR1 of SEQ ID NO: 187, SEQ ID NO:196, SEQ ID NO:205, SEQ ID NO:214, or SEQ ID NO:223, the heavy chain CDR2 of SEQ ID NO: 188, SEQ ID NO:197, SEQ ID NO:206, SEQ ID NO:215, or SEQ ID NO:224, the heavy chain CDR3 of SEQ ID NO: 189, SEQ ID NO:198, SEQ ID NO:207, SEQ ID NO:216 or SEQ ID NO:225, the light chain CDR1 of SEQ ID NO: 254, the light chain CDR2 of SEQ ID NO: 255, and the light chain CDR3 of SEQ ID NO: 256.

In one embodiment the EGFR antigen binding domain comprises a heavy chain variable region sequence that is at least about 95%, 96%, 97%, 98%, 99% or 100% identical to an amino acid sequence selected from the group of: SEQ ID NO: 190, SEQ ID NO:199, SEQ ID NO:208, SEQ ID NO:217 and SEQ ID NO:226, and a light chain variable region sequence that is at least about 95%, 96%, 97%, 98%, 99% 01100% identical to an amino acid sequence selected from the group of: SEQ ID NO: 37 and SEQ ID NO: 40.

In one embodiment the EGFR antigen binding domain comprises the heavy chain variable region of SEQ ID NO: 190, SEQ ID NO:199, SEQ ID NO:208, SEQ ID NO:217 or SEQ ID NO:226 and the light chain variable region comprising the amino acid sequence of SEQ ID NO: 37 or SEQ ID NO:40.

In certain embodiments, the EGFR antigen binding domain comprises the heavy and light chain variable regions of the EGFR antibodies cetuximab (C225, Erbitux®, Lilly®) or panitumumab (Vectibix®, Amgen®).

In certain embodiments, the EGFR antigen binding domain binds the same epitope as the heavy and light chain variable regions of the EGFR antibodies cetuximab (C225, Erbitux®, Lilly®) or panitumumab (Vectibix®, Amgen®).

In certain embodiments, the EGFR antigen binding domain competes for binding to EGFR with the heavy and light chain variable regions of the EGFR antibodies cetuximab (C225, Erbitux®, Lilly®) or panitumumab (Vectibix®, Amgen®).

Common Variable Region

The multivalent antibody of the invention preferably uses a common chain at each of the three or more binding domains. As described, the base antibody portion of the multivalent antibody invention preferably has a first heavy chain variable region/light chain variable region (VH/VL) combination that binds one antigen and a second VH/VL combination that binds a second antigen. Each additional binding domain connected to the base antibody portion may also comprise an additional VH/VL combination that binds a further epitope on an antigen.

A base antibody portion of the invention preferably comprises two heavy chains (one or both comprising one or more additional CH1 and VH domain) and a light chain which pairs with each CH1 and VH domain. Preferably the two heavy chains have compatible heterodimerization domains, and preferably the light chain is a common light chain. Alternatively, the base antibody portion of the multivalent antibody of the invention comprises two light chains (one or both comprising one or more additional CL and VL domain) and a heavy chain variable region which pairs with each CL and VL domain, and the heavy chain variable region comprises a common heavy chain variable region.

Where the embodiment of the invention includes a multivalent antibody comprising a common light chain, where said light chain is expressed within a host cells that includes DNA encoding two or more heavy chain variable regions, said light chain is capable of pairing with each available heavy chains (or CH1-VH1 regions), thereby forming at least three functional antigen binding domains.

A functional antigen binding domain is capable of specifically binding to an epitope on an antigen. Preferably, a common light chain used in a multivalent antibody of the invention is capable of pairing with all heavy chains (or CH1-VH1 regions) produced with a method according to the invention, thereby forming functional antigen binding domains, so that mispairing of unmatched heavy and light chains is avoided or produced at a significantly lower ratio than the multivalent antibody.

It is a preferred aspect of the present invention that a multivalent antibody of the invention has a common light chain (variable region) that can combine with an array of heavy chain variable regions to form an antibody with functional antigen binding domains (WO2004/009618, WO2009/157771).

Figure 8:
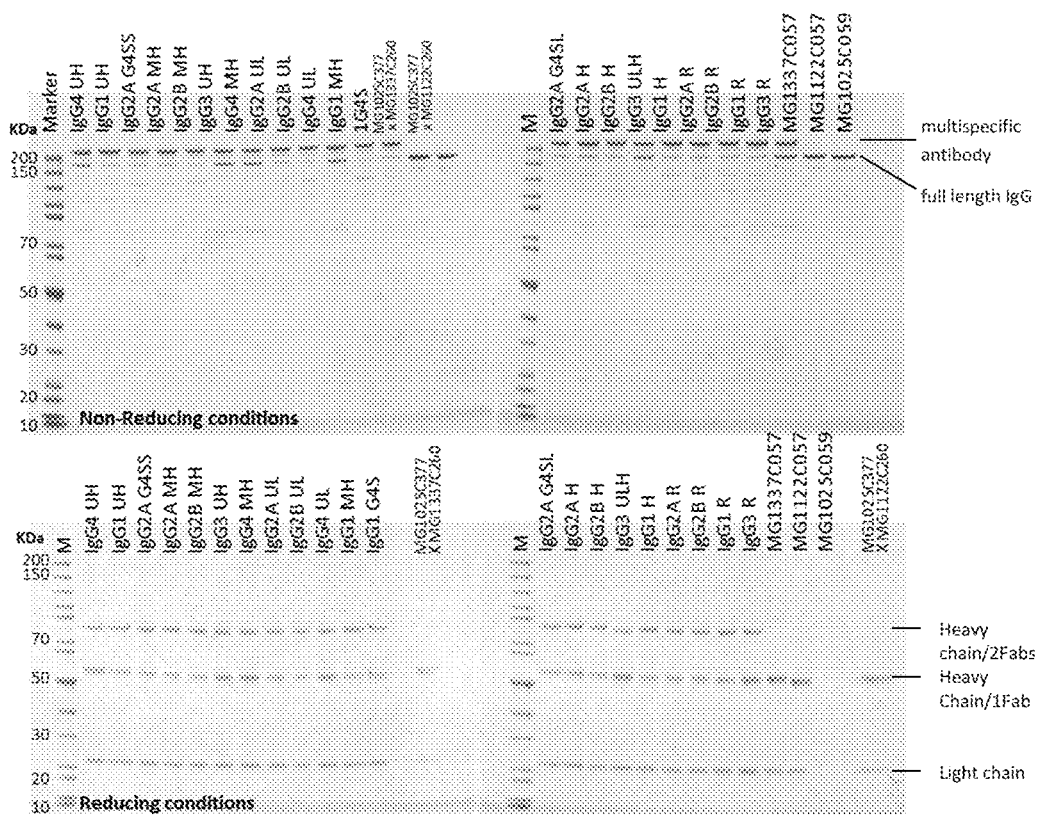
FIG. 8 sets out the SDS-PAGE gels of IgGs in non-reducing (top) and reducing (bottom) conditions.

A common light chain (variable region) for use in the multivalent antibody of the invention is preferably a human light chain (variable region). A common light chain (variable region) preferably has a germline sequence. A preferred germline sequence is a light chain variable region that is frequently used in the human repertoire and has good thermodynamic stability, yield and solubility. A preferred germline light chain is O12. A common light chain is preferably the rearranged germline human kappa light chain IgVκ1-39*01/IGAJκ1*01 (FIG. 11A; SEQ ID NO: 35). The common light chain variable region is preferably the variable region of the rearranged germline human kappa light chain IgVκ1-39*01/IGAJκ1*01 (FIG. 11A; SEQ ID NO: 35). A common light chain preferably comprises a light chain variable region as depicted in FIG. 11B or 8D (SEQ ID NOs: 37 or 40 respectively) with 0-5 amino acid insertions, deletions, substitutions, additions or a combination thereof. The common light preferably further comprises a light chain constant region, preferably a kappa light chain constant region. A nucleic acid that encodes the common light chain can be codon optimized for the cell system used to express the common light chain protein. The encoding nucleic acid can deviate from a germ-line nucleic acid sequence.

The common light chain (variable region) for use in the multivalent antibodies of the invention can be a lambda light chain and this is therefore also provided in the context of the invention, however a kappa light chain is preferred. The common light chain of the invention may comprise a constant region of a kappa or a lambda light chain. It is preferably a constant region of a kappa light chain, preferably wherein said common light chain is a germline light chain, preferably a rearranged germline human kappa light chain comprising the $IgV_{\kappa}I$-39 gene segment, for example the rearranged germline human kappa light chain $IgV_{\kappa}\kappa I$-39*01/$IGJ_{\kappa}I$*01 (FIG. 11). The terms rearranged germline human kappa light chain IgVκ1-39*01/IGJκ1*01, IGKV1-39/$IG_{\kappa}$J1, huVκ1-39 light chain or in short huVκ1-39, or simply 1-39 are used interchangeably throughout the application. Those of skill in the art will recognize that "common" also refers to functional equivalents of the light chain of which the amino acid sequence is not identical. Many variants of said light chain exist wherein mutations (deletions, substitutions, additions) are present that do not materially influence the formation of functional binding regions.

IgVκ1-39 is short for Immunoglobulin Variable Kappa 1-39 Gene. The gene is also known as Immunoglobulin Kappa Variable 1-39; IGKV139; IGKV1-39; O12a or O12. External Ids for the gene are HGNC: 5740; Entrez Gene: 28930; Ensembl: ENSG00000242371. A preferred amino acid sequence for IgW1-39 is given in FIG. 11. This lists the sequence of the V-region. The V-region can be combined with one of five J-regions. FIG. 11 describes two preferred sequences for IgVκ1-39 in combination with a J-region. The joined sequences are indicated as IGKV1-39/jk1 and IGKV1-39/jk5; alternative names are IgVκ1-39*01/

IGJκ1*01 or IgVκ1-39*01/IGJκ5*01 (nomenclature according to the IMGT database worldwide web at imgt.org).

A common light chain variable region is preferably linked to a kappa light chain constant region. In a preferred embodiment the light chain variable region used in the multivalent antibody of the invention comprises the kappa light chain IgVκ1-39*01/IGJκ1*01 or IgVκ1-39*01/IGJκ5*01. In a preferred embodiment the common light chain in the multivalent antibody is IgVκ1-39*01/IGJκ1*01.

A cell that produces a common light chain can produce for instance rearranged germline human kappa light chain IgVκ1-39*01/IGJκ1*01 and a light chain comprising the variable region of the mentioned light chain fused to a lambda constant region. Where herein reference is made to a germ-line sequence it is preferred that the variable region is a germ-line sequence.

A preferred common light chain for use in a multivalent antibody of the invention is one comprising the sequence set out in SEQ ID NO: 29.

The common chain for use in the multivalent antibodies of the invention can also be a heavy chain and this is therefore also provided in the context of the invention. Common heavy chains have been used in the art to make bispecific antibodies, and can be used here in making a multivalent antibody comprising three or more binding domain, two or more of said binding domains comprise a common heavy chain known in the art. For example, the use of antibody libraries in which the heavy chain variable domain is the same for all the library members and thus the diversity is based on the light chain variable domain. Such libraries are described, for example, PCT/US2010/035619, and PCT/US2010/057780, each of which is hereby incorporated by reference in its entirety. These and other techniques to generating binding domains having common heavy chains can be generated by the skilled artisan, and can be employed in the present invention to produce multivalent antibodies having novel formats disclosed herein.

Production of a Multivalent Antibody

A multivalent antibody of the invention may be produced by co-transfection of individual cells with one or more genetic constructs which together encode the three or more proteins that form a multimer comprising the multivalent antibody such as those described above, including in FIGS. 1a-u. For example, a host cell may be co-transfected with nucleic acid encoding three or more heavy chain variable regions and a common light chain variable region to produce a multivalent antibody. Alternatively, a multivalent antibody of the invention may be produced by co-transfection of individual cells with one or more genetic constructs which together encode the three or more light chain variable regions and a common heavy chain.

Several methods have been published to favor the production antibodies which are heterodimers. In the present invention it is preferred that the cell favors the production of the heterodimers over the production of the respective homodimers. This is typically achieved by modifying the constant region of the heavy chains such that they favor heterodimerization (i.e. dimerization with one heavy chain combining with the second heavy chain) over homodimerization. In a preferred embodiment the antibody of the invention comprises two different immunoglobulin heavy chains with compatible heterodimerization domains.

The compatible heterodimerization domains are preferably compatible immunoglobulin heavy chain CH3 heterodimerization domains. When wildtype CH3 domains are used, co-expression of two different heavy chains (A and B) and a common light chain will result in three different antibody species, AA, AB and BB. AA and BB are designations for the two homodimer antibodies and AB is a designation for the heterodimer antibody. To increase the percentage of the desired heterodimer product (AB) CH3 engineering can be employed, or in other words, one can use heavy chains with compatible hetero-dimerization domains, as defined hereunder. The art describes various ways in which such hetero-dimerization of heavy chains can be achieved.

The term 'compatible hetero-dimerization domains' as used herein refers to protein domains that are engineered such that engineered domain A' will preferentially form heterodimers with engineered domain B' and vice versa, homo-dimerization between A'-A' and B'-B' is diminished.

In U.S. Ser. No. 13/866,747 (now issued as U.S. Pat. No. 9,248,181), U.S. Ser. No. 14/081,848 (now issued as U.S. Pat. No. 9,358,286), WO2013/157953 and WO2013/157954, methods and means are disclosed for producing multivalent antibodies using compatible heterodimerization domains. These means and methods can also be favorably employed in the present invention. Specifically, an antibody of the invention preferably comprises mutations to produce essentially only bispecific full length IgG molecules. Preferred mutations are the amino acid substitutions L351K and T366K (EU numbering) in the first CH3 domain or at positions corresponding thereto (the 'KK-variant' heavy chain) and the amino acid substitutions L351D and L368E in the second domain or at positions corresponding thereto (the 'DE-variant' heavy chain), or vice versa. It was previously demonstrated in our U.S. Pat. Nos. 9,248,181 and 9,358,286 patents as well as the WO2013/157954 PCT application that the DE-variant and KK-variant preferentially pair to form heterodimers (so-called 'DEKK' bispecific molecules). Homodimerization of DE-variant heavy chains (DEDE homodimers) or KK-variant heavy chains (KKKK homodimers) hardly occurs due to repulsion between the charged residues in the CH3-CH3 interface between identical heavy chains.

In a preferred host cell of the present invention, capable of expressing proteins that multimerize to form a multivalent antibody, the host cell is transformed with a nucleic acid that encodes three proteins. In order from N-terminus to C-terminus, the encoded proteins include a first protein comprising VH1-CH1-VH2-CH1-CH2-CH3, wherein a linker connects VH2 and CH1 on the first protein, a second encoded protein comprising VLc-CL, a third encoded protein comprising VH3-CH1-CH2-CH3, wherein the CH1 of the first and third encoded protein pairs with the CL of the second encoded protein, and the encoded CH3 region of the first and third proteins encode amino acid L351K and T366K (EU numbering) in the first CH3 protein or at positions corresponding thereto and the amino acids L351D and L368E in the third protein or a corresponding positions thereto respectively, or vice versa. Alternatively, said first and third proteins comprise other compatible hetero-dimerization domains that cause the efficient pairing of the CH3 domains of each of these proteins.

Said nucleic acids encoding said three proteins may be on one or more vectors, to generate a multivalent antibody of the invention. Similarly, host cells can be generated encoding more than three proteins for each of the multivalent antibodies described above, including those in FIGS. 1a-1u.

Said nucleic acids encoding said three proteins may further be stably integrated into the host cell's genome, preferably at chromosomal regions known for high expression and an absence or reduction of gene silencing.

According to the invention, there is thus provided a method for the preparation of a multivalent antibody, which method comprises:
  providing a cell which comprises one or more nucleic acid sequences encoding polypeptides which are capable of assembly into a multivalent antibody according to the invention; and
  cultivating said host cell under conditions to provide for expression of the polypeptides and for their assembly into a multivalent antibody.

A host cell of the present invention may be capable of producing the multivalent antibody at a purity of at least about 50%, at least about 60%, least about 70%, at least about 80%, at least about 90%, at least about 95%, at least about 98% of the multivalent antibody of the invention on the basis of total expressed immunoglobulin.

A host cell of the invention may be capable of producing the multivalent antibody, wherein at least about 50%, at least about 60%, least about 70%, at least about 80%, at least about 90%, at least about 95%, at least about 98% of the multivalent antibody produced comprises a variable rearranged region paired with a cognate common chain for all binding sites.

A host cell of the invention may be capable of producing the multivalent antibody, wherein at least about 50%, at least about 60%, at least about 70%, at least about 80%, at least about 90%, at least about 95%, at least about 98% of the common chain expressed is paired to the multivalent antibody and is not free, unassociated protein.

Suitable cells for antibody production are a hybridoma cell, a Chinese hamster ovary (CHO) cell, an NS0 cell or a PER-C6 cell. In a particularly preferred embodiment said cell is a CHO cell. Cells for the production of an antibody as disclosed herein are also referred to as host cells.

Various institutions and companies have developed cell lines for the large scale production of antibodies, for instance for clinical use. Non-limiting examples of such cell lines are CHO cells, NS0 cells or PER.C6 cells. At least some of these cells are also used for other purposes such as the production of proteins. Cell lines developed for industrial scale production of proteins and antibodies are herein further referred to as industrial cell lines. In a preferred embodiment the invention provides an industrial cell line that produces and an antibody of the invention.

The invention in one embodiment provides a cell (host cell) comprising an antibody according to the invention and/or a nucleic acid according to the invention. Said cell is preferably an animal cell, more preferably a mammal cell, more preferably a primate cell, most preferably a human cell. For the purposes of the invention a suitable cell, suitable host cell is any cell capable of comprising and preferably of producing an antibody according to the invention and/or a nucleic acid according to the invention.

The invention further provides a cell comprising an antibody according to the invention. Preferably said cell (typically an in vitro, isolated or recombinant cell) produces said antibody. In a preferred embodiment said cell is a hybridoma cell, a Chinese hamster ovary (CHO) cell, an NS0 cell or a PER.C6 cell. In a particularly preferred embodiment said cell is a CHO cell. Further provided is a cell culture comprising a cell according to the invention. Various institutions and companies have developed cell lines for the large scale production of antibodies, for instance for clinical use. Non-limiting examples of such cell lines are CHO cells, NS0 cells or PER.C6 cells. These cells are also used for other purposes such as the production of proteins. Cell lines developed for industrial scale production of proteins and antibodies are herein further referred to as industrial cell lines. Thus in a preferred embodiment the invention provides the use of a cell line developed for the large scale production of antibody for the production of a multivalent antibody of the invention. The invention further provides a cell for producing a multivalent antibody comprising one more nucleic acid molecules that alone or together code for a multivalent antibody as claimed.

The invention also provides a method for producing two or more antibodies by the same cell wherein at least one of said antibodies is a multivalent antibody as described herein. This embodiment is now exemplified by the previously described DE/KK heterodimerization system. The invention is, however, not limited to a particular method for enabling heterodimerization of heavy chains. As previously described, the DE-variant and KK-variant preferentially pair to form heterodimers (so-called DEKK' bi/multivalent molecules). Homodimerization of DE-variant heavy chains (DEDE homodimers) or KK-variant heavy chains (KKKK homodimers) hardly occurs due to repulsion between the charged residues in the CH3-CH3 interface between identical heavy chains. Introducing a further heavy chain that has either the DE- or the KK-variant heavy chain, allows the production of a further DEKK bi/multivalent molecule. A newly introduced DE-heavy chain (DE2) can associate with the existing KK heavy chain. The cell thus produces two bi/multivalent antibodies a DE1 KK and a DE2KK bivalent antibody. If a new KK heavy chain (KK2) is introduced instead of the new DE heavy chain, the bivalent antibodies with the combinations DEKK1 and DEKK2 are produced. The levels at which the different antibodies can be produced by the cell is typically best adjusted by adjusting the relative expression of the DE1/2 and KK1/2 chains with respect to each other. The light chain is typically produced sufficiently to reduce the level of single heavy chains and the level at which one chain is produced is typically sufficient to allow efficient pairing with the complementary chains. In the DE1/2; KK example the DE1 and DE2 heavy chains are preferably produced to a level that together matches the level of the KK heavy chain. The level of the respective antibodies can be adjusted by adjusting the levels at which the DE1 and DE2 are produced relative to each other. For the KK1/2 DE variant the situation is of course similar but now for the KK1 and KK2 chains in relation to each other. Depending on the number of binding domains or variable domains associated with each of the heavy chains this method allows the production of a variety of different bi/multivalent antibodies. Several non-limiting examples are now here described. In this example heavy chain DE1 has one heavy chain variable region that together with light chain common to all binding domains for a binding domain or variable domain that binds antigen V, heavy chain DE2 has two heavy chain variable regions that together with the common light chain form two binding domains or variable domains that bind antigens W and X. Heavy chain KK has one heavy chain variable region that together with the common light chain forms a binding domain or variable domain that binds antigen Y. Producing these heavy and light chains in a cell with produce an antibody DE1 KK and an antibody DE2KK wherein antibody DE1 KK is a bivalent antibody that binds antigens V and Y. Antibody DE2KK is a multivalent antibody that binds the antigens W, X and Y. If in the above example DE1 also has two heavy chain variable regions that together with the common light chain form two binding domains or variable domains two multivalent antibodies of the invention are produced. The KK heavy chain can also be provided with an additional heavy chain variable region thereby adding yet further binding domains of the same or different antigen binding specificity. Combination of two or more different heterodimerization domains such as the DE/KK described above and the know in hole domains can add further diversity in the oligoclonic antibody production. For instance adding two heavy chains, one with the knob and the other with the complementary hole allows the production of an independent bi/multivalent antibody comprising of a knob heavy chain and a hole heavy chain. Depending on the number of heavy chain variable regions associated with each heavy chain and depending on whether the are the same or different, a further monospecific antibody, or a further bi or multivalent antibody is produced.

According to the invention, there is provided a composition comprising two or more antibodies, at least one of which may be a multivalent antibody of the invention. Such a composition of the invention may comprise two or more multivalent antibodies of the invention. Such a composition may comprise three, four, five or more antibodies, at least one of which may be a multivalent antibody of the invention. Such a composition may comprise three, four, five or more antibodies, all of which may be a multivalent antibody of the invention. In such a composition, one or more of the antibodies present in the composition may have one heavy chain in common.

A host cell of the invention may express or may be capable of expressing two or more antibodies, at least one of which may be a multivalent antibody of the invention. A host cell of the invention may express or may be capable of expressing two or more multivalent antibodies of the invention. Such host cells may express or may be capable of expressing three, four, five or more antibodies, at least one of which may be a multivalent antibody of the invention. Such host cells may express or may be capable of expressing three, four, five or more antibodies, all of which may be a multivalent antibody of the invention.

According to the invention, there is thus provided a method for the preparation of a composition comprising two or more antibodies, which method comprises: providing a cell which comprises one or more nucleic acid sequences encoding polypeptides which are capable of assembly into two or more antibodies, at least one of which is a multivalent antibody according to the invention; and cultivating said host cell under conditions to provide for expression of the polypeptides and for their assembly into the two or more antibodies, at least one of which is a multivalent antibody according to the invention.

The invention also provides a method for producing two or more antibodies by the same cell wherein at least one of said antibodies is a multivalent antibody as described herein.

The invention provides a method for producing a composition comprising two or more antibodies of which at least one is a multivalent antibody as claimed the method comprising providing a cell with
  nucleic acid that encodes a first heavy chain with a heavy chain variable region that together with a common light chain forms a binding domain or variable domain that binds to a first antigen;
  nucleic acid that encodes a second heavy chain with a heavy chain variable region that together with said common light chain forms a variable domain that binds to a second antigen and a heavy chain variable region that together with said common light chain forms a variable domain that binds a third antigen;
  a nucleic acid that encodes a third heavy chain with a heavy chain variable region that together with said common light chain forms a variable domain that binds to a fourth antigen; and
  a nucleic acid that encodes a polypeptide comprising said common light chain;
wherein two or more of said nucleic acids may be physically linked or not and wherein each of said nucleic acids further comprises an expression control sequence to allow expression of the encoded heavy and light chains in said cell and wherein the method further comprises culturing said cell to allow expression of said heavy and light chains and, optionally collecting said two or more antibodies. In one embodiment said first and second heavy chains have a compatible heterodimerization domain preferably a DE/KK heterodimerization domain. In a preferred embodiment said third heavy chain comprises one of the parts of the compatible heterodimerization domain as a result of which two antibodies are produced. In one embodiment the method further comprises providing a collection of cells with said nucleic acid and selecting from said collection a cell with a desired ratio of expression of the respective heavy and light chains. In a preferred embodiment said two or more antibodies are two or more multispecific antibodies. In a preferred embodiment the cells produce essentially equimolar amounts of the two or more antibodies. In some embodiments the cells produce more of one antibody than of another of said two or more antibodies.

Non-Human Animals

Synthesis and expression of multivalent binding proteins has been problematic, in part due to issues associated with identifying a suitable light chain that can associate and express with two or more different heavy chains, and in part due to isolation issues. Further, the art has lacked an array of linkers that permit a diverse array of antibody valence, flexibility with stability and low immunogenicity.

The methods and compositions described herein allow for making suitable multivalent binding proteins having binding domains obtained from, derived from, or based on suitable methods. Suitable methods may include phage display methods (including modification of germline sequences generated in phage display systems), and other in vitro methods known in the art. A particularly useful method is having a genetically modified non-human animal make, through natural processes of somatic recombination, and affinity maturation, a suitable heavy chain variable domain that can associate and express with a common light chain.

In one embodiment, the variable domains used in a multivalent antibody of the invention are obtained from, derived from or based on heavy and light chain variable regions of a non-human transgenic animal that comprises in its germline an unrearranged heavy chain variable locus and expresses a single rearranged human light chain variable domain, e.g., a common light chain mammal, such as a rodent. Such a non-human, transgenic animal upon exposure to an antigen will express a diversity of heavy chain variable regions paired with a common light chain, which can then be used to develop nucleic acid sequences encoding heavy chain variable regions obtained from, derived from or based on those from said transgenic animal that are able to be efficiently transformed into host cells for the production of multivalent antibodies.

In particular, the human variable region sequences from suitable B cells of an immunized common light chain animal that are genetically engineered to express human light chain variable domains derived from no more than one, or no more than two, human VL gene segments may be used as a source of potential VH domains for a multivalent antibody of the invention. The B cells from said animals that are immunized with one or more antigens of interest, which are, in various embodiments, antigens to which the multivalent antibody will bind. Cells, tissues, or serum, splenic or lymph materials of the said animals are screened to obtain heavy chain variable domains (or B cells that express them) that exhibit desired characteristics with respect to the antigens of interest, e.g., high affinity, low affinity, blocking ability, activation, internalization or other characteristics. Because virtually all of the heavy chain variable domains that are generated in response to an antigenic stimulation in said transgenic animal are made in conjunction with the expresses of a human immunoglobulin light chain derived from no more than one, or no more than two, VL gene segments, the heavy chain variable regions are capable of expressing and associating with common light chain domains that are expressed in the transgenic animal.

In one aspect, an epitope-binding protein as described herein is provided, wherein human VL and VH sequences are encoded by nucleic acid based on nucleic acid obtained from the B-cell of a transgenic mouse described herein, and/or a transgenic animal as disclosed in WO2009/157771, incorporated herein by reference, that has been immunized with an antigen comprising an epitope of interest.

Nucleic Acid Sequences, Polypeptides, Vectors and Cells

The invention further provides: nucleic acid sequences encoding polypeptides or linkers that may be used in the assembly of a multivalent antibody of the invention; vectors comprising such nucleic acid sequences; a cell which is capable of producing a multivalent antibody of the invention; and a method for the preparation of such a multivalent antibody using such a cell.

Multivalent antibodies according to the invention are typically produced by cells that express nucleic acid sequences encoding the polypeptides that together assemble to form an antibody of the invention.

Accordingly, the invention provides a linker which comprises an amino acid sequence as set out in any one of SEQ ID NOs 1 to 3 or 5 to 24 or a polypeptide having at least about 85% sequence identity to any one thereto at least about 85% sequence identity to any one thereto, such as at least about 90% sequence identity to any one thereto, for example at least about 95% sequence identity to any one thereto, such as at least about 98% sequence identity to any one thereto, for example at least about 99% sequence identity to any one thereto.

The invention further provides a polypeptide comprising: a VH1-CH1-hinge-based linker-VH2-CH1.

In certain embodiments VH1 and VH2 bind the same epitope. In certain embodiment the VH1 and VH2 bind the same antigen, but different epitopes. And in certain embodiments, VH1 and VH2 bind separate epitopes and antigens.

Also provided by the invention is a nucleic acid sequence encoding such a linker or polypeptide and a vector comprising such a nucleic acid sequence.

The nucleic acid sequences employed to make the described polypeptides may be placed in any suitable expression vector and, in appropriate circumstances, two or more vectors in a single host cell.

Generally, nucleic acid sequences encoding variable domains are cloned with the appropriate linkers and/or constant regions and the sequences are placed in operable linkage with a promoter in a suitable expression construct in a suitable cell line for expression.

Accordingly, the invention also provides a method for the preparation of an antibody, which method comprises:

providing a cell which comprises one or more nucleic acid sequences encoding polypeptides which are capable of assembly into a multivalent antibody of the invention; and cultivating said host cell under conditions to provide for expression of the polypeptides and for their assembly into a multivalent antibody.

Expression of a Multivalent Antibody

Expression of antibodies in recombinant host cells has been described in the art. The nucleic acid molecules encoding the light and heavy chains of an antibody of the invention may be present as extrachromosomal copies and/or stably integrated into the chromosome of the host cell. The latter is preferred in which case a loci may be targeted that is known for lack of gene silencing.

To obtain expression of nucleic acid sequences encoding the polypeptides which assemble as an antibody of the invention, it is well known to those skilled in the art that sequences capable of driving such expression can be functionally linked to the nucleic acid sequences encoding the polypeptides. Functionally linked is meant to describe that the nucleic acid sequences encoding the polypeptides or precursors thereof are linked to the sequences capable of driving expression such that these sequences can drive expression of the polypeptides or precursors thereof. Useful expression vectors are available in the art, e.g. the pcDNA vector series of Invitrogen. Where the sequence encoding the polypeptide of interest is properly inserted with reference to sequences governing the transcription and translation of the encoded polypeptide, the resulting expression cassette is useful to produce the polypeptide of interest, referred to as expression. Sequences driving expression may include promoters, enhancers and the like, and combinations thereof. These should be capable of functioning in the host cell, thereby driving expression of the nucleic acid sequences that are functionally linked to them. Promoters can be constitutive or regulated, and can be obtained from various sources, including viruses, prokaryotic, or eukaryotic sources, or artificially designed.

Expression of nucleic acid sequences of the invention may be from the natural promoter or a derivative thereof or from an entirely heterologous promoter. Some well-known and much used promoters for expression in eukaryotic cells comprise promoters derived from viruses, such as adenovirus, e.g. the E1A promoter, promoters derived from cytomegalovirus (CMV), such as the CMV immediate early (IE) promoter, promoters derived from Simian Virus 40 (SV40), and the like. Suitable promoters can also be derived from eukaryotic cells, such as methallothionein (MT) promoters, elongation factor Ia (EF-Ia) promoter, actin promoter, an immunoglobulin promoter, heat shock promoters, and the like. Any promoter or enhancer/promoter capable of driving expression of a nucleic acid sequence of the invention in a host cell is suitable in the invention. In one embodiment the sequence capable of driving expression comprises a region from a CMV promoter, preferably the region comprising nucleotides −735 to +95 of the CMV immediate early gene enhancer/promoter. The skilled person will be aware that the expression sequences used in the invention may suitably be combined with elements that can stabilize or enhance expression, such as insulators, matrix attachment regions, STAR elements and the like. This may enhance the stability and/or levels of expression.

Any cell suitable for expressing a recombinant nucleic acid sequence may be used to generate an antibody of the invention. Preferably said cell is adapted for suspension growth.

A multivalent antibody of the invention may be expressed in host cells, typically by culturing a suitable cell of the invention and harvesting said antibody from said culture. Preferably said cell is cultured in a serum free medium. An antibody of the invention may be recovered from the cells or, preferably, from the cell culture medium by methods that are generally known to the person skilled in the art.

Further provided is an antibody obtainable by a method for producing an antibody according to the invention. The antibody is preferably purified from the medium of the culture.

After recovery, an antibody may be purified from the culture by using methods known in the art. Such methods may include precipitation, centrifugation, filtration, size-exclusion chromatography, affinity chromatography, cation- and/or anion-exchange chromatography, hydrophobic interaction, chromatography, and the like. Affinity chromatography, including based on the linker sequence as a means of separating the multivalent antibody of the invention may be used.

Pharmaceutical Compositions and Methods of Use

Also provided by the invention is a pharmaceutical composition which comprises an antibody of the invention and a pharmaceutically acceptable carrier and/or diluent.

Accordingly, the invention provides a multispecific antibody as described herein for use in the treatment of the human or animal body by therapy.

Further provided by the invention is a method for the treatment of a human or animal suffering from a medical condition, which method comprises administering to the human or animal a therapeutically effective amount of an antibody as described herein.

The amount of antibody according to the invention to be administered to a patient is typically in the therapeutic window, meaning that a sufficient quantity is used for obtaining a therapeutic effect, while the amount does not exceed a threshold value leading to an unacceptable extent of side-effects. The lower the amount of antibody needed for obtaining a desired therapeutic effect, the larger the therapeutic window will typically be. An antibody according to the invention exerting sufficient therapeutic effects at low dosage is, therefore, preferred.

A reference herein to a patent document or other matter which is given as prior art is not to be taken as an admission that that document or matter was known or that the information it contains was part of the common general knowledge at the priority date of any of the claims.

The disclosure of each reference set forth herein is incorporated herein by reference in its entirety.

For the purpose of clarity and a concise description features are described herein as part of the same or separate embodiments, however, it will be appreciated that the scope of the invention may include embodiments having combinations of all or some of the features described.

The following Examples illustrate the invention. For ease of reference, for Examples eight to fifteen, when describing trispecific molecules, the following format is used MFAxMFB:MFC or AntigenAxAntigenB:AntigenC, such that MFA or AntigenA followed by x constitutes the "short arm", while the x denotes the dimerization, followed by MFB or AntigenB describes the interior position of the long arm, followed by a ":" designating a linker followed by MFC or AntigenC describes MFC or AntigenC at the distal domain of the long arm.

EXAMPLES

Figure 2A:
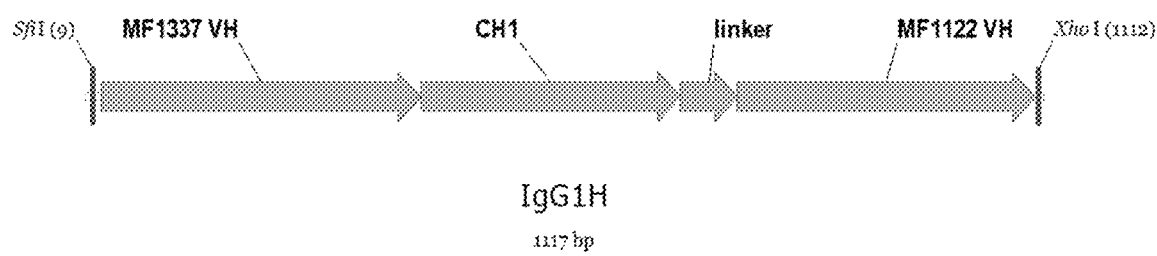
FIG. 2a sets out a schematic diagram of the VH1-CH1-linker-VH2 insert used for cloning the constructs in the vector MV1626. It is understood, though not shown, that the vector also may encode CH3-CH2-CH1 region, which is connected to the VH2.
Figure 3:
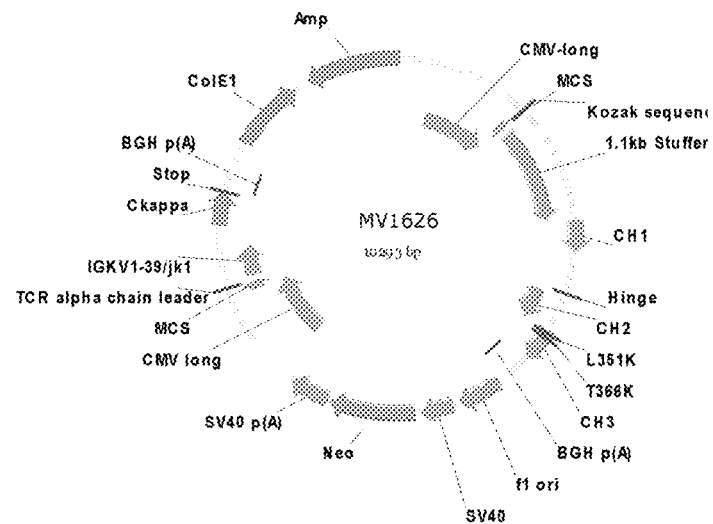
FIG. 3 sets out a schematic diagram of the MV1626 vector.

Example 1: Cloning of the Variable Domains and Linker for the Generation of a Vector Capable of Expressing a Multispecific Antibody 24 linker constructs were cloned in pools according to their size as detailed in Table 2 into the MV1626 vector (see FIG. 3), containing the KK residues (L351K, T366K) in the CH3 region for the generation of IgG heavy chain heterodimers (WO2013/157954 and WO2013/157953). The constructs were cloned into vector MV1626 using restriction enzyme SfiI and XhoI. All constructs contain sequentially the VH gene of MF1337, a CH1 domain, the linker sequences of which the translations are listed in Table 2, and the VH gene of MF1122. As an example, the DNA sequence of construct MF1337xIgG4 UHxMF1122 is provided below in Table 3. Schematically the construct is depicted in FIG. 2a. The constructs are based on both the CH1 and linker sequence of the IgG isotype indicated in the name of the constructs. A translation of all 24 CH1 regions in combination with the linker sequences is provided in FIG. 5. A translation of all three VH genes and the common light chain gene are provided below in Table 4.

TABLE 2

Figure 5:
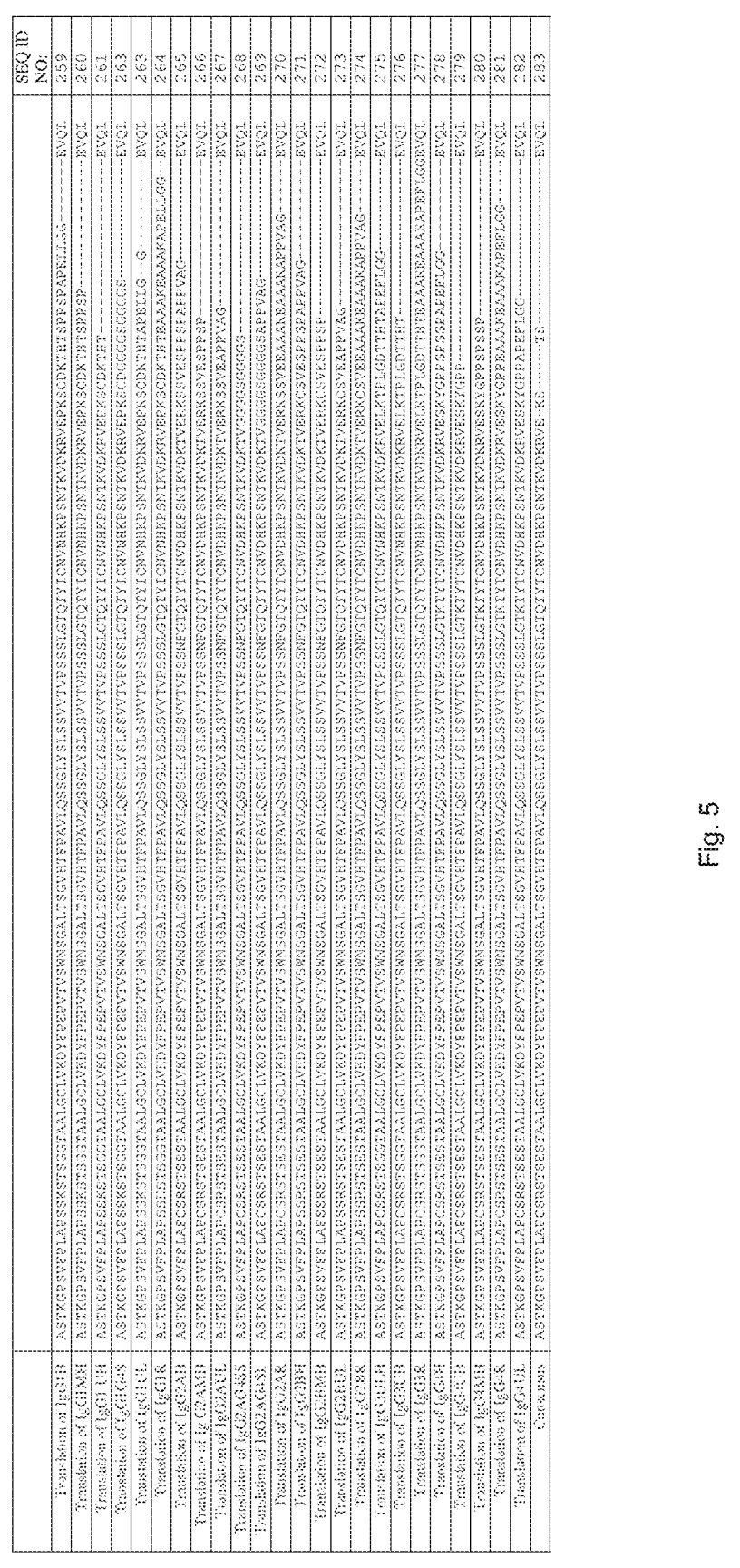

The sequences of the 24 different linkers/
constructs and naming as used; note there
are also differences in CH1 (FIG. 5).
The linker sequence is indicated below.

| | Linker name | Sequence | Linker size (aa) |
|---|---|---|---|
| Pool1 | | | |
| 1 | IgG4 UH | ESKYGPP (SEQ ID NO: 1) | 7 |
| 2 | IgG1 UH | EPKSCDKTHT (SEQ ID NO: 2) | 10 |
| 3 | IgG2A G4SS | GGGGSGGGGS (SEQ ID NO: 3) | 10 |
| 4 | IgG2A MH | ERKSSVESPPSP (SEQ ID NO: 4) | 12 |
| 5 | IgG2B MH | ERKCSVESPPSP (SEQ ID NO: 5) | 12 |
| 6 | IgG3 UH | ELKTPLGDTTHT (SEQ ID NO: 6) | 12 |
| 7 | IgG4 MH | ESKYGPPSPSSP (SEQ ID NO: 7) | 12 |
| 8 | IgG2A UL | ERKSSVEAPPVAG (SEQ ID NO: 8) | 13 |
| 9 | IgG2B UL | ERKCSVEAPPVAG (SEQ ID NO: 9) | 13 |
| 10 | IgG4 UL | ESKYGPPAPEFLGG (SEQ ID NO: 10) | 14 |
| 11 | IgG1 MH | EPKSCDKTHTSPPSP (SEQ ID NO: 11) | 15 |
| 12 | IgG1 G45 | EPKSCDGGGGSGGGGS (SEQ ID NO: 12) | 16 |
| 13 | IgG2 G4SL | GGGGSGGGGSAPPVAG (SEQ ID NO: 13) | 16 |

TABLE 2 -continued

The sequences of the 24 different linkers/
constructs and naming as used; note there
are also differences in CH1 (FIG. 5).
The linker sequence is indicated below.

| Linker name | Sequence | Linker size (aa) |
|---|---|---|
| Pool2 | | |
| 1 IgG1 UL | EPKSCDKTHTAPELLGG (SEQ ID NO: 14) | 17 |
| 2 IgG2A H | ERKSSVESPPSPAPPVAG (SEQ ID NO: 15) | 18 |
| 3 IgG2B H | ERKCSVESPPSPAPPVAG (SEQ ID NO: 16) | 18 |
| 4 IgG3 ULH | ELKTPLGDTTHTAPEFLGG (SEQ ID NO: 17) | 19 |
| 5 IgG4 H | ESKYGPPSPSSPAPEFLGG (SEQ ID NO 18) | 19 |
| 6 IgG1 H | EPKSCDKTHTSPPSPAPELLGG (SEQ ID NO: 19) | 22 |
| 7 IgG2A R | ERKSSVEEAAAKEAAAKAPPVAG (SEQ ID NO: 20) | 23 |
| 8 IgG2B R | ERKCSVEEAAAKEAAAKAPPVAG (SEQ ID NO: 21) | 23 |
| 9 IgG4 R | ESKYGPPEAAAKEAAAKAPEFLGG (SEQ ID NO: 22) | 24 |
| 10 IgG1 R | EPKSCDKTHTEAAAKEAAAKAPELLGG (SEQ ID NO: 23) | 27 |
| 11 IgG3 R | ELKTPLGDTTHTEAAAKEAAAKAPEFLGG (SEQ ID NO: 24) | 29 |

The respective CH1 sequences together with the linker are indicated in FIG. 5.
The "linker name" refers to the sequence of the indicated together with the CH1 domain.

TABLE 3

| DNA sequence of construct MF1337xIgG4_UHxMF1122 | |
|---|---|
| DNA sequence | SEQ ID NO |
| ggcccagccggccatggccgaggtgcagctggtggagactggggctgaggtgaagaagccggggcctca<br>gtgaaggtctcctgcaaggcttctgactacatcttcaccaaatatgacatcaactgggtgcgccaggcc<br>ctggacaagggcttgaatggatggatgagcgctaacactggaaacacgggctatgcacagaagtt<br>ccagggcagagtcaccatgaccagggacacgtccataaacacagcctacatggagctgagcagcctgaca<br>tctggtgacacggccgtttatttctgtgcgaggagtagtcttttcaagacagagacggcgccctactatc<br>acttcgctctggacgtctggggccaagggaccacggtcaccgtctccagtgctagcaccaagggcccag<br>cgtgttccccctggccccctgcagccggagcaccagcgagagcaccgccgccctgggctgcctggtgaag<br>gactactttccccgagcccgtgaccgtgagctggaacagcggcgccctgaccagcggcgtgcacaccttcc<br>ccgccgtgctgcagagcagcggcctgtacagcctgagcagcgtggtgacggtgcccagcagcagcctggg<br>caccaagacctacacctgcaacgtggaccacaagcccagcaacaccaaggtggacaagcgggtggagagc<br>aagtacggccccccgaggtgcagctggtggagtctgggggaggcgtggtccagcctgggaggtccctga<br>gactctcctgtgcagcctctggattcaccttcagtagctatggcatgcactgggtccgccaggctccagg<br>caaggggctggagtgggtggcagttatatcatatgatggaagtaataaatactatgcagactccgtgaag<br>ggccgattcaccatctccagagacaattccaagaacacgctgtatctgcaaatgaacagcctgagagctg<br>aggacacggccgtgtattactgtgcaagagccctcttcacgaccatcgccatggactattggggccaagg<br>tacccttgtcaccgtctcgagt | SEQ ID NO: 25 |
| gaggtgcagctggtggagactggggctgaggtgaagaagccggggcctca<br>gtgaaggtctcctgcaaggcttctgactacatcttcaccaaatatgacatcaactgggtgcgccaggcc<br>ctggacaagggcttgaatggatggatgagcgctaacactggaaacacgggctatgcacagaagtt<br>ccagggcagagtcaccatgaccagggacacgtccataaacacagcctacatggagctgagcagcctgaca<br>tctggtgacacggccgtttatttctgtgcgaggagtagtcttttcaagacagagacggcgccctactatc<br>acttcgctctggacgtctggggccaagggaccacggtcaccgtctccagtgctagcaccaagggcccag<br>cgtgttccccctggccccctgcagccggagcaccagcgagagcaccgccgccctgggctgcctggtgaag<br>gactactttccccgagcccgtgaccgtgagctggaacagcggcgccctgaccagcggcgtgcacaccttcc<br>ccgccgtgctgcagagcagcggcctgtacagcctgagcagcgtggtgacggtgcccagcagcagcctggg<br>caccaagacctacacctgcaacgtggaccacaagcccagcaacaccaaggtggacaagcgggtggagagc<br>aagtacggccccccgaggtgcagctggtggagtctgggggaggcgtggtccagcctgggaggtccctga<br>gactctcctgtgcagcctctggattcaccttcagtagctatggcatgcactgggtccgccaggctccagg<br>caaggggctggagtgggtggcagttatatcatatgatggaagtaataaatactatgcagactccgtgaag<br>ggccgattcaccatctccagagacaattccaagaacacgctgtatctgcaaatgaacagcctgagagctg<br>aggacacggccgtgtattactgtgcaagagccctcttcacgaccatcgccatggactattggggccaagg<br>tacccttgtcaccgtctcgagt | SEQ ID NO: 284 |
| EVQLVETGAEVKKPGASVKVSCKASDYIFTKYDINWVRQAPGQGLEWMGWMS<br>ANTGNTGYAQKFQGRVTMTRDTSINTAYMELSSLTSGDTAVYFCARSSLFKTET<br>APYYHFALDVWGQGTTVIVSSASTKGPSVFPLAPCSRSTSESTAALGCLVKDYF<br>PEPVTVSWNSGALTSGVHTFPAVLQSSGLYSLSSVVIVPSSSLGTKTYTCNVDH<br>KPSNTKVDKRVESKYGPPEVQLVESGGGVVQPGRSLRLSCAASGFTFSSYGM<br>HWVRQAPGKGLEWVAVISYDGSNKYYADSVKGRFTISRDNSKNTLYLQMNSLR<br>AEDTAVYYCARALFTTIAMDYWGQGTLVTVSS | SEQ ID NO: 285<br>Translation of SEQ ID NO: 284 |

TABLE 4

Translations of all three VH genes and the common light chain gene

| Protein sequence | Description | SEQ ID NO |
|---|---|---|
| EVQLVESGGGVVQPGRSLRLSCAASGF TFSSYGMHWVRQAPGKGLEWVAVISYD GSNKYYADSVKGRFTISRDNSKNTLYL QMNSLRAEDTAVYYCARALFTTIAMDY WGQGTLVT | Translation of MF1122 | SEQ ID NO: 26 |
| EVQLVESGGGVVQPGRSLRLSCAASGF TFSSYGMHWVRQAPGKGLEWVAVISYD GSNKYYADSVKGRFTISRDNSKNTLYL QMNSLRAEDTAVYYCARALFTTIAMDY WGQGTLVTVSS | Translation of MF1122 | SEQ ID NO: 286 |
| EVQLVESGGGLVQPGGSLRLSCAASGF TFSSYAMSWVRQAPGKGLEWVSAISGS GGSTYYADSVKGRFTISRDNSKNTLYL QMNSLRAEDTAVYYCARADWWATFDYW GQGTLVT | Translation of MF1025 | SEQ ID NO: 27 |
| EVQLVESGGGLVQPGGSLRLSCAASGF TFSSYAMSWVRQAPGKGLEWVSAISGS GGSTYYADSVKGRFTISRDNSKNTLYL QMNSLRAEDTAVYYCARADWWATFDYW GQGTLVTVSS | Translation of MF1025 | SEQ ID NO: 287 |
| EVQLVETGAEVKKPGASVKVSCKASDY IFTKYDINWVRQAPGQGLEWMGWMSAN TGNIGYAQKFQGRVTMTRDTSINTAYM ELSSLTSGDTAVYFCARSSLFKTETAP YYHFALDVWGQGTTVT | Translation of MF1337 | SEQ ID NO: 28 |
| EVQLVETGAEVKKPGASVKVSCKASDY IFTKYDINWVRQAPGQGLEWMGWMSAN TGNIGYAQKFQGRVTMTRDTSINTAYM ELSSLTSGDTAVYFCARSSLFKTETAP YYHFALDVWGQGTTVTVSS | Translation of MF1337 | SEQ ID NO: 288 |
| DIQMTQSPSSLSASVGDRVTITCRASQ SISSYLNWYQQKPGKAPKLLIYAASSL QSGVPSRFSGSGSGTDFTLTISSLQPE DFATYYCQQSYSTPPTFGQGTKVEIKR TVAAPSVFIFPPSDEQLKSGTASVVCL LNNFYPREAKVQWKVDNALQSGNSQES VTEQDSKDSTYSLSSTLTLSKADYEKH KVYACEVTHQGLSSPVTKSFNRGEC | Translation of common light chain (cLC) | SEQ ID NO: 29 |

The inserts and the vector were digested at 50° C. for 2h using SilI restriction enzyme, followed by 2h at 37° C. with XhoI enzyme. The digested DNA was loaded onto a 0.8% agarose gel and run for 2 hours at 100 volts. The digested vector and inserts were subsequently isolated from the gel using Qiagen QIAquick Gel Extraction kit before overnight ligation at 16° C. using T4 DNA ligase in 1/5 ratio (w/w vector/insert). 50 µL of DH5α-T1R competent *E. coli* is were transformed in presence of 5 µL of the ligation mix following a heat shock procedure of 30 min on ice followed by 2 min at 42° C. and 2 min on ice. Transformed bacteria were plated on LB agar supplemented with Ampicillin and incubated overnight at 37° C. Single colonies were picked and mixed with 100 µL of sterile deionised water and used for colony PCR using primers DO_2130 and DO_1056 to confirm the presence of the insert, followed by sequence PCR with the BigDye® Terminator v1.1 Cycle Sequencing Kit (Thermofisher®) for clone confirmation using primer DO_2130.

Single colonies of confirmed clones were used to inoculate 4 mL of LB-Amp. The overnight cultures at 37"C were prepared in 24 wells format mini-prep using the QIAGEN® Plasmid Mini Kit according to the manufacturer manual. After elution from the column, the purified DNA was precipitated by adding 0.7 volumes of room-temperature Isopropanol. The DNA pellet was washed with 1 ml of 70% Ethanol and air dried in sterile conditions and resuspended in sterile Tris-EDTA buffer before storage at −20'C. The final constructs were dideoxy sequenced using primers DO_1488, DO_1056 and DO_2130 for the insert as well as primers DO_0182 and DO_0091 for the CH2/CH3 region using the BigDye® Terminator v1.1 Cycle Sequencing Kit.

All primer sequences are set out in Table 5.

Sequencing showed that all constructs had successfully been prepared.

TABLE 5 primer sequences

| Primer | Sequence | Description | SEQ ID NO |
|---|---|---|---|
| DO_0091 | CCTCATGCATCACGGAGCATG | CH3_rev | SEQ ID NO: 30 |
| DO_0182 | CAAAGGCCAAACTCTCCACTC | CH2 fwd | SEQ ID NO: 31 |
| DO_1056 | CGCTGTGCCCCCAGAGGTGC | VH_rev | SEQ ID NO: 32 |
| DO_1488 | GTACCGGTGAATTGGCCGG | VH_fwd | SEQ ID NO: 33 |
| DO_2130 | GCGCCCTACTATCACTTCGCT CTGG | MF1337 CDR3 fwd | SEQ ID NO: 34 |

Example 2: Transfection and IgG Purification

Figure 2B:
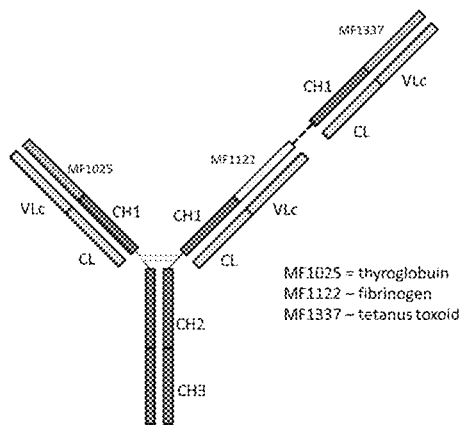
FIG. 2b shows a trispecific antibody, where VH1 binds a tetanus toxoid antigen, VH2 binds a fibrinogen antigen and VH3 binds a thyroglobulin antigen.
Figure 4:
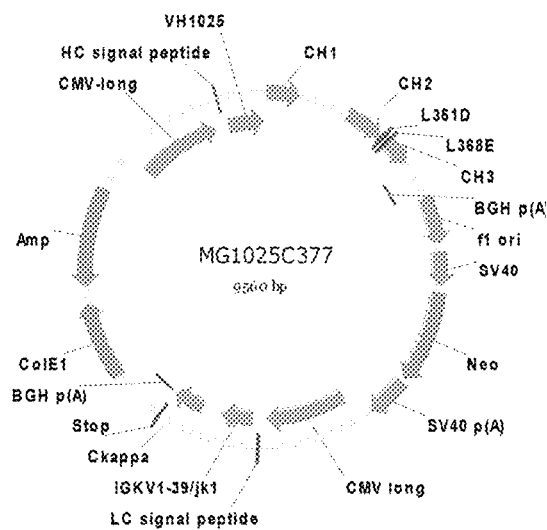
FIG. 4 sets out a schematic diagram of the MG1025C377 expression vector.

The expression vectors generated in Example 1 were combined with the vector MG1025C377 (FIG. 4) expressing the second heavy chain of the base antibody portion of the multispecific antibodies, bearing the L351 D-L368E mutations in the CH3 region (WO2013/157954 and WO2013/157953) and the Thyroglobulin Fab gene of antibody MF1025 (see Example 2 of WO2013/157953). Expression of the two heavy chains together with a common light chain leads to the production of the trispecific antibody as shown in FIG. 2b.

FreeStyle™ 293-F cells (Thermofisher®) were used for expression of the designed antibodies in a 24 wells plate format. Two days before transfection, FreeStyle™ 293-F cell stock was split in 293-F culture medium in a 1:1 ratio and incubated overnight at 37° C. and 8% $CO_2$ at an orbital shaking speed of 155 rpm. Cells were diluted on the day before transfection to a density of $5×10^5$ cells/mL 4 ml of the suspension cells were seeded into a 24 deep wells plate, covered with a breathable seal and incubated overnight at 37° C. and 8% CO2 at an orbital shaking speed of 285 rpm. On transfection day, 4.8 ml 293-F culture medium were mixed with 240 µg of polyethylenimine (PEI) linear (MW 25,000). For each IgG to be produced, 200 uL of the 293F culture medium-PEI mix was added to 8 µl of DNA (for IgG heterodimers 4 µl of DNA encoding each heavy chain) as detailed in Table 6. The mixture was incubated for 20 minutes at room temperature before gently adding to the cells. On the day after transfection Penicillin-Streptomycin (Pen Strep) diluted in 500 µL 293F medium was added to each well. The plates were incubated at 37° C. and 8% CO2 at an orbital shaking speed of 285 rpm until harvest seven days after transfection. Plates were centrifuged 5 min at 500 g, supernatants containing IgGs were filtered using 10-12 µm melt blown polypropylene filter plates and stored at −20° C. prior to purification.

Various control antibodies were also expressed, namely:

Bivalent anti-Tetanus Toxoid antibody using Fab MF1337 (using vector MG1337C057)

Bivalent anti-thyroglobulin antibody using Fab MF1025 (using vector MG1025C059)

Bivalent anti-Fibrinogen antibody using Fab MF1122v (using vector MG1122C057)

Figure 6:
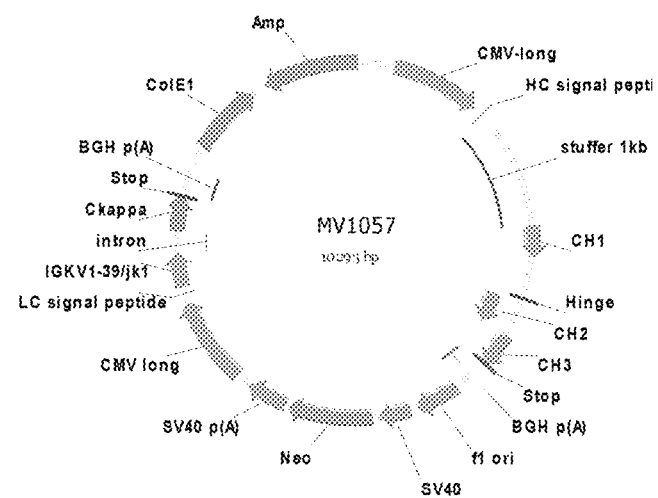
FIG. 6 sets out a schematic diagram of the MV1057 vector.

MG1337C057 indicates a construct expressing the VH region of MF1337 from vector MV1057. MG1025C059 indicates a construct expressing the VH region of MF1025 from vector MV1059. MG1122C057 indicates a construct expressing the VH region of MF1122 from vector MV1057. MV1057 (FIG. 6) and MV1059 are vectors expressing monospecific-bivalent human IgG1 molecules. MV1057 and MV1059 are essentially the same vectors resulting in expression of identical IgG1 molecules.

Bispecific anti-thyroglobulin×anti-Tetanus Toxoid antibody combining Fab MF1337 and Fab MF1025 (using MG1025C377×MG1337C260)

Bispecific anti-thyroglobulin×anti Fibrinogen antibody combining Fab MF1122 and Fab MF1025 (using MG1025C377×MG1122C260)

Figure 7:
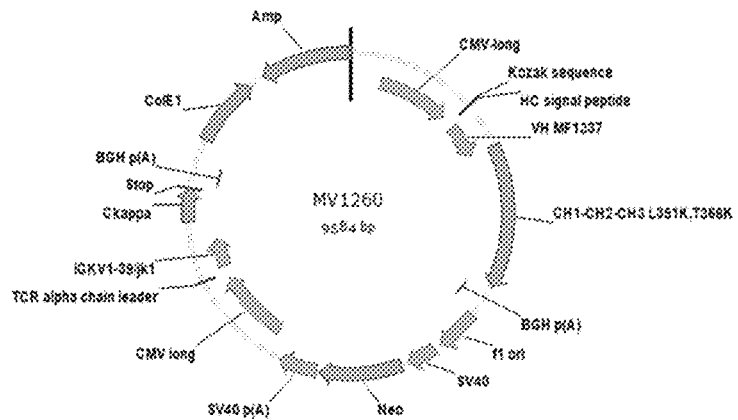
FIG. 7 sets out a schematic diagram of the MV1260 vector.

MG1025C377 (FIG. 4) expresses the heavy chain variable domain of antibody MF1025 in the context of a human IgG1 heavy chain containing the L351D, L368E (DE) mutations. MG1337C260 (FIG. 7) expresses the heavy chain variable domain of antibody MF1337 in the context of a human IgG1 heavy chain containing the L351K, T366K (KK) mutations. MG1122C260 expresses the heavy chain variable domain of antibody MF1122 in the context of a human IgG1 heavy chain containing the L351K, T366K (KK) mutations.

TABLE 6

Transfection scheme for IgG production.

| construct 1 | construct 2 |
|---|---|
| MG1025C377 | MF1337xIgG4 UHxMF1122 |
| MG1025C377 | MF1337xIgG1 UHxMF1122 |
| MG1025C377 | MF1337xIgG2A G4SSxMF1122 |
| MG1025C377 | MF1337xIgG2A MHxMF1122 |
| MG1025C377 | MF1337xIgG2B MHxMF1122 |
| MG1025C377 | MF1337xIgG3 UHxMF1122 |
| MG1025C377 | MF1337xIgG4 MHxMF1122 |
| MG1025C377 | MF1337xIgG2A ULxMF1122 |
| MG1025C377 | MF1337xIgG2B ULxMF1122 |
| MG1025C377 | MF1337xIgG4 ULxMF1122 |
| MG1025C377 | MF1337xIgG1 MHxMF1122 |
| MG1025C377 | MF1337xIgG1 G4SxMF1122 |
| MG1025C377 | MG1337C260 |
| MG1025C377 | MG1122C260 |
| MG1337C057 | —* |
| MG1122C057 | —* |
| MG1025C059 | —* |
| MG1025C377 | MF1337xIgG2 G4SLxMF1122 |
| MG1025C377 | MF1337xIgG1 ULxMF1122 |
| MG1025C377 | MF1337xIgG2A HxMF1122 |
| MG1025C377 | MF1337xIgG2 BHxMF1122 |
| MG1025C377 | MF1337xIgG3 ULHxMF1122 |
| MG1025C377 | MF1337xIgG4 HxMF1122 |
| MG1025C377 | MF1337xIgG1HxMF1122 |
| MG1025C377 | MF1337xIgG2A RxMF1122 |
| MG1025C377 | MF1337xIgG2B RxMF1122 |
| MG1025C377 | MF1337xIgG4 RxMF1122 |
| MG1025C377 | MF1337xIgG1 RxMF1122 |
| MG1025C377 | MF1337xIgG3 RxMF1122 |

*= bivalent controls

Following harvesting, antibodies were purified in 24 well format as follows: supernatants were mixed with 50 µL 1M Trizma® pH8 and 100 µL of ProteinA Sepharose® CL-4B beads (50% v/v, G.E Healthcare Life Sciences) and incubated at 25° C. for 2 h at 600 rpm orbital shaking. Beads were vacuum filtered and washed 2 times with 3 mL PBS pH7.4. The elution of the antibodies was performed by adding 200 uL of citrate buffer 0.1M, pH3 followed by neutralization with 300 uL 1M Trizma® pH8. Purified IgG fractions were immediately buffer exchanged to PBS pH7.4. IgG samples were transferred into a 30 kDa 96 well filter plate, polyethersulfone membrane and centrifuged at 1500 g 4° C. until a volume of 10 µL was left per well. 200 µL of PBS were added in each well, samples were mixed at 500 rpm for 3 min before IgGs are collected for storage at 4° C. IgG concentration was determined by Octet and ProteinA biosensors (Pall ForteBio®). Human IgG was used as standard in seven 2 folds dilutions starting from 192 µg/ml to 3 µg/ml. Concentrations of IgG samples were determined in duplicate.

Reduced and Non-Reduced SDS-PAGE were performed for all thirty produced IgGs thus including the controls. The results are presented in FIG. 8. In NR conditions, the expected product sizes of ~200 kDa for the trispecific, multivalent antibodies and ~150 kDa for the control monoclonal IgGs and Biclonics® were observed. For R conditions, product sizes of ~25 kDa (LC), ~50 kDa (HC/1VH) and ~75 kDa (HC/2VH) for the trivalent antibodies were observed. The control IgGs band sizes of ~25 kDa (LC) and ~50 kDa (HC) were as expected. The results also showed bands at ~150 kDa for the trispecific constructs. These are the homodimers resulting from association of DE heavy chains which may be the result of higher expression levels of the DE containing shorter heavy chain over the longer KK containing heavy chain.

Example 3: Binding Activity of the Fab Domains in the VH1, VH2 and VH3 Position Measured in ELISA Binding activity of the three Fab domain in each construct was checked by ELISA using the tetanus toxoid, fibrinogen and thyroglobulin antigens and huEGFR-Fc antigen as a negative control (see Table 7 for coating conditions, supplier and catalogue numbers).

Each multispecific IgG sample was first diluted to 10 µg/ml in PBS and analysed in titration on Fibrinogen, Tetanus Toxoid and Thyroglobulin; in four 5-fold dilutions, from 10 to 0.08 µg/ml. All 30 samples were analyzed on huEGFR-Fc at 10 µg/mL. Appropriate amounts of antigen in PBS were prepared. 50 µl of diluted antigen solution were added per ELISA plate well and coated o/n at 4° C. Plates were washed twice with wash buffer (PBS/Tween®). Wells were blocked for 1 hour at RT with 300 µl/well block buffer (PBS/2%13SA). During incubation appropriate IgG dilutions were made in block buffer. Plates were emptied by inverting above sink followed by slapping on tissue. 50 µl of diluted IgG samples and controls were added to the wells of the blocked plate, covered with seal and incubated 60 minutes at RT. Plates were washed three times with wash buffer (PBS/0.05% Tween®). Diluted detection antibody (mouse anti-Human IgG HRP-conjugated; Becton Dickinson™, cat. no. 555788), 1/2000 in block buffer was added at 50 µl per well. The plate was covered with seal and incubated for 60 minutes at RT. The plate was washed three times with wash buffer. TMB substrate solution (BD, OptEIA™ cat. no. 51-2606KC) was made by mixing reagents A and B in 1:1 ratio and adding 50 μl per well and developed for (maximal) 10 minutes. 50 μl of 1 M H2SO4 was added to each well to stop the staining reaction.

The plates were read at A450 using a 'BioTek™ EIx808™ ELISA plate reader. Binding curves were plotted using GraphPad Prism 7® and Area Under Curve (AUC) calculated for each antigen ELISA of each construct and listed in Table 8. A small variation in AUC is seen for binding to Thyroglobulin (VH1, on the DE-arm, see FIG. 1) and Tetanus Toxoid (VH3, on the tip of the KK arm, see FIG. 1) of 12% and 8%. A larger variation is seen for the Fibrinogen-arm (this is VH2, FIG. 1). This indicates that accessibility or affinity of the Fab domain in the VH2 position depends on the linker that connects the Fab in the VH2 position to the Fab in the VH3 position. All linkers provide VH2s that are functional.

TABLE 7

List of antigens used for ELISA

| Antigen | Coating concentration (μg/ml) | Coating Buffer | Supplier | Catalogue number |
|---|---|---|---|---|
| Fibrinogen | 10 | PBS | Sigma | F4753 |
| Tetanus toxoid | 2 | PBS | Statens institute | T162-2 |
| Thyroglobulin | 10 | PBS | Sigma | T1126-500MG |
| huEGFR-Fc | 2.5 | PBS | R&D Systems | 344-ER |

TABLE 8

Area Under Curve values resulting from ELISA binding assays of the 24 trispecific, multivalent antibodies listed in Table 6. The antibodies were titrated in ELISA for binding to three different antigens. The resulting AUC values were sorted based on the binding activity towards Fibrinogen, resulting from the Fab in the VH2 position. This identified that a range of binding activities of the Fab in the VH2 position exists. The fifteen constructs with the highest activity for the Fab in the VH2 position were prioritized for further experimentation, the six constructs with the lowest activity are indicated in Italics.

| Construct | Tetanus Toxoid, VH3 | Fibrinogen, VH2 | Thyroglobulin, VH1 |
|---|---|---|---|
| IgG1 MH | 2.50 | 1.68 | 2.29 |
| IgG1 H | 2.55 | 1.64 | 2.44 |
| IgG1 R | 2.46 | 1.63 | 2.44 |
| IgG1 G4S | 2.54 | 1.56 | 2.19 |
| IgG1 UH | 2.33 | 1.42 | 2.31 |
| IgG3 R | 2.48 | 1.34 | 2.48 |
| IgG3 UH | 2.45 | 1.30 | 2.40 |
| IgG2A R | 2.51 | 1.30 | 2.40 |
| IgG2A MH | 2.43 | 1.25 | 2.31 |
| IgG3 ULH | 2.42 | 1.23 | 2.38 |
| IgG2B R | 2.51 | 1.21 | 2.42 |
| IgG4 MH | 2.46 | 1.18 | 2.35 |
| IgG4 UL | 2.50 | 1.17 | 2.25 |
| IgG2A H | 2.39 | 1.16 | 2.37 |
| IgG2B H | 2.42 | 1.16 | 2.36 |
| *IgG2A G4SS* | 2.34 | 1.12 | 2.32 |
| *IgG2B MH* | 2.48 | 1.11 | 2.25 |
| *IgG4 UH* | 2.31 | 1.08 | 2.33 |
| *IgG2A UL* | 2.36 | 1.07 | 2.27 |
| *IgG2B UL* | 2.46 | 1.03 | 2.36 |
| *IgG2 G4SL* | 2.29 | 1.03 | 2.31 |
| IgG1 UL | ND | ND | ND |
| IgG4 H | ND | ND | ND |
| IgG4 R | ND | ND | ND |

ND means Not Done

Example 4: Stability of Binding Activity

Stability of binding activity of the three Fab domains in the trivalent antibody constructs was analyzed following four accelerated stress conditions. The samples were diluted to 10 μg/ml in PBS and incubated for 1 month at 4° C. The samples were diluted to 10 μg/ml in D10F medium and incubated for 7 days at 40° C. The samples were also diluted to 10 μg/ml in D10F medium and incubated for 2 days at 50° C. The samples were also diluted in PBS and subjected to five freeze-thaw cycles (5XFT).

Following these accelerated stress conditions binding activity towards the antigens recognized by the three Fab domains was analyzed in ELISA as described before. Area Under Curve were calculated and tabulated.

Stress applied at 40° C. only significantly affected binding of the Fab in the VH2 position, binding to Fibrinogen to different degrees in the different constructs tested. Stress at 4° C., at 50° C. and 5×FT affected binding of all three Fab domains to different degrees in the different constructs tested.

The binding activities were ranked for each antigen and stress condition and the 16 most optimal constructs under each stress condition identified for each Fab position. The number of times that a construct was amongst the 16 most optimal constructs was added up and used to rank all constructs based on conservation of binding activity of the three Fab under accelerated stress conditions.

Figure 9:
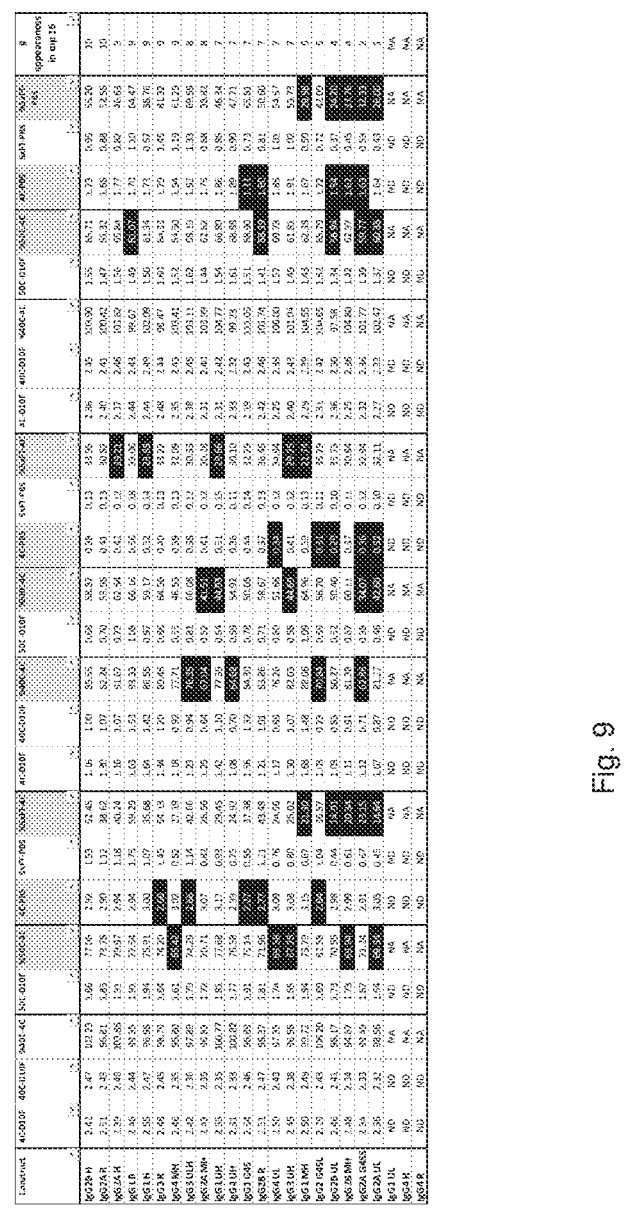

The results are set out in FIG. 9 indicate that there is a range of stabilities of the different constructs under accelerated stress conditions. Stability of binding activity of the three Fab domains in the 21 produced trivalent antibody constructs was analyzed following four accelerated stress conditions. ELISA data (AUC) are tabulated. The binding activities were ranked and the 16 most optimal constructs under each stress condition identified for each Fab position. The number of times that a construct was amongst the 16 most optimal constructs was added up and used to rank all constructs based on conservation of binding activity of the three Fab under accelerated stress conditions.

All antibodies are stable and some are more stable than others.

Example 5: Large Scale Transfection and IgG Purification

Eighteen constructs were selected for a large scale production for further analysis as follows: IgG1 MH, IgG1 H, IgG1 R, IgG1 G4S, IgG1 UH, IgG3 R, IgG3 UH, **IgG2A R, IgG2A MH, IgG3 ULH, IgG2B R, IgG4 MH, IgG4 UL, IgG2A H, IgG2B H, *IgG1 UL, *IgG4 H, *IgG4 R. As a control, the following productions were included: Bispecific anti-thyroglobulin×anti-Tetanus Toxoid (using MG1025C377×MG1337C260 described before in Example 2) and bispecific anti-thyroglobulin×anti-Fibrinogen (using MG1025C377×MG1122C260 described before).

DNA of these constructs was prepared as described before. Multispecific IgGs were transfected as described before by co-transfection of the constructs listed in Table 6. Those constructs selected were produced at larger scale. Two days before transfection, FreeStyle™ HEK293-F cell stock was split in 293-F culture medium in a 1:1 ratio in 100 ml final volume per 500 ml culture flask and incubated at 37° C. and 8% CO2, at an orbital shaking speed of 155 rpm. One day before transfection cells were counted and a cell suspension with a density of $5.0 \times 10^5$ cells/ml prepared by diluting the cells with 293-F culture medium. Cells were then seeded at 100 ml cell suspension per T500 flask and incubated at 37° C. and 8% CO2 at an orbital shaking speed of 155 rpm. Next day the cells were transfected. A mix of 293-F culture medium, PEI and DNA was prepared by mixing 7.5 ml 293-F culture medium, 187.5 µl PEI stock at 1 µg/µl) and 150 µl DNA at 0.5 µg/µl. This was incubated for 20 minutes at RT and then added to the cells that were then incubated at 37° C. and 8% CO2 at an orbital shaking speed of 155 rpm for 7 days.

Supernatant containing antibody protein was centrifuged at 1000 g for 10 minutes to remove the cells. The supernatant was filtered using a 0.45 µm filter. The IgG was purified from the supernatant using an AKTAexplorer™ 100 system (GE™ Health Care) and protein A affinity chromatography followed by desalting. A HiTrap® MabSelect™ SuRe™ 5 ml column and HiTrap® 5 ml Desalting column (GE™ Health Care) were used according to the manufacturers instructions. IgG concentration was determined by OD280 absorption. This yielded 0.8-4.9 mg IgG in PBS for all constructs. The generated proteins were analyzed on SDS-PAGE, reduced and non-reduced, as described above in Example 2. The data confirmed the data as found in Example 2 and are not provided here.

HP-SEC was performed to establish expression ratio's between the two heavy chains that make up base antibody portion of the multispecific antibodies. Because of the size difference of the two heavy chains in the trivalent constructs the halfbodies and homodimers can be identified and quantified in High Performance Size Exclusion Chromatography (HP-SEC). HP-SEC was performed using a Dionex™ HPLC system equipped with a TSK guard column SWXL (Tosoh Bioscience® cat #08543) and a TSK-gel column G3000SWXL (Tosoh Bioscience® cat #08541). For each analysis, 20 µg protein sample in PBS was injected to the column, which was run using 200 mM Sodium Phosphate, 50 mM NaCl as running buffer at a flow speed of 1 mL/min at 4° C. The chromatograms were analyzed for retention times and relative peak areas based on the UV280 results using Chromeleon 6.80 software. The ratio between the amounts of trivalent IgG/DEDE homodimer were calculated and are presented in Table 9 below. The constructs that have a Trivalent/DEDE ratio above average are presented in Italics.

TABLE 9

HP-SEC was performed to establish expression ratio's between the two heavy chains that make up the base antibody portion of the multispecific antibodies The ratio between the amounts of trivalent IgG/DEDE homodimer were calculated and are tabulated

| Construct | Trivalent versus DEDE ratio |
|---|---|
| *IgG1 MH* | 6.1 |
| *IgG1 H* | 5.7 |
| *IgG1 UH* | 5.6 |
| *IgG2B H* | 5.6 |
| *IgG2A MH* | 5.4 |
| *IgG1 UL* | 5.3 |
| *IgG2A H* | 5.3 |
| *IgG1 G4S* | 5.1 |
| *IgG2B R* | 4.4 |
| *IgG1 R* | 4.3 |
| IgG4 H | 3.1 |
| IgG4 UL | 3.1 |
| IgG4 MH | 2 |
| IgG4 R | 2 |
| IgG3 R | 1.7 |
| IgG3 ULH | 1.7 |

TABLE 9-continued

HP-SEC was performed to establish expression ratio's between the two heavy chains that make up the base antibody portion of the multispecific antibodies The ratio between the amounts of trivalent IgG/DEDE homodimer were calculated and are tabulated

| Construct | Trivalent versus DEDE ratio |
|---|---|
| IgG3 UH | 1.7 |
| IgG2A R | NA |

The stability of the large-scale purified IgGs (including the two controls) was assessed after different stress conditions as described before; after five freeze-thaw cycles in PBS, after one week incubation at 40° C. in D10F medium, after one week incubation at 50° C. in D10F medium and after one week incubation at 50° C. in PBS. Performance of the stressed samples was compared to performance of the same samples after a one week incubation at 4° C. (control). To that purpose, purified IgGs from the 100 ml productions were diluted in PBS at 0.2 mg/mL and divided in two batches: one for stability tests in PBS at 0.2 mg/ml (4° C., 3×FT and 50° C.), one diluted to 0.1 mg/ml in D10F for stress tests at 4° C., 40° C. and 50° C. as described above. For sample IgG1 H, a concentration of 0.194 mg/mL was used.

Following these accelerated stress conditions binding activity towards the antigens recognized by the three Fab fragments was analyzed in ELISA as described before. Area Under Curve were calculated and tabulated (see FIG. 10). Percentage remaining binding activity after stress compared to activity of the control sample stored at 4° C. was calculated for each binding activity. The samples were ranked based on these percentages for each binding activity against each target at each stress condition. The percentages above average were indicated and the number of times each sample performed above average was added up and is presented in the last column of the Table in FIG. 10. This shows that there is a range in the stability of the constructs as measured by the binding activity of the three Fab arms after stress.

Example 6: Stability Analysis of 18 Multivalent IgG Constructs

Figure 10:
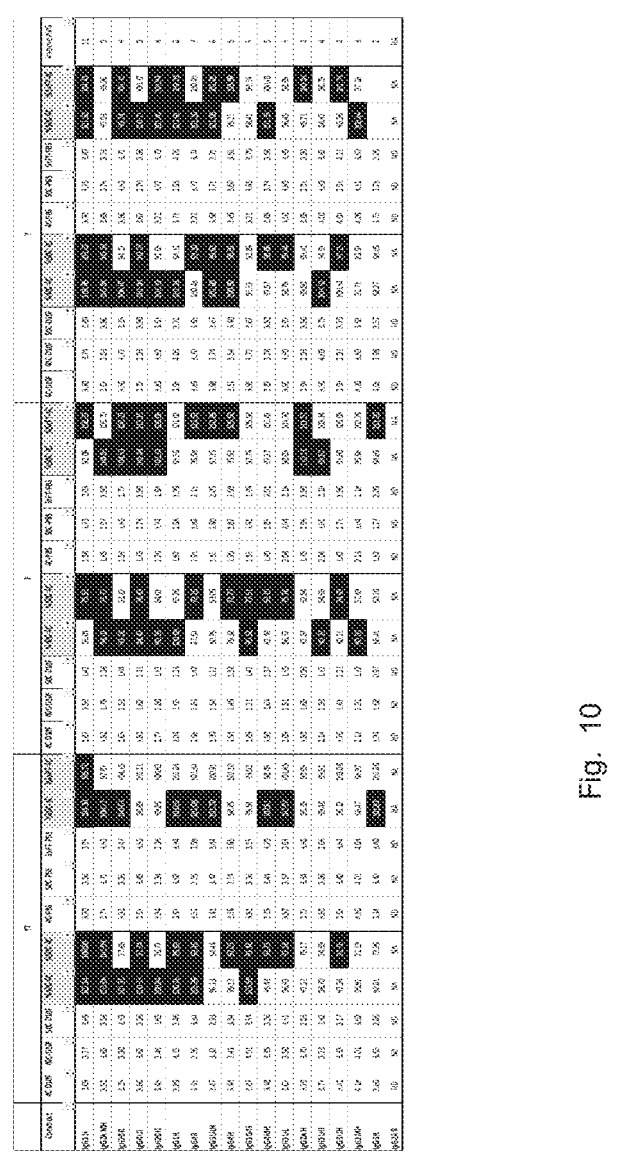

Stability analysis was performed on the 18 multivalent constructs identified in FIG. 10 and as previously described in Example 5. In addition, four control antibodies were used having heavy chain binding domains comprising MF6744 (SEQ ID NO:91), MF1337 (SEQ ID NO: 28 and SEQ ID NO:288) previously described in WO 2018/056821 A1, which is incorporated by reference, and MF1122 (SEQ ID NO:26 and SEQ ID NO:286), coupled to a cLC namely:

monospecific anti-CD137 antibody using Fab MF6744/cLC;

monospecific anti-Fibrinogen antibody using Fab MF1122/cLC;

monospecific anti-Tetanus Toxoid antibody using Fab MF1337/cLC; and bispecific anti-Fibrinogen×anti-Tetanus Toxoid antibody containing Fab MF1122/cLC and Fab MF1337/cLC as a DEKK bispecific control.

The list of samples tested for stability analysis is provided below in Table 10.

TABLE 10

List of samples tested for stability analysis: 18 multivalent antibodies and 4 control antibodies

| IgGs | CH3 | Fab(s) | Comments |
|---|---|---|---|
| Ctrl AA | WT | MF6744 | Monospecific IgG |
| Ctrl BB | WT | MF1122 | Monospecific IgG |
| Ctrl CC | WT | MF1337 | Monospecific IgG |
| Ctrl BC | DE-KK | MF1122-MF1337 | Bispecific - DEKK |
| Sample 1 | DE-KK | MF6744xMF1337:MF1122 | Trispecifics - IgG1 H (SEQ ID NO: 19) |
| Sample 2 | DE-KK | MF6744xMF1337:MF1122 | Trispecifics - IgG2A MH (SEQ ID NO: 4) |
| Sample 3 | DE-KK | MF6744xMF1337:MF1122 | Trispecifics - IgG4 UL (SEQ ID NO: 10) |
| Sample 4 | DE-KK | MF6744xMF1337:MF1122 | Trispecifics - IgG1 G4S (SEQ ID NO: 12) |
| Sample 5 | DE-KK | MF6744xMF1337:MF1122 | Trispecifics - IgG1 MH (SEQ ID NO: 11) |
| Sample 6 | DE-KK | MF6744xMF1337:MF1122 | Trispecifics - IgG1 R (SEQ ID NO: 23) |
| Sample 7 | DE-KK | MF6744xMF1337:MF1122 | Trispecifics - IgG1 UH (SEQ ID NO: 2) |
| Sample 8 | DE-KK | MF6744xMF1337:MF1122 | Trispecifics -IgG1 UL (SEQ ID NO: 14) |
| Sample 9 | DE-KK | MF6744xMF1337:MF1122 | Trispecifics -IgG2A H (SEQ ID NO: 15) |
| Sample 10 | DE-KK | MF6744xMF1337:MF1122 | Trispecifics -IgG2A R (SEQ ID NO: 20) |
| Sample 11 | DE-KK | MF6744xMF1337:MF1122 | Trispecifics -IgG2B H (SEQ ID NO: 16) |
| Sample 12 | DE-KK | MF6744xMF1337:MF1122 | Trispecifics -IgG2B R (SEQ ID NO: 21) |
| Sample 13 | DE-KK | MF6744xMF1337:MF1122 | Trispecifics -IgG3 R (SEQ ID NO: 24) |
| Sample 14 | DE-KK | MF6744xMF1337:MF1122 | Trispecifics -IgG3 UH (SEQ ID NO: 6) |
| Sample 15 | DE-KK | MF6744xMF1337:MF1122 | Trispecifics - IgG3 ULH (SEQ ID NO: 17) |
| Sample 16 | DE-KK | MF6744xMF1337:MF1122 | Trispecifics - IgG4 H (SEQ ID NO: 18) |
| Sample 17 | DE-KK | MF6744xMF1337:MF1122 | Trispecifics - IgG4 MH (SEQ ID NO: 7) |
| Sample 18 | DE-KK | MF6744xMF1337:MF1122 | Trispecifics - IgG4 R (SEQ ID NO: 22) |

Stability of the 18 multivalent constructs and 4 control antibodies was analyzed following 4 different conditions. Accordingly, the 22 samples (18 trivalent+4 controls) were diluted to 0.2 mg/ml in PBS and subjected to:
- 1 month at 4° C. (TO) seen as reference;
- 7 days at 50° C.;
- 5× freeze-thaw (FT) cycles at −80° C.; or
- 4 hours of shaking at 400 rpm at room temperature.

After each of these four conditions, stability was analyzed using 7 different methods, namely:

UV-Vis absorption spectroscopy: after the subtraction of background buffer absorption and light-scatter due to aggregates, absorbance is tested at 350 nm to provide information on the aggregation state of the samples as explained in Eckhardt, 1994: Mulinacci, 2011b and Peters, 2013.

90° light-scattering spectroscopy: in solution, the scatter intensity of light may be affected by different factors, such as protein concentration, refractive index, particle size and shape, and the wavelength of the incident light. This method is used to study protein aggregation as reported in Cappelle, 2005; Demeule, 2007a and b; Mulinacci, 2011a and 2013; Luca, 2010; Patois, 2011 and 2012; Peters 2013.

Tryptophan intrinsic fluorescence emission, expressed as % change compared to T0: changes to the hydrophobicity and rigidity of the environment can be measured through the fluorescence emission of tryptophan (Capelle, 2005; Demeule, 2007a and b and 2009; Mulinacci, 2011a and b; Luca, 2010; Patois, 2011; Peters, 2013).

1,8-ANS fluorescence emission, expressed as % change compared to T0: as an uncharged small hydrophobic fluorescent probe, 1-anilinonaphthalene-8-sulfonic acid (1,8-ANS) becomes fluorescent in water when bound to electrostatic pockets in proteins, protein aggregates, detergent micelles, leachables, membranes and cellular components and can therefore be used to study membrane surfaces and proteins (Demeule, 2009; Mulinacci, 2011a and b; Luca 2010).

Nile Red fluorescence emission, expressed as % change compared to T0: as an uncharged small hydrophobic fluorescence probe, Nile Red is influenced by the polarity of the environment and can be used to analyze protein degradation, protein aggregation, lipid structures, protein unfolding (Sackett and Wolff, 1987).

Nile Red fluorescence microscopy, where the number of particles/1 ul is measured: Nile Red is used to stain the samples in order to visualize protein aggregates for fluorescence microscopy using a Leica® DMi8® microscope (Demeule, 2007a and b, and 2009; Mulinacci, 2011b and 2013; Patois 2011).

Dynamic light-scattering, expressed as % monomer (intensity calculation) change compared to T0: dynamic light-scattering is measured using a Nano-Flex® instrument. The laser passing through the optical fiber is scattered and reflected from particles towards the detector which measures the scattered light intensity in order to determine the size distribution profile of the particles.

The readout of these methods relates to the aggregation, fragmentation and unfolding of the proteins which is a measure of the stability of the proteins. Results showed that 4 hours of shaking at 400 rpm had the biggest impact on the stability of the antibodies. The control monospecific PG1337/MF1337 antibody was the most affected by the stress conditions. Therefore, as all 18 multivalent constructs and the bispecific control contained the PG1337/MF1337 Fab, all results were normalized with PG1337 set as the threshold.

Figure 12:
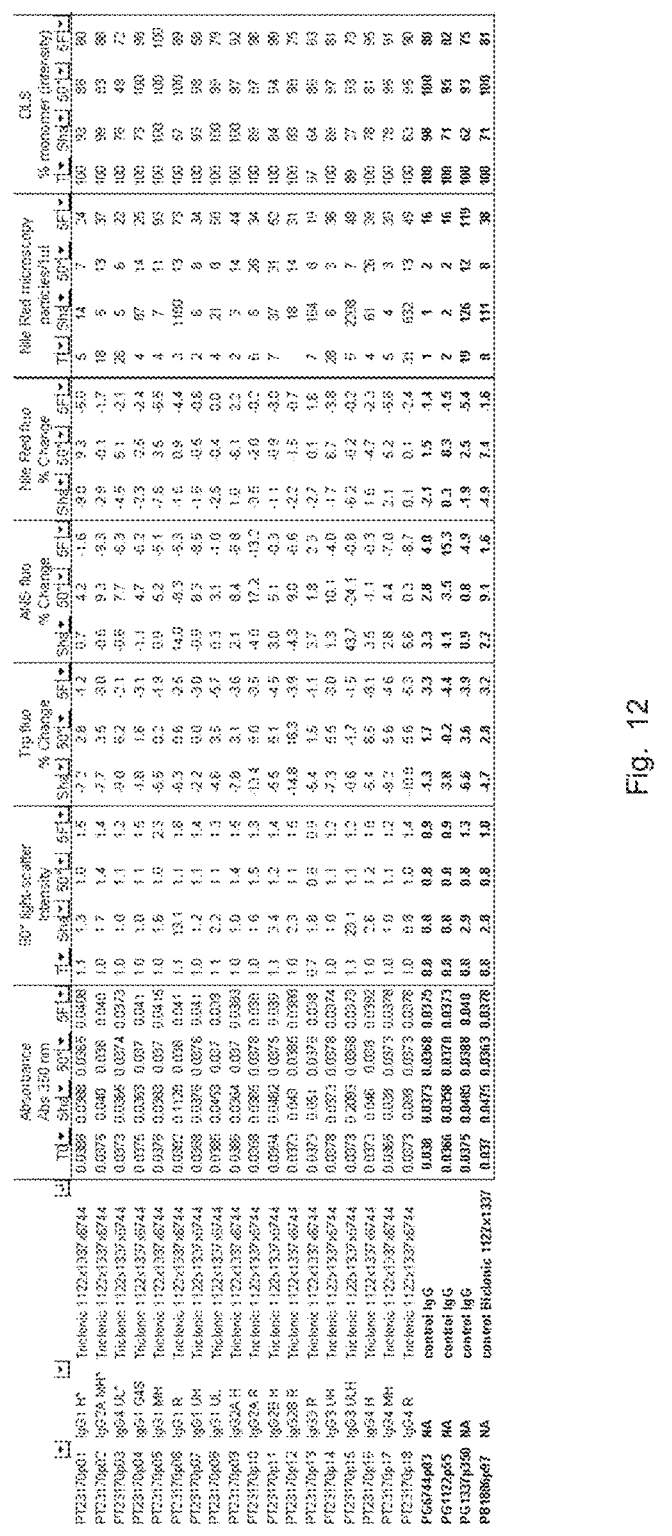

The stability of the molecules was calculated by combining the scores of all the 7 methods during the 4 different conditions. The results can be seen in FIG. 12 and reveal that the constructs have a range of stabilities, which for an array of trispecific molecules demonstrated superior stability to the control bispecific IgG.

Example 7: Bioinformatic Linker Characterization

Eight linkers as set out in Table 11 below and depicted in FIG. 13 were further characterized. A flexibility prediction was obtained for each of these sequences using the Karplus and Schulz flexibility Prediction method (which computes the average of the flexibility index for each amino acid in the sequence). The flexibility index is derived from the average properties of each amino acid in protein structures as described in Karplus P A, Schulz G E. Prediction of Chain Flexibility in Proteins—A tool for the Selection of Peptide Antigens. Naturwissenschaften 1985; 72:212-3; http://tool-s.immuneepitope.org/bcell/). In table 11 we designate a linker as rigid (R) if the KS score is 1.015 or less, partially flexible if the KS-score is from about 1.015 to 1.04. A flexible sequence, for the purposes of this invention, is a sequence having a Karplus and Schulz flexibility Prediction greater than 1.04.

TABLE 11

Eight linkers and flexibility as determined according to Karplus and Schulz

| # | Linker | Sequence | Flexibility | SEQ ID NO |
|---|---|---|---|---|
| 1 | IgG1 G4S | EPKSCDGGGGSGGGGS F | F | 12 |
| 2 | IgG1 H | EPKSCDKTHTSPPSPAPELLGG | F | 19 |
| 3 | IgG1 MH | EPKSCDKTHTSPPSP | F | 11 |
| 4 | IgG1 UH | EPKSCDKTHT | Med | 2 |
| 5 | IgG2A H | ERKSSVESPPSPAPPVAG | F | 15 |
| 6 | IgG2A MH | ERKSSVESPPSP | R | 4 |
| 7 | IgG2B H | ERKCSVESPPSPAPPVAG | Med | 16 |
| 8 | IgG2B R | ERKCSVEEAAAKEAAAKAPPVAG | R | 21 |

A second bioinformatic prediction of these linkers was obtained using Rosetta local structure prediction. Here Rosetta fragment picker was used to provide local structure predictions as described in Gront D, Kulp D W, Vernon R M, Strauss C E M, Baker D (2011) Generalized Fragment Picking in Rosetta: Design, Protocols and Applications. PLoS ONE 6(8): e23294. https://doi.org/10.1371/journal.pone.0023294. For this use of the prediction tool a minimum number of 40 residues is preferred, and accordingly glycine residues were introduced at the termini of the linkers to make the sequences each 40 residues long, with the linker sequence in the middle. These linkers were characterized for secondary structure, running the sequences through the Rosetta fragment pipeline which finds close local sequence matches in structures in the ProteinDataBank and using these close sequence-sequence matches to predict local structure. The centered fragment was then visualized for each of the 8 sequences above. FIG. 13.

The summary of the results is set out below in Table 12: F=flexible; M=medium; R=rigid; C=coil=flexible; H=helix=rigid; and E=strand=medium, which demonstrates general agreement with the Karplus and Schultz score based on predicted secondary structure.

TABLE 12

Summary of flexibility results.

| # | Linker | SEQ ID NO | Karplus Schultz | Fragment Prediction |
|---|---|---|---|---|
| 1 | IgG1 G4S | 12 | F | CE |
| 2 | IgG1 H | 19 | F | CH |
| 3 | IgG1 MH | 11 | F | C |
| 4 | IgG1 UH | 2 | M | H |
| 5 | IgG2A H | 15 | F | C |
| 6 | IgG2A MH | 4 | R | H |
| 7 | IgG2B H | 16 | M | CE |
| 8 | IgG2B R | 21 | R | H |

Example 8: Generation of Anti-CD3, PD-L1, and EGFR Binding Domains

Mice Used for Immunization.

For generation of human antibodies binding to CD3, EGFR and PD-L1, mice transgenic for the human common light chain and for a human heavy chain (HC) minilocus (comprising a selection of human V gene segments, all human Ds and all human Js) (see WO2009/157771 incorporated herein by reference) can be immunized with either DNA encoding the proteins or recombinant DNA, seen below. These mice are referred to as 'MeMo®' mice. For specific heavy chain variable regions, or trivalent multimers having the sequences disclosed herein, they can be produced by any means known to persons of ordinary skill in the art.

Protein Immunizations

'Mello®' mice were immunized by subcutaneous injections with recombinant protein and Gerbu™ adjuvant MM (Gerbu Biotechnik c #3001). Recombinant huPDL1-His (Sino Biological™; cat.no. 10084-H08H) proteins were used for immunizations. Mice were immunized with 40 µg recombinant protein in PBS mixed with 40 µl of adjuvant in a total volume of 100 µl. Subsequently mice were boosted on day 14 and 28 with 20 µg of recombinant protein in PBS together with 20 µl of adjuvant in a total volume of 50 µl. Mouse serum was collected at day 35 to determine serum titers. Mice with low serum titers received additional cycles of booster immunizations and serum analyses. Each cycle consisted of two weekly immunizations using 20 µg of recombinant protein in 50 µl PBS followed one week later by serum collection for titer analysis. Mice showing high serum titers against the human and macaque target received a final boost immunization consisting of daily injections with 20 µg of recombinant protein in 50 µl PBS on three consecutive days. One day after the final injection mouse lymphoid tissue was collected.

DNA Immunizations

MeMo®' mice were immunized by DNA tattooing using a micropigmentation device. DNA tattoo immunizations were performed with 20 µg plasmid DNA encoding the target antigen. Mice were immunized with DNA encoding the human target PD-L1. For PD-L1 immunizations, Treg cells were depleted four days prior to the start of immunization by injection of mice with 0.5 mg anti-CD25 antibody PC61.5 to break tolerance. Mice were immunized at day 0, 3, 6, 14, 17, 28 and 31. Mouse serum was collected at day 35 to determine serum titers. Mice with low serum reactivity against the human and/or macaque target received additional cycles of booster immunizations with human, rat or macaque DNA antigen and serum analyses. Each cycle consisted of two weekly DNA immunizations followed one week later by serum collection for titer analysis. Mice showing serum reactivity against cells expressing the human and macaque target received a final boost immunization followed after 3 days by collection of lymphoid tissue.

Recovery of Lymphoid Tissue

Spleen and draining lymph nodes were removed from all mice that were successfully immunized. Single cell suspensions were generated from both spleen and inguinal lymph nodes and subsequently these tissues were lysed in Trizol LS reagent and stored at −80° C. until use. Generation of 'immune' phage antibody repertoires by RT-PCR cloning of VH genes From successfully immunized mice, the inguinal lymph nodes were used for the construction of 'immune' phage antibody repertoires. To this end, RNA was extracted from Trizol LS lysed lymphoid tissue and 1 µg of total RNA was used in a RT reaction using an IgG-CH1 specific primer. The resulting cDNA was then used to amplify the polyclonal pool of VH-encoding cDNA using in-house developed VH-specific primers essentially as described in Marks et al. (J Mol Biol. 1991 Dec. 5; 222(3):581-97). The resulting PCR product was then cloned in a phagemid vector for the display of Fab fragments on phage, as described in de Haard et al.

(J Biol Chem. 1999 Jun. 25; 274(26):18218-30) with the exception that the light chain was the same for every antibody and was encoded by the vector. After ligation, the phagemids were used to transform E. coli TG1 bacteria and transformed bacteria were plated onto LB-agar105 plates containing ampicillin and glucose. All phage libraries contained >10⁶ transformants and had an insert frequency of >80%. Bacteria were harvested after overnight growth and used to prepare phage according to established protocols (de Haard et al., J Biol Chem. 1999 Jun. 25; 274(26):18218-30).

Targeting Antibodies

EGFR- and PD-L1 cLC antibodies were obtained using previously described methods from phage antibody repertoires generated from successfully target-immunised MeMo® mice. Further, methods to generate antibody variable domain VH chains for the EGFR antibodies, including synthetic human anti-EGFR antibodies, have also been described in pending applications that are incorporated herein by reference: WO 2015/130173 A1; WO 2015/130172 A1.

Immunization of Memo® Mice with CDR3

For generation of human antibodies binding to CD3, mice transgenic for the human common light chain and for a human heavy chain (HC) minilocus (comprising a selection of human V gene segments, all human Ds and all human Js) (see WO2009/157771 incorporated herein by reference) were immunized with TCR/CD3 containing lipoparticles (Intergral Molecular). These mice are referred to as 'MeMo®' mice. For specific heavy chain variable regions, or trivalent multimers having the sequences disclosed herein, they can be produced by any means known to persons of ordinary skill in the art.

MeMo® mice were immunized with Hek293T-derived human 5D5M TCR/CD3 containing lipoparticles, followed by human T-cells for the generation of an anti-TCR/CDR3 immune response and anti-TCR/CD3 antibody panel generation.

Lipoparticles concentrate conformationally intact membrane proteins directly from the cell surface, permitting these complex proteins to be manipulated as soluble, high-concentration proteins for antibody immunization and screening The lipoparticles used in the present study for immunisation contain the 5D5M TCRαβ combination. The amino acid sequences (SEQ ID NO: 289 and SEQ ID: 290)

Hek293T-derived TCR/CD3 lipoparticles of the 5D5M TCRαβ combination were synthesized, cloned and used to generate lipoparticles containing this TCR/CD3 combination by transient transfection into HEK293T cells (Intergral Molecular).

5D5M TCRα

(SEQ ID NO: 289)
MWGVFLLYVSMKMGGTTGQNIDQPTEMTATEGAIVQINCTYQTSGFNGLF

WYQQHAGEAPTFLSYNVLDGLEEKGRFSSFLSRSKGYSYLLLKELQMKDS

ASYLCAVMDSNYQLIWGAGTKLIIKPDIQNPDPAVYQLRDSKSSDKSVCL

FTDFDSQTNVSQSKDSDVYITDKTVLDMRSMDFKSNSAVAWSNKSDFACA

NAFNNSIIPEDTFFPSPESSCDVKLVEKSFETDTNLNFQNLSVIGFRILL

LKVAGFNLLMTLRLWSS

5D5M TCRβ

(SEQ ID NO: 290)
MRIRLLCCVAFSLLWAGPVIAGITQAPTSQILAAGRRMTLRCTQDMRHNA

MYWYRQDLGLGLRLIHYSNTAGTTGKGEVPDGYSVSRANTDDFPLTLASA

VPSQTSVYFCASSEAGGNTGELFFGEGSRLTVLEDLNKVFPPEVAVFEPS

EAEISHTQKATLVCLATGFFPDHVELSWWVNGKEVHSGVSTDPQPLKEQP

ALNDSRYCLSSRLRVSATFWQNPRNHFRCQVQFYGLSENDEVVTQDRAKP

VTQIVSAEAWGRADCGFTSVSYQQGVLSATILYEILLGKATLYAVLVSAL

VLMAMVKRKDF

MeMo® mice were used for immunizations using TCR/CD3 lipoparticles and primary human T cells The immunization schedule contains points on day 35, 56, 77 and 98, where the antigen-specific Ig serum titer was determined by ELISA using QTG-derived 3SDX TCR/CD3 positive and -negative lipoparticles using anti mouse IgG detection and by ELISA using CD3c5E-Fc fusion protein as a positive control. The reactivity was observed in sera drawn at day 35 will determine which mice developed a relevant anti-TCR/CD3 response.

For all immunized mice, lymphoid material for antibody discovery was collected and stored when:

Titers are 1/300 for human TCR/CD3 (in ELISA using lipoparticles), or:

Titers are <1/300 and >1/100 for human TCR/CD3 and did not increase during the last booster immunization.

Priming Immunisation Using Lipoparticles

To prime the humoral immune response in the MeMo® mice for TCR/CD3, lipoparticles containing the human 5D5M TCRαβ combination was used for immunization. Lipoparticles were used together with Gerbu adjuvant for the first and second injection.

Booster Immunizations Using Polyclonal T-Cells

Mice were immunised by sub-cutaneous injection of cell suspension. The first booster immunisations (day 28) comprised a mix of cells in PBS with adjuvant and all subsequent injections are only composed of cells in PBS. Mice that have developed at day 35 serum IgG titers of 1/300 against human TCR/CD3 (determined by ELISA using lipoparticles) received additional injections with cells on days 42, 43 and 44. Mice that failed to meet these criteria receive booster immunisations (day 42 and 49) with cells. All subsequent immunisations are given as sub-cutaneous injections of cells in PBS. After the final immunisation, mice are sacrificed, bled for serum and the spleen and left inguinal lymph nodes are collected.

Screening Sera from Immunised Mice in ELISA

Interim serum IgG titers were screened by ELISA using TCR/CD3-containing lipoparticles and 'null' lipoparticles. Serum IgG titers were determined using anti-mouse IgG staining, as this staining was shown to be the most sensitive.

CD3 binding variable domains were made using the amino acid sequence of the heavy chain variable region of a CD3 MF of the CDR regions thereof as indicated in SEQ ID NO: 92-154.

Re-cloning of VH-encoding cDNA's from the phagemid vector to IgG-expression vectors The VH-encoding cDNA's of all target-specific clones were sequenced. A selection of unique clones based on sequence identity and cluster analysis was then re-cloned to different IgG expression vectors using Sfi1-BstEII or a Sfi/XhoI digestion and ligation of the pool of digested cDNA's into the IgG expression plasmid was done according to standardised molecular biological techniques.

Purification of Antibodies from Culture Supernatant

Medium containing antibodies is harvested and centrifuged to remove the cell debris. Subsequently Protein A Sepharose® beads are added to the medium. Medium and Protein A Sepharose® beads are incubated with the antibodies to allow binding.

After incubation the beads are isolated from the medium and washed, by a vacuum filter. The antibodies are eluted from the beads by incubation with elution buffer.

Optionally, the buffer of the purified IgG is exchanged/desalted.

Buffer Exchange

In order to desalt the purified antibodies the antibody fraction is centrifuged using a filter plate or filter column. The plate or column is centrifuged to reduce the volume of the antibody fraction. Subsequently, PBS or the required buffer is added to the fraction to replace the buffer with a low salt buffer. Optionally this centrifugation step followed by adding buffer is repeated in order to further desalt the storage buffer of the antibodies.

Example 9: Generation of Trispecific Antibodies with a Tumor Cell Antigen on the Short or Long Arm Trispecific antibodies were generated by transient co-transfection of two plasmids encoding IgG with different VH domains, using CH3 engineering technology for efficient hetero-dimerisation and formation of trispecific antibodies. The common light chain is also co-transfected in the same cell, either on the same plasmid or on another plasmid. In our co-pending applications (e.g. WO2013/157954 and WO2013/157953; incorporated herein by reference) we have disclosed methods and means for producing multispecific antibodies from a single cell, whereby means are provided that favor the formation of multispecific antibodies over the formation of monospecific antibodies. These methods can also be favorably employed in the present invention for the generation of multivalent multimers, including trispecific antibodies.

Specifically, preferred variations to predominantly produce trispecific full length IgG molecules are amino acid substitutions in reference to a human wild type sequence at positions 351 and 366, e.g. L351K and T366K (numbering according to EU numbering) in the first CH3 domain (the 'KK-variant' heavy chain) and amino acid substitutions at positions 351 and 368, e.g. L351D and L368E in the second CH3 domain (the 'DE-variant' heavy chain), or vice versa. It was previously demonstrated in our co-pending applications that the negatively charged DE-variant heavy chain and positively charged KK-variant heavy chain preferentially pair to form heterodimers (so-called 'DEKK' molecules). Homodimerization of DE-variant heavy chains (DE-DE homodimers) or KK-variant heavy chains (KK-KK homodimers) hardly occurs due to strong repulsion between the charged residues in the CH3-CH3 interface between identical heavy chains.

According to the present invention, the immune cell engaging binding domain or tumor antigen binding domain can be placed at any position on the multivalent molecule, including the distal or interior position of the long arm or the short arm, and the heterodimerization technology can be utilized to favorably generate the trispecific molecule over the monospecific, bivalent homodimer, or quadrospecific homodimer.

First, it was demonstrated that a tumor cell antigen binding domain may be placed at either the distal or interior region of the long arm or the short arm.

For each of the trispecific and/or trivalent antibodies described herein, expression is accomplished through suspension growth adapted 293 cells were cultivated in T125 flasks on a shaker plateau until a density of 3.0×10⁶ cells/ml. Cells were seeded at a density of 0.3-0.5×10⁶ viable cells/ml in each well of a 24-deep well plate. The cells were transiently transfected with a mix of two plasmids encoding different antibodies, cloned into the proprietary vector system. Seven days after transfection, the cellular supernatant was harvested and filtered through a 0.22 µM filter. The sterile supernatant was stored at 4° C. until purification of the trispecific antibodies.

Figure 15A:
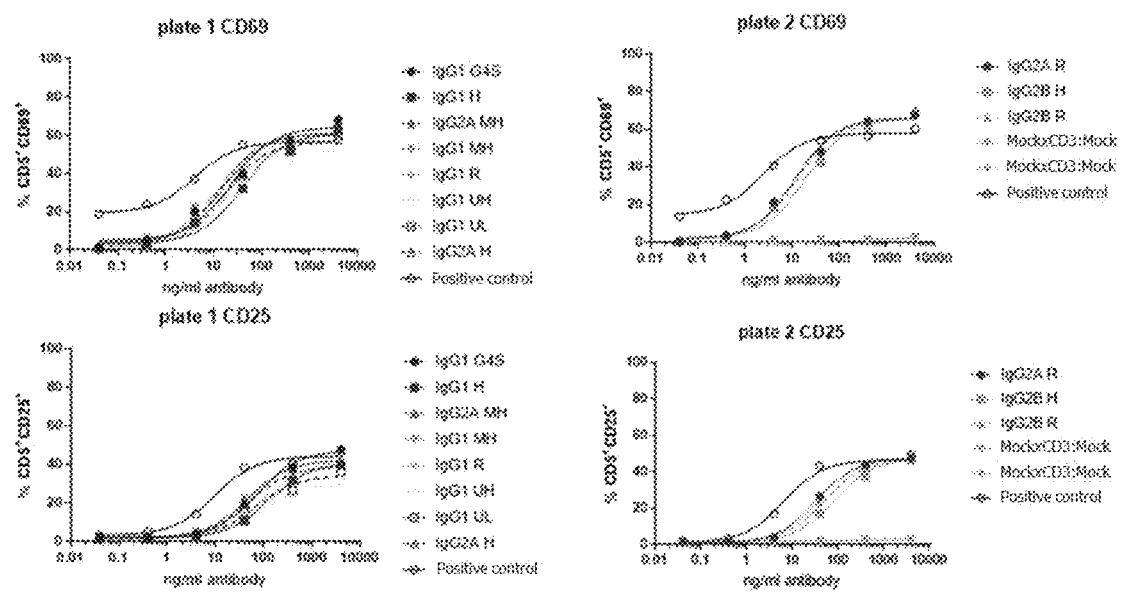
FIG. 15: T cell activation in BxPC3 cells (median EGFR expression) by flow cytometry with the expression of CD25 and CD69 as a read out for both formats: EGFR on the short arm (EGFRxCD3:TT at FIG. 15a) and EGFR on the long arm (ThyroxCD3:EGFR at FIG. 15b). The bispecific antibody (EGFRxCD3) is used as a positive control.
Figure 16A:
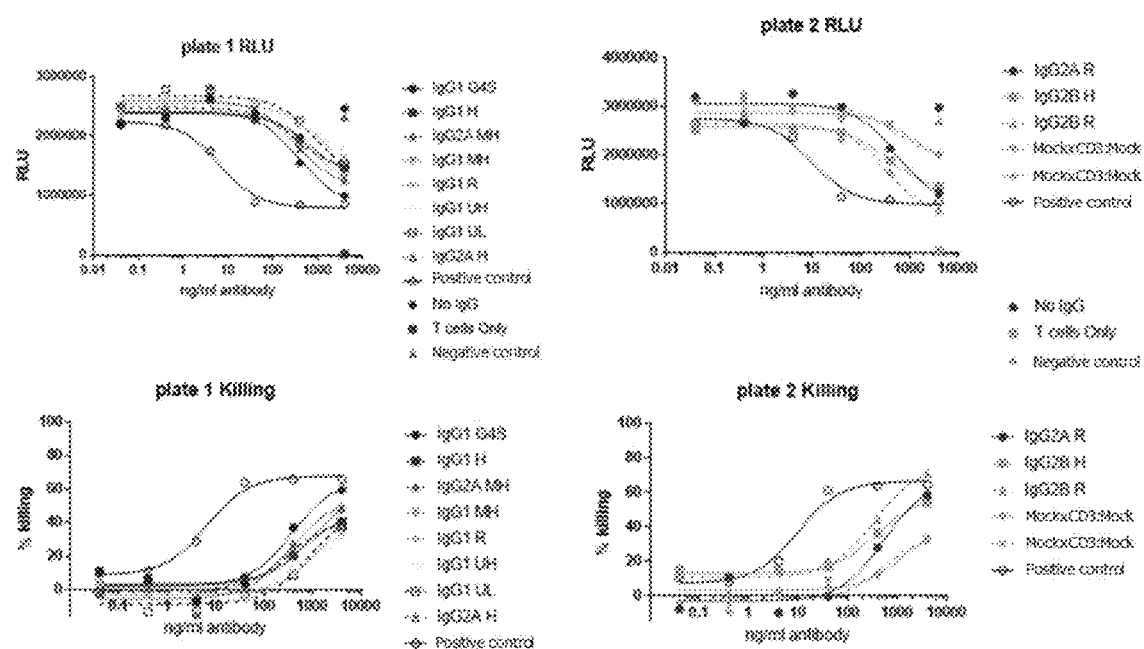
FIG. 16: T cell cytotoxicity in HCT116 cells (median EGFR expression) was determined by measuring ATP levels assessed by CellTiter-Glo® for both EGFRxCD3:TT (FIG. 16a) and ThyroxCD3:EGFR (FIG. 16b). The top charts ATP levels, measured by luminescence on an EnVision® Microplate reader results in Relative light unit (RLU) values, which were analyzed using GraphPad Prism®, which the bottom chart correlates to percent killing based on the following equation, % Killing=(100−(RLU sample/RLU no IgG)×100).

For an example of a trispecific molecule having an immune engaging binding domain at the interior position of the long arm and a tumor cell antigen at the short arm, DNA encoding the VH gene for the CD3 binding domain (MF8078), a linker of the invention and a tetanus toxoid (TT) binding domain (MF1337) are cloned into a vector encoding the positively charged CH3 domain (KK), where DNA encoding the VH gene for the EGFR binding domain (MF8233) is cloned into a vector encoding the negatively charged CH3 domain (DE) encoding a trispecific molecule of EGFR×CD3:TT. The heavy chain variable regions for the three binding domains are set out in Table 13, with activity for these trispecific molecules described in FIGS. 15a and 16a. For these trispecific molecules, each heavy chain variable region pairs with a common light chain. SEQ ID NO: 29.

TABLE 13

| EGFR x CD3: Mock | | | | |
|---|---|---|---|---|
| | KK arm | | | |
| DE arm | Linker used | Linker SEQ ID | | Purpose |
| MF8233 | MF8078 | IgG1 G4S | 12 | MF1337 | sample |
| MF8233 | MF8078 | IgG1 H | 19 | MF1337 | sample |
| MF8233 | MF8078 | IgG2A MH | 4 | MF1337 | Sample |
| MF8233 | MF8078 | IgG1 MH | 11 | MF1337 | sample |
| MF8233 | MF8078 | IgG1 R | 23 | MF1337 | sample |
| MF8233 | MF8078 | IgG1 UH | 2 | MF1337 | sample |
| MF8233 | MF8078 | IgG1 UL | 14 | MF1337 | sample |
| MF8233 | MF8078 | IgG2A H | 15 | MF1337 | sample |
| MF8233 | MF8078 | IgG2A R | 20 | MF1337 | sample |
| MF8233 | MF8078 | IgG2B H | 16 | MF1337 | sample |
| MF8233 | MF8078 | IgG2B R | 21 | MF1337 | sample |
| MF1025 | MF8078 | IgG1 H* | 19 | MF1337 | Neg Contr |
| MF1025 | MF8078 | IgG2 AMH | 4 | MF1337 | Neg Contr |

Figure 15B:
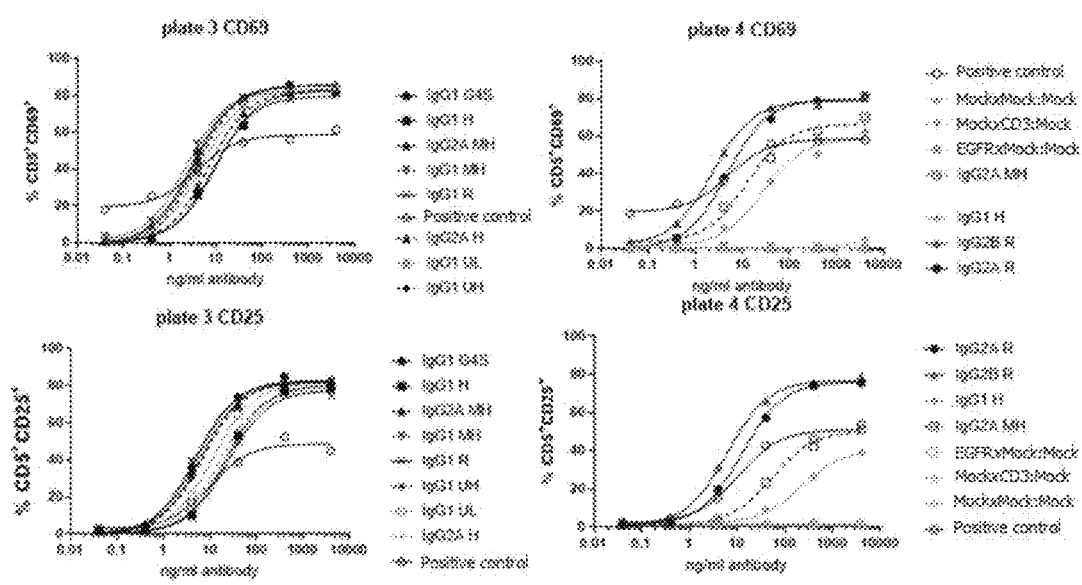
Figure 16B:
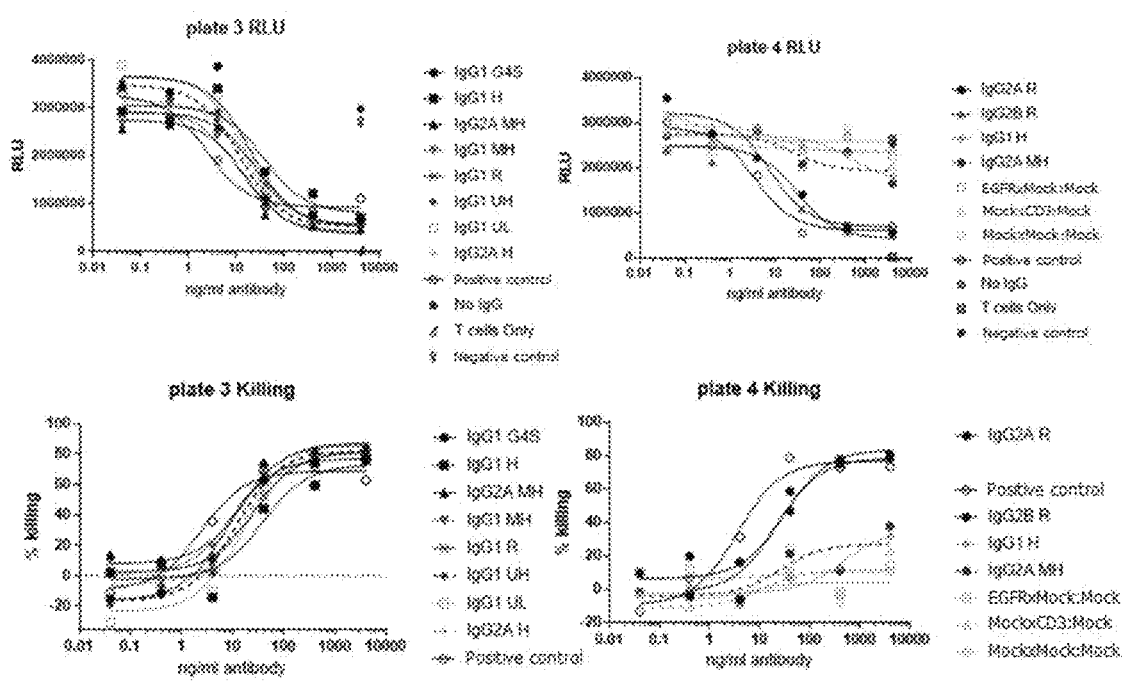

For an example of a trispecific antibody having an immune engaging binding domain at the interior position and a tumor cell antigen at the distal position of the long arm, DNA encoding the VH gene for the CD3 binding domain (MF8078), a linker of the invention and DNA encoding the VH gene for the EGFR binding domain (MF8233) are cloned into a vector encoding the positively charged CH3 domain (KK), where DNA encoding the VH gene for the Thyroglobulin binding domain ("Thyro") (MF1025) is cloned into a vector encoding the negatively charged CH3 domain (DE) encoding a trispecific molecule of Thyro×CD3:EGFR. FIG. 14b. The heavy chain variable regions for the three binding domains are set out in Table 14, with activity for these trispecific molecules described in FIGS. 15b and 16b. For these trispecific molecules, each heavy chain variable region pairs with a common light chain. SEQ ID NO: 29.

TABLE 14

Mock x CD3: EGFR

KK arm

| DE arm | | Linker used | Linker SEQ ID | | Purpose |
|---|---|---|---|---|---|
| MF1025 | MF8078 | IgG1 G4S | 12 | MF8233 | sample |
| MF1025 | MF8078 | IgG1 H | 19 | MF8233 | sample |
| MF1025 | MF8078 | IgG2A MH | 4 | MF8233 | sample |
| MF1025 | MF8078 | IgG1 MH | 11 | MF8233 | sample |
| MF1025 | MF8078 | IgG1 R | 23 | MF8233 | sample |
| MF1025 | MF8078 | IgG1 UH | 2 | MF8233 | sample |
| MF1025 | MF8078 | IgG1 UL | 14 | MF8233 | sample |
| MF1025 | MF8078 | IgG2A H | 15 | MF8233 | sample |
| MF1025 | MF8078 | IgG2A R | 20 | MF8233 | sample |
| MF1025 | MF8078 | IgG2B H | 16 | MF8233 | sample |
| MF1025 | MF8078 | IgG2B R | 21 | MF1337 | Comparator type A |
| MF1025 | MF8078 | IgG1 H | 19 | MF1337 | Comparator type A |
| MF1025 | MF1122 | IgG2 AMH | 4 | MF1337 | Neg contr |
| MF1025 | MF8078 | IgG1 H | 19 | MF1337 | Neg contr |
| MF1025 | MF1122 | IgG2 AMH | 4 | MF1337 | Neg contr |

Example 10: Effect of Positioning the Tumor Cell Antigen Binding Domain on Short or Long Arm for T-Cell Engaging Trivalent Molecules Cell Lines BxPC3 is a human pancreatic cancer cell line.

HCT-116 is a human colon carcinoma cell line.

The above series of trispecific IgGs were generated at 24 well production which incorporated eleven different linkers in trispecifics containing an anti-EGFR binding domain on the short arm (FIG. 14a and Table 13) and an anti-EGFR binding domain on the long arm (FIG. 14b and Table 14) and an array of control antibodies. These molecules have been assessed for their capacity to cause T-cell activation and in a cytotoxicity assay.

Using Ficoll® and EasySep® human T cell isolation kit according to standard techniques resting T cells were isolated from whole blood from healthy donors, checked for >95% T cell purity by anti-CD3 antibody using flow cytometric analysis and subsequently cryopreserved. For a cytotoxicity assay the cryopreserved T cells were thawed and used if their viability was >90% upon thawing, determined by standard Trypan Blue staining. Cytotoxicity assay in short, thawed resting T cells and BxPC3 (FIG. 15) or HCT116 (FIGS. 16 and 17) target cells were co-cultured in an E:T ratio of 5:1 for 48 hours. For the trivalent antibodies, a 6-step 3 fold dilution series starting at a concentration of 4 ug/ml was used. EGFRxCD3 bispecific antibodies were used as a positive control; MockxMock:Mock, MockxCD3:Mock and EGFRxMock:Mock trivalent antibodies were used for specificity controls. T cell activation was quantified using flow cytometry; CD4 and CD8 T cells were gated based on CD4 and CD8 expression and subsequently analyzed for their activation status by measuring CD25 and CD69 expression on T cells. Target cell lysis was determined by measuring the fraction of alive cells by measuring ATP levels assessed by CellTiter-Glo® (Promega®). ATP levels, measured by luminescence on an EnVision® Microplate reader results in Relative light unit (RLU) values, which were analyzed using GraphPad Prism®.

Target cell lysis for each sample was calculated as follows:

% Killing=(100−(RLU sample/RLU no IgG)×100).

These data pertaining to T-cell activation (see FIG. 15) and cytotoxicity (FIG. 16) demonstrate that the trispecific antibodies are functional. As shown in FIGS. 15 and 16, MockxCD3:EGFR and EGFRxCD3:Mock trispecific molecules are demonstrated to be capable of inducing EGFR target specific T cell activation and cytotoxicity. When the anti-EGFR Fab was positioned on the distal position in the long arm the MockxCD3:EGFR trispecific showed enhanced activity over both the bispecific EGFRxCD3 and the trispecific having the EGFR binding domain on the short arm and the CD3 and mock TT (MF1337) binding domain on the long arm (see FIG. 14a), both in terms of T cell activation (FIG. 15) and cytotoxicity (FIG. 16).

Figure 17A:
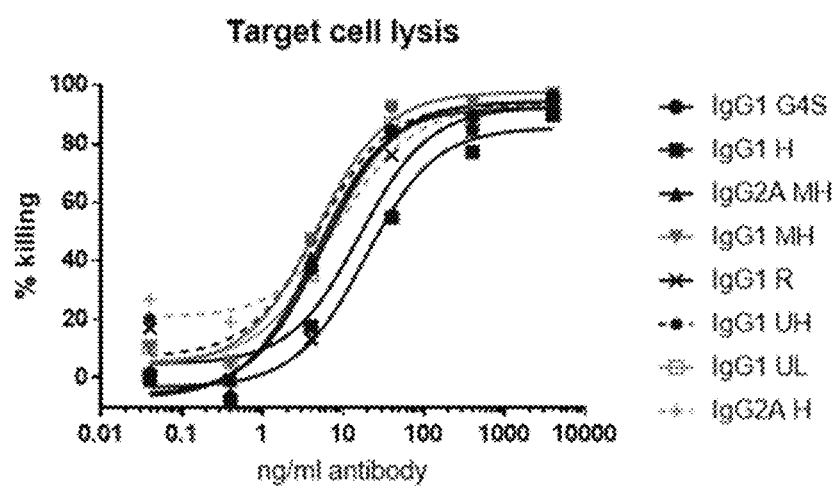
FIG. 17: Effect of linkers on T-cell cytotoxicity in HCT116 cells (FIG. 17a). Comparison of target cell lysis versus cytokine release for a range of linkers were demonstrated for IL-2 (FIG. 17b), IFN-g (FIG. 17c) and TNF-α (FIG. 17d).
Figure 17B:
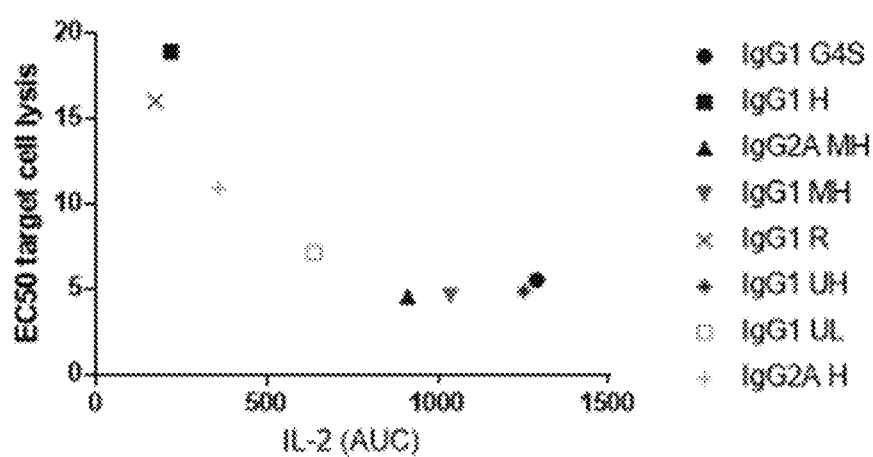
Figure 17C:
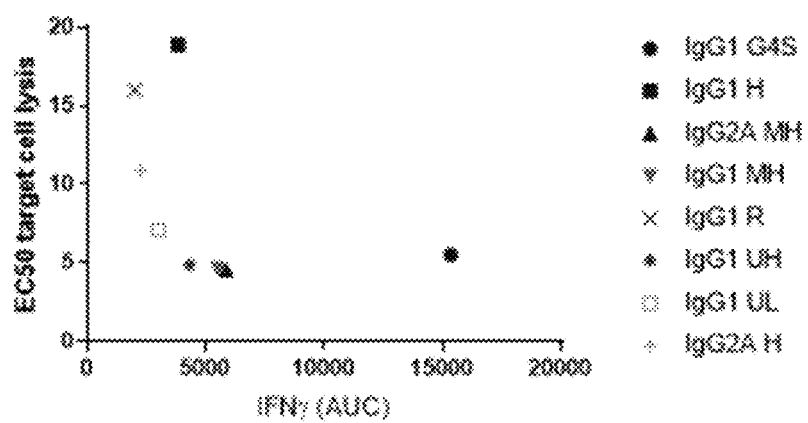
Figure 17D:
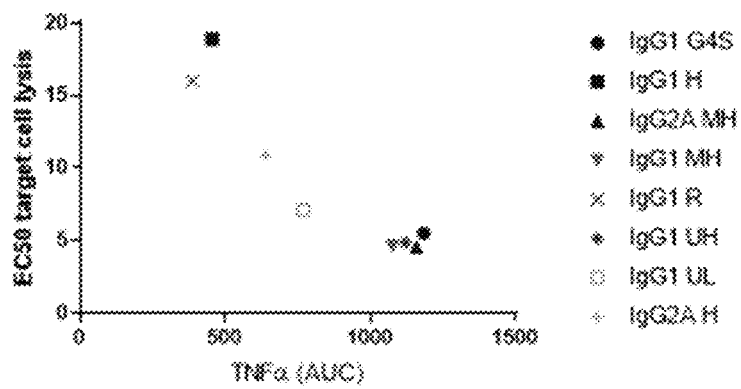

Further, based on the activity of the trispecific antibodies having EGFR and CD3 on the long arm, the linkers can be binned into those that correlate with relatively high cytokine production (IgG1 UH (SEQ ID NO: 2), IgG1 MH (SEQ ID NO: 11), IgG2A MH (SEQ ID NO: 4) and IgG1 G4S (SEQ ID NO: 12)) and those that correlate with relatively low cytokine production (IgG1 UL (SEQ ID NO: 14), IgG2A H (SEQ ID NO: 15), IgG2B R (SEQ ID NO: 21), IgG2A R (SEQ ID NO: 20), IgG1 H (SEQ ID NO: 19), IgG1R (SEQ ID NO: 23)) as show in FIGS. 17b-d. The change in linker use and impact on cytotoxicity was less pronounced. FIG. 17a.

Example 11: Generation of Trispecific Antibodies with an Immune Cell Engaging Binding Domain on the Short or Long Arm According to the present invention, the immune cell engaging binding domain can be placed at any position on the multivalent molecule, including the distal or interior position of the long arm or the short arm, and the heterodimerization technology can be utilized to favorably generate the trivalent molecule. See FIG. 18 (CD3 binding domain on the short arm), FIG. 19 (CD3 binding domain on the interior long arm) and FIG. 25 (CD3 binding domain on the distal long arm).

Figure 18:
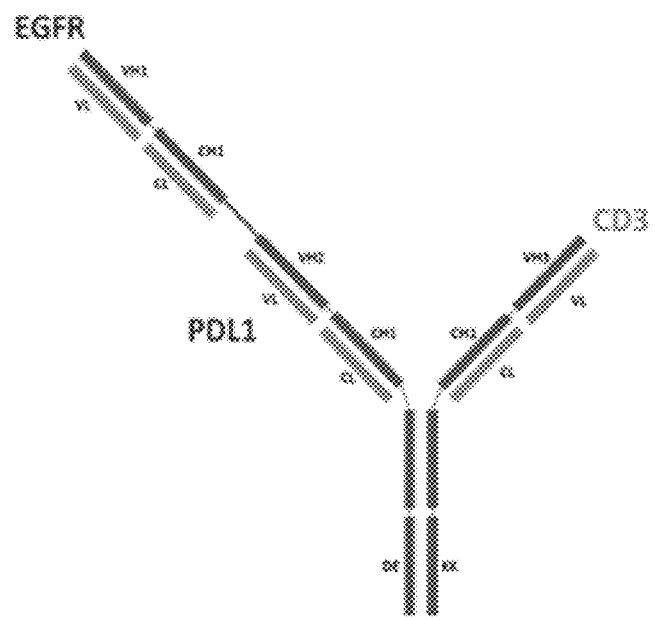
FIG. 18: Configuration of the CD3xPD-L1:EGFR trispecific T cell engager molecule with CD3 binding domain located on the short arm.

For example, an immune engaging domain is positioned at the short arm, where DNA encoding the VH gene for the CD3 binding domain (MF8078) is cloned into a vector encoding the positively charged CH3 domain (KK), where DNA encoding the VH gene for the EGFR binding domain (MF9988 (SEQ ID NO:218) or MF9891 (SEQ ID NO:191)), the linker IgG2A MH and the VH gene for the PD-L1 binding domain (MF5380 (SEQ ID NO:173) or MF5444 (SEQ ID NO:164)) is cloned into a vector encoding the negatively charged CH3 domain (DE). FIG. 18 (CD3xPD-L1:EGFR).

TABLE 15

CD3xPD-L1: EGFR

| KK arm | DE arm | |
|---|---|---|
| MF8078 | MF5380 | MF9988 |
| MF8078 | MF5380 | MF9891 |
| MF8078 | MF5444 | MF9988 |
| MF8078 | MF5444 | MF9891 |

Figure 19:
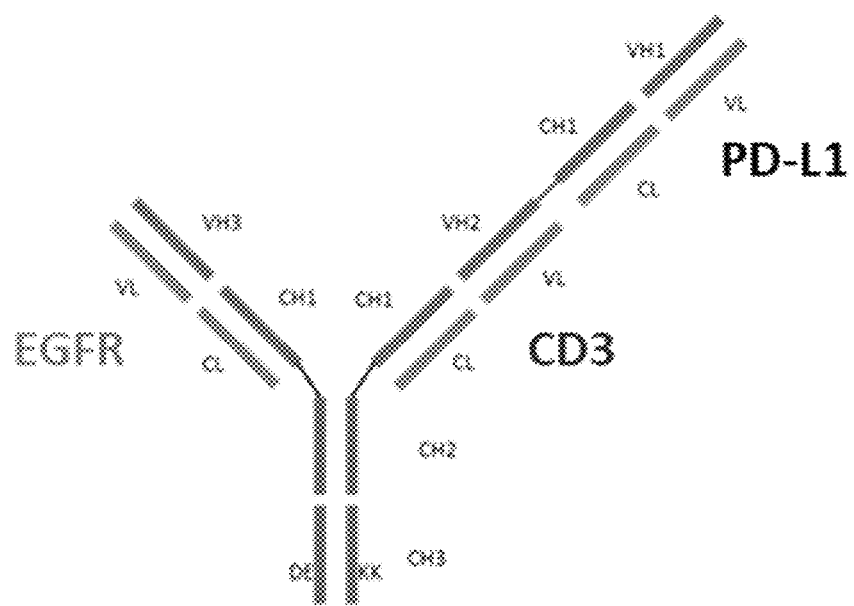
FIG. 19: Configuration of the EGFRxCD3:PD-L1 trispecific T cell engager molecule with CD3 binding domain located on the internal region of the long arm.

Alternatively, an immune engaging domain is positioned at the interior position of the long arm, where DNA encoding the VH gene for a CD3 binding domain (MF8078), the linker IgG2A MH (SEQ ID NO:4) and a VH gene for a PD-L1 binding domain (MF5444 (SEQ ID NO:164), MF5380 (SEQ ID NO:173), MF5377 (SEQ ID NO:155)) is cloned into a vector encoding the positively charged CH3 domain (KK), where DNA encoding the VH gene for a EGFR binding domain (MF9886 (SEQ ID NO:200), MF9988 (SEQ ID NO:218), MF9891 (SEQ ID NO:191) or MF9873 (SEQ ID NO:209)) is cloned into a vector encoding the negatively charged CH3 domain (DE). FIG. 19 (EGFRxCD3:PD-L1).

TABLE 16

EGFRxCD3: PD-L1

| DE arm | KK arm | |
|---|---|---|
| MF9988 | MF8078 | MF5444 |
| MF9988 | MF8078 | MF5380 |
| MF9886 | MF8078 | MF5380 |
| MF9988 | MF8078 | MF5377 |
| MF9886 | MF8078 | MF5377 |
| MF9891 | MF8078 | MF5377 |
| MF9873 | MF8078 | MF5377 |
| MF9891 | MF8078 | MF5380 |
| MF9873 | MF8078 | MF5380 |
| MF9891 | MF8078 | MF5444 |
| MF9873 | MF8078 | MF5444 |
| MF1337 | MF8078 | MF5377 |
| MF1337 | MF8078 | MF5380 |
| MF1337 | MF8078 | MF5444 |
| MF9886 | MF8078 | MF1337 |
| MF9988 | MF8078 | MF1337 |
| MF9891 | MF8078 | MF1337 |
| MF9873 | MF8078 | MF1337 |
| Control Antibodies | | |
| MF1337 | MF8078 | — |
| MF8233 | MF8078 | — |

Figure 24:
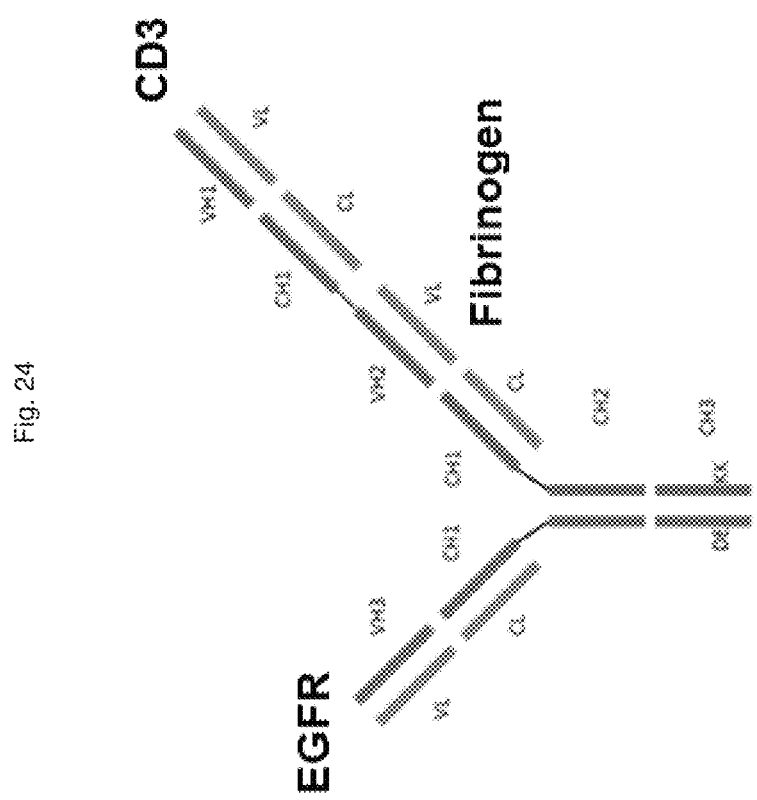
FIG. 24: Configuration of the EGFRxFibrinogen:CD3 trispecific T cell engager molecule with the CD3 binding domain located on the distal region of the long arm.

Alternatively, an immune engaging domain is positioned at the distal position of the long arm, where DNA encoding the VH gene for a CD3 binding domain (MF8078 (SEQ ID NO:110), MF8508 (SEQ ID NO: 128) or MF8057 (SEQ ID NO: 92)) a linker IgG 1H (SEQ ID NO:19) and a VH gene for a Fibrinogen binding domain ("Fibri") (MF1025) is cloned into a vector encoding the positively charged CH3 domain (KK), where DNA encoding the VH gene for a EGFR binding domain (MF8233) is cloned into a vector encoding the negatively charged CH3 domain (DE). FIG. 24 (EGFRxFibri:CD3).

TABLE 17

EGFRxFibri: CD3

| | | KK arm | | |
|---|---|---|---|---|
| DE arm | | Linker used | Linker seq | |
| MF8233 | MF1122 | IgG1H | 19 | MF8078 |
| MF8233 | MF1122 | IgG1H | 19 | MF8508 |
| MF8233 | MF1122 | IgG1H | 19 | MF8057 |

For each of the trispecific molecules described above, and set out in FIGS. 18, 19 and 24, each heavy chain variable region pairs with a common light chain. SEQ ID NO: 29.

As described further below, each CD3 binding domain placement was demonstrated to be effective at generating T-cell cytotoxicity or activation against cells expressing one or more extracellularly exposed tumor cell antigens.

Example 12: Effective Dual Tumor Antigen Binding and T Cell Engagement Via CD3 for the Trispecific Format of EGFRxCD3:PD-L1

Cell Lines:

MDA-MB-231 cells (ATCC® HTB-26) are breast cancer cells; derived from metastatic site.

Trispecific antibodies were produced according to the format at FIG. 19 to analyze the capacity of such molecules to achieve simultaneous tumor antigen targeting and T-cell engagement via cytotoxicity. These antibodies were generated by techniques described above.

Four anti-EGFR Fabs (MF9886, MF9988, MF9891, MF9873) with a range of affinities from relatively low to high were used for the short arm and were combined with different anti-PD-L1 Fabs (MF5444, MF5380 and MF5377) that also contain a range of affinities from low to high for the distal long arm. The anti-CD3 Fab and linker were kept constant, using MF8078, and linker IgG2 AMH (SEQ ID NO: 4).

Ranking for EGFR and PD-L1 affinities was based on binding data from Table 18 and 19, respectively; the ranking was based on binding relative to a reference anti-EGFR and anti-PD-L1 antibody as described below.

TABLE 18

EGFR panel Monospecific, Bivalent EGFR antibodies having the heavy chains MF9886, MF9988, MF9891, MF9873.

| MF | MDA-MB-231 cells (%) |
|---|---|
| 9886 | 10.7 |
| 9988 | 21.0 |
| 9891 | 44.2 |
| 9873 | 82.5 |
| 8233 | 100 |

The affinity ranking of EGFR heavy chains is based on the relative ability of these monospecific, bivalent antibodies to bind EGFR expressing cells as set out above as compared to the positive control of a monospecific, bivalent antibody having heavy chain MF8233.

TABLE 19

PD-L1 panel Monospecific, Bivalent PD-L1 antibodies, having the heavy chains MF5444, MF5380 and MF5377

| Anti-PD-L1 heavy chain | Binds to huPD-L1 | Ratio EC50/ EC50 RG7446 |
|---|---|---|
| MF5377 | Yes | 3.09 |
| MF5380 | Yes | 3.67 |
| MF5444 | Yes | 5.46 |

The relative affinity ranking of the PD-L1 heavy chain arms is based on capacity to bind human PD-L1 in ELISA. To this end, ELISA plates were coated with huPD-L1-His (Sinobiological) in an 8-step, 3-fold titration diulation range, starting at 10 µg/ml. Subsequently, binding of each PD-L1 Fab was evaluated as a PD-L1xTT IgG 5 ug/ml. EC50s for binding were determined, and normalized to the binding EC50 as determined for anti-PD-L1 RG7446 MPDL3280A, see US 2010/0203056, present on each ELISA plate.

These trispecific EGFRxCD3:PD-L1 molecules were then tested for their capacity to induce cytotoxicity based on methods previously described herein against two cell lines (HCT116 and MDA-MB-231) having different antigen densities for the tumor cell antigens. The expression profiles of these cell lines were determined using FACS staining by use of control antibodies (cetuximab for EGFR, and MPDL3280A for PD-L1) were considered positive for expression of the antigen of interest when the mean fluorescence intensity (MFI) was 3× higher than the background signal. Triplicates were performed for PD-L1 and quadruplicates for EGFR, and results were reported as MFI as set out below.

TABLE 20

| Cell line | EGFR (MFI) | PD-L1 (MFI) |
| --- | --- | --- |
| HCT116 | 178,523 | 10,876 |
| MDA-MB-231 | 276,915 | 74,581 |

Figure 20:
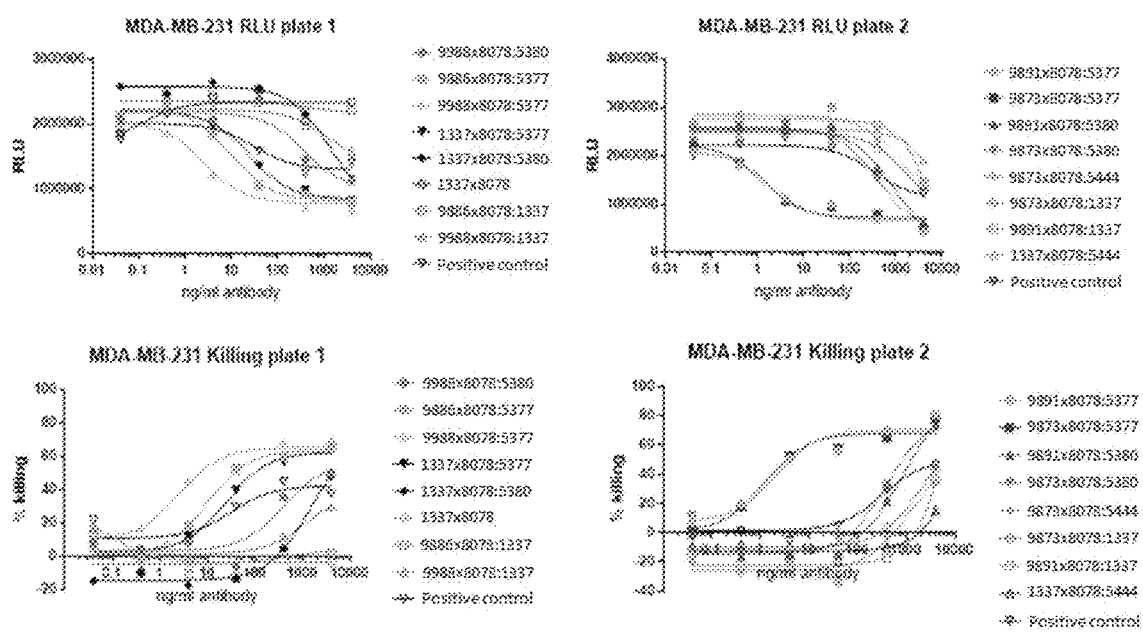
FIG. 20: T cell cytotoxicity activity data is provided against MDA-MB-231 cells comparing trispecific molecules combining a CD3 binding domain and two tumor cell antigen binding domains to trispecific controls with one tumor cell antigen binding domain, a mock domain and a CD3 binding domain, and the positive control described above.
Figure 21:
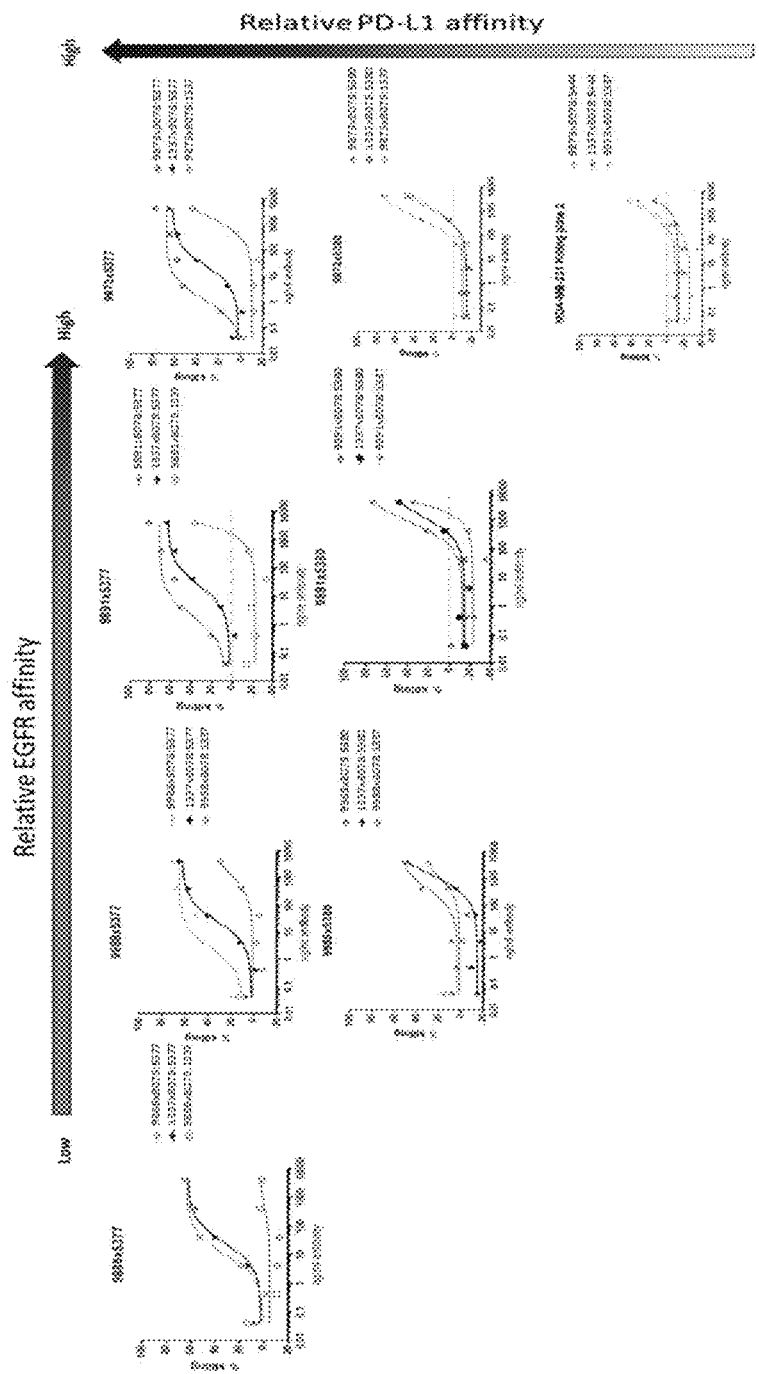
FIG. 21: T cell cytotoxicity activity data is provided against MDA-MB-231 cells comparing trispecific molecules combining a CD3 binding domain and two tumor cell antigen binding domains versus trispecific controls with one tumor cell antigen binding domain, a mock domain and a CD3 binding domain, where the trispecific molecules comprise tumor cell antigen binding domains comprising a range of affinities for targeting EGFR and PD-L1.
Figure 22:
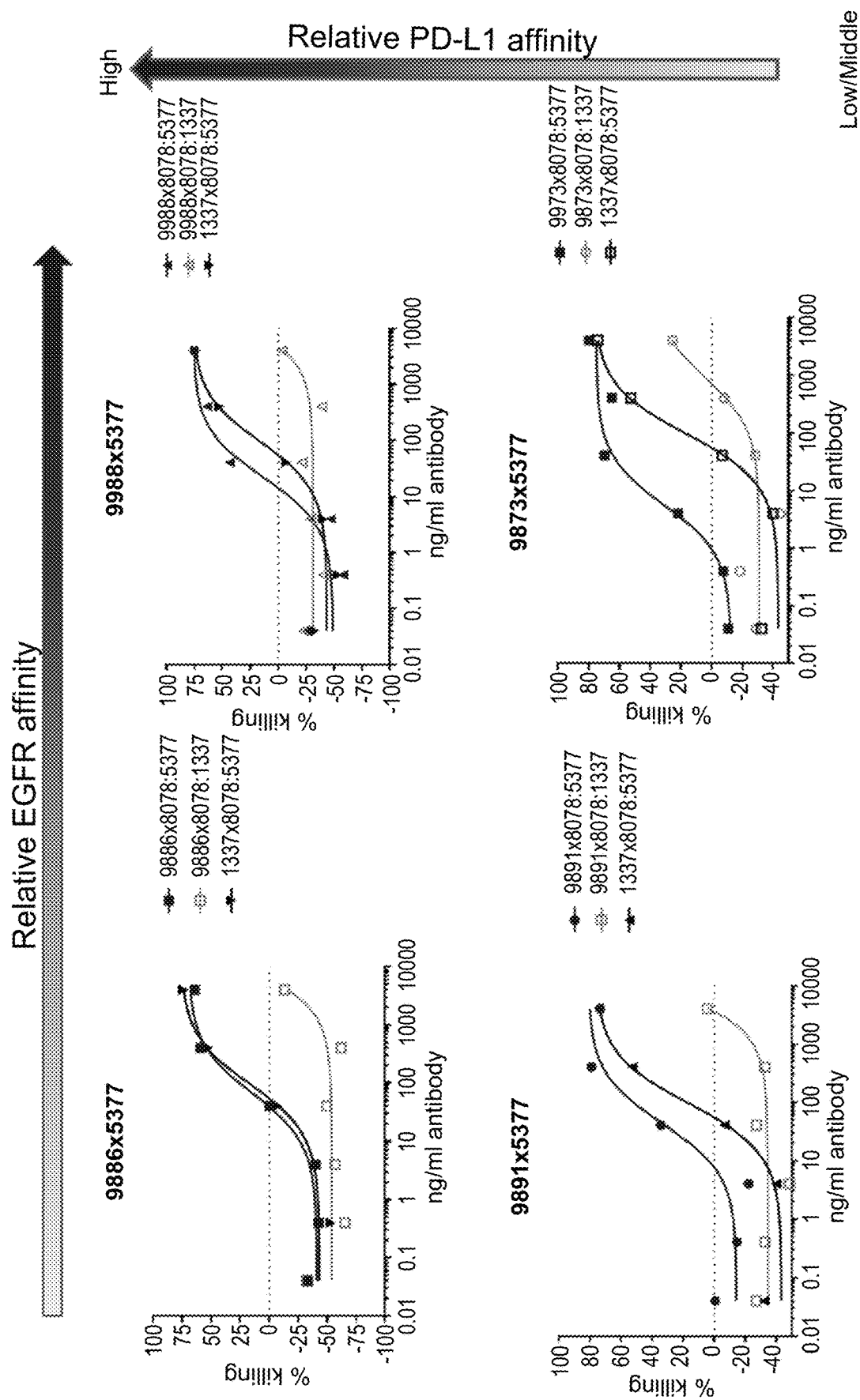
FIG. 22: T cell cytotoxicity activity data is provided against HCT116 cells comparing trispecific molecules combining a CD3 binding domain and two tumor cell antigen binding domains versus trispecific controls with one tumor cell antigen binding domain, a mock domain and a CD3 binding domain, where the trispecific molecules comprise tumor cell antigen binding domains comprising a range of affinities for targeting EGFR and PD-L1.
Figure 22:
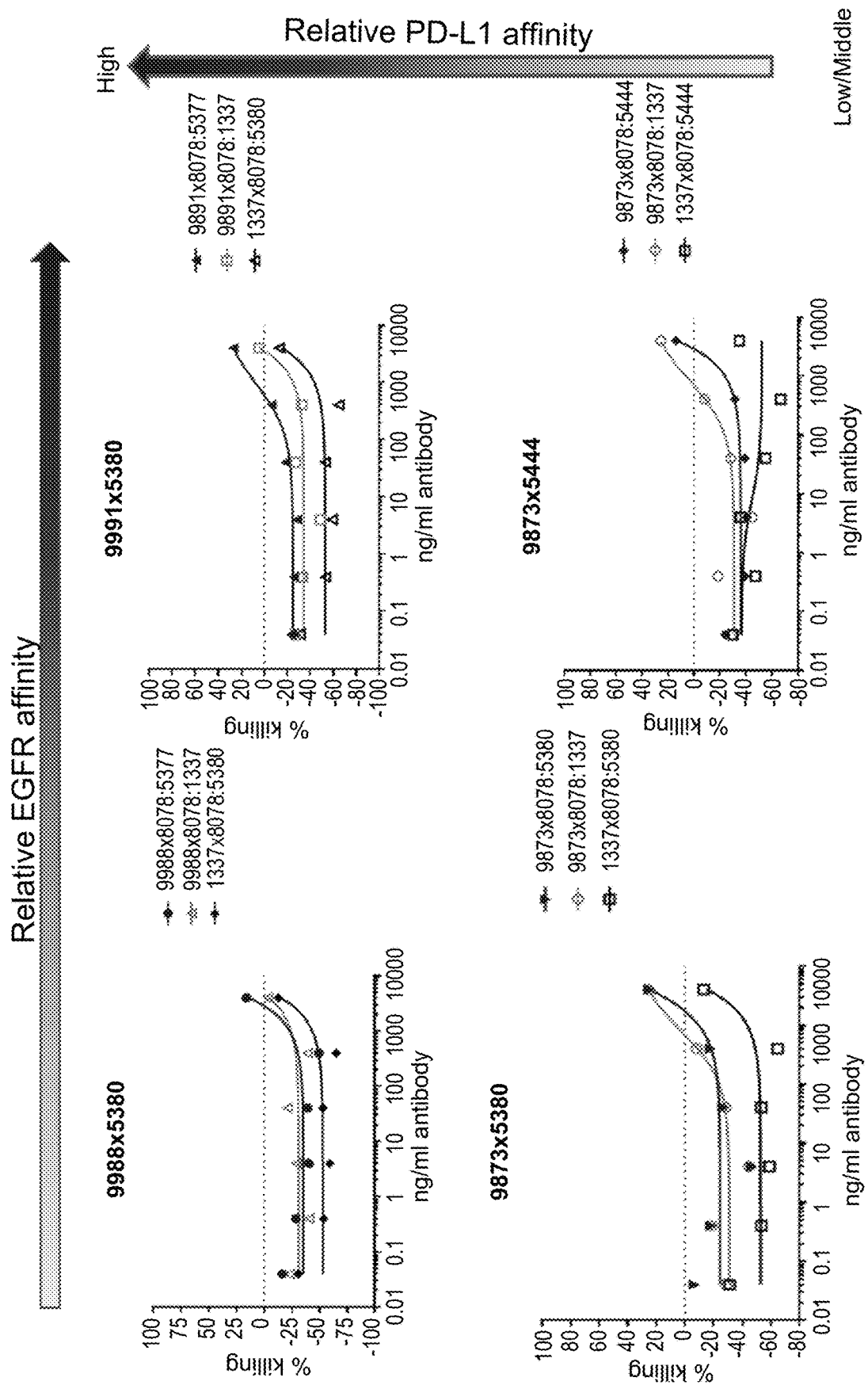

This study examining cytotoxicity of the trispecific molecules against these cell lines show all three binding domains of the EGFRxCD3:PD-L1 trispecific molecules are capable of simultaneous binding the two tumor cell antigens and CD3, such that both tumor antigen binding domains of the trispecific molecule contribute to cytotoxicity upon T-cell engagement. FIGS. 20 and 21 (against MDA-MB-231 cells) and FIG. 22 (against HCT116 cells). These trispecific molecules generally showed enhanced functional activity over the bispecific EGFRxCD3×Mock and the MockxCD3× PD-L1 controls, with the trispecific molecule 9873×8078: 5377 showing the largest percent lysis. FIG. 21. The trispecifics tested here are more potent against MDA-MB-231 cells which have relatively high target antigen levels compared to HCT116 cells. FIG. 21 and FIG. 22.

Example 13: Effective Dual Tumor Antigen Binding and T Cell Engagement Via CD3 for Trispecific Format of CD3×PD-L1:EGFR Trispecific antibodies were produced according to the format at FIG. 18 to further show simultaneous tumor antigen targeting where the immune engaging domain is present on the short arm. These antibodies were generated by techniques described above. For this format, dual antigen targeting-correlated binding was demonstrated, such that with increasing PD-L1 affinity there was a continued enhancement of target cell binding as measured by FACs on MDA-MB-231 cells as observed for CD3×PD-L1:EGFR molecules. FIG. 23a. For certain of these trispecific molecules having the format of CD3×PD-L1:EGFR, simultaneous dual antigen binding and immune cell engagement have been demonstrated to have an additive effect on cytotoxicity of BxPC3 cells over molecules binding a single antigen and CD3 (heavy chain sequences not shown) verifying the capability of these molecules to engage all three binding arms simultaneously. FIG. 23b. The protocol for the cytotoxicity assay for these data have been described above.

Example 14: Effective T Cell Activation Via CD3 at the Distal Long Arm, for Trispecific Format of EGFRxFibrinogen:CD3

Jurkat-NFAT-RE-luc2 cells (Promega®) are a genetically engineered Jurkat T cell line that expresses a luciferase reporter driven by an NFAT-response element (NFAT-RE). HT29 (ATCC HTB-38) is a human colon cancer cell.

Figure 25:
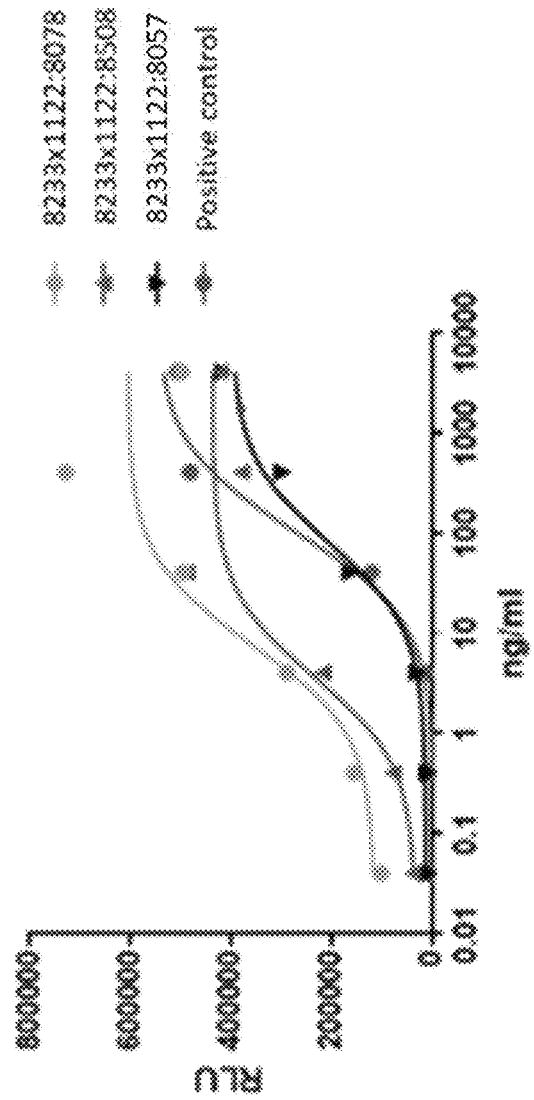
FIG. 25: T-cell activiation data is provided against HT29 cells, and demonstrating T-cell activiation by a variety of EGFRxFibrinogen:CD3 trispecific T cell engager molecules using different CD3 binding domains as compared to the positive control EGFRxCD3 bispecific antibody used in FIG. 15.

A study was performed for placing the CD3 binding domain on the distal region of the long arm, with a trivalent molecule of EGFR (MF8233)×Fibrinogen(MF1122):CD3 (MF8078). FIG. 24. Performing a T-cell activation assay on Jurkat-NFAT-RE-luc2 cells against target cell HT29 to establish functional T-cell activation capacity for this format. The reporter assay in short: Jurkat effector T cells were co-incubated with target cells in the presence of a concentration range of trisprecific antibodies and control antibodies. After 5 hours of incubation the Luciferase activity of the reporter cells was measured as a read-out for T cell activation, using the Bio-Glo™ Luciferase Assay System (Promega®). Luminescence activity was measured on an EnVision® Microplate reader resulting in Relative light unit (RLU) values, which were analyzed using GraphPad Prism®. As shown in FIG. 25, activiation of T-cells by the EGFRxFibri:CD3 trispecific molecules was demonstrated at levels equal to or greater than the positive control, which is a EGFRxCD3 antibody previously demonstrated to engender T-cell activation in FIG. 15a.

Figure 26:
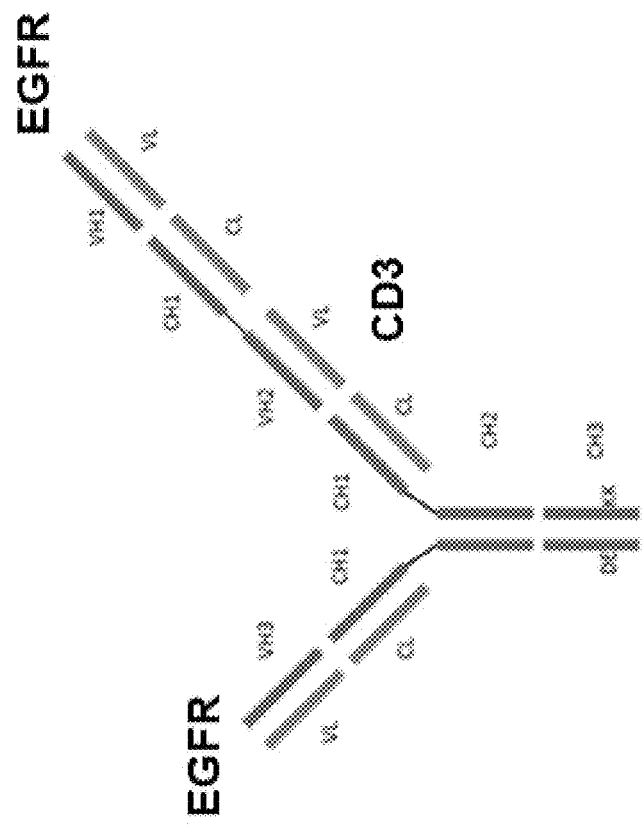
FIG. 26: Configuration of the EGFRxCD3:EGFR bispecific, trivalent molecule with the same EGFR binding domains (MF9891).

Example 15: Effective Tumor Antigen Binding and T Cell Engagement Via CD3 for an Array of CD3 Binding Domains and Linkers A panel of EGFRxCD3:EGFR bispecific, trivalent molecules were generated (FIG. 26) to demonstrate the efficacy of tumor targeting and T-cell engagement across a variety of different CD3, immune-cell engaging binding domains and eight different linkers. Each trivalent molecule contained two of the same anti-EGFR binding domains (MF9891) at the short arm and distal long arm position, with the CD3 binding domain at the interior, long arm position. For this study, a reporter cell line of Jurkat-NFAT-RE-luc2 cells and target cells HCT116 (intermediate EGFR expression) and MDA-MB-231 were used to measure T-cell activation, by methods previously described. For a negative control, trivalent molecules using a CD3 binding domain from different superclusters were produced MockxCD3×Mock or the bispecific (EGFR (MF8233) xTT(MF1337)) (4,000 ng/ml). The read-out relied on reporter activation after 5 hours of incubation.

Figure 27:
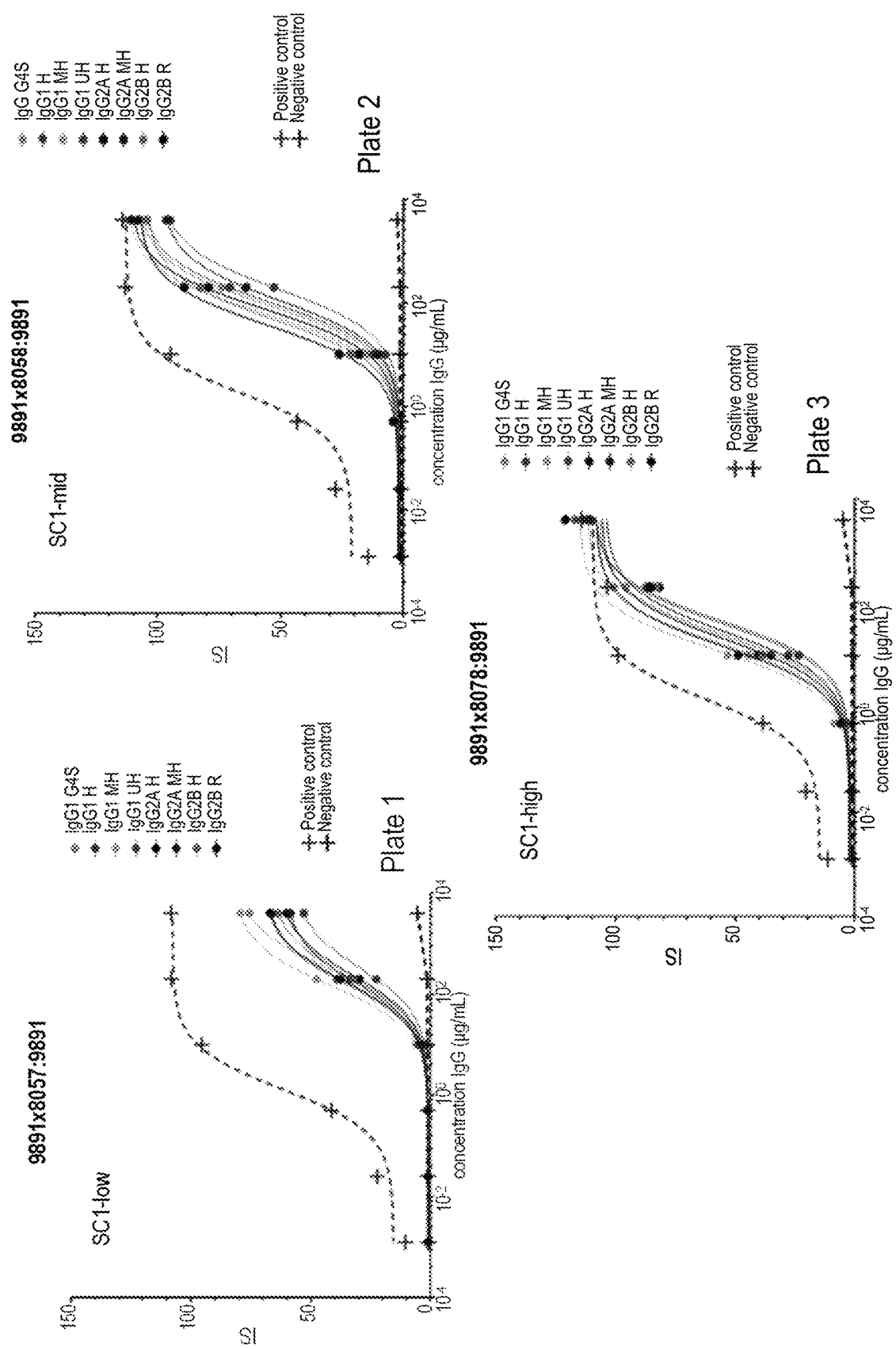
FIG. 27: T cell activation activity in HCT116 cells was measured for a series of bispecific trivalent EGFRxCD3: EGFR molecules with the same EGFR binding domains (MF9891) and different CD3 binding domains from different superclusters with a range of linkers.
Figure 27:
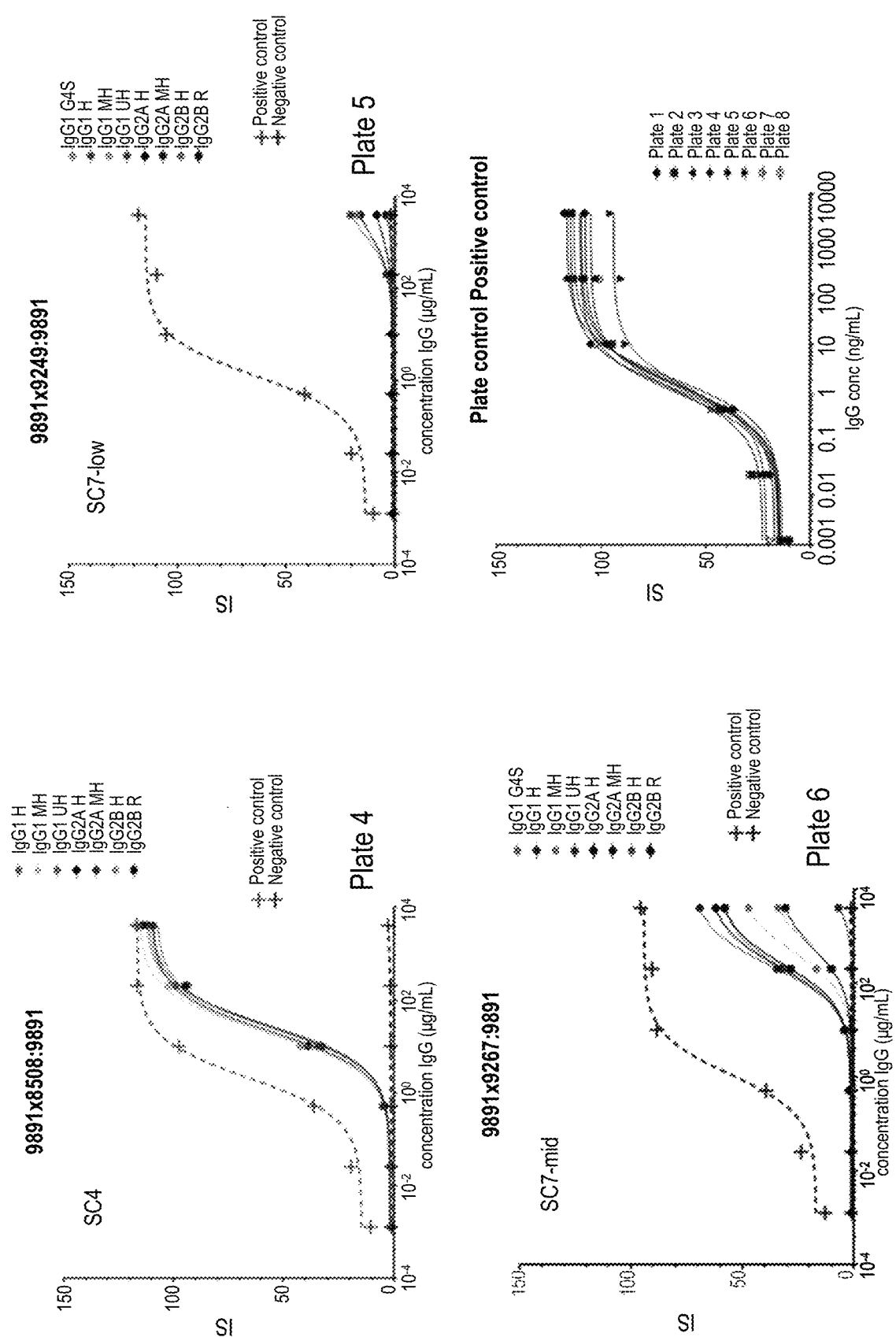

Each CD3 tested from varying superclusters demonstrated reporter activity using HCT116 cells, with a CD3 binding domain from supercluster 7 demonstrating the lowest relative reporter activity, while evidencing a spectrum of activity based on linker arms. In contrast, the two CD3 binding domains from supercluster 1 (MF8058 and MF8078) and a CD3 binding domain from supercluster 4 (MF8508) demonstrated relatively consistent activity irrespective of linker arm. Finally, one CD3 binding domain of supercluster 1 (MF8057) evidenced relatively low reporter activity, which provided some differentiation associated with different linkers. See FIG. 27. A review of these data indicate that trivalents containing the IgG1 MH linker appear consistently to be the most potent across superclusters.

Figure 28:
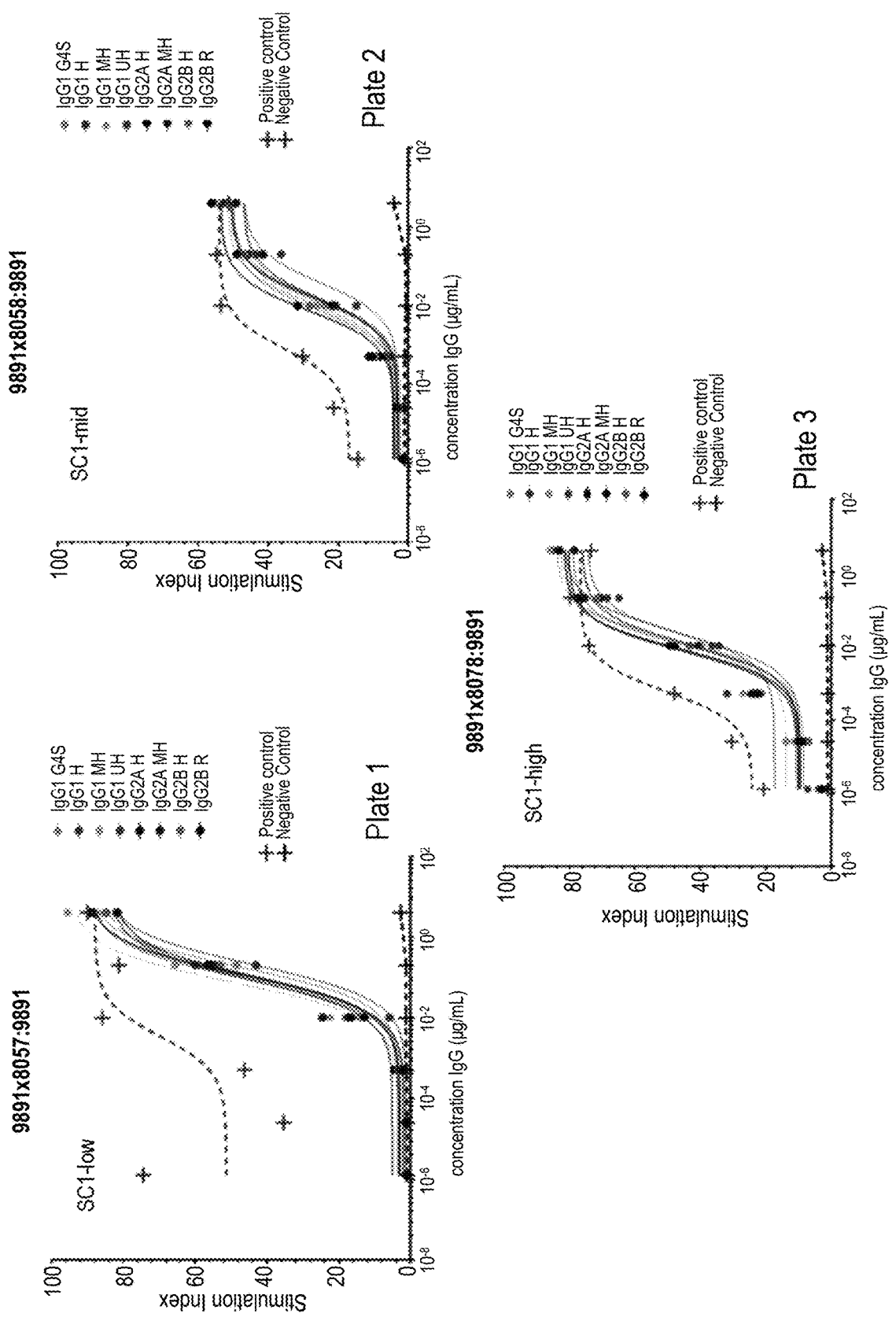
FIG. 28: T cell activation activity in MDA-MB-231 cells was measured for a series of bispecific trivalent EGFRxCD3:EGFR molecules with the same EGFR binding domains (MF9891) and different CD3 binding domains from different superclusters with a range of linkers.
Figure 28:
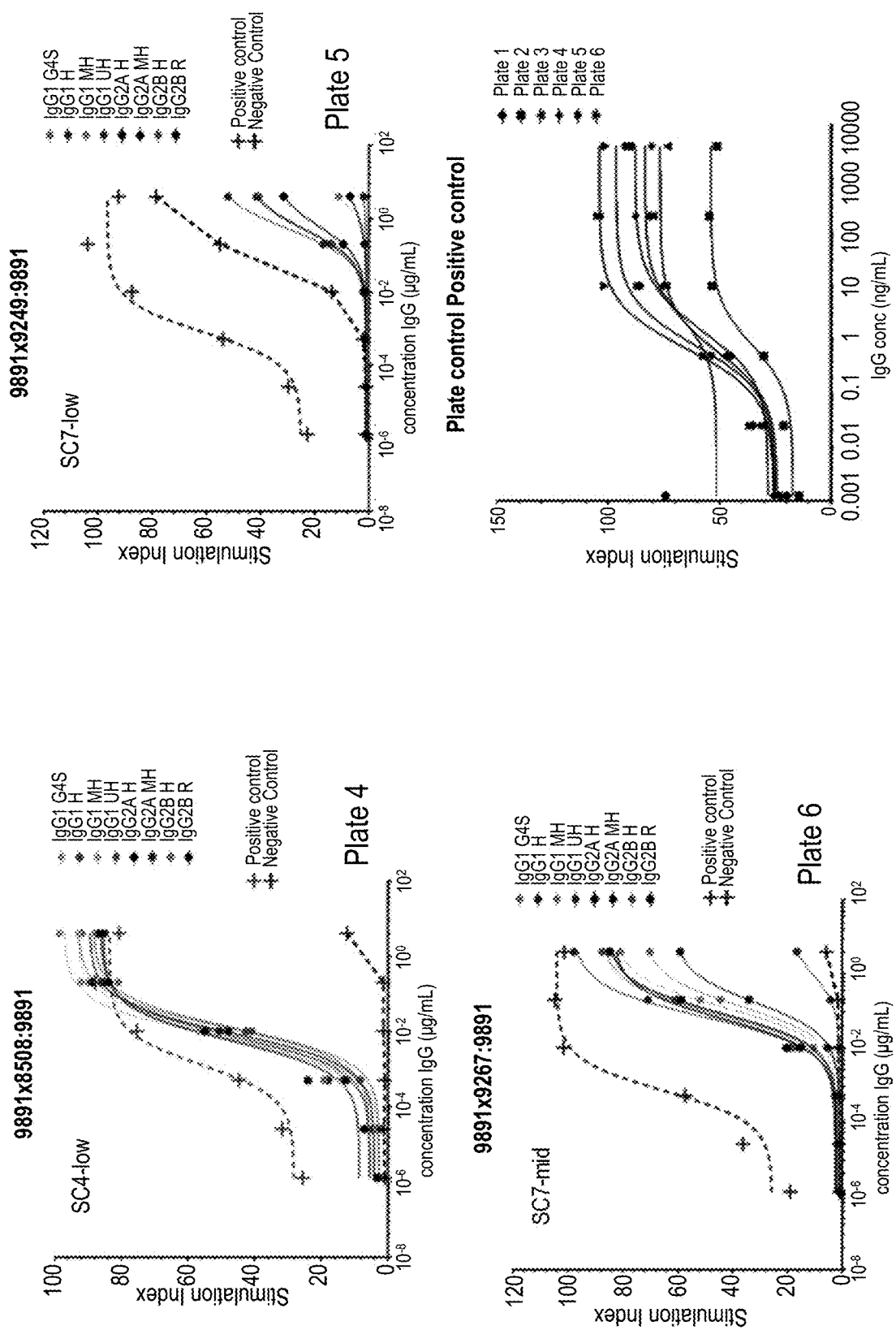

Similarly, each CD3 binding domain tested from varying superclusters demonstrated reporter activity using MDA-MB-231 cells, with the CD3 binding domains from supercluster 7 demonstrating relatively low reporter activity, with a spectrum of activity based on the linker used. In contrast, the three CD3 binding domains from supercluster 1 (MF8057, MF8058 and MF8078) and CD3 binding domain from supercluster 4, demonstrated relatively similar activity irrespective of linker used. See FIG. 28.

TABLE 21

IgG heavy chains for the generation of bispecific molecules.

Table 21A
CH1:
gctagcaccaagggcccatcggtcttccccctggcaccctcctccaagagcacctctggg
A S T K G P S V F P L A P S S K S T S G
ggcacagcggccctgggctgcctggtcaaggactacttccccgaaccggtgacggtgtcg
G T A A L G C L V K D Y F P E P V T V S
tggaactcaggcgccctgaccagaggcgtgcacaccttcccggctgtcctacagtcctca
W N S G A L T S G V H T F P A V L Q S S
ggactctactccctcagcagcgtcgtgaccgtgccctccagcagcttgggcacccagacc
G L Y S L S S V V T V P S S S L G T Q T
Tacatctgcaacgtgaatcacaagcccagcaacaccaaggtggacaagagagtt
(SEQ ID NO: 291)
Y I C N V N H K P S N T K V D K R V (SEQ ID NO: 292)

Table 21B
Hinge:
Gagcccaaatcttgtgacaaaactcacacatgcccaccgtgccca (SEQ ID NO: 293)
E P K S C D K T H T C P P C P (SEQ ID NO: 294)

Table 21C
CH2:
gcacctgaactcctggggggaccgtcagtcttcctcttccccccaaaacccaaggacacc
A P E L L G G P S V F L F P P K P K D T
ctcatgatctcccggacccctgaggtcacatgcgtggtggtggacgtgagccacgaagac
L M I S R T P E V T C V V V D V S H E D
cctgaggtcaagttcaactggtacgtggacggcgtggaggtgcataatgccaagacaaag
P E V K F N W Y V D G V E V H N A K T K
ccgcggggaggagcagtacaacagcacgtaccgtgtggtcagcgtcctcaccgtcctgcac
P R E E Q Y N S T Y R V V S V L T V L H
caggactggctgaatggcaaggagtacaagtgcaaggtctccaacaaagcccctcccagcc
Q D W L N G K E Y K C K V S N K A L P A
Cccatcgagaaaaccatctccaaagccaaa (SEQ ID NO: 295)
P I E K T I S K A K (SEQ ID NO: 296)

Table 21D
CH2 containing L235G and G236R silencing substitutions:
gcacctgaactcggcaggggaccgtcagtcttcctcttccccccaaaacccaaggacacc
A P E L G R G P S V F L F P P K P K D T
ctcatgatctcccggacccctgaggtcacatgcgtggtggtggacgtgagccacgaagac
L M I S R T P E V T C V V V D V S H E D
cctgaggtcaagttcaactggtacgtggacggcgtggaggtgcataatgccaagacaaag
P E V K F N W Y V D G V E V H N A K T K
ccgcggggaggagcagtacaacagcacgtaccgtgtggtcagcgtcctcaccgtcctgcac
P R E E Q Y N S T Y R V V S V L T V L H
caggactggctgaatggcaaggagtacaagtgcaaggtctccaacaaagcccctcccagcc
Q D W L N G K E Y K C K V S N K A L P A
Cccatcgagaaaaccatctccaaagccaaa (SEQ ID NO: 297)
P I E K T I S K A K (SEQ ID NO: 298)

Table 21E
CH3: KK of DEKK
gggcagccccgagaaccacaggtgtacaccaagcccccatcccgggaggagatgaccaag
G Q P R E P Q V Y T K P P S R E E M T K
aaccaggtcagcctgaagtgcctggtcaaaggcttctatcccagcgacatcgccgtggag
N Q V S L K C L V K G F Y P S D I A V E
tgggagagcaatgggcagccggagaacaactacaagaccacgcctcccgtgctggactcc
W E S N G Q P E N N Y K T T P P V L D S
gacggctccttcttcctctatagcaagctcaccgtggacaagagcaggtggcagcagggg
D G S F F L Y S K L T V D K S R W Q Q G
aacgtcttctcatgctccgtgatgcatgaggctctgcacaaccactacacgcagaagagc
N V F S C S V M H E A L H N H Y T Q K S
ctctccctgtctccgggttga (SEQ ID NO: 299)
L S L S P G - (SEQ ID NO: 300)

Table 21F
CH3: DE of DEKK
gggcagccccgagaaccacaggtgtacaccgacccccatcccgggaggagatgaccaag
G Q P R E P Q V Y T D P P S R E E M T K
aaccaggtcagcctgacctgcgaggtcaaaggcttctatcccagcgacatcgccgtggag
N Q V S L T C E V K G F Y P S D I A V E
tgggagagcaatgggcagccggagaacaactacaagaccacgcctcccgtgctggactcc
W E S N G Q P E N N Y K T T P P V L D S

TABLE 21 -continued

IgG heavy chains for the generation of bispecific molecules.

```
gacggctccttcttcctctatagcaagctcaccgtggacaagagcaggtggcagcagggg
 D  G  S  F  F  L  Y  S  K  L  T  V  D  K  S  R  W  Q  Q  G
aacgtcttctcatgctccgtgatgcatgaggctctgcacaaccactacacgcagaagagc
 N  V  F  S  C  S  V  M  H  E  A  L  H  N  H  Y  T  Q  K  S
ctctccctgtctccgggttga (SEQ ID NO: 301)
 L  S  L  S  P  G  -  (SEQ ID NO: 302)
```

Table 21A: CH1 region.
Table 21B: hinge region.
Table 21O: CH2 region.
Table 21O: CH2 containing L235G and G236R silencing substitutions.
Table 21E: CH3 domain containing substitutions L351K and T366K (KK).
Table 21F; CH3 domain containing substitutions L351O and L368E (DE).

The invention claimed is:

1. A multivalent antibody which comprises:
   a base antibody portion which comprises two binding domains; and
   one or two additional binding domains,
   wherein the base antibody portion is a full length immunoglobulin,
   wherein the one or two additional binding domains are Fab domains comprising a CH1 region, each Fab domain being connected to the base antibody portion by a linker, linking a variable region of the base antibody portion and the CH1 region,
   wherein each binding domain of the base antibody portion and each of the one or two additional binding domains all have the same light chain, the light chain comprising the complementarity determining regions (CDRs) of IGKV1-39/jk1 or IGKV1-39/jk5, and
   wherein the multivalent antibody binds to at least three different epitopes or antigens.

2. The multivalent antibody according to claim 1, wherein the linker comprises a sequence as set out in any one of SEQ ID NOs:1 to 24, or a linker having at least about 85% sequence identity to any one thereof.

3. The multivalent antibody according to claim 1, wherein the base portion of the antibody comprises a first CH3 domain that dimerizes with a second CH3 domain, the first of which comprises an amino acid residue lysine at positions 351 and 366 or at positions corresponding thereto and the second of which comprises the amino acid residues of aspartic acid at 351 and glutamic acid at 368 or at positions corresponding thereto.

4. The multivalent antibody according to claim 1, wherein the amino acid sequence of the linker comprises a naturally-occurring sequence.

5. The multivalent antibody according to claim 1, wherein the linker comprises a middle hinge region sequence.

6. The multivalent antibody according to claim 1, wherein the linker comprises an upper and a lower hinge region sequence.

7. The multivalent antibody according to claim 1, wherein the linker comprises a helix-forming sequence.

8. The multivalent antibody according to claim 1, wherein the linker comprises an amino acid sequence according to any one of SEQ ID NOs: 1 to 24.

9. The multivalent antibody according to claim 1, wherein at least one of the binding domains specifically binds to an epitope within an antigen on an immune effector cell.

10. The multivalent antibody according to claim 9, wherein at least one of the binding domains specifically binds to an epitope within an antigen on an aberrant cell.

11. The multivalent antibody according to claim 1, wherein a first binding domain specifically binds PD-L1; a second binding domain specifically binds CD3, and a third binding domain specifically binds to EGFR.

12. A pharmaceutical composition which comprises an antibody according to claim 1 and a pharmaceutically acceptable carrier and/or diluent.

13. The multivalent antibody according to claim 1, wherein the light chain comprises the sequence of SEQ ID NO:29.

14. The multivalent antibody according to claim 1, wherein the linker comprises the sequence of SEQ ID NO:1.

15. The multivalent antibody according to claim 1, wherein the linker comprises the sequence of SEQ ID NO:2.

16. The multivalent antibody according to claim 1, wherein the linker comprises the sequence of SEQ ID NO:3.

17. The multivalent antibody according to claim 1, wherein the linker comprises the sequence of SEQ ID NO:4.

18. The multivalent antibody according to claim 1, wherein the linker comprises the sequence of SEQ ID NO:5.

19. The multivalent antibody according to claim 1, wherein the linker comprises the sequence of SEQ ID NO:6.

20. The multivalent antibody according to claim 1, wherein the linker comprises the sequence of SEQ ID NO:7.

21. The multivalent antibody according to claim 1, wherein the linker comprises the sequence of SEQ ID NO:8.

22. The multivalent antibody according to claim 1, wherein the linker comprises the sequence of SEQ ID NO:9.

23. The multivalent antibody according to claim 1, wherein the linker comprises the sequence of SEQ ID NO:10.

24. The multivalent antibody according to claim 1, wherein the linker comprises the sequence of SEQ ID NO:11.

25. The multivalent antibody according to claim 1, wherein the linker comprises the sequence of SEQ ID NO:12.

26. The multivalent antibody according to claim 1, wherein the linker comprises the sequence of SEQ ID NO:13.

27. The multivalent antibody according to claim 1, wherein the linker comprises the sequence of SEQ ID NO:14.

28. The multivalent antibody according to claim 1, wherein the linker comprises the sequence of SEQ ID NO:15.

29. The multivalent antibody according to claim 1, wherein the linker comprises the sequence of SEQ ID NO:16.

30. The multivalent antibody according to claim 1, wherein the linker comprises the sequence of SEQ ID NO:17.

31. The multivalent antibody according to claim 1, wherein the linker comprises the sequence of SEQ ID NO:18.

32. The multivalent antibody according to claim 1, wherein the linker comprises the sequence of SEQ ID NO:19.

33. The multivalent antibody according to claim 1, wherein the linker comprises the sequence of SEQ ID NO:20.

34. The multivalent antibody according to claim 1, wherein the linker comprises the sequence of SEQ ID NO:21.

35. The multivalent antibody according to claim 1, wherein the linker comprises the sequence of SEQ ID NO:22.

36. The multivalent antibody according to claim 1, wherein the linker comprises the sequence of SEQ ID NO:23.

37. The multivalent antibody according to claim 1, wherein the linker comprises the sequence of SEQ ID NO:24.

38. The multivalent antibody according to claim 1, wherein the light chain comprises a CDR1 comprising the amino acid sequence QSISSY (SEQ ID NO: 254), a CDR2 comprising the amino acid sequence AAS (SEQ ID NO: 255), and a CDR3 region comprising the amino acid sequence QQSYSTP (SEQ ID NO: 256).

39. The multivalent antibody according to claim 1, wherein the light chain comprises a light chain variable region comprising the sequence of SEQ ID NO: 37 or 40, with 0-5 conservative amino acid substitutions at one or more positions other than the CDRs.

40. The multivalent antibody according to claim 38, wherein the light chain comprises a light chain variable region comprising the sequence of SEQ ID NO: 37 or 40, with 0-5 conservative amino acid substitutions at one or more positions other than the CDRs.

41. The multivalent antibody according to claim 1, wherein the multivalent antibody binds to three different epitopes or antigens.

42. The multivalent antibody according to claim 1, wherein the multivalent antibody binds to four different epitopes or antigens.

43. The multivalent antibody according to claim 1, wherein the multivalent antibody binds to at least three epitopes within two different antigens.

44. The multivalent antibody according to claim 9, wherein the immune effector cell is a T cell.

45. The multivalent antibody according to claim 44, wherein the antigen on said T cell is CD3.

46. The multivalent antibody according to claim 10, wherein the aberrant cell is a tumor cell.

47. The multivalent antibody according to claim 9, wherein the two binding domains of the base antibody are binding domains 1 and 2 and one additional binding domain is binding domain 3, wherein binding domain 3 is linked to binding domain 1 and binding domain 1 is a CD3 binding domain and binding domains 2 and 3 bind to epitopes within different target cell antigens.

* * * * *

UNITED STATES PATENT AND TRADEMARK OFFICE
CERTIFICATE OF CORRECTION

| | |
|---|---|
| PATENT NO. | : 11,952,424 B2 |
| APPLICATION NO. | : 16/370346 |
| DATED | : April 9, 2024 |
| INVENTOR(S) | : Cornelis Adriaan de Kruif et al. |

It is certified that error appears in the above-identified patent and that said Letters Patent is hereby corrected as shown below:

On the Title Page

Column 1, Item (73), under "Assignee:", Line 1, delete "merus n.v." and insert -- MERUS N.V. --, therefor.

Signed and Sealed this
Twenty-eighth Day of May, 2024

Katherine Kelly Vidal
*Director of the United States Patent and Trademark Office*